(12) United States Patent
Fairhurst et al.

(10) Patent No.: US 8,114,877 B2
(45) Date of Patent: Feb. 14, 2012

(54) ORGANIC COMPOUNDS

(75) Inventors: Robin A Fairhurst, Horsham (GB); Roger J Taylor, Horsham (GB)

(73) Assignee: Novartis AG, Basel (CH)

( * ) Notice: Subject to any disclaimer, the term of this patent is extended or adjusted under 35 U.S.C. 154(b) by 421 days.

(21) Appl. No.: 11/722,835

(22) PCT Filed: Jan. 12, 2006

(86) PCT No.: PCT/EP2006/000217
§ 371 (c)(1), (2), (4) Date: Jun. 26, 2007

(87) PCT Pub. No.: WO2006/074925
PCT Pub. Date: Jul. 20, 2006

(65) Prior Publication Data
US 2008/0207648 A1 Aug. 28, 2008

(30) Foreign Application Priority Data
Jan. 14, 2005 (GB) .................................. 0500785.1

(51) Int. Cl.
C07D 473/16 (2006.01)
C07D 473/40 (2006.01)
C07D 473/34 (2006.01)
A61K 31/52 (2006.01)
A61P 11/06 (2006.01)

(52) U.S. Cl. ........... 514/252.16; 514/263.2; 514/263.22; 514/263.21; 544/277

(58) Field of Classification Search .................. None
See application file for complete search history.

(56) References Cited

U.S. PATENT DOCUMENTS

| | | | |
|---|---|---|---|
| 4,008,125 A | 2/1977 | Kurozumi et al. | |
| 4,738,954 A | 4/1988 | Hamilton et al. | |
| 4,873,360 A | 10/1989 | Johnson et al. | |
| 4,954,504 A | 9/1990 | Chen et al. | |
| 5,688,774 A | 11/1997 | Jacobson et al. | |
| 6,307,054 B1 | 10/2001 | Truesdale et al. | |
| 6,376,472 B1 | 4/2002 | Myers et al. | |
| 6,403,567 B1 | 6/2002 | Zablocki et al. | |
| 6,429,315 B1 | 8/2002 | Sledeski et al. | |
| 6,492,348 B1 * | 12/2002 | Bays et al. ................. 514/263.2 |
| 6,559,313 B2 | 5/2003 | Myers et al. | |
| 6,677,316 B2 | 1/2004 | Bays et al. | |
| 7,553,823 B2 | 6/2009 | Zablocki | |
| 7,737,126 B2 | 6/2010 | Blatcher | |
| 2003/0092668 A1 | 5/2003 | Liang et al. | |
| 2003/0176390 A1 | 9/2003 | Herling et al. | |
| 2004/0106572 A1 | 6/2004 | Fishman et al. | |
| 2004/0162422 A1 | 8/2004 | Hall et al. | |
| 2005/0101551 A1 | 5/2005 | Sevillano et al. | |
| 2005/0182018 A1 | 8/2005 | Linden et al. | |
| 2006/0142237 A1 | 6/2006 | Fishman et al. | |
| 2006/0189636 A1 | 8/2006 | Critchley et al. | |
| 2007/0099865 A1 | 5/2007 | Fishman et al. | |
| 2007/0191293 A1 | 8/2007 | Langston et al. | |
| 2007/0232626 A1 | 10/2007 | Jacobson et al. | |
| 2008/0027022 A1 | 1/2008 | Linden | |
| 2008/0051364 A1 | 2/2008 | Fishman et al. | |
| 2008/0051404 A1 | 2/2008 | Claiborne et al. | |
| 2008/0200483 A1 * | 8/2008 | Fairhurst et al. ............... 544/277 |
| 2008/0214581 A1 | 9/2008 | Allen | |
| 2008/0242683 A1 | 10/2008 | Fairhurst | |
| 2008/0262001 A1 | 10/2008 | Kranenburg | |
| 2008/0300213 A1 | 12/2008 | Fishman | |
| 2008/0312160 A1 | 12/2008 | Guerrant | |
| 2009/0012035 A1 | 1/2009 | Jacobson | |
| 2009/0054476 A1 | 2/2009 | Goblyos et al. | |
| 2009/0081764 A1 | 3/2009 | Pausch | |
| 2009/0093633 A1 * | 4/2009 | Fairhurst et al. ............... 544/277 |
| 2009/0099214 A1 * | 4/2009 | Fairhurst et al. ......... 514/263.22 |
| 2009/0105476 A1 | 4/2009 | Fairhurst et al. | |
| 2009/0123510 A1 | 5/2009 | Cronstein | |
| 2009/0181920 A1 | 7/2009 | Watkins | |
| 2009/0181934 A1 | 7/2009 | Fairhurst | |
| 2009/0240045 A1 | 9/2009 | Fairhurst et al. | |
| 2009/0281126 A1 * | 11/2009 | Fairhurst et al. ........... 514/263.2 |
| 2009/0281127 A1 * | 11/2009 | Fairhurst et al. ............... 544/277 |

(Continued)

FOREIGN PATENT DOCUMENTS
EP 0 267 878 5/1988
(Continued)

OTHER PUBLICATIONS

Baraldi et al., "Recent improvements in the field of A3 adenosine receptor ligands", Expert Opinion on Therapeutic Patents, vol. 15, No. 11 (2005), pp. 1507-1519.

(Continued)

Primary Examiner — Mark Berch
(74) Attorney, Agent, or Firm — Paul D. Strain; Strain & Strain PLLC

(57) ABSTRACT

Compounds of formula I

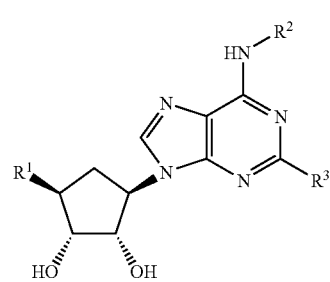

in free or salt form, wherein $R^1$, $R^2$ and $R^3$ have the meanings as indicated in the specification, are useful for treating conditions mediated by activation of the adenosine $A_{2A}$ receptor, especially inflammatory or obstructive airways diseases. Pharmaceutical compositions that contain the compounds and a process for preparing the compounds are also described.

31 Claims, No Drawings

U.S. PATENT DOCUMENTS

| | | | |
|---|---|---|---|
| 2009/0325967 A1 | 12/2009 | Fairhurst et al. | |
| 2010/0041918 A1 | 2/2010 | Laumen | |
| 2010/0190784 A1* | 7/2010 | Fairhurst et al. | 514/232.5 |
| 2010/0197914 A1* | 8/2010 | Fairhurst | 544/277 |
| 2010/0240680 A1* | 9/2010 | Fairhurst et al. | 514/263.22 |
| 2010/0286126 A1* | 11/2010 | Fairhurst et al. | 514/218 |

FOREIGN PATENT DOCUMENTS

| | | |
|---|---|---|
| JP | 63-219387 | 9/1988 |
| WO | 92/05177 | 4/1992 |
| WO | WO 93/22328 A1 | 11/1993 |
| WO | WO 98/50047 A1 | 11/1998 |
| WO | 99/67263 | 12/1999 |
| WO | 99/67266 | 12/1999 |
| WO | WO 99/67265 A1 | 12/1999 |
| WO | WO 00/23457 A1 | 4/2000 |
| WO | WO 00/78774 A2 | 12/2000 |
| WO | WO 00/78779 A2 | 12/2000 |
| WO | WO 01/60835 A1 | 8/2001 |
| WO | 02/22630 | 3/2002 |
| WO | WO 02/055085 A2 | 7/2002 |
| WO | WO 02/070534 A1 | 9/2002 |
| WO | WO 03/029264 A2 | 4/2003 |
| WO | WO 03/086408 A1 | 10/2003 |
| WO | WO 2005/063246 A1 | 7/2005 |
| WO | WO 2005/084653 A2 | 9/2005 |
| WO | WO 2005/107463 A1 | 11/2005 |
| WO | WO 2005/116037 A1 | 12/2005 |
| WO | WO 2006/011130 A1 | 2/2006 |
| WO | WO 2006/045552 A1 | 5/2006 |
| WO | WO 2006/074925 A1 | 7/2006 |
| WO | WO 2006/097260 A1 | 9/2006 |
| WO | WO 2007/121917 A2 | 11/2007 |
| WO | WO 2007/121919 A1 | 11/2007 |
| WO | WO 2007/121920 A2 | 11/2007 |
| WO | WO 2007/121921 A2 | 11/2007 |
| WO | WO 2007/121923 A1 | 11/2007 |
| WO | WO 2007/121924 A2 | 11/2007 |
| WO | WO 2007/147659 A1 | 12/2007 |
| WO | WO 2008006563 A1 * | 1/2008 |

OTHER PUBLICATIONS

Barnard et al., "Inhibition of measles virus replication by 5'-nor carbocyclic adenosine analogues", Antiviral Chemistry & Chemotherapy, vol. 12, No. 4 (2001), pp. 241-250.

Broadley et al., "Drugs Modulating Adenosine Receptors as Potential Therapeutic Agents for Cardiovascular Diseases", Expert Opinion on Therapeutic Patents, vol. 10, No. 11 (2000), pp. 1669-1692.

Cowart et al., "Synthesis of Novel Carbocyclic Adenosine Analogues as Inhibitors of Adenosine Kinase", J. Org. Chem., vol. 64, No. 7 (1999), pp. 2240-2249.

Curran et al., "The Preparation of Optically Active 2, Cyclopenten-1,4-Diol Derivatives from Furfuryl Alcohol", Tetrahedron, vol. 53, No. 6 (1997), pp. 1983-2004.

Duhamel et al., "Acylation Enatioselective D'un Diol, Meso: Le Cis-Cyclopenthen-2 Diol-1,4", Tetrahedron Letters, vol. 26, No. 26 (1985), pp. 3099-3102.

Galkina et al., "Studies on an Oixdative, 1,4-Addition to s-trans-1,3-Dienes, a Key Reaction in a Strigol Total Synthesis", Eur. J. Org. Chem., (2003), pp. 4640-4653.

Ghosh et al. "Synthesis of Enantiomerically Pure 5'-Aza Noraristeromycin Analogs", J. Org. Chem., vol. 60, No. 18 (1995), pp. 5808-5813.

Hegde et al., "5'-Amino-5'-deoxy-5'-noraristeromycin", Chemical Abstracts Index entry for Journal of Organic Chemistry, vol. 63, No. 20 (1998), pp. 7092-7094.

Hegde et al., "5'-Amino-5'-deoxy-5'noraristeromycin", J. Org. Chem., vol. 63, No. 20 (1998), pp. 7092-7094.

Kikugawa et al., "Platelet Aggregation Inhibitors. 6. 12-Thioadenosine Derivatives", Journal of Medicinal Chemistry, vol. 16, No. 12 (1973), pp. 1381-1388.

Marlene A Jacobsen, "Adenosine receptor agonists", Expert Opinion Therapeutic Targets, vol. 12, No. 4 (2002), pp. 489-501.

Marumoto et al., "Synthesis and Coronary Vasodilating Activity of 2-Substituted Adenosines", Chemical and Pharmaceutical Bulletin, vol. 23, No. 4 (1975), pp. 759-774.

Oriyama et al., "Catalytic Asymmetrization of CIS-2-Cyclopentene-1,4-Diol. Highly Efficient and Practical Synthesis . . . ", Heterocycles, vol. 52, No. 3 (2000), pp. 1055-1069.

Palle et al., "Structure-Affinity Relationships of the Affinity of 2-Pyrazolyl Adenosine Analogues for the Adenosine A2A Receptor", Bioorganic & Medicinal Chemistry Letters, vol. 12, No. 20 (2002), pp. 2935-2939.

Silverman J, Rheumatol, vol. 35, No. 4(2008), pp. 1-8.

Terashima et al., "Novel Use of Meso-Compound for the Preparation of Optically Active Compounds . . . ", Tetrahedron Letters, vol. 11 (1977), pp. 1001-1004.

Yang et al., "Amino substituted derivatives of 5'-amino-5'-deoxy-5'-noraristeromycin", Bioorganic & Medicinal Chemistry, vol. 13, No. 3 (2005), pp. 877-882.

Fairhurst et al., U.S. PTO Office Action, U.S. Appl. No. 12/297,727, Oct. 4, 2010, 13 pgs.

Fairhurst, U.S. PTO Office Action, U.S. Appl. No. 12/297,291, Dec. 1, 2010, 21 pgs.

Fairhurst, U.S. PTO Office Action, U.S. Appl. No. 11/576,607, Jan. 11, 2010, 39 pgs.

Fairhurst, U.S. PTO Office Action, U.S. Appl. No. 11/576,607, Dec. 23, 2009, 43 pgs.

Fairhurst, U.S. PTO Office Action, U.S. Appl. No. 11/576,607, Jul. 16, 2010, 40 pgs.

Fairhurst, U.S. PTO Office Action, U.S. Appl. No. 12/296,714, Jan. 5, 2010, 4 pgs.

Fairhurst, U.S. PTO Office Action, U.S. Appl. No. 12/296,714, May 19, 2010, 63 pgs.

Fairhurst, U.S. PTO Office Action, U.S. Appl. No. 12/296,714, Dec. 23, 2009, 12 pgs.

Fairhurst, U.S. PTO Office Action, U.S. Appl. No. 12/296,714, Dec. 30, 2009, 10 pgs.

Fairhurst, U.S. PTO Office Action, U.S. Appl. No. 12/297,373, Dec. 22, 2009, 8 pgs.

Fairhurst, U.S. PTO Office Action, U.S. Appl. No. 12/297,373, Jul. 15, 2010, 8 pgs.

Fairhurst, U.S. PTO Office Action, U.S. Appl. No. 12/297,404, Dec. 30, 2009, 18 pgs.

Fairhurst, U.S. PTO Office Action, U.S. Appl. No. 12/297,404, Jul. 15, 2010, 38 pgs.

Fairhurst, U.S. PTO Office Action, U.S. Appl. No. 12/297,940, Jan. 22, 2010, 15 pgs.

Fairhurst, U.S. PTO Office Action, U.S. Appl. No. 12/297,007, Dec. 23, 2009, 11 pgs.

Fairhurst, U.S. PTO Office Action, U.S. Appl. No. 12/297,007, Jul. 15, 2010, 32 pgs.

International Search Report, PCT/EP2007/006156, Oct. 12, 2007, 3 pgs.

International Search Report, PCT/EP2007/059666, Jan. 18, 2008, 3 pgs.

Kerns et al., "Drug-like Properties: Concepts, Structure Design and Methods: from ADME to Toxicity Optimization", Elsevier (2008), pp. 92-93.

Goosen et al., "Physicochemical Characterization and Solubility Analysis of Thalidomide and Its N-Alkyl Analogs", Pharmaceutical Research, vol. 19, No. 1 (2002), pp. 13-19.

Fourie et al., "Percutaneous delivery of carbamazepine and selected N-alkyl and N-hydroxyalkyl analogues", International Journal of Pharmaceutics, vol. 279, Issues 1-2 (2004), pp. 59-66.

Edwards et al., "Nonpeptidic Inhibitors of Human Neutrophil Elastase. 7. Design, Synthesis, and in Vitro Activity of a Series of Pyridopyrimidine Trifluoromethyl Ketones", J. Med. Chem., vol. 39 (1996), pp. 1112-1124.

Rautio et al., "Piperazinylalkyl prodrugs of naproxen improve in vitro skin permeation", European Journal of Pharmaceutical Sciences, vol. 11 (2000), pp. 157-163.

Unpublished Pending U.S. Appl. No. 12/297,291, Fairhurst et al., filed Oct. 15, 2008.

Unpublished Pending U.S. Appl. No. 12/297,491, Fairhurst et al., filed Oct. 17, 2008.

Bressi et al., "Adenosine Analogues as Inhibitors of Trypanosoma brucei Phosphoglycerate Kinase: Elucidation of a Novel Binding Mode for a 2-Amino-N$^6$-Substituted Adenosine", Journal of Medicinal Chemistry, vol. 43, No. 22 (2000), pp. 4135-4150.
Fairhurst, U.S. PTO Office Action, U.S. Appl. No. 11/576,607, Feb. 17, 2011, 12 pgs.
Fairhurst, U.S. PTO Office Action, U.S. Appl. No. 12/296,714, Jan. 3, 2011, 16 pgs.
Fairhurst, U.S. PTO Office Action, U.S. Appl. No. 12/296,714, Apr. 28, 2011, 7 pgs.
Fairhurst, U.S. PTO Office Action, U.S. Appl. No. 12/297,291, Mar. 21, 2011, 41 pgs.
Fairhurst, U.S. PTO Office Action, U.S. Appl. No. 12/297,491, Mar. 24, 2011, 20 pgs.
Fairhurst, U.S. PTO Office Action, U.S. Appl. No. 12/308,637, Feb. 24, 2011, 23 pgs.
Fairhurst, U.S. PTO Office Action, U.S. Appl. No. 12/310,254, Mar. 24, 2011, 18 pgs.
Fairhurst, U.S. PTO Office Action, U.S. Appl. No. 12/679,663, Feb. 28, 2011, 21 pgs.
Ghosh et al., "Synthesis and Biological Evaluation of a Carbocyclic Azanoraristeromycin Siderophore Conjugate", Nucleosides & Nucleotides, vol. 18, No. 2 (1999), pp. 217-225.
Wanner et al., "Synthesis and properties of 2-nitrosoadenosine", J. Chem. Soc., Perkin Trans., vol. 1 (2001), pp. 1908-1915.
Fairhurst, U.S. PTO Notice of Allowance, U.S. Appl. No. 11/576,607, Jun. 9, 2011, 7 pgs.
Fairhurst, U.S. Notice of Allowance, U.S. Appl. No. 12/297,291, Jul. 14, 2011, 9 pgs.
Fairhurst, U.S. PTO Restriction Requirement, U.S. Appl. No. 12/247,764, Jul. 15, 2011, 14 pgs.
International Search Report, PCT/EP2008/063869, Jul. 21, 2009, 7 pgs.
Laumen, U.S. PTO Office Action, U.S. Appl. No. 12/312,311, Aug. 9, 2011, 20 pgs.
Siddiqi et al., "Enantiospecific Synthesis of the Fluoro and Epimeric Derivatives of 5'- Noraristeromycin", J. Chem. Soc. Chem. Commun., 1993, pp. 708-709.
Unpublished pending U.S. Appl. No. 13/218,865, Robin Alec Fairhurst et al., filed Aug. 26, 2011.
Unpublished pending U.S. Appl. No. 13/218,887, Robin Alec Fairhurst et al., filed Aug. 26, 2011.
Fairhurst, U.S. PTO Notice of Allowance, U.S. Appl. No. 12/308,637, Sep. 26, 2011, 13 pgs.
Fairhurst, U.S. PTO Office Action, U.S. Appl. No. 12/297,491, Oct. 12, 2011, 11 pgs.
Fairhurst, U.S. PTO Office Action, U.S. Appl. No. 12/310,254, Oct. 12, 2011, 11 pgs.
Fairhurst, U.S. PTO Office Action, U.S. Appl. No. 12/247,764, Oct. 26, 2011, 17 pgs.

* cited by examiner

ORGANIC COMPOUNDS

This invention relates to organic compounds, their preparation and use as pharmaceuticals.

In one aspect, the present invention provides compounds of formula I

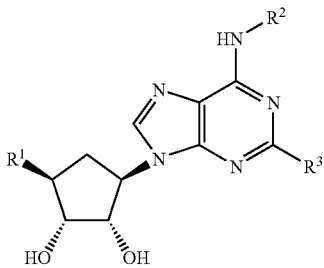

in free or salt form, wherein $R^1$ denotes a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by oxo, $C_1$-$C_8$-alkoxy, $C_6$-$C_{10}$-aryl, $R^4$ or by $C_1$-$C_8$-alkyl optionally substituted by hydroxy;

$R^2$ is hydrogen or $C_1$-$C_8$-alkyl optionally substituted by hydroxy or $C_6$-$C_{10}$-aryl;

$R^3$ is hydrogen, halo, $C_2$-$C_8$-alkenyl, $C_2$-$C_8$-alkynyl or $C_1$-$C_8$-alkoxycarbonyl, or $R^3$ is amino optionally substituted by $C_3$-$C_8$-cycloalkyl optionally substituted by amino, hydroxy, $C_7$-$C_{14}$-aralkyloxy, —$SO_2$—$C_6$-$C_{10}$-aryl or —NH—C(=O)—NH—$R^6$, or $R^3$ is amino substituted by $R^4$, —$R^4$—$C_7$-$C_{14}$-aralkyl or a $C_5$-$C_{15}$-carbocyclic group optionally substituted by hydroxy, $C_1$-$C_8$-alkyl or $C_1$-$C_8$-alkoxycarbonyl, or $R^3$ is aminocarbonyl optionally substituted by $R^5$, or $R^3$ is $C_1$-$C_8$-alkylamino optionally substituted by hydroxy, $R^5$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^6$, —NH—C(=O)—NH—$C_1$-$C_8$-alkyl-$R^5$, a $C_5$-$C_{15}$-carbocyclic group or by $C_6$-$C_{10}$-aryl optionally substituted by $C_6$-$C_{10}$-aryloxy, or $R^3$ is a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by amino, $C_1$-$C_8$-alkyl, $C_1$-$C_8$-alkoxy, $C_1$-$C_8$-alkylamino, di($C_1$-$C_8$-alkyl)amino, $R^4$, —$R^4$—C(=O)—$C_7$-$C_{14}$-aralkyloxy, —NH—C(=O)—NH—$R^6$, —NH—C(=O)—$C_1$-$C_8$-alkoxy, —NH—C(=O)—$C_3$-$C_8$-cycloalkyl, —NH—$SO_2$—$C_1$-$C_8$-alkyl, —NH—C(=O)—NH—$C_1$-$C_4$-alkyl-$R^4$, —NH—C(=O)—NH—$C_1$-$C_4$-alkyl-$R^4$—$C_6$-$C_{10}$-aryl, —NH—C(=O)—NH—$C_1$-$C_4$-alkyl-di($C_1$-$C_4$-alkyl)amino, —NH—C(=O)—NH—$C_6$-$C_{10}$-aryl-$R^4$, —NH—C(=O)—NH—$C_6$-$C_{10}$-aryl-$SO_2NH_2$, —NH—C(=O)—NH—$R^6$—$C_7$-$C_{14}$-aralkyloxy or —NH—C(=O)—NH—$C_7$-$C_{14}$-aralkyl optionally substituted by halo, hydroxyl, carboxy, —C(=NH)$NH_2$ or $C_1$-$C_4$-alkoxycarbonyl, or $R^3$ is $C_1$-$C_8$-alkylaminocarbonyl or $C_3$-$C_8$-cycloalkylaminocarbonyl in either case being optionally substituted by amino, $C_1$-$C_8$-alkylamino, di($C_1$-$C_8$-alkyl)amino, —NH—C(=O)-di($C_1$-$C_8$-alkyl)amino, —NH—C(=O)—$C_1$-$C_4$-alkyl-di($C_1$-$C_4$-alkyl)amino, —NH—C(=O)—$C_1$-$C_4$-alkyl-$R^4$—$C_7$-$C_{14}$-aralkyl, —NH—C(=O)—NH—$R^6$, —NH—C(=O)—NH—$C_1$-$C_8$-alkyl, —NH—C(=O)—NH—$C_1$-$C_9$-alkylamino, —NH—C(=O)—NH-di($C_1$-$C_4$-alkyl)amino, —NH—C(=O)—NH—$C_7$-$C_{14}$-aralkyl or —NH—C(=O)—NH—$R^6$—$C_7$-$C_{14}$-aralkyloxy;

$R^4$ and $R^5$ are each independently a 5- to 12-membered heterocyclic group containing at least one ring heteroatom selected from the group consisting of nitrogen, oxygen and sulfur; and $R^6$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur.

Terms used in the specification have the following meanings:

"Optionally substituted" means the group referred to can be substituted at one or more positions by any one or any combination of the radicals listed thereafter.

"N-bonded 3- to 10-membered heterocyclic group containing from 1 to 4 ring nitrogen atoms and optionally containing from 1 to 4 other heteroatoms selected from the group consisting of oxygen and sulfur" as used herein, that is attached to the cyclopentyl moiety of the compound of formula I through a ring nitrogen atom. The N-bonded 3- to 10-membered heterocyclic group may be, for example a saturated or saturated, monocyclic or bicyclic heterocyclic group that is attached to the bound to that contains one, two, three or four ring nitrogen atoms. Preferably the N-bonded 3- to 10-membered heterocyclic group is a N-bonded 5- to 6-membered heterocyclic group containing from 1 to 4 ring nitrogen atoms, especially N-bonded pyrazolyl, N-bonded tetrazolyl, N-bonded triazolyl or N-bonded pyridinyl.

"Halo" or "halogen" as used herein may be fluorine, chlorine, bromine or iodine. Preferably halo is chlorine.

"$C_1$-$C_8$-alkyl" as used herein denotes straight chain or branched alkyl having 1 to 8 carbon atoms. Preferably $C_1$-$C_8$-alkyl is $C_1$-$C_8$-alkyl.

"$C_2$-$C_8$-alkenyl" as used herein denotes straight chain or branched hydrocarbon chains that contain 2 to 8 carbon atoms and one or more carbon-carbon double bonds. Preferably $C_2$-$C_8$-alkenyl is $C_2$-$C_4$-alkenyl".

"$C_2$-$C_8$-alkynyl" as used herein denotes straight chain or branched hydrocarbon chains that contain 2 to 8 carbon atoms and one or more carbon-carbon triple bonds and optionally one or more carbon-carbon double bonds. Preferably $C_2$-$C_8$-alkynyl is $C_2$-$C_6$-alkynyl".

"$C_1$-$C_8$-alkoxy" as used herein denotes straight chain or branched alkoxy having 1 to 8 carbon atoms. Preferably $C_1$-$C_8$-alkoxy is $C_1$-$C_4$-alkoxy.

"$C_3$-$C_8$-cycloalkyl" as used herein denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably $C_3$-$C_8$-cycloalkyl" is $C_3$-$C_6$-cycloalkyl.

"$C_1$-$C_8$-alkylamino" and "di($C_1$-$C_8$-alkyl)amino" as used herein denote amino substituted respectively by one or two $C_1$-$C_8$-alkyl groups as hereinbefore defined, which may be the same or different. Preferably $C_1$-$C_8$-alkylamino and di($C_1$-$C_8$-alkyl)amino are respectively $C_1$-$C_4$-alkylamino and di($C_1$-$C_4$-alkyl)amino.

"$C_1$-$C_8$-alkylcarbonyl" and "$C_1$-$C_8$-alkoxycarbonyl" as used herein denote $C_1$-$C_8$-alkyl or $C_1$-$C_8$-alkoxy respectively as hereinbefore defined attached by a carbon atom to a carbonyl group. Preferably $C_1$-$C_8$-alkylcarbonyl and $C_1$-$C_8$-alkoxycarbonyl are $C_1$-$C_4$-alkylcarbonyl and $C_1$-$C_4$-alkoxycarbonyl respectively.

"$C_3$-$C_8$-cycloalkylcarbonyl" as used herein denotes $C_3$-$C_8$-cycloalkyl as hereinbefore defined attached by a carbon atom to a carbonyl group. Preferably $C_3$-$C_8$-cycloalkylcarbonyl is $C_3$-$C_5$-cycloalkylcarbonyl.

"$C_3$-$C_8$-cycloalkylamino" as used herein denotes $C_3$-$C_8$-cycloalkyl as hereinbefore defined attached by a carbon atom to the nitrogen atom of an amino group. Preferably $C_3$-$C_8$-cycloalkylamino is $C_3$-$C_5$-cycloalkylamino.

"$C_6$-$C_{10}$-aryl" as used herein denotes a monovalent carbocyclic aromatic group that contains 6 to 10 carbon atoms and which may be, for example, a monocyclic group such as phenyl or a bicyclic group such as naphthyl. Preferably $C_6$-$C_{10}$-aryl is $C_6$-$C_8$-aryl, especially phenyl.

"$C_7$-$C_{14}$-aralkyl" as used herein denotes alkyl, for example $C_1$-$C_4$-alkyl as hereinbefore defined, substituted by $C_6$-$C_{10}$-aryl as hereinbefore defined. Preferably $C_7$-$C_{14}$-aralkyl is $C_7$-$C_{10}$-aralkyl, especially phenyl-$C_1$-$C_4$-alkyl.

"$C_1$-$C_8$-alkylaminocarbonyl" and "$C_3$-$C_8$-cycloalkylaminocarbonyl" as used herein denote $C_1$-$C_8$-alkylamino and $C_3$-$C_8$-cycloalkylamino respectively as hereinbefore defined attached by a carbon atom to a carbonyl group. Preferably $C_1$-$C_8$-alkylaminocarbonyl and $C_3$-$C_8$-cycloalkyl-aminocarbonyl are $C_1$-$C_4$-alkylaminocarbonyl and $C_3$-$C_9$-cycloalkylaminocarbonyl respectively.

"$C_5$-$C_{15}$-carbocyclic group" as used herein denotes a carbocyclic group having 5 to 15 ring carbon atoms, for example a monocyclic group, either aromatic or non-aromatic, such as a cyclopentyl, cyclohexyl, cycloheptyl, cyclooctyl or phenyl, or a bicyclic group such as bicyclooctyl, bicyclononyl, bicyclodecyl, indanyl or indenyl, again any of which can be substituted by one or more, usually one or two, $C_1$-$C_4$-alkyl groups. Preferably the $C_5$-$C_{15}$-carbocyclic group is a $C_6$-$C_{10}$-carbocyclic group, especially phenyl, cyclohexyl or indanyl. The $C_5$-$C_{15}$-carbocyclic group can unsubstituted or substituted. Preferred substituents on the heterocyclic ring include halo, cyano, hydroxy, carboxy, amino, aminocarbonyl, nitro, $C_1$-$C_{10}$-alkyl, $C_1$-$C_{10}$-alkoxy and $C_3$-$C_{10}$-cycloalkyl, especially hydroxy or amino.

"5- to 12-membered heterocyclic group containing at least one ring heteroatom selected from the group consisting of nitrogen, oxygen and sulphur" as used herein may be, for example, a saturated or unsaturated monocyclic heterocyclic group such as furanyl, pyrrolyl, pyrrolidinyl, pyrazolyl, imidazolyl, triazolyl, isotriazolyl, tetrazolyl, thiadiazolyl, isothiazolyl, oxadiazolyl, pyridinyl, piperidinyl, pyrazinyl, oxazolyl, isoxazolyl, pyrazinyl, pyridazinyl, pyrimidinyl, piperazinyl, pyrrolidinyl, morpholinyl, triazinyl, oxazinyl or thiazolyl, or a saturated or unsaturated bicyclic heterocyclic group such as indolyl, indazolyl, benzothiazolyl, benzothiofurazanyl, benzimidazolyl, quinolinyl, isoquinolinyl. Preferred monocyclic heterocyclic groups include pyrazolyl, imidazolyl, pyrrolidinyl, pyridinyl and piperidinyl.

Preferred bicyclic heterocyclic groups include indolyl, quinolinyl and benzimidazolyl. The 5- to 12-membered heterocyclic group can be unsubstituted or substituted. Preferred substituents include halo, cyano, oxo, hydroxy, carboxy, amino, nitro, $C_1$-$C_8$-alkyl (optionally substituted by hydroxy), $C_1$-$C_8$-alkylsulfonyl, aminocarbonyl, $C_1$-$C_8$-alkylcarbonyl, $C_1$-$C_8$-alkoxycarbonyl, and $C_1$-$C_8$-alkoxy optionally substituted by aminocarbonyl. Especially preferred substituents include chloro, cyano, carboxy, amino, $C_1$-$C_8$-alkoxycarbonyl, $C_1$-$C_4$-alkoxy and $C_1$-$C_4$-alkyl optionally substituted by hydroxy.

"5- or 6-membered heterocyclic group containing at least one ring heteroatom selected from the group consisting of nitrogen, oxygen and sulphur" as used herein may be, for example, a saturated or unsaturated heterocyclic group such as furanyl, pyrrolyl, pyrrolidinyl, pyrazolyl, imidazolyl, triazolyl, isotriazolyl, tetrazolyl, thiadiazolyl, isothiazolyl, oxadiazolyl, pyridinyl, piperidinyl, pyrazinyl, oxazolyl, isoxazolyl, pyrazinyl, pyridazinyl, pyrimidinyl, piperazinyl, pyrrolidinyl, morpholinyl, triazinyl, oxazinyl or thiazolyl. Preferred 5- or 6-membered heterocyclic groups include pyrazolyl, imidazolyl, pyrrolidinyl, pyridinyl and piperidinyl. The 5- or 6-membered heterocyclic group can be unsubstituted or substituted. Preferred substituents include halo, cyano, oxo, hydroxy, carboxy, amino, nitro, $C_1$-$C_8$-alkyl (optionally substituted by hydroxy), $C_1$-$C_8$-alkylsulfonyl, aminocarbonyl, $C_1$-$C_8$-alkylcarbonyl, $C_1$-$C_8$-alkoxycarbonyl, and $C_1$-$C_8$-alkoxy optionally substituted by aminocarbonyl. Especially preferred substituents include chloro, cyano, carboxy, amino, $C_1$-$C_8$-alkoxycarbonyl, $C_1$-$C_4$-alkoxy and $C_1$-$C_4$-alkyl optionally substituted by hydroxy.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

In compounds of formula I the following are suitable or preferred aspects of the invention either independently or in any combination:

$R^1$ suitably denotes a N-bonded 5- or 6-membered heterocyclic group containing 1, 2, 3 or 4 ring nitrogen atoms that is optionally substituted at one position by oxo, methyl, ethyl, phenyl, or methyl substituted by hydroxyl. However $R^1$ is preferably a N-bonded 5-membered heterocyclic group containing 2, 3 or 4 ring nitrogen atoms that is substituted at one position by methyl, ethyl, phenyl, or methyl substituted by hydroxyl.

$R^2$ is suitably hydrogen or $C_1$-$C_5$-alkyl optionally substituted at one or two positions by hydroxy or $C_6$-$C_8$-aryl optionally substituted by hydroxy. $C_6$-$C_8$-aryl is preferably phenyl. However $R^2$ is preferably hydrogen or $C_2$-$C_5$-alkyl optionally substituted at one or two positions by hydroxy or phenyl optionally substituted by hydroxy. In one especially preferred aspect $R^2$ is 2,2-diphenyl-ethyl, 2,2-bis-(4-hydroxy-phenyl)-ethyl, 6-phenethyl or 1-hydroxymethyl-2-phenyl-ethyl. In another especially preferred aspect $R^2$ is hydrogen or propyl.

Preferred compounds of formula I in free or salt form include those where $R^1$ denotes a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by oxo, $C_6$-$C_{10}$-aryl or by $C_1$-$C_9$-alkyl optionally substituted by hydroxy;

$R^2$ is hydrogen or $C_1$-$C_8$-alkyl optionally substituted at one or two positions by hydroxy or $C_6$-$C_{10}$-aryl optionally substituted at one or two positions by hydroxy;

$R^3$ is halo, $C_2$-$C_8$-alkynyl or $C_1$-$C_8$-alkoxycarbonyl, or $R^3$ is amino optionally substituted by $C_3$-$C_8$-cycloalkyl optionally substituted by amino, hydroxy, $C_7$-$C_{14}$-aralkyloxy or —NH—C(=O)—NH—$R^6$, or $R^3$ is amino substituted by $R^4$, —$R^4$—$C_7$-$C_{14}$-aralkyl or a $C_5$-$C_{15}$-carbocyclic group optionally substituted by hydroxy or $C_1$-$C_8$-alkoxycarbonyl, or $R^3$ is aminocarbonyl optionally substituted by $R^5$, or $R^3$ is $C_1$-$C_8$-alkylamino optionally substituted by hydroxy, $R^5$, —NH—C(=O)—$C_1$-$C_8$-alkyl, —NH—$SO_2$—$C_1$-$C_8$-alkyl, —NH—C(=O)—NH—$R^6$, a $C_5$-$C_{15}$-carbocyclic group or by $C_6$-$C_{10}$-aryl optionally substituted by $C_6$-$C_{10}$-aryloxy, or $R^3$ is a N-bonded 5-membered heterocyclic group containing 1 or 2 ring nitrogen atoms, that group being optionally substituted by amino, di($C_1$-$C_8$-alkyl)amino, $R^4$, —$R^4$—C(=O)—$C_7$-$C_{14}$-aralkyloxy, —NH—C(=O)—NH—$R^6$, —NH—C(=O)—$C_1$-$C_8$-alkoxy, —NH—C(=O)—$C_3$-$C_8$-cycloalkyl, —NH—$SO_2$—$C_1$-$C_8$-alkyl, —NH—C(=O)—NH—$C_1$-$C_4$-alkyl-$R^4$, —NH—C(=O)—NH—$C_1$-$C_4$-alkyl-$R^4$—$C_6$-$C_{10}$-aryl, —NH—C(=O)—NH—$C_1$-$C_4$-alkyl-di($C_1$-$C_4$-alkyl)amino, —NH—C(=O)—NH—$C_6$-$C_{10}$-aryl-$R^4$, —NH—C(=O)—NH—$C_6$-$C_{10}$-aryl-$SO_2NH_2$, or —NH—C(=O)—NH—$C_7$-$C_{14}$-aralkyl optionally substituted by halo, hydroxyl, carboxy, —C(=NH)$NH_2$ or $C_1$-$C_4$-alkoxycarbonyl, or $R^3$ is $C_1$-$C_8$-alkylaminocarbonyl or $C_3$-$C_8$-cycloalkylaminocarbonyl in either case being optionally substituted by amino, —NH—C(=O)-di($C_1$-$C_8$-alkyl)amino, —NH—C(=O)—$C_1$-$C_4$-alkyl-di($C_1$-$C_4$-alkyl)amino, —NH—C(=O)—$C_1$-$C_4$-alkyl-$R^4$—$C_7$-$C_{14}$-aralkyl, —NH—C(=O)—NH—$R^6$, —NH—C(=O)—NH—$C_1$-$C_8$-alkyl, —NH—C(=O)—NH—$C_1$-$C_8$-alkylamino, —NH—C(=O)—NH-di($C_1$-$C_4$-alkyl)amino, or —NH—C(=O)—NH—$C_7$-$C_{14}$-aralkyl;

$R^4$ and $R^5$ are each independently a 5- to 12-membered heterocyclic group containing at least one ring heteroatom selected from the group consisting of nitrogen, oxygen and sulfur; and $R^6$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur.

Especially preferred compounds of formula I in free or salt form include those where $R^1$ denotes a N-bonded 5- to 6-membered heterocyclic group containing from 1 to 4 ring nitrogen atoms, that group being optionally substituted by oxo, phenyl, methyl, ethyl or by methyl substituted by hydroxy;

$R^2$ is hydrogen or $C_1$-$C_8$-alkyl optionally substituted at one or two positions by hydroxy or phenyl optionally substituted at one or two positions by hydroxy;

$R^3$ is halo, $C_2$-$C_6$-alkynyl or $C_1$-$C_4$-alkoxycarbonyl, or $R^3$ is amino optionally substituted by $C_3$-$C_6$-cycloalkyl optionally substituted by amino, hydroxy, $C_7$-$C_{10}$-aralkyloxy or —NH—C(=O)—NH—$R^6$, or $R^3$ is amino substituted by $R^4$, —$R^4$-benzyl or a $C_5$-$C_{15}$-carbocyclic group optionally substituted by hydroxy or $C_1$-$C_4$-alkoxycarbonyl, or $R^3$ is aminocarbonyl optionally substituted by $R^5$, or $R^3$ is $C_1$-$C_4$-alkylamino optionally substituted by hydroxy, $R^5$, —NH—C(=O)—$C_1$-$C_4$-alkyl, —NH—$SO_2$—$C_1$-$C_4$-alkyl, —NH—C(=O)—NH—$R^6$, a $C_5$-$C_{15}$-carbocyclic group or by phenyl optionally substituted by phenoxy, or $R^3$ is a N-bonded 5-membered heterocyclic group containing from 1 ring nitrogen atom, that group being optionally substituted by amino, di($C_1$-$C_4$-alkyl)amino, $R^4$, —$R^4$—C(=O)-benzyloxy, —NH—C(=O)—NH—$R^6$, —NH—C(=O)—$C_1$-$C_4$-alkoxy, —NH—C(=O)—$C_3$-$C_6$-cycloalkyl, —NH—$SO_2$—$C_1$-$C_4$-alkyl, —NH—C(=O)—NH—$C_1$-$C_4$-alkyl-$R^4$, —NH—C(=O)—NH—$C_1$-$C_4$-alkyl-$R^4$-phenyl, —NH—C(=O)—NH—$C_1$-$C_4$-alkyl-di($C_1$-$C_4$-alkyl)amino, —NH—C(=O)—NH-phenyl-$R^4$, —NH—C(=O)—NH-phenyl-$SO_2NH_2$, or —NH—C(=O)—NH—$C_7$-$C_{10}$-aralkyl optionally substituted by halo, hydroxyl, carboxy, —C(=NH)$NH_2$ or $C_1$-$C_4$-alkoxycarbonyl, or $R^3$ is $C_1$-$C_4$-alkylaminocarbonyl or $C_3$-$C_6$-cycloalkylaminocarbonyl in either case being optionally substituted by amino, —NH—C(=O)-di($C_1$-$C_4$-alkyl)amino, —NH—C(=O)—$C_1$-$C_4$-alkyl-di($C_1$-$C_4$-alkyl)amino, —NH—C(=O)—$C_1$-$C_4$-alkyl-$R^4$-benzyl, —NH—C(=O)—NH—$R^6$, —NH—C(=O)—NH—$C_1$-$C_4$-alkyl, —NH—C(=O)—NH—$C_1$-$C_4$-alkylamino, —NH—C(=O)—NH-di($C_1$-$C_4$-alkyl)amino, or —NH—C(=O)—NH-benzyl;

$R^4$ and $R^5$ are each independently a 5- to 12-membered heterocyclic group containing at least one ring heteroatom selected from the group consisting of nitrogen, oxygen and sulfur; and $R^6$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur.

In a second aspect, the present invention provides compounds of formula I in free or salt form, wherein $R^1$ denotes a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by oxo, $C_1$-$C_8$-alkoxy, $C_6$-$C_{10}$-aryl, $R^4$ or by $C_1$-$C_8$-alkyl optionally substituted by hydroxy;

$R^2$ is hydrogen or $C_1$-$C_8$-alkyl optionally substituted by hydroxy or $C_6$-$C_{10}$-aryl;

$R^3$ is hydrogen, halo, $C_2$-$C_8$-alkenyl, $C_2$-$C_8$-alkynyl or $C_1$-$C_8$-alkoxycarbonyl, or $R^3$ is amino optionally substituted by $C_3$-$C_8$-cycloalkyl optionally substituted by amino, hydroxy, $C_7$-$C_{14}$-aralkyloxy, —$SO_2$—$C_6$-$C_{10}$-aryl or —NH—C(=O)—NH—$R^6$, or $R^3$ is amino substituted by a $C_5$-$C_{15}$-carbocyclic group optionally substituted by hydroxy, $C_1$-$C_8$-alkyl or $C_1$-$C_8$-alkoxycarbonyl, or $R^3$ is aminocarbonyl optionally substituted by $R^5$, or $R^3$ is $C_1$-$C_8$-alkylamino optionally substituted by hydroxy, $R^5$, amino, di($C_1$-$C_8$-alkyl)amino, —NH—C(=O)—$C_1$-$C_8$-alkyl, —NH—$SO_2$—$C_1$-$C_8$-alkyl, —NH—C(=O)—NH—$R^6$, —NH—C(=O)—NH—$C_1$-$C_8$-alkyl-$R^5$, a $C_5$-$C_{15}$-carbocyclic group or by $C_6$-$C_{10}$-aryl optionally substituted by $C_6$-$C_{10}$-aryloxy, or $R^3$ is a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by amino, $C_1$-$C_8$-alkyl or $C_1$-$C_8$-alkoxy, $C_1$-$C_8$-alkylamino, di($C_1$-$C_8$-alkyl)amino, —NH—C(=O)—NH—$R^6$, —NH—C(=O)—NH—$C_7$-$C_{14}$-aralkyl or —NH—C(=O)—NH—$R^6$—$C_7$-$C_{14}$-aralkyloxy;

or $R^3$ is $C_1$-$C_8$-alkylaminocarbonyl or $C_3$-$C_8$-cycloalkylaminocarbonyl in either case being optionally substituted by amino, $C_1$-$C_9$-alkylamino, di($C_1$-$C_8$-alkyl)amino, —NH—C(=O)—NH—$R^6$, —NH—C(=O)—NH—$C_7$-$C_{14}$-aralkyl or —NH—C(=O)—NH—$R^6$—$C_7$-$C_{14}$-aralkyloxy;

$R^4$ and $R^5$ are each independently a 5- to 12-membered heterocyclic group containing at least one ring heteroatom selected from the group consisting of nitrogen, oxygen and sulfur; and $R^6$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur.

Preferred compounds of formula I in free or salt form include those where $R^1$ denotes a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by oxo, $C_6$-$C_{10}$-aryl or by $C_1$-$C_8$-alkyl optionally substituted by hydroxy;

$R^2$ is hydrogen or $C_1$-$C_8$-alkyl optionally substituted by hydroxy or $C_6$-$C_{10}$-aryl;

$R^3$ is halo, $C_2$-$C_8$-alkynyl or $C_1$-$C_8$-alkoxycarbonyl, or $R^3$ is amino optionally substituted by $C_3$-$C_8$-cycloalkyl optionally substituted by amino, hydroxy, $C_7$-$C_{14}$-aralkyloxy or —NH—C(=O)—NH—$R^6$, or $R^3$ is amino substituted by a $C_6$-$C_{10}$-carbocyclic group optionally substituted by hydroxy or $C_1$-$C_8$-alkoxycarbonyl, or $R^3$ is aminocarbonyl optionally substituted by $R^5$, or $R^3$ is $C_1$-$C_8$-alkylamino optionally substituted by hydroxy, $R^5$, —NH—C(=O)—$C_1$-$C_8$-alkyl, —NH—$SO_2$—$C_1$-$C_8$-alkyl, —NH—C(=O)—NH—$R^6$, a $C_5$-$C_{10}$-carbocyclic group or by $C_6$-$C_{10}$-aryl optionally substituted by $C_6$-$C_{10}$-aryloxy, or $R^3$ is a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by amino or —NH—C(=O)—NH—$R^6$, or $R^3$ is $C_1$-$C_8$-alkylaminocarbonyl optionally substituted by amino, —NH—C(=O)—NH—$R^6$ or —NH—C(=O)—NH—$C_7$-$C_{14}$-aralkyl;

$R^5$ is a 5- to 12-membered heterocyclic group containing at least one ring heteroatom selected from the group consisting of nitrogen, oxygen and sulfur; and $R^6$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur.

Especially preferred compounds of formula I in free or salt form include those where $R^1$ denotes a N-bonded 5- to 6-membered heterocyclic group containing from 1 to 4 ring nitrogen atoms, that group being optionally substituted by oxo, $C_6$-$C_8$-aryl or by $C_1$-$C_4$-alkyl optionally substituted by hydroxy;

$R^2$ is hydrogen or $C_1$-$C_4$-alkyl optionally substituted by hydroxy or $C_6$-$C_8$-aryl; and $R^3$ is halo, $C_2$-$C_6$-alkynyl or $C_1$-$C_4$-alkoxycarbonyl, or $R^3$ is amino optionally substituted by $C_3$-$C_6$-cycloalkyl optionally substituted by amino, hydroxy, $C_7$-$C_{10}$-aralkyloxy or —NH—C(=O)—NH—$R^6$, or $R^3$ is amino substituted by a $C_5$-$C_{15}$-carbocyclic group optionally substituted by hydroxy or $C_1$-$C_4$-alkoxycarbonyl, or $R^3$ is aminocarbonyl optionally substituted by $R^5$, or $R^3$ is $C_1$-$C_4$-alkylamino optionally substituted by hydroxy, $R^5$, —NH—C(=O)—$C_1$-$C_4$-alkyl, —NH—$SO_2$—$C_1$-$C_4$-alkyl, —NH—C(=O)—NH—$R^6$, a $C_5$-$C_{15}$-carbocyclic group or by $C_6$-$C_8$-aryl optionally substituted by $C_6$-$C_8$-aryloxy, or $R^3$ is pyrrolidinyl optionally substituted by amino, or $R^3$ is a N-bonded 5- to 6-membered heterocyclic group containing from 1 to 4 ring nitrogen atoms, that group being optionally substituted by amino or —NH—C(=O)—NH—$R^6$, or $R^3$ is $C_1$-$C_4$-alkylaminocarbonyl optionally substituted by amino, —NH—C(=O)—NH—$R^6$ or —NH—C(=O)—NH—$C_7$-$C_{10}$-aralkyl;

$R^5$ is a 5- to 12-membered heterocyclic group containing at least one ring heteroatom selected from the group consisting of nitrogen, oxygen and sulfur; and $R^6$ is a 5- or 6-membered heterocyclic group containing at least one ring heteroatom selected from the group consisting of nitrogen, oxygen and sulfur, which is optionally substituted by a 5- or 6-membered heterocyclic group containing at least one ring heteroatom selected from the group consisting of nitrogen, oxygen and sulfur.

Especially preferred specific compounds of formula I include those described hereinafter in the Examples.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid, para-biphenyl benzoic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, cinnamic acids such as 3-(2-naphthalenyl)propenoic acid, para-methoxy cinnamic acid or para-methyl cinnamic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

The invention provides, in another aspect, a method of preparing a compound of formula I in free or salt form which comprises (i) (A) for the preparation of compounds of formula I where $R^3$ is amino optionally substituted by $C_3$-$C_8$-cycloalkyl optionally substituted by amino, hydroxy, $C_7$-$C_{14}$-aralkyloxy, —$SO_2$—$C_6$-$C_{10}$-aryl or —NH—C(=O)—NH—$R^6$, or $R^3$ is amino substituted by $R^4$, —$R^4$—$C_7$-$C_{14}$-aralkyl or a $C_5$-$C_{15}$-carbocyclic group optionally substituted by hydroxy, $C_1$-$C_8$-alkyl or $C_1$-$C_8$-alkoxycarbonyl, or R³ is C₁-C₈-alkylamino optionally substituted by hydroxy, R⁵, amino, di(C₁-C₈-alkyl)amino, —NH—C(=O)—C₁-C₈-alkyl, —NH—SO₂—C₁-C₈-alkyl, —NH—C(=O)—NH—R⁶, —NH—C(=O)—NH—C₁-C₈-alkyl-R⁵, a C₅-C₁₅-carbocyclic group or by C₆-C₁₀-aryl optionally substituted by C₆-C₁₀-aryloxy, or R³ is a N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by amino, C₁-C₈-alkyl, C₁-C₈-alkoxy, C₁-C₈-alkylamino, di(C₁-C₈-alkyl)amino, R⁴, —R⁴—C(=O)—C₇-C₁₄-aralkyloxy, —NH—C(=O)—NH—R⁶, —NH—C(=O)—C₁-C₈-alkoxy, —NH—C(=O)—C₃-C₈-cycloalkyl, —NH—SO₂—C₁-C₈-alkyl, —NH—C(=O)—NH—C₁-C₄-alkyl-R⁴, —NH—C(=O)—NH—C₁-C₄-alkyl-R⁴—C₆-C₁₀-aryl, —NH—C(=O)—NH—C₁-C₄-alkyl-di(C₁-C₄-alkyl)amino, —NH—C(=O)—NH—C₆-C₁₀-aryl-R⁴, —NH—C(=O)—NH—C₆-C₁₀-aryl-SO₂NH₂, —NH—C(=O)—NH—R⁶—C₇-C₁₄-aralkyloxy or —NH—C(=O)—NH—C₇-C₁₄-aralkyl optionally substituted by halo, hydroxyl, carboxy, —C(=NH)NH₂ or C₁-C₄-alkoxycarbonyl, reacting a compound of formula II

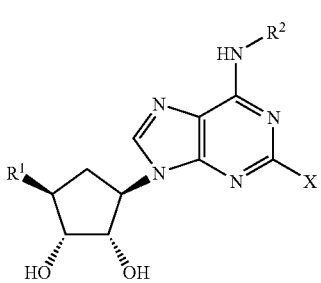

II or a protected form thereof, wherein R¹ and R² are as hereinbefore defined and X is halo, with either a compound of formula III

  III or a compound of formula IV

  IV wherein R⁷ is C₃-C₈-cycloalkyl optionally substituted by amino, hydroxy, C₇-C₁₄-aralkyloxy, —SO₂—C₆-C₁₀-aryl or —NH—C(=O)—NH—R⁶, or R⁷ is R⁴, —R⁴—C₇-C₁₄-aralkyl or a C₅-C₁₅-carbocyclic group optionally substituted by hydroxy, C₁-C₈-alkyl or C₁-C₈-alkoxycarbonyl, or R⁷ is C₁-C₈-alkyl optionally substituted by hydroxy, R⁵, amino, di(C₁-C₈-alkyl)amino, —NH—C(=O)—C₁-C₈-alkyl, —NH—SO₂—C₁-C₈-alkyl, —NH—C(=O)—NH—R⁶, —NH—C(=O)—NH—C₁-C₈-alkyl-R⁵, a C₅-C₁₅-carbocyclic group or by C₆-C₁₀-aryl optionally substituted by C₆-C₁₀-aryloxy, and T is an N-bonded 3- to 10-membered heterocyclic group containing from 1 to 4 ring nitrogen atoms and optionally containing from 1 to 4 other heteroatoms selected from the group consisting of oxygen and sulfur, that group being optionally substituted by amino, C₁-C₈-alkyl, C₁-C₈-alkoxy, C₁-C₈-alkylamino, di(C₁-C₈-alkyl)amino, R⁴, —R⁴—C(=O)—C₇-C₁₄-aralkyloxy, —NH—C(=O)—NH—R⁶, —NH—C(=O)—C₁-C₈-alkoxy, —NH—C(=O)—C₃-C₈-cycloalkyl, —NH—SO₂—C₁-C₈-alkyl, —NH—C(=O)—NH—C₁-C₄-alkyl-R⁴, —NH—C(=O)—NH—C₁-C₄-alkyl-R⁴—C₆-C₁₀-aryl, —NH—C(=O)—NH—C₁-C₄-alkyl-di(C₁-C₄-alkyl)amino, —NH—C(=O)—NH—C₆-C₁₀-aryl-R⁴, —NH—C(=O)—NH—C₆-C₁₀-aryl-SO₂NH₂, —NH—C(=O)—NH—R⁶—C₇-C₁₄-aralkyloxy or —NH—C(=O)—NH—C₇-C₁₄-aralkyl optionally substituted by halo, hydroxyl, carboxy, —C(=NH)NH₂ or C₁-C₄-alkoxycarbonyl;

(B) for the preparation of compounds of formula I where R³ is C₁-C₈-alkylamino or C₃-C₈-cycloalkyl substituted by —NH—C(=O)—C₁-C₈-alkyl, reacting a compound of formula V

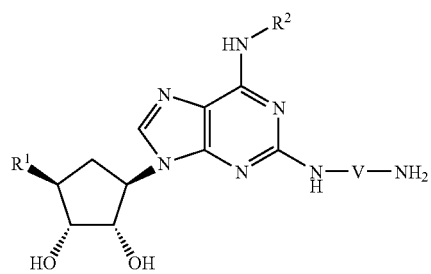  V wherein R¹ and R² are as hereinbefore defined and V is C₁-C₈-alkylene or C₃-C₈-cycloalkyl, with a compound of formula VI

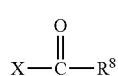  VI or an amide forming derivative of formula VII

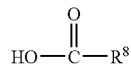  VII wherein X is a halogen, preferably chloro, and R⁸ is C₁-C₈-alkyl, in the presence of a base;

(C) for the preparation of compounds of formula I where R³ is C₁-C₈-alkylamino substituted by —NH—SO₂—C₁-C₈-alkyl, reacting a compound of formula IV wherein R¹ and R² are as hereinbefore defined and V is C₁-C₈-alkylene, with a compound of formula VIII

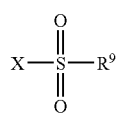  VIII wherein X is a halogen, preferably chloro, and $R^9$ is $C_1$-$C_8$-alkyl, in the presence of a base;

(D) for the preparation of compounds of formula I wherein $R^3$ is $C_2$-$C_8$-alkynyl, reacting a compound of formula II or a protected form thereof, where $R^1$ and $R^2$ are as hereinbefore defined, with a compound of formula IX

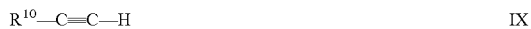   IX wherein $R^{10}$ is $C_1$-$C_8$-alkyl, in the presence of a base and a catalyst;

(E) for the preparation of compounds of formula I wherein $R^3$ is amino substituted by $C_3$-$C_8$-cycloalkyl substituted by —NH—C(=O)—NH—$R^6$, or $R^3$ is $C_1$-$C_8$-alkylamino substituted by —NH—C(=O)—NH—$R^6$, where $R^6$ is as hereinbefore defined, reacting a compound of formula V where $R^1$, $R^2$ and V are as hereinbefore defined, with either a compound of formula X

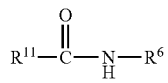   X or a compound of formula XI

O=C=N—$R^6$   XI wherein $R^{11}$ is a 5- or 6-membered heterocyclic ring containing at least one ring heteroatom selected from the group consisting of nitrogen, oxygen and sulphur and $R^6$ is as hereinbefore defined;

(F) for the preparation of compounds of formula I wherein $R^3$ is a N-bonded 3- to 10-membered heterocyclic group containing from 1 to 4 ring nitrogen atoms and optionally containing from 1 to 4 other heteroatoms selected from the group consisting of oxygen and sulfur, that group being substituted by —NH—C(=O)—NH—$R^6$, where $R^6$ is as hereinbefore defined, reacting a compound of formula XI

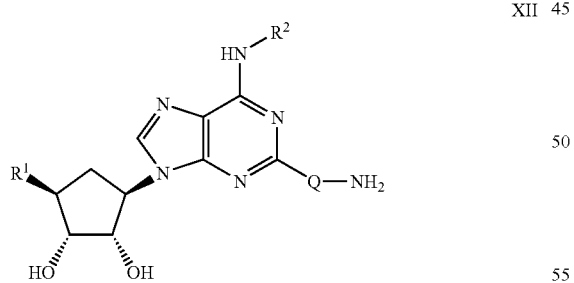   XII wherein $R^1$ and $R^2$ are as hereinbefore defined and Q is a N-bonded 3- to 10-membered heterocyclic group containing from 1 to 4 ring nitrogen atoms and optionally containing from 1 to 4 other heteroatoms selected from the group consisting of oxygen and sulfur, with either a compound of formula X or a compound of formula XI, wherein $R^6$ and $R^{11}$ are as hereinbefore defined;

(G) for the preparation of compounds of formula I where $R^3$ is $C_1$-$C_8$-alkoxycarbonyl, dihydroxylating a compound of formula XIII

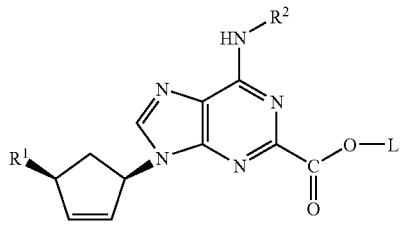   XIII where $R^1$ and $R^2$ is as hereinbefore defined and L is $C_1$-$C_8$-alkyl;

(H) for the preparation of compounds of formula I wherein $R^3$ is $C_1$-$C_8$-alkylaminocarbonyl or $C_3$-$C_8$-cycloalkylaminocarbonyl in either case optionally substituted by amino, or $R^3$ is aminocarbonyl optionally substituted by $R^5$, reacting a compound of formula XIII where $R^1$ and $R^2$ is as hereinbefore defined and $R^{12}$ is $C_1$-$C_8$-alkyl, with a compound of formula XIV $H_2N$—Y   XIV wherein Y is $R^1$ and $R^2$ are as hereinbefore defined and Y is $C_1$-$C_8$-alkyl or $C_3$-$C_8$-cycloalkyl in either case optionally substituted by amino, or Y is $R^5$; or (I) for the preparation of compounds of formula I wherein $R^3$ is $C_1$-$C_8$-alkylamino-carbonyl or $C_3$-$C_8$-cycloalkylaminocarbonyl in either case substituted by —NH—C(=O)—NH—$R^6$, where $R^6$ is as hereinbefore defined, reacting a compound of formula XV

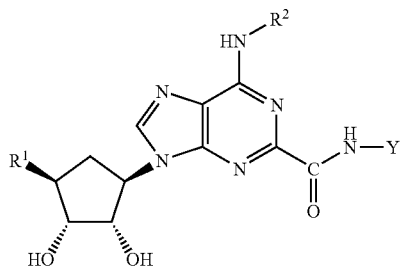   XV wherein $R^1$ and $R^2$ are as hereinbefore defined and Y is $C_1$-$C_8$-alkyl or $C_3$-$C_8$-cycloalkyl in either case substituted by amino, or Y is $R^5$, $C_1$-$C_8$-alkyl or $C_3$-$C_8$-cycloalkyl in the presence of a base, with a compound of formula X or a compound of formula XI, wherein $R^{11}$ is a 5- or 6-membered heterocyclic ring containing at least one ring heteroatom selected from the group consisting of nitrogen, oxygen and sulphur and $R^6$ is as hereinbefore defined; and (ii) removing any protecting groups and recovering the resultant compound of formula I in free or salt form.

Process variant (A) may be carried out using known procedures for reacting halides with amines, or analogously as hereinafter described in the Examples. The reaction is conveniently carried out using an organic solvent, for example dichlorobenzene, dimethylsulfoxide, acetonitrile, N-methylpyrrolidone (NMP), or 1,4-dioxane or mixtures thereof optionally in the presence of a catalyst, such as sodium iodide, and a base, such as triethylamine. Suitable reaction temperatures from 100° C. to 250° C., preferably between 100° C. to 240° C., for example by heating with microwave radiation.

Process variant (B) may be carried out using known procedures for reacting amines with carboxylic acids or acid halides to form amides, or analogously as hereinafter described in the Examples. The base is preferably diisopropylethylamine (DIPEA). The reaction is conveniently carried out using an organic solvent, such as dry tetrahydrofuran (THF). Suitable reaction temperatures from 0° C. to 40° C., preferably room temperature.

Process variant (C) may be carried out using known procedures for reacting amines with alkylsulfonyl-halides to form alkylsulfonylamines, or analogously as hereinafter described in the Examples. The base is preferably diisopropylethylamine (DIPEA). The reaction is conveniently carried out using an organic solvent, such as dry tetrahydrofuran (THF). Suitable reaction temperatures from 0° C. to 40° C., preferably room temperature.

Process variant (D) may be carried out using known procedures for reacting halides with alkynes, or analogously as hereinafter described in the Examples. The catalyst is preferably a palladium catalyst (together with a CuI salt) and the base is preferably butylamine. The reaction is conveniently carried out using an organic solvent, such as dimethylformamide (DMF). Suitable reaction temperatures from 40° C. to 200° C., preferably 80° C. to 160° C., especially about 120° C.

Process variant (E) may be carried out using known procedures for reacting amines with acyl-imidazoles or isocyanates, or analogously as hereinafter described in the Examples. $R^{11}$ in formula X is preferably imidazolyl. The reaction is conveniently carried out using an organic solvent, for example toluene and/or isopropyl alcohol. Suitable reaction temperatures from 0° C. to 40° C., preferably room temperature.

Process variant (F) may be carried out using known procedures for reacting amines with acyl-imidazoles or isocyanates, or analogously as hereinafter described in the Examples. $R^{11}$ in formula XII is preferably imidazolyl. The reaction is conveniently carried out using an organic solvent, for example toluene and/or isopropyl alcohol. Suitable reaction temperatures from 0° C. to 40° C., preferably room temperature.

Process variant (G) may be carried out using known procedures for dihydroxylating unsaturated carbocyclic compounds, or analogously as hereinafter described in the Examples. Preferably a dihydroxylating agent is used, such as osmium tetroxide ($OsO_4$), either in a stoichiometrical amount or a catalytic amount, preferably together with a re-oxidant, such as N-methylmorpholine N-oxide (NMO), or alternatively using AD-mix-α or AD-mix-β. The reaction is conveniently carried out using an organic solvent, for example THF. Suitable reaction temperatures from 0° C. to 40° C., preferably room temperature.

Process variant (H) may be carried out using known procedures for reacting esters with amines to form amides, or analogously as hereinafter described in the Examples. The reaction is conveniently carried out using an organic solvent, such as dry THF. Suitable reaction temperatures from 0° C. to 40° C., preferably room temperature.

Process variant (I) may be carried out using known procedures for reacting primary or second amines with acyl-imidazoles or isocyanates, or analogously as hereinafter described in the Examples. The reaction is conveniently carried out using an organic solvent, for example toluene and/or isopropyl alcohol. Suitable reaction temperatures from 0° C. to 40° C., preferably room temperature.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as stereoisomers, may be obtained in a conventional manner, e.g. by fractional crystallisation or asymmetric synthesis from correspondingly asymmetrically substituted, e.g. optically active, starting materials.

Compounds of formula II may be prepared by dihydroxylating a compound of formula XVI

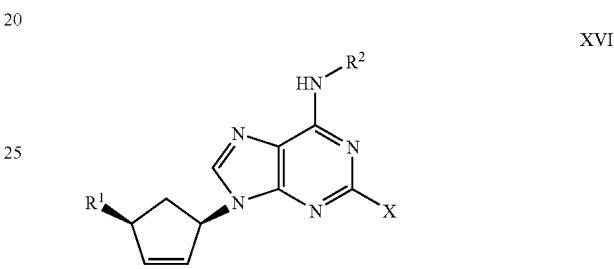

XVI where $R^1$ and $R^2$ are as hereinbefore defined and X is halo, preferably chloro, or analogously as hereinafter described in the Examples. Preferably a dihydroxylating agent is used, such as osmium tetroxide ($OsO_4$), either in a stoichiometrical amount or a catalytic amount, preferably together with a re-oxidant, such as N-methylmorpholine N-oxide (NMO), or alternatively using AD-mix-α or AD-mix-β. The reaction is conveniently carried out using an organic solvent, for example THF. Suitable reaction temperatures from 0° C. to 40° C., preferably room temperature.

Compounds of formula III or IV are commercially available or may be obtained by known procedures for preparing such compounds, or analogously as herein described in the Examples.

Compounds of formula V may be prepared by reacting a compound of formula II where $R^1$, $R^2$ and X are as hereinbefore defined, with a compound of formula XVII $H_2N\diagdown_V\diagup NH_2$

XVII where V is $C_1$-$C_8$-alkylene or $C_3$-$C_8$-cycloalkyl, or analogously as herein described in the Examples. The reaction is conveniently carried out using an organic solvent, for example NMP or $CH_3CN$. Suitable reaction temperatures from 150° C. to 220° C.

Compounds of formula VI, VII, VIII, IX, X or XI are commercially available or may be obtained by known procedures for preparing such compounds, or analogously as herein described in the Examples.

Compounds of formula XII may be prepared by reacting a compound of formula II where where $R^1$, $R^2$ and X are as hereinbefore defined, with a compound of formula XVIII

XVIII where Q is a N-bonded 3- to 10-membered heterocyclic group containing from 1 to 4 ring nitrogen atoms and optionally containing from 1 to 4 other heteroatoms selected from the group consisting of oxygen and sulfur, or analogously as herein described in the Examples. The reaction is conveniently carried out using an organic solvent, for example DMSO. Suitable reaction temperatures from 80° C. to 150° C.

Compounds of formula XIII may be prepared by reacting a compound of formula XIX

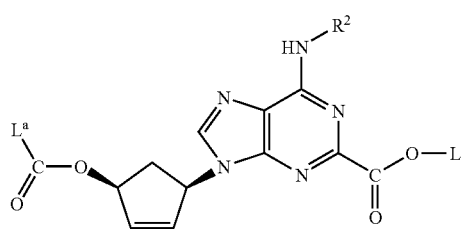

XIX where $R^2$ and L are as hereinbefore defined and $L^a$ is $C_1$-$C_8$-alkyl, preferably methyl, with a compound of formula XX

H—$R^1$     XX where $R^1$ is as hereinbefore defined, or analogously as herein described in the Examples. The reaction is conveniently carried out using an organic solvent, for example THF. Suitable reaction temperatures from 20° C. to 80° C.

Compounds of formula XIV are commercially available or may be obtained by known procedures for preparing such compounds, or analogously as herein described in the Examples.

Compounds of formula XV may be prepared by reacting a compound of formula XXI

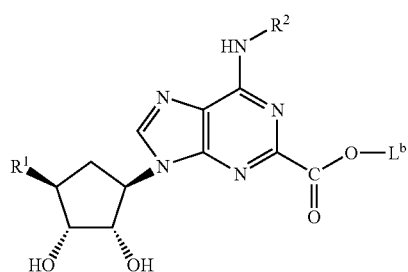

XXI where $R^1$ and $R^2$ are as hereinbefore defined, and $L^b$ is $C_1$-$C_8$-alkyl, preferably methyl, with compound of formula XVII where V is as hereinbefore defined, or analogously as herein described in the Examples. Suitable reaction temperatures from 80° C. to 120° C.

Compounds of formula XVI may be prepared by reacting a compound of formula XXII

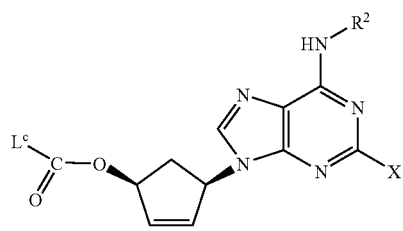

XXII where $R^1$, $R^2$ and X are as hereinbefore defined with a compound of formula XX where $R^1$ is as hereinbefore defined, or analogously as herein described in the Examples. The reaction is conveniently carried out using an organic solvent, for example THF. Suitable reaction temperatures from 0° C. to 50° C.

Compounds of formula XVII or XVIII are commercially available or may be obtained by known procedures for preparing such compounds, or analogously as herein described in the Examples.

Compounds of formula XIX are prepared by reacting a compound of formula XXIII

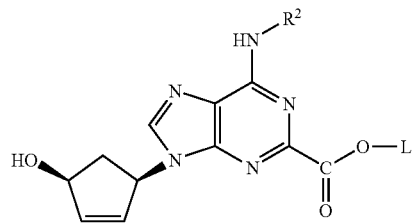

XXIII where $R^2$ and L are as hereinbefore defined, with a compound of formula XXIV

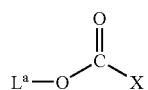

XXIV where $L^a$ is $C_1$-$C_8$-alkyl and X is halo, preferably chloro, or analogously as herein described in the Examples. The reaction is conveniently carried out in an inert environment, for example in argon, using an organic solvent, for example deoxygenated tetrahydrofuran, preferably in the presence of a base, for example pyridine. Suitable reaction temperatures from 0° C. to 40° C., preferably room temperature.

Compounds of formula XX are commercially available or may be obtained by known procedures for preparing such compounds, or analogously as herein described in the Examples.

Compounds of formula XXI may be prepared by dihydroxylating a compound of formula XXV

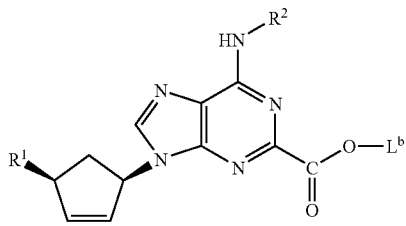

XXV where $R^1$, $R^2$ and $L^b$ are as hereinbefore defined, or analogously as hereinafter described in the Examples. Preferably a dihydroxylating agent is used, such as osmium tetroxide ($OsO_4$), either in a stoichiometrical amount or a catalytic amount, preferably together with a re-oxidant, such as N-methylmorpholine N-oxide (NMO), or alternatively using AD-mix-α or AD-mix-β. The reaction is conveniently carried out using an organic solvent, for example THF. Suitable reaction temperatures from 0° C. to 40° C., preferably room temperature. Compounds of XXII may be prepared by reacting a compound of formula XXVI

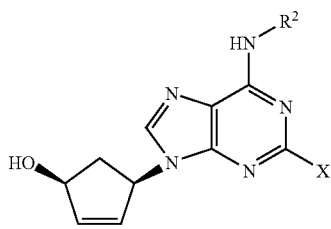

XXVI where $R^2$ and X are as hereinbefore defined, with a compound of formula XXVII

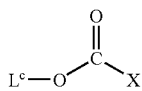

XXVII where $L^c$ is $C_1$-$C_8$-alkyl and X is halo, preferably chloro, or analogously as herein described in the Examples. The reaction is conveniently carried out in an inert environment, for example in argon, using an organic solvent, for example deoxygenated tetrahydrofuran, preferably in the presence of a base, for example pyridine. Suitable reaction temperatures from 0° C. to 40° C., preferably room temperature.

Compounds of formula XXIII may be prepared by reacting a compound of formula XXVIII

XXVIII

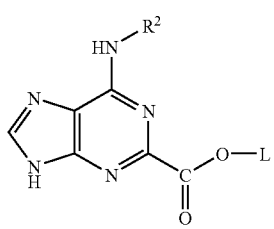

where $R^2$ and L are as hereinbefore defined, with (1S,4R)-cis 4-acetoxy-2-cyclopenten-1-ol in the presence of a base, such sodium hydride, and a catalyst, such as that generated from tetrakis(triphenylphosphine)palladium and triphenylphosphine, or analogously as herein described in the Examples. The reaction is conveniently carried out in an inert environment, for example in argon, using an organic solvent, for example deoxygenated tetrahydrofuran or dimethyl sulfoxide. Suitable reaction temperatures from 60° C. to 100° C., preferably about 80° C.

Compounds of formula XXIV are commercially available or may be obtained by known procedures for preparing such compounds, or analogously as herein described in the Examples.

Compounds of formula XXV may be prepared by reacting a compound of formula XXIX

XXIX

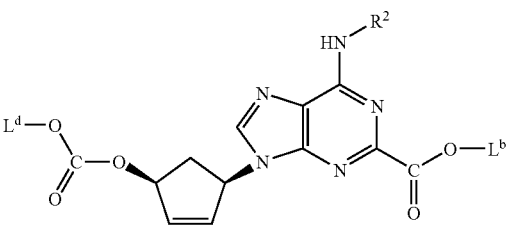

where $R^2$ and $L^b$ are as hereinbefore defined and $L^d$ is $C_1$-$C_8$-alkyl, preferably methyl, with a compound of formula XX where $R^1$ is as hereinbefore defined, or analogously as herein described in the Examples. The reaction is conveniently carried out using an organic solvent, for example THF. Suitable reaction temperatures from 0° C. to 50° C.

Compounds of formula XXVI may be prepared by reacting a compound of formula XXX

XXX where $R^2$ and X are as hereinbefore defined and $L^e$ is $C_1$-$C_8$-alkyl, preferably methyl, with a compound of formula XX where $R^1$ is as hereinbefore defined, or analogously as herein described in the Examples. The reaction is conveniently carried out using an organic solvent, for example THF. Suitable reaction temperatures from 0° C. to 50° C.

Compounds of formula XXVII are commercially available or may be obtained by known procedures for preparing such compounds, or analogously as herein described in the Examples.

Compounds of XXVIII may be prepared by reacting a salt compound of formula XXVIII where $R^2$ and L are as hereinbefore defined with a silating agent, for example (N,O-bis(trimethylsilyl)acetamide), or analogously as herein described in the Examples. The reaction is conveniently carried out in an inert environment, for example in argon, using an organic solvent, for example dry dichloromethane. Suitable reaction temperatures from 60° C. to 100° C., preferably about 80° C. A preferred salt is 6-(2,2-Diphenyl-ethylamino)-9H-purine-2-carboxylic acid methyl ester hydrochloride, which is prepared using the method described in international patent application WO 01/94368.

Compounds of formula XXIX may be prepared by reacting a compound of formula XXI

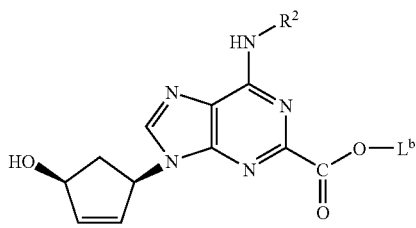

XXXI where $R^2$ and $L^b$ are as hereinbefore defined, with a compound of formula XXXII

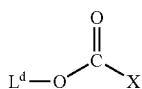

XXXII where $L^d$ is $C_1$-$C_8$-alkyl and X is halo, preferably chloro, or analogously as herein described in the Examples. The reaction is conveniently carried out in an inert environment, for example in argon, using an organic solvent, for example deoxygenated tetrahydrofuran, preferably in the presence of a base, for example pyridine. Suitable reaction temperatures from 0° C. to 50° C., preferably room temperature.

Compounds of formula XXX may be prepared by reacting a compound of formula XXXIII

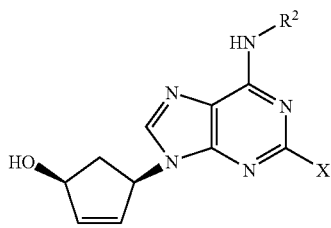

XXXII where $R^2$ and X are as hereinbefore defined, with a compound of formula XXXIV

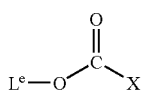

XXXIV where $L^e$ is $C_1$-$C_8$-alkyl and X is halo, preferably chloro, or analogously as herein described in the Examples. The reaction is conveniently carried out in an inert environment, for example in argon, using an organic solvent, for example deoxygenated tetrahydrofuran, preferably in the presence of a base, for example pyridine. Suitable reaction temperatures from 0° C. to 40° C., preferably room temperature.

Compounds of formula XXXI may be prepared by reacting a compound of formula XXXV

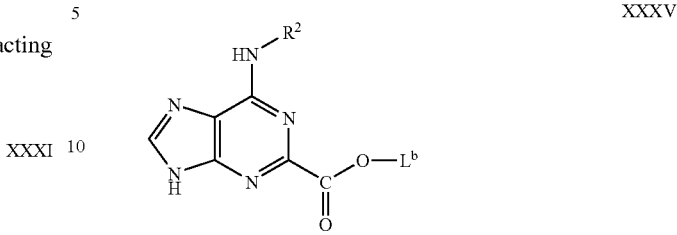

XXXV where $R^2$ and $L^b$ are as hereinbefore defined, with (1S,4R)-cis 4-acetoxy-2-cyclopenten-1-ol in the presence of a base, such sodium hydride, and a catalyst, such as that generated from tetrakis(triphenylphosphine)palladium and triphenylphosphine, or analogously as herein described in the Examples. The reaction is conveniently carried out in an inert environment, for example in argon, using an organic solvent, for example deoxygenated tetrahydrofuran or dimethyl sulfoxide. Suitable reaction temperatures from 60° C. to 100° C., preferably about 80° C.

Compounds of formula XXXII are commercially available or may be obtained by known procedures for preparing such compounds, or analogously as herein described in the Examples.

Compounds of formula XXXIII may be prepared by reacting a compound of formula XXXVI

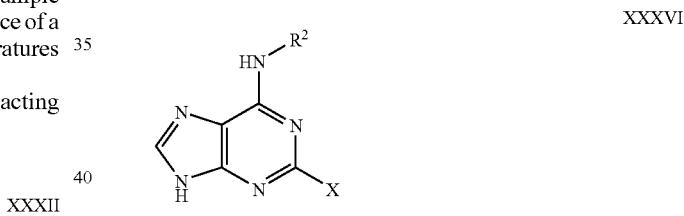

XXXVI where $R^2$ and X are as hereinbefore defined, with (1S,4R)-cis 4-Acetoxy-2-cyclopenten-1-ol in the presence of a base, such sodium hydride, and a catalyst, such as that generated from tetrakis(triphenylphosphine)palladium and triphenylphosphine, or analogously as herein described in the Examples. The reaction is conveniently carried out in an inert environment, for example in argon, using an organic solvent, for example deoxygenated tetrahydrofuran or dimethylsulfoxide (DMSO). Suitable reaction temperatures from 40° C. to 60° C., preferably about 50° C.

Compounds of formula XXXIV are commercially available or may be obtained by known procedures for preparing such compounds, or analogously as herein described in the Examples.

Compounds of formula XXXV may be prepared by reacting a salt compound of formula XXVV where $R^2$ and $L^b$ are as hereinbefore defined with a silating agent, for example (N,O-bis(trimethylsilyl)acetamide), or analogously as herein described in the Examples. The reaction is conveniently carried out in an inert environment, for example in argon, using an organic solvent, for example dry dichloromethane. Suitable reaction temperatures from 60° C. to 100° C., preferably about 80° C. A preferred salt is 6-(2,2-Diphenyl-ethylamino)-9H-purine-2-carboxylic acid methyl ester hydrochloride, which is prepared using the method described in international patent application WO 01/94368.

Compounds of formula XXXVI are commercially available or may be obtained by known procedures for preparing such compounds, or analogously as herein described in the Examples.

Compounds of formula I and their pharmaceutically acceptable salts are useful as pharmaceuticals. In particular, they activate the adenosine $A_{2A}$ receptor, i.e. they act as $A_{2A}$ receptor agonists. Their properties as $A_{2A}$ agonists may be demonstrated using the method described by L. J. Murphree et al in *Molecular Pharmacology* 61, 455-462 (2002).

Compounds of the Examples hereinbelow have $K_i$ values below 3.0 µM in the above assay, and in most cases below 1.0 µM. For example, the compounds of Examples 1, 4, 7, 12, 22, 37, 40, 45, 47, 54, 64, 67, 77, 86, 96, 109, 127, 150 and 157 have $K_i$ values of 0.197, 0.172, 0.043, 0.272, 0.138, 0.121, 0.067, 0.017, 0.010, 0.072, 0.049, 0.071, 0.020, 0.040, 0.002, 0.005, 0.003, 0.006 and 0.003 µM respectively.

Having regard to their activation of the adenosine $A_{2A}$ receptor, compounds of formula I in free or pharmaceutically acceptable salt form, hereinafter alternately referred to as "agents of the invention", are useful in the treatment of conditions which respond to the activation of the adenosine $A_{2A}$ receptor, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction. Agents of the invention are also useful in the treatment of inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, scleredoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunct-ivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, conditions characterised by elevated intraocular pressure or secretion of ocular aqueous humor, such as glaucoma, ischemic tissue/organ damage from reperfusion and bedsores.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; Cernadas et al (1999) *Am. J. Respir. Cell Mol. Biol.* 20:1-8; and Fozard et al (2002) *European Journal of Pharmacological* 438, 183-188.

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs.

An agent of the invention may be mixed with the other drug substance in a fixed pharmaceutical composition or it may be administered separately, before, simultaneously with or after the other drug substance.

Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030725, WO 05/030212, WO 05/087744, WO 05/087745, WO 05/087749 and WO 05/090345; and adenosine $A_{2B}$ receptor antagonists such as those described in WO 02/42298.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 0075114, which document is incorporated herein by reference, preferably compounds of the Examples thereof, especially a compound of formula

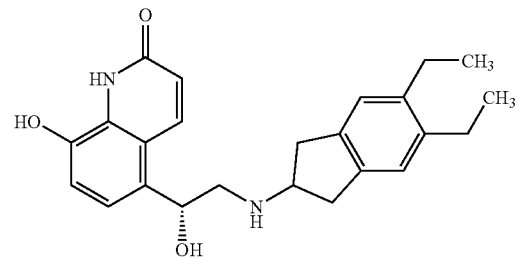

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/089892, WO 04/108675, WO 04/108676, WO 05/033121, WO 05/040103, WO 05/044787, WO 05/058867, WO 05/065650, WO 05/066140 and WO 05/07908.

Suitable dual anti-inflammatory and bronchodilatory drugs include dual beta-2 adrenoceptor agonist/muscarinic antagonists such as those disclosed in US 2004/0167167, WO 04/74246, WO 04/74812 and US 2004/0242622.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition responsive to activation of the adenosine $A_{2A}$ receptor, for example an inflammatory or allergic condition, particularly an inflammatory or obstructive airways disease, which comprises administering to a subject, particularly a human subject, in need thereof a compound of formula I in free form or in the form of a pharmaceutically acceptable salt. In another aspect the invention provides a compound of formula I, in free form or in the form of a pharmaceutically acceptable salt, for use in the manufacture of a medicament for the treatment of a condition responsive to activation of the adenosine $A_{2A}$ receptor, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate, typically 0.05-2.0% magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) a compound of formula I in inhalable form, e.g. in an aerosol or other atomisable composition or in inhalable particulate, e.g. micronised, form, (B) an inhalable medicament comprising a compound of formula I in inhalable form; (C) a pharmaceutical product comprising a compound of formula I in inhalable form in association with an inhalation device; and (D) an inhalation deviceccontaining a compound of formula I in inhalable form.

Dosages of compounds of formula I employed in practising the present invention will of course vary depending, for example, on the particular condition to be treated, the effect desired and the mode of administration. In general, suitable daily dosages for administration by inhalation are of the order of 0.005 to 10 mg, while for oral administration suitable daily doses are of the order of 0.05 to 100 mg.

The invention is illustrated by the following Examples.

EXAMPLES

Abbreviations used are as follows: CDI is 1,1'-carbonyldiimidazole, DCM is dichloromethane, DIPEA is diisopropylethylamine, DMF is dimethylformamide, THF is tetrahydrofuran, HPLC is high Performance Liquid Chromatography, DMSO is dimethyl sulfoxide, HCl is hydrochloric acid, TFA is trifluoroacetic acid, and DMAP is 4-dimenthylaminopyridine.

Preparation of Intermediates

The following intermediates of formula (A)

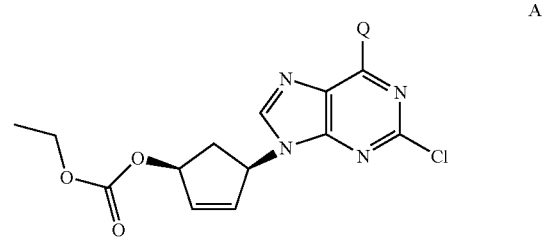

A are shown in Table 1 below, their method of preparation being described hereinafter.

TABLE 1

| Intermediate | Q | M/s (MH+) |
|---|---|---|
| AA | (diphenylmethyl-aminomethyl group) | 504 |
| AB | (bis(4-methoxyphenyl)methyl-amino group) | — |
| AC | Cl | 343 |

Intermediate AA

Carbonic Acid (1S,4R)-4-[2-chloro-6-(2,2-diphenyl-ethylamino)-purin-9-yl]-cyclopent-2-enyl Ester Ethyl Ester AA1) (2-Chloro-9H-purin-6-yl)-(2,2-diphenyl-ethyl)-amine 2,6-Dichloroputrine (20.00 g, 106 mmol) is dissolved in THF (250 ml) under an atmosphere of argon. Diisopropylamine (16.38 g, 127 mmol) is added followed by 2,2-diphenylethyl-amine (25.00 g, 127 mmol) and the reaction mixture is stirred at 50° C. The reaction is shown to be complete by LCMS after 6 hours. 50% of the solvent is removed in vacuo and replaced with MeOH. The resulting precipitate is filtered off and dried to give the title compound. $^1$H nmr (d$_6$-DMSO, 400 MHz); 8.05 (br s, 1H), 7.35-7.10 (m, 10H), 4.55 (m, 1H), 4.10 (m, 2H), MS (ES+) m/e 350 (MH$^+$).

AA2) (1S,4R)-4-[2-Chloro-6-(2,2-diphenyl-ethylamino)-purin-9-yl]-cyclopent-2-enol (2-Chloro-9H-purin-6-yl)-(2,2-diphenyl-ethyl)-amine (12.92 g, 36.97 mmol) is placed in an oven-dried flask under an atmosphere of argon. Dry deoxygenated THF (100 mL) and dry DMSO (2 mL) are added and the suspension is cooled on an ice-bath. Sodium hydride 95% (0.89 g, 36.97 mmol) is then slowly added and the solution is stirred at room temperature for 30 minutes. (1S,4R)-cis 4-Acetoxy-2-cyclopenten-1-ol (5.00 g. 35.20 mmol) and triphenyl-phosphine (1.38 g, 5.28 mmol) are placed in an oven-dried flask under an atmosphere of argon. Dry deoxygenated THF (50 mL) is added. This solution is added to the anion solution via syringe. Tetrakis (triphenylphosphine)palladium(0) (2.03 g, 1.76 mmol) is then added and the reaction mixture is stirred at 50° C. for 3 hours. The reaction mixture is allowed to cool and the solvent is removed in vacuo. The residue is taken up in dichloromethane (50 ml) and poured into vigorously stirring diethyl ether (300 mL). The precipitate is filtered off, the filtrate is taken and the solvent is removed in vacuo to give the title compound. $^1$H nmr (CDCl$_3$, 400 MHz); 7.65 (m, 1H), 7.35-7.15 (m, 10H), 6.35 (m, 1H), 5.90 (m, 1H), 5.80 (m, 1H), 5.50 (m, 1H), 5.25 (d, 1H), 4.85 (t, 1H), 4.35 (t, 1H), 4.25 (m, 2H), 2.95 (m, 1H), 2.15 (d, 1H), MS (ES+) m/e 432 (MH$^+$).

AA3) Carbonic acid (1S,4R)-4-[2-chloro-6-(2,2-diphenyl-ethylamino)-purin-9-yl]-cyclopent-2-enyl ester ethyl ester (1S,4R)-4-[2-Chloro-6-(2,2-diphenyl-ethylamino)-purin-9-yl]-cyclopent-2-enol (3.00 g, 6.95 mmol) is placed in an oven-dried flask under an atmosphere of argon. Dry THF (100 mL) is added followed by dry pyridine (1.10 g, 13.90 mmol). Ethyl chloroformate (3.02 g, 27.80 mmol) is added slowly and the reaction mixture is stirred at room temperature for 4 hours. The solvent is removed in vacuo and the residue is partitioned between dichloromethane (200 mL) and 10% citric acid (200 mL). The organic layer is washed with water (150 ml) and brine (150 ml), dried over MgSO$_4$, filtered and the solvent is removed in vacuo. The title compound is obtained after purification by flash column chromatography (silica, iso-hexane/ethyl acetate 2:1). $^1$H nmr (CDCl$_3$, 400 MHz); 7.70 (br s, 1H), 7.35-7.15 (m, 10H), 6.35 (m, 1H), 6.15 (m, 1H), 5.80 (m, 1H), 5.65 (m, 2H), 4.35 (t, 1H), 4.25 (m, 2H), 4.20 (q, 2H), 3.10 (m, 1H), 1.95 (d, 1H), 1.30 (t, 3H), MS (ES+) m/e 504 (MH$^+$).

Intermediate AB

Carbonic acid (1S,4R)-4-(6-{[bis-(4-methoxy-phenyl)-methyl]-amino}-2-chloro-purin-9-yl)-cyclopent-2-enyl Ester Ethyl Ester AB1) Bis-(4-methoxy-phenyl)-methanone Oxime 4,4'-Dimethoxybenzophenone (25 g, 103 mmol) is suspended in ethanol (150 mL) and pyridine (30 mL). Hydroxylamine hydrochloride (21.50 g, 310 mmol) is added and the reaction mixture is refluxed for 3 hours. The reaction mixture is allowed to cool and the solvent is removed in vacuo. The residue is partitioned between ethyl acetate (500 mL) and water (500 mL). The organic layer dried is over MgSO$_4$, filtered and the solvent removed in vacuo. The title compound is obtained following crystallisation from ethylacetate/cyclohexane. $^1$H nmr (CDCl$_3$, 400 MHz); 7.70 (s, 1H), 7.40 (d of d, 4H), 6.95 (d, 2H), 6.85 (d, 2H), 3.85 (s, 3H), 3.80 (s, 3H).

AB2) C,C-Bis-(4-methoxy-phenyl)-methylamine

Bis-(4-methoxy-phenyl)-methanone oxime (20 g, 77.82 mmol) is suspended in ammonia (450 mL) and ethanol (90 mL). Ammonium acetate (3.00 g, 38.91 mmol) is added followed by the portion-wise addition of zinc dust (25.29 g, 389.1 mmol). Once the addition is complete the reaction mixture is slowly heated to 50° C. When the effervescence has ceased the reaction mixture is refluxed for 4 hours. The reaction mixture is allowed to cool and ethyl acetate is added (250 mL). The reaction mixture is filtered through Celite® and the phases are separated. The organic layer dried is over MgSO$_4$, filtered and the solvent removed in vacuo to give the title compound. $^1$H nmr (CDCl$_3$, 400 MHz); 7.25 (d, 4H), 6.80 (d, 4H), 5.10 (s, 1H), 3.75 (s, 6H).

AB3) Bis-(4-methoxy-phenyl)-methyl]-(2-chloro-9H-purin-6-yl)-amine

The title compound is prepared from 2,6-dichloropurine and C,C-Bis-(4-methoxy-phenyl)-methylamine (AB2) using a procedure analogous to that of Intermediate AA1. $^1$H nmr (d$_6$-DMSO, 400 MHz); 8.20 (br s, 1H), 7.25 (d, 4H), 6.90 (d, 4H), 3.75 (s, 6H), 3.15 (m, 1H), MS (ES+) m/e 396 (MH$^+$).

AB4) (1S,4R)-4-(6-{[Bis-(4-methoxy-phenyl)-methyl]-amino}-2-chloro-purin-9-yl)-cyclopent-2-enol The title compound is prepared from Bis-(4-methoxy-phenyl)-methyl]-(2-chloro-9H-purin-6-yl)-amine (AB3) using a procedure analogous to that of Intermediate AA2. $^1$H nmr (CDCl$_3$, 400 MHz); 9.10 (m, 1H), 8.10 (m, 1H), 7.30 (d, 4H), 6.90 (d, 4H), 6.55 (d, 1H), 6.20 (m, 1H), 5.95 (m, 1H), 5.40 (m, 1H), 5.30 (d, 1H), 4.70 (m, 1H), 3.70 (s, 6H), 2.90 (m, 1H), 1.70 (m, 1H), MS (ES+) m/e 478 (MH$^+$).

AB5) 3-Oxy-benzotriazole-1-carboxylic Acid Ethyl Ester

The title compound is prepared from 1-hydroxybenzotriazole by the procedure of Wuts, Peter G. M. et al Organic Letters (2003), 5(9), 1483-1485. $^1$H nmr (CDCl$_3$, 400 MHz); 8.20 (d, 1H), 8.00 (d, 1H), 7.75 (t, 1H), 7.55 (t, 1H), 4.60 (q, 2H), 1.55 (t, 3H).

AB6) Carbonic acid (1S,4R)-4-(6-{[bis-(4-methoxy-phenyl)-methyl]-amino}-2-chloro-purin-9-yl)-cyclopent-2-enyl ester ethyl ester (1S,4R)-4-(6-{[Bis-(4-methoxy-phenyl)-methyl]-amino}-2-chloro-purin-9-yl)-cyclopent-2-enol (8.00 g, 16.75 mmol) is placed in an oven-dried flask under an atmosphere of argon. Dry pyridine (80 mL) is added followed by diisopropylamine (16 mL). A catalytic amount of DMAP is added followed by 3-oxy-benzotriazole-1-carboxylic acid ethyl ester (6.94 g, 33.50 mmol). The reaction mixture is stirred at room temperature. The reaction is shown to be complete by TLC after 18 hours. The solvent is removed in vacuo and the residue is partitioned between ethyl acetate (500 mL) and 2M HCl (200 mL). The organic layer is washed with water (150 ml) and brine (150 ml), dried over MgSO$_4$, filtered and the solvent is removed in vacuo. The title compound is obtained after purification by flash column chromatography (silica, dichloro-methane/methanol 50:1). $^1$H nmr (CDCl$_3$, 400 MHz); 7.80 (s, 1H), 7.25 (d of d, 4H), 6.85 (d of d, 4H), 6.65 (m, 1H), 6.50 (m, 1H), 6.35 (m, 1H), 6.15 (m, 1H), 5.65 (m, 2H), 4.25 (q, 2H), 3.80 (s, 6H), 3.10 (m, 1H), 1.95 (m, 1H), 1.35 (t, 3H).

Intermediate AC

Carbonic acid (1S,4R)-4-(2,6-dichloro-purin-9-yl)-cyclopent-2-enyl ester ethyl ester AC1) (1S,4R)-4-(2,6-Dichloro-purin-9-yl)-cyclopent-2-enol 2,6-Dichloropurine (10 g, 52.90 mmol), (1S,4R)-cis 4-Acetoxy-2-cyclopenten-1-ol (10 g. 70.40 mmol), tris(dibenzylideneacetone)dipalladium(0) (3.20 g, 3.50 mmol) and polymer supported triphenylphosphine (~3 mmol/g, 11.60 g, 35.00 mmol) are placed in an oven-dried flask under an atmosphere of argon. Dry deoxygenated THF (80 mL) is added and the reaction mixture is stirred gently for 5 minutes. Triethylamine (20 mL) is added and the reaction mixture is stirred at 50° C. The reaction is shown to be complete by LCMS after 1 hour. The reaction mixture is allowed to cool, the polymer supported triphenylphosphine is filtered off and the solvent is removed in vacuo. The title compound is obtained after purification by flash column chromatography (silica, dichloromethane/methanol 25:1). $^1$H nmr (CDCl$_3$, 400 MHz); 8.30 (s, 1H), 6.40 (m, 1H), 5.90 (m, 1H), 5.50 (m, 1H), 4.95 (m, 1H), 3.05 (m, 1H), 2.10 (m, 1H), MS (ES+) m/e 271 (MH$^+$).

AC2) Carbonic acid (1S,4R)-4-(2,6-dichloro-purin-9-yl)-cyclopent-2-enyl ester ethyl ester The title compound is prepared from (1S,4R)-4-(2,6-Dichloro-purin-9-yl)-cyclopent-2-enol (AC1) using a procedure analogous to that of Intermediate AA3. Purification by crystallisation from MeOH. $^1$H nmr (CDCl$_3$, 400 MHz); 8.20 (s, 1H), 6.45 (m, 1H), 6.25 (m, 1H), 5.75 (m, 1H), 5.70 (m, 1H), 4.25 (q, 2H), 3.20 (m, 1H), 2.05 (m, 1H), 1.35 (t, 3H), MS (ES+) m/e 343 (MH$^+$).

The following intermediates of formula (B)

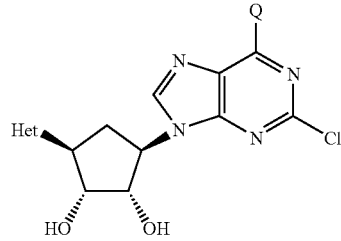

are shown in the Table 2 below, the method of preparation being described hereinafter.

TABLE 2

| Intermediate | Het | Q |
|---|---|---|
| BA1 | H$_3$C-pyrazole (N-methyl) | diphenylmethyl-CH$_2$-NH- |
| BA2 | H$_3$C-pyrazole (N-methyl) | diphenylmethyl-CH$_2$-NH- |
| BA3 | triazole | diphenylmethyl-CH$_2$-NH- |

TABLE 2-continued
| Intermediate | Het | Q |
|---|---|---|
| BA4 | 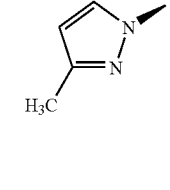 | 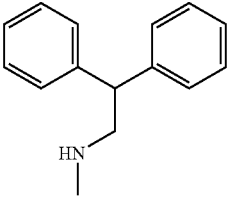 |
| BA5 | 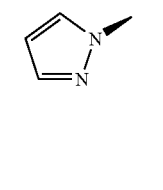 | 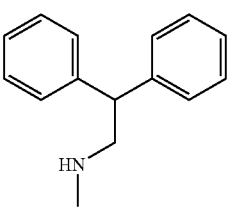 |
| BA6 | 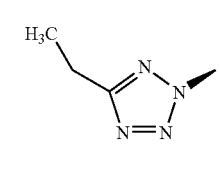 | 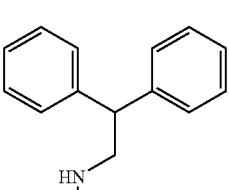 |
| BA7 | 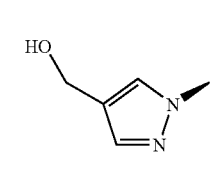 | 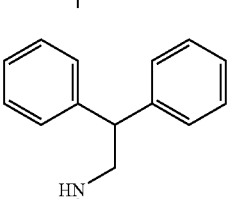 |
| BA8 | 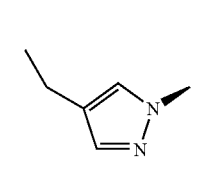 | 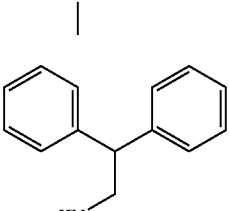 |
| BA9 | 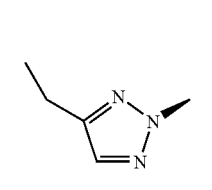 | 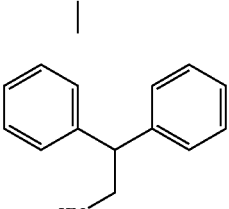 |
| BB1 | 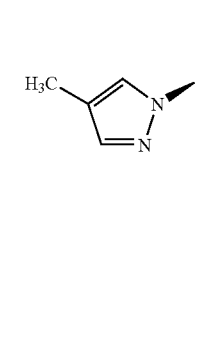 | 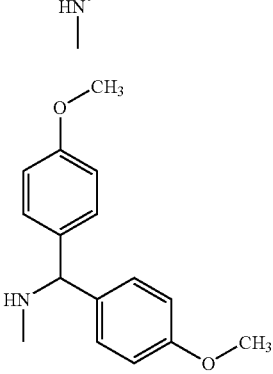 |

TABLE 2-continued
| Intermediate | Het | Q |
|---|---|---|
| BB2 | 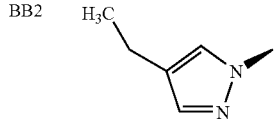 | 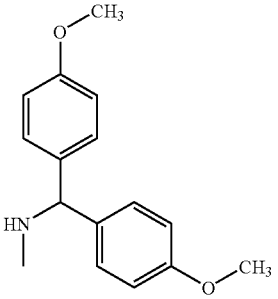 |
| BB3 | 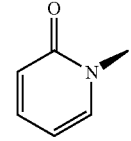 | 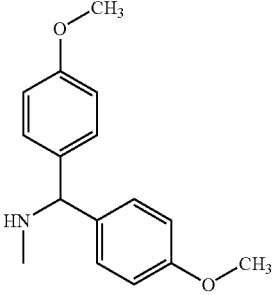 |
| BB4 | 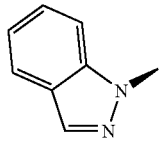 | 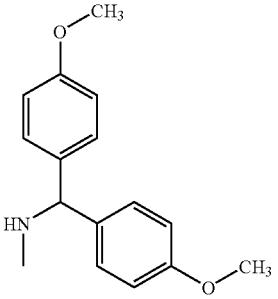 |
| BB5 | 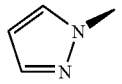 | 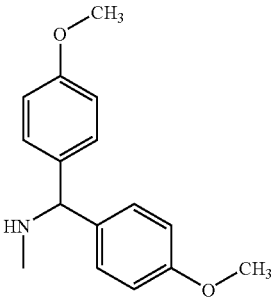 |
| BB6 | 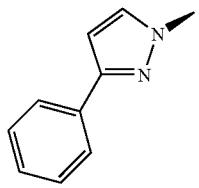 | 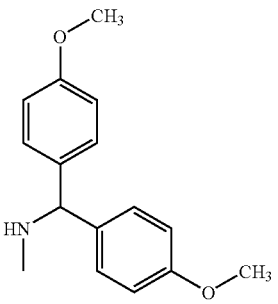 |

TABLE 2-continued

| Intermediate | Het | Q |
|---|---|---|
| BB7 | 4-(hydroxymethyl)-1-methyl-1H-pyrazole | bis(4-methoxyphenyl)methyl-N-methylamine |
| BC1 | 4-ethyl-1-methyl-1H-pyrazole | (2S)-2-(methylamino)-3-phenylpropan-1-ol |
| BD1 | 4-ethyl-1-methyl-1H-pyrazole | N-methyl-2-phenylethan-1-amine |
| BE1 | 4-ethyl-1-methyl-1H-pyrazole | N,3-dimethylpentan-3-amine (sec-butyl methylamine variant) |
| BF1 | 5-ethyl-2-methyl-2H-tetrazole | 2,2-bis(4-hydroxyphenyl)-N-methylethan-1-amine |

Intermediate BA1

(1R,2S,3R,5S)-3-[2-Chloro-6-(2,2-diphenyl-ethylamino)-purin-9-yl]-5-(4-methyl-pyrazol-1-yl)-cyclopentane-1,2-diol a) {2-Chloro-9-[(1R,4S)-4-(4-methyl-pyrazol-1-yl)-cyclopent-2-enyl]-9H-purin-6-yl}-(2,2-diphenyl-ethyl)-amine Carbonic acid (1S,4R)-4-[2-chloro-6-(2,2-diphenyl-ethylamino)-purin-9-yl]-cyclopent-2-enyl ester ethyl ester (Intermediate AA) (2.00 g, 3.97 mmol) is placed in an oven-dried flask under an atmosphere of argon. Dry deoxygenated THF (20 mL) is added followed by 4-methyl-pyrazole (0.36 g, 4.37 mmol) and triphenylphosphine (0.16 g, 0.60 mmol). Tetrakis (triphenyl-phosphine)palladium(0) (0.23 g, 0.20 mmol) is then added and the reaction mixture is stirred at room temperature for 18 hours. The solvent is removed in vacuo and the title compound is obtained after purification by flash column chromatography (silica, iso-hexane/ethyl acetate 1:2). $^1$H nmr (CDCl$_3$, 400 MHz); 8.10 (br s, 1H), 7.35-7.15 (m, 12H), 6.25 (m, 1H), 6.10 (m, 1H), 5.80 (m, 1H), 5.70 (m, 1H), 5.35 (m, 1H), 4.35 (t, 1H), 4.25 (m, 2H), 3.25 (m, 1H), 2.20 (m, 1H), 2.05 (s, 3H), MS (ES+) m/e 496 (MH$^+$).

b) (1R,2S,3R,5S)-3-[2-Chloro-6-(2,2-diphenyl-ethylamino)-purin-9-yl]-5-(4-methyl-pyrazol-1-yl)-cyclopentane-1,2-diol {2-Chloro-9-[(1R,4S)-4-(4-methyl-pyrazol-1-yl)-cyclopent-2-enyl]-9H-purin-6-yl}-(2,2-diphenyl-ethyl)-amine (step 1)(1.50 g, 3.03 mmol) is dissolved in THF (30 mL)-N-methyl-morpholine N-oxide (0.71 g, 6.06 mmol) is added followed by osmium tetroxide (3 mL, 4% in water). The reaction mixture is stirred at room temperature for 18 hours.

The solvent is removed in vacuo and the title compound is obtained after purification by flash column chromatography (silica, dichloromethane/methanol 25:1). $^1$H nmr (CDCl$_3$, 400 MHz); 7.90 (br s, 1H), 7.40-7.15 (m, 12H), 5.95 (m, 1H), 5.65 (m, 1H), 4.80 (m, 1H), 4.65 (m, 2H), 4.35 (t, 1H), 4.30 (m, 2H), 3.70 (m, 1H), 3.40 (m, 1H), 3.00 (m, 1H), 2.70 (m, 1H), 2.40 (m, 1H), 2.10 (s, 3H), MS (ES+) m/e 531 (MH$^+$).

Intermediate BA2-BA5

These compounds are namely,
(1R,2S,3R,5S)-3-[2-Chloro-6-(2,2-diphenyl-ethylamino)-purin-9-yl]-5-(5-methyl-tetrazol-2-yl)-cyclopentane-1,2-diol (Intermediate BA2);
(1R,2S,3R,5S)-3-[2-Chloro-6-(2,2-diphenyl-ethylamino)-purin-9-yl]-5-[1,2,3]triazol-1-yl-cyclopentane-1,2-diol (Intermediate BA3);
(1R,2S,3R,5S)-3-[2-Chloro-6-(2,2-diphenyl-ethylamino)-purin-9-yl]-5-(3-methyl-pyrazol-1-yl)-cyclopentane-1,2-diol (Intermediate BA4);
(1R,2S,3R,5S)-3-[2-Chloro-6-(2,2-diphenyl-ethylamino)-purin-9-yl]-5-pyrazol-1-yl-cyclo-pentane-1,2-diol (Intermediate BA5);
are prepared by an analogous procedure to (1R,2S,3R,5S)-3-[2-Chloro-6-(2,2-diphenyl-ethylamino)-purin-9-yl]-5-(4-methyl-pyrazol-1-yl)-cyclopentane-1,2-diol (Intermediate BA1) by replacing 4-methylpyrazole in step 1 with the appropriate 5 membered nitrogen heterocycle.

Intermediate BA6

(1R,2S,3R,5S)-3-[2-Chloro-6-(2,2-diphenyl-ethylamino)-purin-9-yl]-5-(5-ethyl-tetrazol-2-yl)-cyclopentane-1,2-diol a) 2,6-Dichloro-9-[(1R,4S)-4-(5-ethyl-tetrazol-2-yl)-cyclopent-2-enyl]-9H-purine Carbonic acid (1S,4R)-4-(2,6-dichloro-purin-9-yl)-cyclopent-2-enyl ester ethyl ester (Intermediate AC) (3 g, 8.75 mmol), 5-Ethyl-2H-tetrazole (0.94 g. 9.62 mmol), tris(dibenzylideneacetone)dipalladium(0) (0.40 g, 0.44 mmol) and triphenylphosphine (0.35 g, 1.32 mmol) are placed in an oven-dried flask under an atmosphere of argon. Dry deoxygenated THF (40 mL) is added and the reaction mixture is stirred gently for 5 minutes. Triethylamine (20 mL) is added and the reaction mixture is stirred at room temperature for 1 hour. The reaction mixture is allowed to cool and the solvent is removed in vacuo. The residue was taken up in methanol (50 mL) and the solid was filtered off-product. $^1$H nmr (CDCl$_3$, 400 MHz); 8.55 (s, 1H), 6.35 (m, 1H), 6.25 (m, 1H), 6.05 (m, 1H), 5.90 (m, 1H), 3.45 (m, 1H), 2.85 (q, 2H), 2.30 (m, 1H), 1.30 (t, 3H), MS (ES+) m/e 351 (MH$^+$).

b) {2-Chloro-9-[(1R,4S)-4-(5-ethyl-tetrazol-2-yl)-cyclopent-2-enyl]-9H-purin-6-yl}-(2,2-diphenyl-ethyl)-amine 2,6-Dichloro-9-[(1R,4S)-4-(5-ethyl-tetrazol-2-yl)-cyclopent-2-enyl]-9H-purine (step 1) (0.2 g, 0.57 mmol) is dissolved in THF (5 ml) under an atmosphere of argon. Diisopropylamine (0.088 g, 0.68 mmol) is added followed by 2,2-diphenylethylamine (0.123 g, 0.63 mmol) and the reaction mixture is stirred at 50° C. for 4 hours. The solvent is removed in vacuo and residue is partitioned between dichloromethane (20 mL) and 2M HCl (20 mL). The organic layer is washed with sat. NaHCO$_3$ (20 mL), water (20 ml) and brine (20 ml), dried over MgSO$_4$, filtered and the solvent is removed in vacuo to give the title compound. $^1$H nmr (CDCl$_3$, 400 MHz); 8.20 (br s, 1H), 7.30-7.10 (m, 10H), 6.30 (m, 1H), 6.20 (m, 1H), 5.95 (m, 1H), 5.80 (m, 1H), 4.35 (m, 1H), 4.20 (m, 2H), 3.35 (m, 1H), 2.85 (q, 2H), 2.20 (m, 1H), 1.30 (t, 3H), MS (ES+) m/e 512 (MH$^+$).

c) (1R,2S,3R,5S)-3-[2-Chloro-6-(2,2-diphenyl-ethylamino)-purin-9-yl]-5-(5-ethyl-tetrazol-2-yl)-cyclopentane-1,2-diol The title compound is prepared from {2-chloro-9-[(1R,4S)-4-(5-ethyl-tetrazol-2-yl)-cyclopent-2-enyl]-9H-purin-6-yl}1-(2,2-diphenyl-ethyl)-amine (step 1) using a procedure analogous to that of Intermediate BA1, step 2. Purification by reverse phase column chromatography (Isolute™ C18, 0-100% acetonitrile in water—0.1% TFA). $^1$H nmr (MeOD, 400 MHz); 8.20 (s, 1H), 7.45-7.15 (m, 10H), 5.30 (m, 1H), 4.95 (m, 1H), 4.70 (m, 1H), 4.60 (m, 1H), 4.50 (m, 1H), 4.20 (m, 2H), 4.10 (q, 2H), 3.05 (m, 1H), 2.75 (m, 1H), 1.25 (t, 3H), MS (ES+) m/e 546 (MH$^+$).

Intermediate BA7

(1R,2S,3R,5S)-3-[2-Chloro-6-(2,2-diphenyl-ethylamino)-purin-9-yl]-5-(4-hydroxymethyl-pyrazol-1-yl)-cyclopentane-1,2-diol This compound is prepared from carbonic acid (1S,4R)-4-(2,6-dichloro-purin-9-yl)-cyclopent-2-enyl ester ethyl ester (Intermediate AC) using the same procedure as Intermediate BA6, by replacing 5-Ethyl-2H-tetrazole with (1H-Pyrazol-4-yl)-methanol (step 1). MS (ES+) m/e 546 (MH$^+$).

Intermediate BA8

(1R,2S,3R,5S)-3-[2-Chloro-6-(2,2-diphenyl-ethylamino)-purin-9-yl]-S-(4-ethyl-pyrazol-1-yl)-cyclopentane-1,2-diol This compound is prepared from carbonic acid (1S,4R)-4-(2,6-dichloro-purin-9-yl)-cyclopent-2-enyl ester ethyl ester (Intermediate AC) using a procedure analogous to that of (1R,2S,3R,5S)-3-[2-chloro-6-(2,2-diphenyl-ethylamino)-purin-9-yl]-5-(5-ethyl-tetrazol-2-yl)-cyclopentane-1,2-diol (Intermediate BA6) by replacing 5-ethyl-2H-tetrazole with 4-ethyl-1H-pyrazole (Intermediate CA) (first step a). MS (ES+) m/e 544.23 (MH$^+$)

Intermediate BA9

3-[2-Chloro-6-(2,2-diphenyl-ethylamino)-purin-9-yl]-5-(4-ethyl-[1,2,3]triazol-1-yl)-cyclopentane-1,2-diol This compound is prepared from carbonic acid (1S,4R)-4-(2,6-dichloro-purin-9-yl)-cyclopent-2-enyl ester ethyl ester (Intermediate AC) using a procedure analogous to that of (1R,2S,3R,5S)-3-[2-chloro-6-(2,2-diphenyl-ethylamino)-purin-9-yl]-5-(5-ethyl-tetrazol-2-yl)-cyclopentane-1,2-diol (Intermediate BA6) by replacing 5-ethyl-2H-tetrazole with 4-ethyl-2H-[1,2,3]triazole (first step a). MS (ES+) m/e 545.24 (MH$^+$)

Intermediate BB1-BB6

These compounds, namely, (1R,2S,3R,5S)-3-(6-([Bis-(4-methoxy-phenyl)-methyl]-amino)-2-chloro-purin-9-yl)-5-(4-methyl-pyrazol-1-yl)-cyclopentane-1,2-diol (Intermediate BB1);

(1R,2S,3R,5S)-3-(6-{[Bis-(4-methoxy-phenyl)-methyl]-amino}-2-chloro-purin-9-yl)-5-(4-ethylpyrazol-1-yl)-cyclopentane-1,2-diol (Intermediate BB2);

1-((1S,2R,3S,4R)-4-{6-[2,2-Bis-(4-methoxy-phenyl)-ethylamino]-2-chloro-purin-9-yl}-2,3-dihydroxy-cyclopentyl)-1H-pyridin-2-one (Intermediate BB3);

(1R,2S,3R,5S)-3-{6-[2,2-Bis-(4-methoxy-phenyl)-ethylamino]-2-chloro-purin-9-yl}-5-indazol-1-yl-cyclopentane-1,2-diol (Intermediate BB4);

(1R,2S,3R,5S)-3-{6-[2,2-Bis-(4-methoxy-phenyl)-ethylamino]-2-chloro-purin-9-yl}-5-pyrazol-1-yl-cyclopentane-1,2-diol (Intermediate BB5);

(1R,2S,3R,5S)-3-{6-[2,2-Bis-(4-methoxy-phenyl)-ethylamino]-2-chloro-purin-9-yl}-5-(3-phenyl-pyrazol-1-yl)-cyclopentane-1,2-diol (Intermediate BB6);

are prepared by an analogous procedure to 1R,2S,3R,5S)-3-[2-Chloro-6-(2,2-diphenyl-ethylamino)-purin-9-yl]-5-(4-methyl-pyrazol-1-yl)-cyclopentane-1,2-diol (Intermediate BA1) by replacing Carbonic acid (1S,4R)-4-[2-chloro-6-(2,2-diphenyl-ethylamino)-purin-9-yl]-cyclopent-2-enyl ester ethyl ester (Intermediate AA) in step (a) with carbonic acid (1S,4R)-4-(6-{[bis-(4-methoxy-phenyl)-methyl]-amino}-2-chloro-purin-9-yl)-cyclopent-2-enyl ester ethyl ester (Intermediate AB) and by replacing 4-methylpyrazole with the appropriate 5 membered nitrogen heterocycle.

Intermediate BB7

(1R,2S,3R,5S)-3-(6-{[Bis-(4-methoxy-phenyl)-methyl]-amino}-2-chloro-purin-9-yl)-5-(4-hydroxymethyl-pyrazol-1-yl)-cyclopentane-1,2-diol a) (1R,2S,3R,5S)-3-(6-[[Bis-(4-methoxy-phenyl)-methyl]-amino]-2-chloro-purin-9-yl)-5-[4-(tert-butyl-diphenyl-silanyloxymethyl)-pyrazol-1-yl]-cyclopentane-1,2-diol The title compound is prepared by an analogous procedure to 1R,2S,3R,5S)-3-[2-Chloro-6-(2,2-diphenyl-ethylamino)-purin-9-yl]-5-(4-methyl-pyrazol-1-yl)-cyclopentane-1,2-diol (Intermediate BA1) by replacing Carbonic acid (1S,4R)-4-[2-chloro-6-(2,2-diphenyl-ethylamino)-purin-9-yl]-cyclopent-2-enyl ester ethyl ester (Intermediate AA) in step 1 with Carbonic acid (1S,4R)-4-(6-{[bis-(4-methoxy-phenyl)-methyl]-amino}-2-chloro-purin-9-yl)-cyclopent-2-enyl ester ethyl ester (Intermediate AB) and by replacing 4-methylpyrazole with 4-(tert-Butyl-diphenyl-silanyloxymethyl)-1H-pyrazole. $^1$H nmr (CDCl$_3$, 400 MHz); 7.70 (m, 4H), 7.50-7.20 (m, 13H), 6.85 (m, 4H), 6.60 (s, 1H), 5.60 (s, 1H), 4.80 (m, 1H), 4.70 (m, 4H), 4.30 (m, 1H), 3.80 (s, 6H), 3.00 (m, 1H), 2.70 (m, 1H), 1.10 (s, 9H).

b) (1R,2S,3R,5S)-3-(6-{[Bis-(4-methoxy-phenyl)-methyl]-amino}-2-chloro-purin-9-yl)-5-(4-hydroxymethyl-pyrazol-1-yl)-cyclopentane-1,2-diol (1R,2S,3R,5S)-3-(6-{[Bis-(4-methoxy-phenyl)-methyl]-amino}-2-chloro-purin-9-yl)-5-[4-(tert-butyl-diphenyl-silanyloxymethyl)-pyrazol-1-yl]-cyclopentane-1,2-diol (step 1) (0.2 g, 0.24 mmol) is placed in a flask with THF (0.5 mL). Tetrabutylammonium fluoride (1M in THF, 0.26 mL, 0.26 mmol) is added and the reaction mixture is stirred at room temperature for 2 hours. The solvent is removed in vacuo and the title compound is obtained after purification by flash column chromatography (silica, dichloromethane/methanol 25:1). MS (ES+) m/e 592 (MH$^+$).

Intermediate BC1

(1R,2S,3R,5S)-3-[2-Chloro-6-((S)-1-hydroxymethyl-2-phenyl-ethylamino)-purin-9-yl]-5-(4-ethyl-pyrazol-1-yl)-cyclopentane-1,2-diol This compound is prepared from carbonic acid (1S,4R)-4-(2,6-dichloro-purin-9-yl)-cyclopent-2-enyl ester ethyl ester (Intermediate AC) using the same procedure as Intermediate BA6, by replacing 5-ethyl-2H-tetrazole with 4-ethyl pyrazole (step 1) and by replacing 2,2-diphenylethylamine with (S)-2-amino-3-phenyl-propan-1-ol. LCMS (electrospray): m/z [MH$^+$] 498.25 $^1$H NMR (MeOD): 1.25 (t, 3H), 2.55 (q, 2H), 2.55 (m, 1H), 2.95 (m, 2H), 3.05 (m, 1H), 3.70 (m, 3H), 4.25 (m, 1H), 4.60 (m, 2H), 4.70 (m, 1H), 7.20 (m, 5H), 7.40 (s, 1H), 7.80 (s, 1H), 8.30 (s, 1H).

Intermediate BD1

(1S,2R,3S,5R)-3-(2-Chloro-6-phenethylamino-purin-9-yl)-5-(4-ethyl-pyrazol-1-yl)-cyclopentane-1,2-diol This is prepared from carbonic acid (1S,4R)-4-(2,6-dichloro-purin-9-yl)-cyclopent-2-enyl ester ethyl ester (Intermediate AC) using the same procedure as Intermediate BA6, by replacing 5-ethyl-2H-tetrazole with 4-ethyl pyrazole (step 1) and by replacing 2,2-diphenyl-ethylamine with phenylethylamine. LCMS (electrospray): m/z [MH$^+$] 468.20 $^1$H NMR (MeOD): 1.25 (t, 3H), 2.55 (q, 2H), 2.65 (m, 1H), 2.95 (m, 1H), 3.00 (t, 2H), 3.70 (m, 1H), 3.85 (m, 2H), 4.30 (m, 1H), 4.70 (m, 2H), 7.30 (m, 5H), 7.40 (s, 1H), 7.70 (s, 1H), 8.30 (s, 1H).

Intermediate BE1

(1R,2S,3R,5S)-3-(2-Chloro-6-(1-ethyl-propylamino-purin-9-yl)-5-(4-ethyl-pyrazol-1-yl)-cyclopentane-1,2-diol This is prepared from carbonic acid (1S,4R)-4-(2,6-dichloro-purin-9-yl)-cyclopent-2-enyl ester ethyl ester (Intermediate AC) using the same procedure as Intermediate BA6, by replacing 5-ethyl-2H-tetrazole with 4-ethyl pyrazole (step 1) and by replacing 2,2-diphenyl-ethylamine with 1-ethyl-propylamine. LCMS (electrospray): m/z [MH$^+$] 434.23 $^1$H NMR (MeOD): 0.85 (t, 9H), 1.15 (q, 2H), 1.50 (m, 2H), 1.60 (m, 2H), 2.45 (m, 1H), 2.55 (m, 1H), 2.80 (m, 1H), 4.10 (m, 1H), 4.15 (m, 1H), 4.60 (m, 2H), 7.30 (s, 1H), 7.70 (s, 1H), 8.20 (s, 1H).

Intermediate BF1

(1R,2S,3R,5S)-3-{6-[2,2-Bis-(4-hydroxy-phenyl)-ethylamino]-2-chloro-purin-9-yl}-5-(5-ethyl-tetrazol-2-yl)-cyclopentane-1,2-diol This compound is prepared from carbonic acid (1S,4R)-4-(2,6-dichloro-purin-9-yl)-cyclopent-2-enyl ester ethyl ester (Intermediate AC) using a procedure analogous to that of (1R,2S,3R,5S)-3-[2-chloro-6-(2,2-diphenyl-ethylamino)- purin-9-yl]-5-(5-ethyl-tetrazol-2-yl)-cyclopentane-1,2-diol (Intermediate BA6) by replacing 2,2-diphenylethylamine with 4,4'-(2-aminoethylidene)bis-phenol (second step b). MS (ES+) m/e 578.34 (MH+)

The following N-heterocyclic intermediates shown in Table 3 are used in the synthesis of intermediates of formula B the method of preparation being described hereinafter.

TABLE 3

| Intermediate | Structure |
| --- | --- |
| CA | (4-ethyl-1H-pyrazole structure) |
| CB | (4-(tert-butyl-diphenyl-silanyloxy)-1H-pyrazole structure) |
| CC | (5-ethyl-2H-tetrazole structure) |
| CD | (1-methyl-4-(2-aminoethyl)-imidazole structure) |

Intermediate CA

4-Ethyl-1H-pyrazole a) 4-Trimethylsilanylethynyl-1H-pyrazole

4-Iodo-1H-pyrazole (20.0 g, 103 mmol) is dissolved in anhydrous THF (150 ml) and trimethylsilyl acetylene (72.8 ml, 515 mmol) is added under an inert atmosphere. Diethylamine (150 ml), bis-(triphenylphosphine) palladium (II) chloride (10.8 g, 15 mmol) and copper iodide (2.9 g, 15 mmol) are added and the reaction mixture is left to stir at room temperature for 3 hours. The solvent is removed under reduced pressure. The residue is dissolved in diethyl ether and the insoluble impurities are filtered off. The solvent is removed under reduced pressure. The residue is dissolved in methanol and the insoluble impurities removed. The solvent is removed under reduced pressure. The residue is purified by dry flash chromatography on silica gel eluting with a gradient system of diethyl ether: iso-hexane (20:80 to 100:0) to afford the title compound [MH+] 165.07 $^1$H NMR (DMSO): 0.00 (s, 9H), 7.45 (s, 1H), 7.90 (s, 1H), 12.90 (br s, 1H)

b) 4-Ethynyl-1H-pyrazole

A solution of 4-trimethylsilanylethynyl-1H-pyrazole (6.5 g, 0.040 mol) in THF (50 ml) is treated with a solution of lithium hydroxide (0.95 g, 0.040 mol) in water (10 ml) and is left to stir at room temperature for 2 days. The reaction mixture is neutralized with acetic acid and the solvent removed under reduced pressure. Water and dichloromethane are added to the residue. The precipitate is filtered off and the aqueous layer separated. The aqueous layer is washed with n-butanol and evaporated under reduced pressure to afford the title compound. [MH+] 93.04 $^1$H NMR (MeOD): 3.30 (s, 1H), 7.70 (br s, 2H).

c) 4-Ethyl-1H-pyrazole

A solution of 4-ethynyl-1H-pyrazole (0.74 g, 0.008 mol) in ethanol (40 ml) is treated with palladium on carbon (0.074 g, 10% by wt). The reaction mixture is hydrogenated for 18 hours, then the catalyst is filtered off and the filtrate is evaporated under reduced pressure to afford the title compound. [MH+] 97.07 $^1$H NMR (MeOD): 1.20 (t, 3H), 2.55 (q, 2H), 7.40 (s, 2H).

Intermediate CB 4-(tert-Butyl-diphenyl-silanyloxymethyl)-1H-pyrazole a) (1H-Pyrazol-4-yl)-methanol 4-Ethylpyrazole carboxylate (10 g, 71.40 mmol) is placed in an oven-dried flask under an atmosphere of argon. Dry THF (100 mL) is added followed by the dropwise addition of lithium aluminium hydride (1M in THF, 100 mL, 100 mmol). Once the addition is complete the reaction mixture is stirred at 50° C. The reaction is shown to be complete by NMR after 4 hours. The reaction mixture is cooled on an ice-bath and the reaction mixture is quenched with water (3.8 mL) then 15% sodium hydroxide (3.8 mL) and finally water again (11.4 mL). The solvent is removed in vacuo and the solid is placed in a Soxhlet apparatus. THF is refluxed through the system for 24 hours. The solvent is removed in vacuo to give the title compound. $^1$H nmr (MeOD, 400 MHz); 7.60 (s, 2H), 4.55 (s, 2H).

b) 4-(tert-Butyl-diphenyl-silanyloxymethyl)-1H-pyrazole (1H-Pyrazol-4-yl)-methanol (0.55 g, 5.61 mmol) and imidazole (0.953 g, 14.00 mmol) are placed in an oven-dried flask under an atmosphere of argon. Dry DMF (2.2 mL) is added followed by tert-butyldiphenylsilyl chloride (1.85 g, 6.73 mmol). The reaction mixture is stirred at room temperature. The reaction is shown to be complete by TLC after 18 hours. The reaction mixture is partitioned between dichloromethane (50 mL) and water (50 mL). The organic layer is washed with water (20 mL) and brine (20 mL), dried over MgSO$_4$, filtered and the solvent is removed in vacuo. The title compound is obtained after purification by flash column chromatography (silica, ethyl acetate/isohexane 1:8). $^1$H nmr (CDCl$_3$, 400 MHz); 7.70 (m, 4H), 7.50 (m, 2H), 7.40 (m, 6H), 4.75 (s, 2H), 1.10 (s, 9H).

Intermediate CC

5-Ethyl-2H-tetrazole a) 5-Vinyl-2H-tetrazole

This compound is prepared from acrylonitrile, sodium azide and aluminium chloride by the procedure of C. Arnold, Jr and D. N. Thatcher *J. Org. Chem.* 1969, 34, 1141. $^1$H nmr (CDCl$_3$, 400 MHz); 6.95 (d of d, 1H), 6.45 (d of d, 1H), 5.95 (d of d, 1H).

b) 5-Ethyl-2H-tetrazole

5-Vinyl-2H-tetrazole (1.20 g, 12.50 mmol) is dissolved in methanol (75 ml) and the compound is hydrogenated by adding a catalytic amount of 10% palladium on charcoal and placing the solution under an atmosphere of H$_2$. The reaction is shown to be complete by TLC after 1 hour. The catalyst is filtered off and the solvent is removed in vacuo to give the title compound. $^1$H nmr (acetone-d$_6$, 400 MHz); 3.00 (q, 2H), 1.35 (t, 3H).

Intermediate CD

2-(1-Ethyl-1H-imidazol-4-yl)-ethylamine a) 7,8-Dihydro-6H-imidazo[1,5-c]pyrimidin-5-one

This is prepared from histamine by the procedure of Rahul Jain and Louis A. Cohen Tetrahedron 1996, 52, 5363. $^1$H nmr (MeOD, 400 MHz); 8.15 (s, 1H), 6.85 (s, 1H), 3.50 (t, 2H), 3.00 (t, 2H).

b) 2-Ethyl-5-oxo-5,6,7,8-tetrahydro-imidazo[1,5-c]pyrimidin-2-ium iodide 7,8-Dihydro-6H-imidazo[1,5-c]pyrimidin-5-one (1.00 g, 7.30 mmol) and ethyl iodide (3.42 g, 21.90 mmol) are placed in a 10-20 mL microwave vial. Acetonitrile (10 mL) is added and the reaction mixture is heated to 120° C. using microwave radiation. The reaction is shown to be complete by NMR after 1 hour. The crystalline material is filtered off and washed with ice-cold acetonitrile to give the title compound. $^1$H nmr (MeOD, 400 MHz); 7.60 (s, 1H), 4.35 (q, 2H), 3.65 (t, 2H), 3.15 (t, 2H), 1.60 (t, 3H).

c) 2-(1-Ethyl-1H-imidazol-4-yl)-ethylamine

The title compound is prepared from 2-Ethyl-5-oxo-5,6,7,8-tetrahydro-imidazo[1,5-c]pyrimidin-2-ium iodide by the procedure of Rahul Jain and Louis A. Cohen *Tetrahedron* 1996, 52, 5363. $^1$H nmr (MeOD, 400 MHz); 7.60 (s, 1H), 6.95 (s, 1H), 4.00 (q, 2H), 2.90 (t, 2H), 2.70 (t, 2H), 1.45 (t, 3H).

Intermediate DA

6-(2,2-Diphenyl-ethylamino)-9H-purine-2-carboxylic Acid Methyl Ester 6-(2,2-Diphenyl-ethylamino)-9H-purine-2-carboxylic acid methyl ester hydrochloride (which is prepared using the method described in international patent application WO 01/94368)(18.2 g, 40.9 mmol) is placed in an oven-dried flask under an atmosphere of argon. Dry CHCl$_3$ (250 mL) and N,O-bis(trimethylsilyl)acetamide (50 mL) are added to the reaction mixture. The reaction mixture is refluxed for 1 hour. The reaction mixture is allowed to cool and the solvent is removed in vacuo. The resulting solid is taken up in MeOH (200 mL) and filtered the white solid is washed with MeOH (2×200 mL). The solid is suspended in water and sonicated for 30 minutes, filtered, washed with water (100 mL), MeOH (2×100 mL) and dried in vac oven to give the title compound.

$^1$H NMR (DMSO, 400 MHz); 8.30 (m, 1H), 8.50 (m, 1H) 7.45-7.20 (m, 10H), 4.80-4.55 (m, 2H), 4.20 (m, 2H), 4.00 (m, 2H), 3.4 (s, 2H).

Intermediate DB

6-(2,2-Diphenyl-ethylamino)-9-((1R,4S)-4-hydroxy-cyclopent-2-enyl)-9H-purine-2-carboxylic Acid Methyl Ester 6-(2,2-Diphenyl-ethylamino)-9H-purine-2-carboxylic acid methyl ester (Intermediate DA) (10.8 g 28.9 mmol) is placed in an oven-dried flask under an atmosphere of argon. Dry deoxygenated tetrahydrofuran (200 mL) and dry dimethyl sulfoxide (5 mL) are added and the suspension is cooled on an ice-bath. Sodium hydride 95% (0.69 g, 28.9 mmol) is then slowly added and the solution is stirred at room temperature for 30 minutes. (1S,4R)-cis 4-Acetoxy-2-cyclopenten-1-ol (3.9 g, 27.5 mmol), triphenylphosphine (1.08 g, 4.13 mmol) and tetrakis(triphenyl-phosphine)palladium(0) (1.27 g, 1.38 mmol) are placed in an oven-dried flask under an atmosphere of argon. Dry deoxygenated tetrahydrofuran (20 mL) is added and stirred at room temperature for 30 minutes. This solution is added to the anion solution via syringe and is then stirred at 50° C. for 6 hours. The reaction mixture is allowed to cool and the solvent is removed in vacuo. The title compound is obtained after purification by flash column chromatography (silica, 0% to 10% MeOH in DCM). $^1$H NMR (MeOD, 400 MHz); 8.15 (s, 1H), 7.40-7.15 (m, 10H), 6.30 (m, 1H), 5.95 (m, 1H), 5.60 (m, 1H), 5.50 (m, 1H), 4.85 (m, 1H), 4.55 (m, 1H), 4.30 (m 2H), 4.00 (s, 2H), 2.65 (s, 3H).

Intermediate DC

6-(2,2-Diphenyl-ethylamino)-9-((1R,4S)-4-ethoxy-carbonyloxy-cyclopent-2-enyl)-9H-purine-2-carboxylic acid methyl ester This compound is prepared by an analogous procedure to carbonic acid (1S,4R)-4-[2-chloro-6-(2,2-diphenyl-ethylamino)-purin-9-yl]-cyclopent-2-enyl ester ethyl ester (Intermediate AA3) by replacing (1S,4R)-4-[2-chloro-6-(2,2-diphenyl-ethylamino)-purin-9-yl]-cyclopent-2-enol with 6-(2,2-Diphenyl-ethylamino)-9-((1R,4S)-4-hydroxy-cyclopent-2-enyl)-9H-purine-2-carboxylic acid methyl ester (step 2) MS (ES+) m/e 528.3 (MH$^+$).

Intermediate E

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (2-aminoethyl)-amide 9-[(1R,4S)-2,3-Dihydroxy-4-(4-hydroxymethyl-pyrazol-1-yl)-cyclopentyl]-6-(2,2-diphenylethylamino)-9H-purine-2-carboxylic acid methyl ester (361 mg, 0.63 mmol) is dissolved in ethyl-1,2-diamine (3.8 g, 63.4 mmol). The reaction mixture is heated at 105° C. for 1½ hour. The reaction mixture is reduced in vacuo. The crude product is purified by flash column chromatography (C18, 0% MeCN to 100% MeCN in H$_2$O+0.1% trifluoroacetic acid as a gradient). The trifluoroacetic acid salt of the title compound partitioning between NaOH$_{(aq)}$ and dichloromethane. The organics are dried over MgSO$_4$, filtered and the solvent is reduced in vacuo to give the title compound. (MH$^+$ 598.39).

Intermediate EA

Pyridin-4-yl-carbamic Acid Phenyl Ester

4-Amino pyridine (500 mg, 5.3 mmol) and N,N-diisopropylethylamine (685 mg, 5.3 mmol) are dissolved in dichloromethane (5 ml). Phenyl chloroformate (830 mg, 5.3 mmol) is added to the reaction mixture. The reaction mixture is stirred at room temperature for 72 hours. The reaction mixture is partitioned between dichloromethane and saturated NaHCO$_3$ (aq). The aqueous is washed with dichloromethane (×2). The organics are combined, dried (MgSO$_4$), filtered and reduced in vacuo to give the title compound.

Intermediate EB

(R)-[1,3']Bipyrrolidinyl a) (R)-1'-Benzyl-[1,3']bipyrrolidinyl

An ice-cooled solution of 2,5-dimethoxytetrahydrofuran (19.11 ml, 0.147 mol) and 6 M sulphuric acid (37.2 ml) in THF (200 ml) is treated dropwise with (R)-(1)-benzyl-3-amino-pyrrolidine (10 g, 0.057 mol). 6M Sulphuric acid (37.2 ml) in THF (150 ml) and sodium borohydride pellets (8.62 g, 0.227 mol) are added simultaneously, ensuring the temperature remains below 10° C. The reaction mixture is allowed to warm to room temperature and water (10 ml) is added to aid dissolution of the sodium borohydride pellets. After stirring at room temperature for 12 days, the mixture is cooled with the use of an ice-bath and water is added (500 ml). The solution is basified by addition of sodium hydroxide pellets (pH<10) and then filtered under vacuum. The filtrate is extracted with diethyl ether and dichloromethane, the organic portions combined and concentrated in vacuo. The crude residue is sonicated in diethyl ether and filtered under vacuum. The filtrate is reduced in vacuo again and the resulting crude is dissolved in acetonitrile (8 ml). The title compound is obtained after purification by reverse phase column chromatography (Isolute™ C18, 0-100% MeCN in water—0.1% TFA).

b) (R)-[1,3']Bipyrrolidinyl

A solution of (R)-1'-benzyl-[1,3']bipyrrolidinyl (0.517 g, 2.24 mmol) in methanol (25 ml) under an atmosphere of argon is treated with palladium hydroxide on carbon (0.1 g). The reaction mixture is placed under an atmosphere of hydrogen, stirred at room temperature overnight and then filtered through Celite™ filter material. The filtrate is concentrated in vacuo to yield the title compound as a dark orange oil.

Intermediate EC

1,3-Di(R)-pyrrolidin-3-yl-urea a) 1,3-Bis-((R)-1-benzyl-pyrrolidin-3-yl)-urea A solution comprising (R)-1-benzyl-pyrrolidin-3-ylamine (5.0 g, 28.4 mmol) in DCM (10 ml) is treated with CDI (2.3 g, 14.2 mmol) and the reaction mixture is stirred at room temperature for 48 hours. The solvent is removed in vacuo and the resulting residue is dissolved in ethyl acetate. This portion is washed with water followed by brine, dried (MgSO$_4$) and concentrated in vacuo to yield the title compound as a pale orange solid.

b) 1,3-Di(R)-pyrrolidin-3-yl-urea

To a solution of 1,3-bis-((R)-1-benzyl-pyrrolidin-3-yl)-urea (5.34 g, 14.1 mmol) in ethanol (80 ml) under an inert atmosphere of argon is added palladium hydroxide on carbon (1.07 g). The reaction mixture is purged with argon and placed under an atmosphere of hydrogen for two days after which time, the mixture is filtered and the catalyst washed with ethanol. The organic portions are combined and concentrated in vacuo to yield the title compound as a white solid.

Intermediate ED

3-Isocyanato-benzenesulfonamide

To a vigorously stirred solution of 3-aminobenzenesulphonamide (1 g, 5.8 mmol) in dry 1,4-dioxane (25 ml) is added trichloromethyl chloroformate (1.72 g, 8.7 mmol) and the reaction mixture is heated to reflux for 3 hours. The solvent is removed in vacuo to yield the title compound which is used without further purification.

Intermediate EE

4-Isocyanato-benzenesulfonamide

This compound is prepared from 4-aminobenzenesulphonamide using a procedure analogous to that of 3-isocyanato-benzenesulfonamide (Intermediate ED) by replacing 3-aminobenzene-sulphonamide with 4-aminobenzenesulphonamide.

Intermediate FB

(1R,2S,3R,5S)-3-[2-((R)-3-Amino-pyrrolidin-1-yl)-6-(2,2-diphenyl-ethylamino)-purin-9-yl]-5-(4-hydroxymethyl-pyrazol-1-yl)-cyclopentane-1,2-diol a) {(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-carbamic Acid Tert-Butyl Ester This compound is prepared from (1R,2S,3R,5S)-3-[2-chloro-6-(2,2-diphenyl-ethylamino)-purin-9-yl]-5-(4-hydroxymethyl-pyrazol-1-yl)-cyclopentane-1,2-diol (Intermediate BA7) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 46) by replacing trans-1,4-diaminocyclohexane with (R)-pyrrolidin-3-yl-carbamic acid tert-butyl ester.

b) (1R,2S,3R,5S)-3-[2-((R)-3-Amino-pyrrolidin-1-yl)-6-(2,2-diphenyl-ethylamino)-purin-9-yl]-5-(4-hydroxymethyl-pyrazol-1-yl)-cyclopentane-1,2-diol {(R)-1-[9-[(1R,2S,3R,4S)-2,3-dihydroxy-4-(4-hydroxymethyl-pyrazol-1-yl)-cyclopentyl]-6-(2,2-diphenyl-ethylamino)-9H-purin-2-yl]-pyrrolidin-3-yl}-carbamic acid tert-butyl ester (first step a) is dissolved in methanol (2 ml). (4 M) HCl in 1,4-dioxane (15 ml) is added and the reaction mixture is stirred at room temperature over night. The compound is purified by reverse phase column chromatography (Isolute™ C18, 0-100% MeCN in water—0.1% HCl). The compound is partitioned between DCM and saturated NaHCO$_{3(aq)}$. The organics are dried (MgSO$_4$), filtered and reduced in vacuo to yield the title compound. MS (ES+) m/e 596.38 (MH$^+$).

Intermediate FC

(1R,2S,3R,5S)-3-[2-((R)-3-Amino-pyrrolidin-1-yl)-6-(2,2-diphenyl-ethylamino)-purin-9-yl]-5-(4-ethyl-[1,2,3]triazol-2-yl)-cyclopentane-1,2-diol a) ((R)-1-{6-(2,2-diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-carbamic Acid Tert-Butyl Ester This compound is prepared from 3-[2-chloro-6-(2,2-diphenyl-ethylamino)-purin-9-yl]-5-(4-ethyl-[1,2,3]triazol-1-yl)-cyclopentane-1,2-diol (Intermediate BA9) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) by replacing trans-1,4-diaminocyclohexane with (R)-pyrrolidin-3-yl-carbamic acid tert-butyl ester.

b) (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol This compound is prepared from ((R)-1-{6-(2,2-diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-carbamic acid tert-butyl ester (step a) using a procedure analogous to that of (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol. (Intermediate FB, second step b). MS (ES+) m/e 595.40 (MH$^+$).

Preparation of Final Compounds

Compounds of formula I

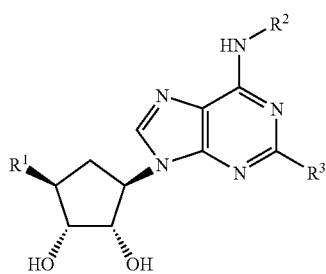

are shown in the following table. Methods for preparing such compounds are described hereinafter. The table also shows mass spectrometry, MH$^+${ESMS}, data. The Examples are prepared as trifluoroacetate salts, except for Examples 39 and 55 which are in free form.

TABLE 4

| Ex. | R$^1$ | R$^2$ | R$^3$ | MH+ |
|---|---|---|---|---|
| 1 | 4-methylpyrazol-1-yl | 2,2-diphenylethyl | trans-4-(methylamino)cyclohexylamine | 608.39 |
| 2 | 4-methylpyrazol-1-yl | 2,2-diphenylethyl | (S)-2-(methylamino)-3-phenylpropan-1-ol | 645.37 |
| 3 | 4-methylpyrazol-1-yl | 2,2-diphenylethyl | N-methyl-2-(piperidin-1-yl)ethylamine | 622.37 |
| 4 | 4-methylpyrazol-1-yl | 2,2-diphenylethyl | N-methyl-2-(1H-imidazol-4-yl)ethylamine | 605.35 |
| 5 | 4-methylpyrazol-1-yl | 2,2-diphenylethyl | N-methyl-2-phenylethylamine | 615.35 |

TABLE 4-continued

| Ex. | R¹ | R² | R³ | MH+ |
|---|---|---|---|---|
| 6 | 5-methyl-2H-tetrazol-2-yl (H₃C on tetrazole) | 1,1-diphenylpropyl | trans-4-(methylamino)cyclohexylamine | 610.34 |
| 7 | 5-methyl-2H-tetrazol-2-yl | 1,1-diphenylpropyl | (3R)-3-amino-1-methylpyrrolidine | 582.28 |
| 8 | 5-methyl-2H-tetrazol-2-yl | 1,1-diphenylpropyl | N-methyl-2-(1-isopropyl-1H-imidazol-4-yl)ethanamine | 649.13 |
| 9 | 5-methyl-2H-tetrazol-2-yl | 1,1-diphenylpropyl | (3S)-3-amino-1-methylpyrrolidine | 582.25 |
| 10 | 2H-1,2,3-triazol-2-yl | 1,1-diphenylpropyl | trans-4-(methylamino)cyclohexylamine | 595.34 |
| 11 | 3-methyl-1H-pyrazol-1-yl | 1,1-diphenylpropyl | trans-4-(methylamino)cyclohexylamine | 608.33 |
| 12 | 1H-pyrazol-1-yl | 1,1-diphenylpropyl | trans-4-(methylamino)cyclohexylamine | 594.37 |
| 13 | 5-methyl-2H-tetrazol-2-yl | 1,1-diphenylpropyl | N-methyl-2-(piperidin-1-yl)ethanamine | 624.22 |
| 14 | 5-methyl-2H-tetrazol-2-yl | 1,1-diphenylpropyl | N-methyl-2-(1H-imidazol-4-yl)ethanamine | 607.19 |

TABLE 4-continued
| Ex. | R¹ | R² | R³ | MH+ |
|---|---|---|---|---|
| 15 | 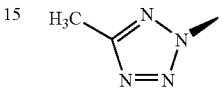 | 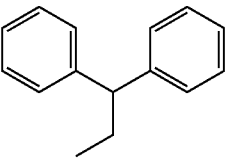 | 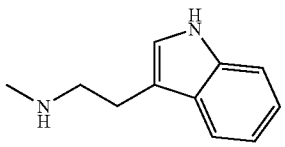 | 656.37 |
| 16 | 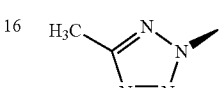 | 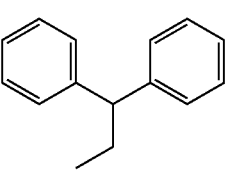 | 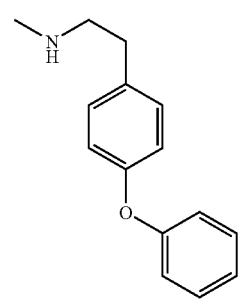 | 709.41 |
| 17 | 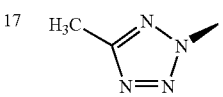 | 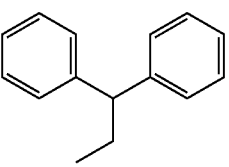 | 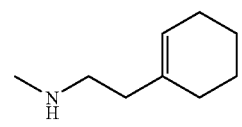 | 621.40 |
| 18 | 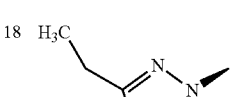 | 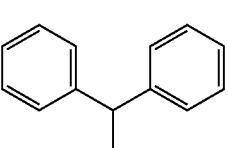 | 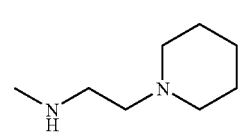 | 638.22 |
| 19 | 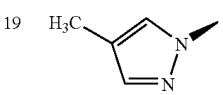 | H | 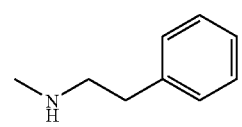 | 435.19 |
| 20 | 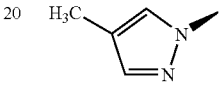 | H | 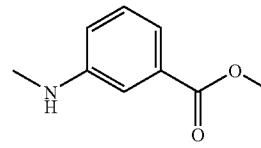 | 479.23 |
| 21 | 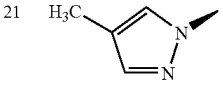 | H | 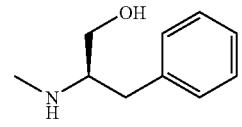 | 465.27 |
| 22 | 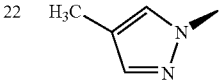 | H | 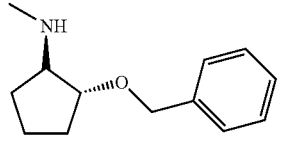 | 505.26 |
| 23 | 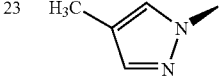 | H | 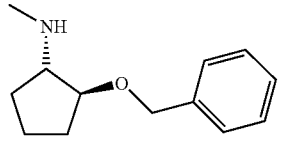 | 505.27 |

TABLE 4-continued
| Ex. | R¹ | R² | R³ | MH+ |
|---|---|---|---|---|
| 24 | 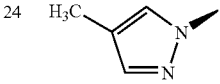 | H | 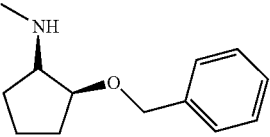 | 505.28 |
| 25 | 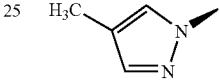 | H | 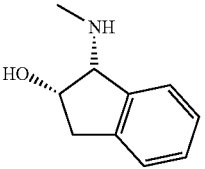 | 463.25 |
| 26 | 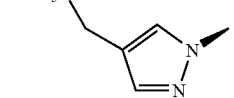 | H | 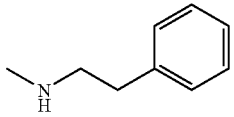 | 449.22 |
| 27 | 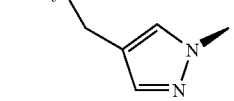 | H | 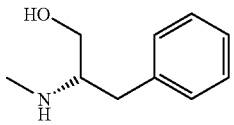 | 479.25 |
| 28 | 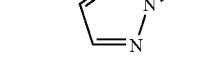 | H | 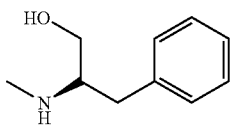 | 451.25 |
| 29 | 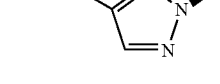 | H | 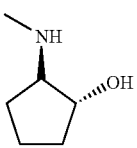 | 415.23 |
| 30 | 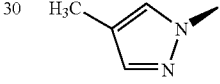 | H | 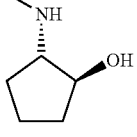 | 415.22 |
| 31 | 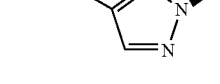 | 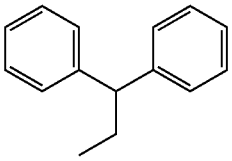 | 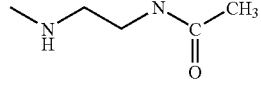 | 596.33 |
| 32 | 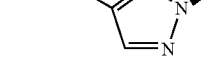 | 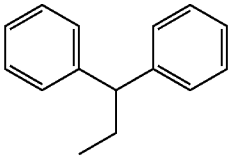 | 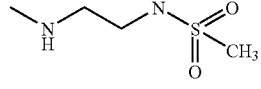 | 632.33 |
| 33 | 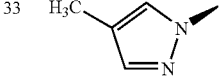 | H | Cl | 350.13 |

TABLE 4-continued
| Ex. | R¹ | R² | R³ | MH+ |
|---|---|---|---|---|
| 34 | 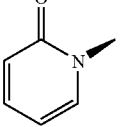 | H | Cl | 363 |
| 35 | 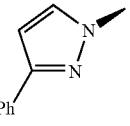 | H | Cl | 412 |
| 36 | 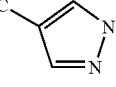 | H | 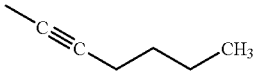 | 396.23 |
| 37 | 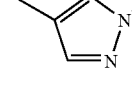 | H | 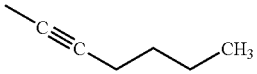 | 410.27 |
| 38 | 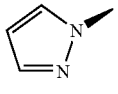 | H | 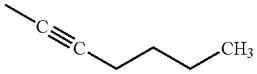 | 382.23 |
| 39 | 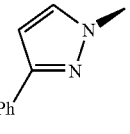 | H | 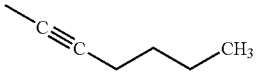 | 458 |
| 40 | 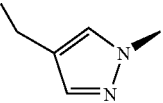 | H |  | 412.26 |
| 41 | 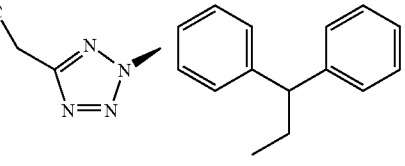 | 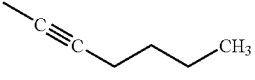 | 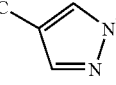 | 592.28 |
| 42 | 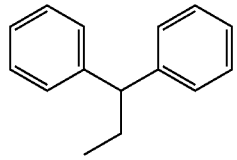 | 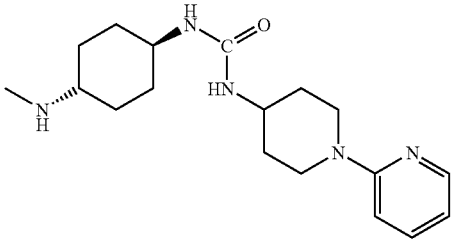 | 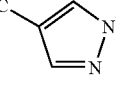 | 811.5 |
| 43 | 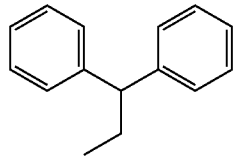 | 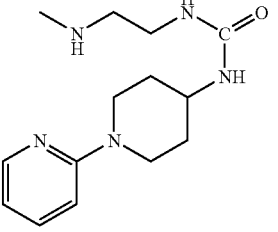 | | 757 |

TABLE 4-continued

| Ex. | R¹ | R² | R³ | MH+ |
|---|---|---|---|---|
| 44 | 5-methyl-2H-tetrazol-2-yl (CH₃) | 1,1-diphenylpropyl | N-(1-(pyridin-2-yl)piperidin-4-yl)-N'-((3S)-1-methylpyrrolidin-3-yl)urea | 785.59 |
| 45 | 5-ethyl-2H-tetrazol-2-yl | 1,1-diphenylpropyl | N-(1-(pyridin-2-yl)piperidin-4-yl)-N'-((3S)-1-methylpyrrolidin-3-yl)urea | 799.59 |
| 46 | (4-hydroxymethyl)-1H-pyrazol-1-yl | 1,1-diphenylpropyl | N-methyl-2-(piperidin-1-yl)ethylamine | 638.5 |
| 47 | (4-hydroxymethyl)-1H-pyrazol-1-yl | 1,1-diphenylpropyl | N-methyl-2-(1-ethyl-1H-imidazol-4-yl)ethylamine | 649.46 |
| 48 | 5-ethyl-2H-tetrazol-2-yl | 1,1-diphenylpropyl | (3S)-3-amino-1-methylpyrrolidine | 596.42 |
| 49 | 4-ethyl-1H-pyrazol-1-yl (H₃C) | (2S)-2-benzyl-3-hydroxypropyl | N-methyl-2-phenylethylamine | 583.4 |

TABLE 4-continued

| Ex. | R¹ | R² | R³ | MH+ |
|---|---|---|---|---|
| 50 | H₃C-ethyl-N-methylpyrazole | (S)-2-methyl-3-phenylpropan-1-ol | N-methyl-2-(1-ethylimidazol-4-yl)ethylamine | 601.4 |
| 51 | H₃C-ethyl-N-methylpyrazole | (S)-2-methyl-3-phenylpropan-1-ol | (3R)-1-methylpyrrolidin-3-amine | 548.4 |
| 52 | H₃C-ethyl-N-methylpyrazole | (S)-2-methyl-3-phenylpropan-1-ol | trans-N-methylcyclohexane-1,4-diamine | 576.4 |
| 53 | H₃C-ethyl-N-methylpyrazole | (S)-2-methyl-3-phenylpropan-1-ol | (S)-2-(methylamino)-3-phenylpropan-1-ol | 613.4 |
| 54 | H₃C-ethyl-N-methylpyrazole | 3-phenylpropyl | N-methyl-2-(1-ethylimidazol-4-yl)ethylamine | 571.4 |
| 55 | H₃C-ethyl-N-methylpyrazole | 3-phenylpropyl | (3R)-1-methylpyrrolidin-3-amine | 518.3 |
| 56 | H₃C-ethyl-N-methylpyrazole | 3-phenylpropyl | trans-N-methylcyclohexane-1,4-diamine | 546.4 |

TABLE 4-continued

| Ex. | R¹ | R² | R³ | MH+ |
|---|---|---|---|---|
| 57 | 4-ethyl-1-methyl-pyrazole | 3-phenylpropyl | (S)-2-(methylamino)-3-phenylpropan-1-ol | 583.4 |
| 58 | 4-ethyl-1-methyl-pyrazole | 2-methylbutyl | 2-(1-ethyl-1H-imidazol-4-yl)-N-methylethanamine | 537.4 |
| 59 | 4-ethyl-1-methyl-pyrazole | 2-methylbutyl | (3)-1-methylpyrrolidin-3-amine | 484.4 |
| 60 | 4-ethyl-1-methyl-pyrazole | 2-methylbutyl | N-methyl-cyclohexane-1,4-diamine | 512.4 |
| 61 | 4-ethyl-1-methyl-pyrazole | 2-methylbutyl | (S)-2-(methylamino)-3-phenylpropan-1-ol | 549.4 |
| 62 | 4-(hydroxymethyl)-1-methyl-pyrazole | 1,1-diphenylpropyl | methyl acetate | 536.4 |
| 63 | 4-(hydroxymethyl)-1-methyl-pyrazole | 1,1-diphenylpropyl | N-(3-aminopropyl)acetamide | 306.84 (MH+/2) |
| 64 | 4-(hydroxymethyl)-1-methyl-pyrazole | 1,1-diphenylpropyl | (S)-N-(pyrrolidin-3-yl)acetamide | 624.42 |

TABLE 4-continued

| Ex. | R¹ | R² | R³ | MH+ |
|---|---|---|---|---|
| 65 | hydroxymethyl-pyrazolyl | 1,1-diphenylpropyl | acetamido-ethyl-urea-piperidinyl-pyridinyl | 401.32 (MH+/2) |
| 66 | hydroxymethyl-pyrazolyl | 1,1-diphenylpropyl | acetamido-ethyl-urea-phenethyl | 745.55 |

Example 1

(1R,2S,3R,5S)-3-[2-(4-Amino-cyclohexylamino)-6-(2,2-diphenyl-ethylamino)-purin-9-yl]-5-(4-methyl-pyrazol-1-yl)-cyclopentane-1,2-diol trifluoroacetate (1R,2S,3R,1S)-3-[2-Chloro-6-(2,2-diphenyl-ethylamino)-purin-9-yl]-5-(4-methyl-pyrazol-1-yl)-cyclopentane-1,2-diol (Intermediate BA1) (0.25 g, 0.47 mmol) and trans-1,4-diaminocyclohexane (0.27 g, 2.36 mmol) are placed in a flask with dry DMSO (2 mL). The reaction mixture is stirred at 120° C. The reaction is shown to be complete by LCMS after 48 hours. The reaction mixture is allowed to cool and the title compound is obtained after purification by reverse phase column chromatography (Isolute™ C18, 0-100% acetonitrile in water—0.1% TFA). MS (ES+) m/e 608 (MH+).

Examples 2-12

These compounds namely,
(1R,2S,3R,5S)-3-[6-(2,2-Diphenyl-ethylamino)-2-((S)-1-hydroxymethyl-2-phenyl-ethylamino)-purin-9-yl]-5-(4-methyl-pyrazol-1-yl)-cyclopentane-1,2-diol (Example 2);
(1R,2S,3R,5S)-3-[6-(2,2-Diphenyl-ethylamino)-2-(2-piperidin-1-yl-ethylamino)-purin-9-yl]-5-(4-methyl-pyrazol-1-yl)-cyclopentane-1,2-diol (Example 3);
(1R,2S,3R,5S)-3-{6-(2,2-Diphenyl-ethylamino)-2-[2-(3H-imidazol-4-yl)-ethylamino]-purin-9-yl}-5-(4-methyl-pyrazol-1-yl)-cyclopentane-1,2-diol (Example 4);
(1R,2S,3R,5S)-3-[6-(2,2-Diphenyl-ethylamino)-2-phenethylamino-purin-9-yl]-5-(4-methyl-pyrazol-1-yl)-cyclopentane-1,2-diol (Example 5);
(1R,2S,3R,5S)-3-[2-(4-Amino-cyclohexylamino)-6-(2,2-diphenyl-ethylamino)-purin-9-yl]-5-(5-methyl-tetrazol-2-yl)-cyclopentane-1,2-diol (Example 6);
(1R,2S,3R,5S)-3-[6-(2,2-Diphenyl-ethylamino)-2-((R)-pyrrolidin-3-ylamino)-purin-9-yl]-5-(5-methyl-tetrazol-2-yl)-cyclopentane-1,2-diol trifluoroacetate (Example 7);
(1R,2S,3R,5S)-3-{6-(2,2-Diphenyl-ethylamino)-2-[2-(1-isopropyl-1H-imidazol-4-yl)-ethylamino]-purin-9-yl}-5-(5-methyl-tetrazol-2-yl)-cyclopentane-1,2-diol trifluoroacetate (Example 8);
(1R,2S,3R,5S)-3-[6-(2,2-Diphenyl-ethylamino)-2-((S)-pyrrolidin-3-ylamino)-purin-9-yl]-5-(5-methyl-tetrazol-2-yl)-cyclopentane-1,2-diol trifluoroacetate (Example 9);
(1R,2S,3R,5S)-3-[2-(4-Amino-cyclohexylamino)-6-(2,2-diphenyl-ethylamino)-purin-9-yl]-5-[1,2,3]triazol-1-yl-cyclopentane-1,2-diol (Example 10);
(1R,2S,3R,5S)-3-[2-(4-Amino-cyclohexylamino)-6-(2,2-diphenyl-ethylamino)-purin-9-yl]-5-(3-methyl-pyrazol-1-yl)-cyclopentane-1,2-diol (Example 11);
(1R,2S,3R,1S)-3-[2-(4-Amino-cyclohexylamino)-6-(2,2-diphenyl-ethylamino)-purin-9-yl]-5-pyrazol-1-yl-cyclopentane-1,2-diol (Example 12);
(1R,2S,3R,5S)-3-[6-(2,2-Diphenyl-ethylamino)-2-(2-piperidin-1-yl-ethylamino)-purin-9-yl]-5-(5-methyl-tetrazol-2-yl)-cyclopentane-1,2-diol trifluoroacetate (Example 13);
(1R,2S,3R,5S)-3-{6-(2,2-Diphenyl-ethylamino)-2-[2-(1H-imidazol-4-yl)-ethylamino]-purin-9-yl}-5-(5-methyl-tetrazol-2-yl)-cyclopentane-1,2-diol trifluoroacetate (Example 14);
(1R,2S,3R,5S)-3-[6-(2,2-Diphenyl-ethylamino)-2-[2-(1H-indol-3-yl)-ethylamino]-purin-9-yl]-5-(5-methyl-tetrazol-2-yl)-cyclopentane-1,2-diol trifluoroacetate (Example 15);
(1R,2S,3R,1S)-3-{6-(2,2-Diphenyl-ethylamino)-2-[2-(4-phenoxy-phenyl)-ethylamino]-purin-9-yl}-5-(5-methyl-tetrazol-2-yl)-cyclopentane-1,2-diol (Example 16);
(1R,2S,3R,5S)-3-[2-(2-Cyclohex-1-enyl-ethylamino)-6-(2,2-diphenyl-ethylamino)-purin-9-yl]-S-(5-methyl-tetrazol-2-yl)-cyclopentane-1,2-diol (Example 17);
(1R,2S,3R,5S)-3-[6-(2,2-Diphenyl-ethylamino)-2-(2-piperidin-1-yl-ethylamino)-purin-9-yl]-5-(5-ethyl-tetrazol-2-yl)-cyclopentane-1,2-diol trifluoroacetate (Example 18);
are prepared from intermediates shown in Table 2 using an analogous procedure to (1R,2S,3R,5S)-3-[2-(4-amino-cyclohexylamino)-6-(2,2-diphenyl-ethylamino)-purin-9-yl]-5-(4- methyl-pyrazol-1-yl)-cyclopentane-1,2-diol trifluoroacetate (Example 1) by replacing the trans-1,4-diaminocyclohexane with the appropriate amine.

Examples 19

(1R,2S,3R,5S)-3-(6-Amino-2-phenethylamino-purin-9-yl)-5-(4-methyl-pyrazol-1-yl)-cyclopentane-1, 2-diol trifluoroacetate (1R,2S,3R,5S)-3-(6-{[Bis-(4-methoxy-phenyl)-methyl]-amino}-2-chloro-purin-9-yl)-5-(4-methyl-pyrazol-1-yl)-cyclopentane-1,2-diol (Intermediate BB1) (0.04 g, 69.5 µmol) and phenethylamine (0.042 g, 350 µmol) are placed in a 0.5-2.5 mL microwave vial. Dichlorobenzene (0.5 mL) is added and the reaction mixture is heated to 240° C. using microwave radiation. The reaction is shown to be complete by LCMS after 1 hour. The solvent is removed in vacuo and the title compound is obtained after purification by reverse phase column chromatography (Isolute™ C18, 0-100% acetonitrile in water—0.1% TFA). $^1$H nmr (MeOD, 400 MHz); 8.20 (s, 1H), 7.50 (s, 1H), 7.30-7.15 (m, 6H), 4.85 (m, 1H), 4.70 (m, 1H), 4.65 (m, 1H), 4.35 (m, 1H), 3.75 (m, 2H), 2.95 (t, 2H), 2.80 (m, 1H), 2.70 (m, 1H), 2.05 (s, 3H), MS (ES+) m/e 435 (MH$^+$).

Examples 20-28

These compounds namely,
3-{6-Amino-9-[(1R,2S,3R,4S)-2,3-dihydroxy-4-(4-methyl-pyrazol-1-yl)-cyclopentyl]-9H-purin-2-ylamino}-benzoic acid ethyl ester (Example 20);
(1R,2S,3R,5S)-3-[6-Amino-2-((S)-1-hydroxymethyl-2-phenyl-ethylamino)-purin-9-yl]-5-(4-methyl-pyrazol-1-yl)-cyclopentane-1,2-diol (Example 21);
(1R,2S,3R,5S)-3-[6-Amino-2-((1R,2R)-2-benzyloxy-cyclopentylamino)-purin-9-yl]-5-(4-methyl-pyrazol-1-yl)-cyclopentane-1,2-diol (Example 22);
(1R,2S,3R,5S)-3-[6-Amino-2-((1S,2S)-2-benzyloxy-cyclopentylamino)-purin-9-yl]-5-(4-methyl-pyrazol-1-yl)-cyclopentane-1,2-diol (Example 23);
(1R,2S,3R,5S)-3-[6-Amino-2-((1R,2S)-2-benzyloxy-cyclopentylamino)-purin-9-yl]-5-(4-methyl-pyrazol-1-yl)-cyclopentane-1,2-diol (Example 24);
(1R,2S,3R,5S)-3-[6-Amino-2-((1R,2S)-2-hydroxy-indan-1-ylamino)-purin-9-yl]-5-(4-methyl-pyrazol-1-yl)-cyclopentane-1,2-diol (Example 25);
(1R,2S,3R,5S)-3-(6-Amino-2-phenethylamino-purin-9-yl)-5-(4-ethyl-pyrazol-1-yl)-cyclopentane-1,2-diol (Example 26);
(1R,2S,3R,5S)-3-[6-Amino-2-((S)-1-hydroxymethyl-2-phenyl-ethylamino)-purin-9-yl]-5-(4-ethyl-pyrazol-1-yl)-cyclopentane-1,2-diol DB (Example 27);
(1R,2S,3R,5S)-3-[6-Amino-2-((S)-1-hydroxymethyl-2-phenyl-ethylamino)-purin-9-yl]-5-pyrazol-1-yl-cyclopentane-1,2-diol (Example 28);
are prepared from intermediates shown in Table 2 using an analogous procedure to (1R,2S,3R,5S)-3-(6-amino-2-phenethylamino-purin-9-yl)-5-(4-methyl-pyrazol-1-yl)-cyclopentane-1,2-diol trifluoroacetate (Example 13) by replacing the phenethylamine with the appropriate amine.

Example 29

(1R,2S,3R,5S)-3-[6-Amino-2-((1R,2R)-2-hydroxy-cyclopentylamino)-purin-9-yl]-5-(4-methyl-pyrazol-1-yl)-cyclopentane-1,2-diol trifluoroacetate (1R,2S,3R,5S)-3-[6-Amino-2-((1R,2R)-2-benzyloxy-cyclopentylamino)-purin-9-yl]-5-(4-methyl-pyrazol-1-yl)-cyclopentane-1,2-diol (Example 22) (0.060 g, 0.10 mmol) is dissolved in methanol (2 ml) and the compound is deprotected by adding a catalytic amount of 20% palladium hydroxide on charcoal and placing the solution under an atmosphere of H$_2$. The reaction is shown to be complete by LCMS after 18 hours. The catalyst is filtered off and the solvent is removed in vacuo to give the title compound. MS (ES+) m/e 415 (MH$^+$).

Example 30

(1R,2S,3R,5S)-3-[6-Amino-2-((1S,2S)-2-hydroxy-cyclopentylamino)-purin-9-yl]-5-(4-methyl-pyrazol-1-yl)-cyclopentane-1,2-diol The title compound is prepared from (1R,2S,3R,5S)-3-[6-Amino-2-((1S,2S)-2-benzyloxy-cyclopentylamino)-purin-9-yl]-5-(4-methyl-pyrazol-1-yl)-cyclopentane-1,2-diol (Example 23) using a procedure analogous to that of (1R,2S,3R,5S)-3-[6-Amino-2-((1R,2R)-2-hydroxy-cyclopentylamino)-purin-9-yl]-5-(4-methyl-pyrazol-1-yl)-cyclopentane-1,2-diol trifluoroacetate (Example 29). MS (ES+) m/e 415 (MH$^+$).

Example 31

N-{2-[9-[(1R,2S,3R,4S)-2,3-Dihydroxy-4-(4-methyl-pyrazol-1-yl)-cyclopentyl]-6-(2,2-diphenyl-ethylamino)-9H-purin-2-ylamino]-ethyl}-acetamide trifluoroacetate (1R,2S,3R,5S)-3-[2-(2-Amino-ethylamino)-6-(2,2-diphenyl-ethylamino)-purin-9-yl]-5-(4-methyl-pyrazol-1-yl)-cyclopentane-1,2-diol (0.020 g, 36 µmol) is dissolved in dry THF (1 mL). Diisopropylethylamine (0.023 g, 180 µmol) is added followed by acetyl chloride (0.002 g, 36 µmol). The reaction mixture is stirred at room temperature. The reaction is shown to be complete by LCMS after 1 hour. The solvent is removed in vacuo and the title compound is obtained after purification by reverse phase column chromatography (Isolute™ C18, 0-100% acetonitrile in water—0.1% TFA). MS (ES+) m/e 596 (MH$^+$).

Example 32

N-{2-[9-[(1R,2S,3R,4S)-2,3-Dihydroxy-4-(4-methyl-pyrazol-1-yl)-cyclopentyl]-6-(2,2-diphenyl-ethylamino)-9H-purin-2-ylamino]-ethyl}-methane-sulfonamide The title compound is prepared from (1R,2S,3R,5S)-3-[2-(2-Amino-ethylamino)-6-(2,2-diphenyl-ethylamino)-purin-9-yl]-5-(4-methyl-pyrazol-1-yl)-cyclopentane-1,2-diol and mesyl chloride using a procedure analogous to that of Example 31. MS (ES+) m/e 632 (MH$^+$).

Example 33

(1R,2S,3R,5S)-3-(6-Amino-2-chloro-purin-9-yl)-5-(4-methyl-pyrazol-1-yl)-cyclopentane-1,2-diol trifluoroacetate (1R,2S,3R,5S)-3-(6-{[Bis-(4-methoxy-phenyl)-methyl]-amino}-2-chloro-purin-9-yl)-5-(4-methyl-pyrazol-1-yl)-cyclopentane-1,2-diol (Intermediate BB1) (0.020 g, 35 µmol) is dissolved in TFA (200 µL). The reaction mixture is stirred at room temperature. The reaction is shown to be complete by LCMS after 2 hours. The solvent is removed in vacuo and the title compound is obtained after purification by reverse phase column chromatography (Isolute™ C18, 0-100% acetonitrile in water—0.1% TFA). $^1$H nmr (MeOD, 400 MHz); 8.50 (s, 1H), 7.85 (s, 1H), 7.55 (s, 1H), 4.95 (m, 1H), 4.70 (m, 1H), 4.65 (m, 1H), 4.30 (m, 1H), 2.95 (m, 1H), 2.65 (m, 1H), 2.15 (s, 3H), MS (ES+) m/e 350 (MH$^+$).

Examples 34 and 35

These compounds, namely,
1-[(1S,2R,3S,4R)-4-(6-Amino-2-chloro-purin-9-yl)-2,3-dihydroxy-cyclopentyl]-1H-pyridin-2-one (Example 34); and
(1R,2S,3R,5S)-3-(6-Amino-2-chloro-purin-9-yl)-5-(3-phenyl-pyrazol-1-yl)-cyclopentane-1,2-diol (Example 35),
are prepared from Intermediates BB1, BB3-BB5 (Table 2) using an analogous procedure to (1R,2S,3R,5S)-3-(6-amino-2-chloro-purin-9-yl)-5-(4-methyl-pyrazol-1-yl)-cyclopentane-1,2-diol trifluoroacetate (Example 33).

Example 36

(1R,2S,3R,5S)-3-(6-Amino-2-hex-1-ynyl-purin-9-yl)-5-(4-methyl-pyrazol-1-yl)-cyclopentane-1,2-diol trifluoroacetate a) (1R,2S,3R,5S)-3-(6-{[Bis-(4-methoxy-phenyl)-methyl]-amino}-2-hex-1-ynyl-purin-9-yl)-5-(4-methyl-pyrazol-1-yl)-cyclopentane-1,2-diol (1R,2S,3R,5S)-3-(6-{[Bis-(4-methoxy-phenyl)-methyl]-amino}-2-chloro-purin-9-yl)-5-(4-methyl-pyrazol-1-yl)-cyclopentane-1,2-diol (Intermediate BB1) (0.1 g, 0.17 mmol), 1-hexyne (0.42 g, 1.70 mmol), copper (I) iodide (0.008 g, 43 µmol), dichlorobis(triphenylphosphine)palladium(II) (0.031 g, 43 µmol), triphenylphosphine (0.023 g, 86 µmol), diethylamine (1 mL) and DMF (0.5 mL) are placed in a 0.5-2.5 mL microwave vial. The reaction mixture is heated to 120° C. using microwave radiation. The reaction is shown to be complete by LCMS after 1 hour. The reaction mixture is partitioned between dichloromethane (20 mL) and 2M HCl (20 mL). The organic layer is washed with sat. NaHCO$_3$ (20 mL), water (20 ml) and brine (20 ml), dried over MgSO$_4$, filtered and the solvent is removed in vacuo. The title compound is obtained after purification by flash column chromatography (silica, dichloromethane/methanol 25:1). MS (ES+) m/e 622 (MH$^+$).

b) (1R,2S,3R,5S)-3-(6-Amino-2-hex-1-ynyl-purin-9-yl)-5-(4-methyl-pyrazol-1-yl)-cyclopentane-1,2-diol trifluoroacetate The title compound is prepared from (1R,2S,3R,5S)-3-(6-{[Bis-(4-methoxy-phenyl)-methyl]-amino}-2-hex-1-ynyl-purin-9-yl)-5-(4-methyl-pyrazol-1-yl)-cyclopentane-1,2-diol (step 1) using a procedure analogous to that of Example 44. $^1$H nmr (MeOD, 400 MHz); 8.60 (s, 1H), 7.70 (s, 1H), 7.40 (s, 1H), 5.00 (m, 1H), 4.70 (m, 2H), 4.25 (m, 1H), 2.95 (m, 1H), 2.60 (m, 1H), 2.45 (t, 2H), 2.15 (s, 3H), 1.65 (m, 2H), 1.55 (m, 2H), 1.00 (t, 3H), MS (ES+) m/e 396 (MH$^+$).

Examples 37-40

These compounds, namely,
(1R,2S,3R,5S)-3-(6-Amino-2-hex-1-ynyl-purin-9-yl)-5-(4-ethyl-pyrazol-1-yl)-cyclopentane-1,2-diol (Example 37);
(1R,2S,3R,5S)-3-(6-Amino-2-hex-1-ynyl-purin-9-yl)-5-pyrazol-1-yl-cyclopentane-1,2-diol (Example 38);
(1R,2S,3R,5S)-3-(6-Amino-2-hex-1-ynyl-purin-9-yl)-5-(3-phenyl-pyrazol-1-yl)-cyclopentane-1,2-diol (Example 39);
(1R,2S,3R,5S)-3-(6-Amino-2-hex-1-ynyl-purin-9-yl)-5-(4-hydroxymethyl-pyrazol-1-yl)-cyclopentane-1,2-diol (Example 40);
are prepared from Intermediates BB1, BB2, BB4-BB7 (Table 2) using an analogous procedure to ((1R,2S,3R,5S)-3-(6-Amino-2-hex-1-ynyl-purin-9-yl)-5-(4-methyl-pyrazol-1-yl)-cyclopentane-1,2-diol trifluoroacetate (Example 36).

Example 41

(1R,2S,3R,15S)-3-[6-(2,2-Diphenyl-ethylamino)-2-hex-1-ynyl-purin-9-yl]-5-(5-ethyl-tetrazol-2-yl)-cyclopentane-1,2-diol This compound is prepared from (1R,2S,3R,5S)-3-[2-Chloro-6-(2,2-diphenyl-ethylamino)-purin-9-yl]-5-(5-ethyl-tetrazol-2-yl)-cyclopentane-1,2-diol (Intermediate BA6) using a procedure analogous to that (1R,2S,3R,5S)-3-(6-{[Bis-(4-methoxy-phenyl)-methyl]-amino}-2-hex-1-ynyl-purin-9-yl)-5-(4-methyl-pyrazol-1-yl)-cyclopentane-1,2-diol (Example 36, Step 1).

Example 42

1-{4-[9-[(1R,2S,3R,4S)-2,3-Dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea Trifluoroacetate (1R,2S,3R,5S)-3-[2-(4-Amino-cyclohexylamino)-6-(2,2-diphenyl-ethylamino)-purin-9-yl]-5-(4-methyl-pyrazol-1-yl)-cyclopentane-1,2-diol trifluoroacetate (Example 1) (0.020 g, 0.028 mmol) is dissolved in DCM (2 ml). Toluene (2 ml) and iPrOH (1 ml) are added followed by N-[1-(2-pyridinyl)-4-piperidinyl]-1H-imidazole-1-carboxamide (which is prepared using the method described in international patent application WO 01/94368) (0.03 mmol of a 0.1 M solution in DCM). The dichloromethane is removed by vacuo and the reaction mixture is stirred at room temperature. The reaction is shown to be complete by LCMS after 48 hours. The solvent is removed in vacuo. The title compound is obtained by flash column chromatography (Isolute™ C18, 0-100% acetonitrile in water—0.1% TFA). MS (ES+) m/e 811.5 (MH$^+$).

Example 43

1-{2-[9-[(1R,2S,3R,4S)-2,3-Dihydroxy-4-(4-methyl-pyrazol-1-yl)-cyclopentyl]-6-(2,2-diphenyl-ethylamino)-9H-purin-2-ylamino]-ethyl}-3-(3,4,5,6-tetrahydro-2H-[1,2']bipyridinyl-4-yl)-urea Trifluoroacetate This compound is prepared from (1R,2S,3R,5S)-3-[2-(2-Amino-ethylamino)-6-(2,2-diphenyl-ethylamino)-purin-9-yl]-5-(4-methyl-pyrazol-1-yl)-cyclopentane-1,2-diol trifluoroacetate using procedures analogous to Example 43. MS (ES+) m/e 757.4 (MH+).

Example 44

1-{(R)-1-[9-[(1R,2S,3R,4S)-2,3-Dihydroxy-4-(5-methyl-tetrazol-2-yl)-cyclopentyl]-6-(2,2-diphenyl-ethylamino)-9H-purin-2-yl]-pyrrolidin-3-yl}-3-(3,4,5,6-tetrahydro-2H-[1,2']bipyridinyl-4-yl)-urea This compound is prepared from (1R,2S,3R,5S)-3-[6-(2,2-Diphenyl-ethylamino)-2-((R)-pyrrolidin-3-ylamino)-purin-9-yl]-5-(5-methyl-tetrazol-2-yl)-cyclopentane-1,2-diol trifluoroacetate (Example 7) using procedures analogous to Example 42.

Example 45

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(3,4,5,6-tetrahydro-2H-[1,2']bipyridinyl-4-yl)-urea This compound is prepared from (1R,2S,3R,5S)-3-[2-((R)-3-Amino-pyrrolidin-1-yl)-6-(2,2-diphenyl-ethylamino)-purin-9-yl]-5-(5-ethyl-tetrazol-2-yl)-cyclopentane-1,2-diol (Example 49 described later) using procedures analogous to Example 42.

Example 46

(1R,2S,3R,5S)-3-[6-(2,2-Diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (1R,2S,3R,1S)-3-[2-Chloro-6-(2,2-diphenyl-ethylamino)-purin-9-yl]-5-(4-hydroxymethyl-pyrazol-1-yl)-cyclopentane-1,2-diol (Intermediate BA7) (0.020 g, 37 μmol), 1-(2-amino-ethyl)piperidine (0.047 g, 370 μmol) and sodium iodide (0.0055 g, 37 μmol) are placed in a 0.5-2.5 mL microwave vial. Acetonitrile (0.25 mL) and NMP (0.25 mL) are added and the reaction mixture is heated to 200° C. for 1 hour using microwave radiation. The title compound is obtained after purification by reverse phase column chromatography (Isolute™ C18, 0-100% acetonitrile in water—0.1% TFA). MS (ES+) m/e 638 (MH$^+$).

Examples 47 to 61

These compounds, namely,
(1R,2S,3R,5S)-3-{6-(2,2-Diphenyl-ethylamino)-2-[2-(1-ethyl-1H-imidazol-4-yl)-ethylamino]-purin-9-yl}-5-(4-hydroxymethyl-pyrazol-1-yl)-cyclopentane-1,2-diol (Example 47);
(1R,2S,3R,5S)-3-[2-((R)-3-Amino-pyrrolidin-1-yl)-6-(2,2-diphenyl-ethylamino)-purin-9-yl]-5-(5-ethyl-tetrazol-2-yl)-cyclopentane-1,2-diol (Example 48);
(1S,2R,3S,5R)-3-(4-Ethyl-pyrazol-1-yl)-5-[6-((S)-1-hydroxymethyl-2-phenyl-ethylamino)-2-phenethylamino-purin-9-yl]-cyclopentane-1,2-diol (Example 49);
(1R,2S,3R,5S)-3-[2-[2-(1-Ethyl-1H-imidazol-4-yl)-ethylamino]-6-((S)-1-hydroxymethyl-2-phenyl-ethylamino)-purin-9-yl]-5-(4-ethyl-pyrazol-1-yl)-cyclopentane-1,2-diol (Example 50);
(1S,2R,3S,5R)-3-(4-Ethyl-pyrazol-1-yl)-5-[6-((S)-1-hydroxymethyl-2-phenyl-ethylamino)-2-((R)-pyrrolidin-3-ylamino)-purin-9-yl]-cyclopentane-1,2-diol (Example 51);
(1R,2S,3R,5S)-3-[2-(4-Amino-cyclohexylamino)-6-((S)-1-hydroxymethyl-2-phenyl-ethylamino)-purin-9-yl]-5-(4-ethyl-pyrazol-1-yl)-cyclopentane-1,2-diol (Example 52);
(1R,2S,3R,5S)-3-[2,6-Bis-((S)-1-hydroxymethyl-2-phenyl-ethylamino)-purin-9-yl]-5-(4-ethyl-pyrazol-1-yl)-cyclopentane-1,2-diol (Example 53);
(1R,2S,3R,5S)-3-{2-[2-(1-Ethyl-1H-imidazol-4-yl)-ethylamino]-6-phenethylamino-purin-9-yl}-5-(4-ethyl-pyrazol-1-yl)-cyclopentane-1,2-diol (Example 54);
(1S,2R,3S,5R)-3-(4-Ethyl-pyrazol-1-yl)-5-[6-phenethylamino-2-((R)-pyrrolidin-3-ylamino)-purin-9-yl]-cyclopentane-1,2-diol (Example 55);
(1R,2S,3R,5S)-3-[2-(4-Amino-cyclohexylamino)-6-phenethylamino-purin-9-yl]-5-(4-ethyl-pyrazol-1-yl)-cyclopentane-1,2-diol (Example 56);
(1S,2R,3S,5R)-3-(4-Ethyl-pyrazol-1-yl)-5-[2-((S)-1-hydroxymethyl-2-phenyl-ethylamino)-6-phenethylamino-purin-9-yl]-cyclopentane-1,2-diol (Example 57);
(1R,2S,3R,5S)-3-[2-[2-(1-Ethyl-1H-imidazol-4-yl)-ethylamino]-6-(1-ethyl-propylamino)-purin-9-yl]-5-(4-ethyl-pyrazol-1-yl)-cyclopentane-1,2-diol (Example 58);
(1R,2S,3R,5S)-3-[6-(1-Ethyl-propylamino)-2-((R)-pyrrolidin-3-ylamino)-purin-9-yl]-5-(4-ethyl-pyrazol-1-yl)-cyclopentane-1,2-diol (Example 59);
(1R,2S,3R,5S)-3-[2-(4-Amino-cyclohexylamino)-6-(1-ethyl-propylamino)-purin-9-yl]-5-(4-ethyl-pyrazol-1-yl)-cyclopentane-1,2-diol (Example 60);
(1R,2S,3R,5S)-3-[6-(1-Ethyl-propylamino)-2-((S)-1-hydroxymethyl-2-phenyl-ethylamino)-purin-9-yl]-5-(4-ethyl-pyrazol-1yl)-cyclopentane-1,2-diol (Example 61);
are prepared from intermediates shown in Table 2 using an analogous procedure to (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) by replacing the 1-(2-aminoethyl)piperidine with the appropriate amine.

Example 62

9-[(1R,4S)-2,3-Dihydroxy-4-(4-hydroxymethyl-pyrazol-1-yl-cyclopentyl]-6-(2,2-diphenyl-ethylamino)-9H-purine-2-carboxylic Acid Methyl Ester a) 6-(2,2-Diphenyl-ethylamino)-9-[(1R,4S)-4-(4-hydroxymethyl-pyrazol-1-yl)-cyclopent-2-enyl]-9H-purine-2-carboxylic Acid Methyl Ester 6-(2,2-Diphenyl-ethylamino)-9-((1R,4S)-4-ethoxycarbonyloxy-cyclopent-2-enyl)-9H-purine-2-carboxylic acid methyl ester (4.91 g, 9.3 mmol), (1H-Pyrazol-4-yl)-methanol (1.0 g, 10.2 mmol) and Ph$_3$P (0.73 g, 2.8 mmol) are dissolved in dry, deoxygenated tetrahydrofuran under argon. Pd$_2$(dba)$_3$ (0.85 g, 0.93 mmol) is added to the reaction mixture. The reaction mixture is heated at 45° C. for 1 hour. The solvent is removed in vacuo. The title material is obtained by flash column chromatography (silica, eluent 0% MeOH to 3% MeOH in DCM) (MH$^+$ 536.42).

b) 9-[(1R,4S)-2,3-Dihydroxy-4-(4-hydroxymethyl-pyrazol-1-yl)-cyclopentyl]-6-(2,2-diphenyl-ethylamino)-9H-purine-2-carboxylic acid methyl ester 6-(2,2-Diphenyl-ethylamino)-9-[(1R,4S)-4-(4-hydroxymethyl-pyrazol-1-yl)-cyclopent-2-enyl]-9H-purine-2-carboxylic acid methyl ester (500 mg, 0.93 mmol) and 4-methyl-morpholine-4-oxide (218 mg, 1.86 mmol) are dissolved tetrahydrofuran (10 ml). OsO$_4$ (4% in H$_2$O) (1.5 ml) is added and the reaction mixture is stirred at room temperature overnight. The reaction mixture is partitioned between H₂O and EtOAc. The aqueous layers are then extracted with EtOAc. The organics are combined, dried over MgSO₄, filtered and the solvent reduced in vacuo. The title material is obtained by flash column chromatography (silica, eluent 3% to 7% MeOH in dichloromethane) (MH⁺ 570.36).

Examples 63 and 64

These compounds, namely,
9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (3-amino-propyl)-amide (Example 63); and
9-[(1R,4S)-2,3-Dihydroxy-4-(4-hydroxymethyl-pyrazol-1-yl)-cyclopentyl]-6-(2,2-diphenyl-ethylamino)-9H-purine-2-carboxylic acid (R)-pyrrolidin-3-yl amide (Example 64);
are prepared from 9-[(1R,4S)-2,3-dihydroxy-4-(4-hydroxymethyl-pyrazol-1-yl)-cyclopentyl]-6-(2,2-diphenyl-ethylamino)-9H-purine-2-carboxylic acid methyl ester (Example 62) using an analogous procedure to 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide.

Example 65

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid {2-[3-(3,4,5,6-tetrahydro-2H-[1,2']bipyridinyl-4-yl)-ureido]-ethyl}-amide This compound is prepared from 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide using an analogous procedure to Example 42.

Example 66

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid [2-(3-phenethyl-ureido)-ethyl]-amide The titled compound is prepared from 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide using an analogous procedure to Example 42 by replacing N-[1-(2-pyridinyl)-4-piperidinyl]-1H-imidazole-1-carboxamide with imidazole-1-carboxylic acid phenethyl-amide.

Further compounds of formula I

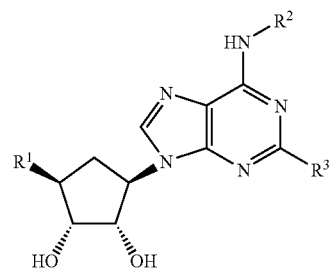

are shown in the Table 5 below. Methods for preparing such compounds are described hereinafter. The table also shows mass spectrometry, MH⁺ {ESMS}, data. The Examples are prepared as trifluoroacetate salts or in free form as indicated.

TABLE 5

| Ex. | R¹ | R² | R³ | MH+ or MH+/2* |
|---|---|---|---|---|
| 67 | 1-methyl-5-methyl-tetrazol-2-yl | 1,1-diphenyl-propan-2-yl (-CH(CH₂Ph)Ph via -CH₂CH(Ph)₂) | 1-methylpyrrolidin-3-yl-NH-S(O)₂-CH₃ | 660 |
| 68 | 1-methyl-5-(methylmethyl)-tetrazol-2-yl (5-ethyl) | 2,2-diphenyl-ethyl | 1-methylpyrrolidin-3-yl-NH-S(O)₂-CH₃ | 674 |

TABLE 5-continued

| Ex. | R¹ | R² | R³ | MH+ or MH+/2* |
|---|---|---|---|---|
| 69 | 4-ethyl-1-methylpyrazole | 3-methylpentan-3-yl (sec-pentyl) | (3S)-1-methylpyrrolidin-3-yl urea linked to 1-(pyridin-2-yl)piperidin-4-yl | 344* |
| 70 | 4-ethyl-1-methylpyrazole | 2-benzyl-3-hydroxypropyl | (3S)-1-methylpyrrolidin-3-yl urea linked to 1-(pyridin-2-yl)piperidin-4-yl | 376* |
| 71 | 4-ethyl-1-methylpyrazole | 3-phenylpropyl | (3S)-1-methylpyrrolidin-3-yl urea linked to 1-(pyridin-2-yl)piperidin-4-yl | 361* |
| 72 | 4-ethyl-1-methylpyrazole | 2-benzyl-3-hydroxypropyl | (3S)-1-methylpyrrolidin-3-yl urea linked to 1-(6-chloropyridin-2-yl)piperidin-4-yl | 393* |

TABLE 5-continued
| Ex. | R¹ | R² | R³ | MH+ or MH+/2* |
|---|---|---|---|---|
| 73 | 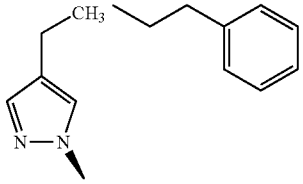 | 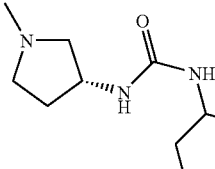 | 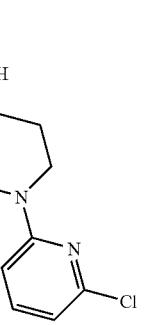 | 378* |
| 74 | 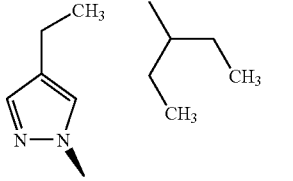 | 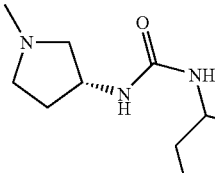 | 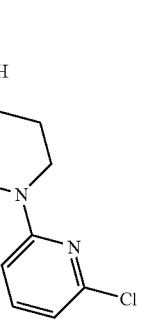 | 361* |
| 75 | 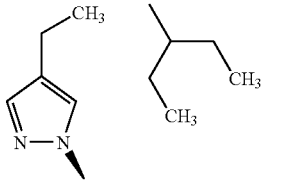 | 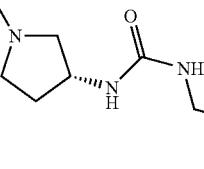 | 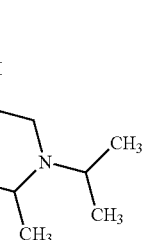 | 688 |
| 76 | 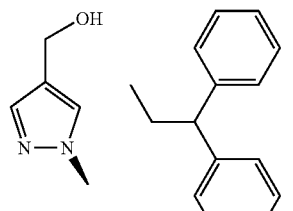 | 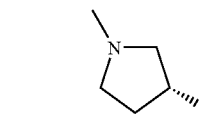 | 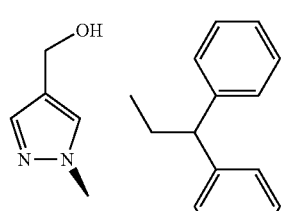 | 596 |
| 77 | 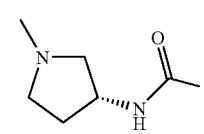 | 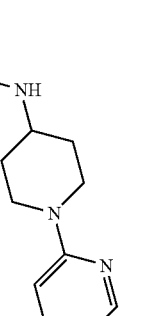 | | 400* |

TABLE 5-continued

| Ex. | R¹ | R² | R³ | MH+ or MH+/2* |
|---|---|---|---|---|
| 78 | 1-methyl-4-(hydroxymethyl)pyrazole | 1,1-diphenylpropyl | 1-benzylpiperidin-4-yl(methyl)amino | 700 |
| 79 | 1-methyl-4-(hydroxymethyl)pyrazole | 1,1-diphenylpropyl | 3-[(1-methylpyrrolidin-3-yl)ureido]-1-[5-(ethoxycarbonyl)pyridin-2-yl]piperidin-4-yl | 436* |
| 80 | 1-methyl-4-(hydroxymethyl)pyrazole | 1,1-diphenylpropyl | N-(2-acetamidoethyl)-N'-[1-(pyridin-2-yl)pyrrolidin-3-yl]urea | 786 |
| 81 | 1-methyl-4-(hydroxymethyl)pyrazole | 1,1-diphenylpropyl | N-(2-acetamidoethyl)-N'-[1-(pyridin-2-yl)pyrrolidin-3-yl]urea | 394* |

TABLE 5-continued

| Ex. | R¹ | R² | R³ | MH+ or MH+/2* |
|---|---|---|---|---|
| 82 | (1-methyl-1H-pyrazol-4-yl)methanol | 1,1-diphenylpropyl | N-(3-{[(1-(pyridin-2-yl)piperidin-4-yl)carbamoyl]amino}propyl)acetamide | 815 |
| 83 | (1-methyl-1H-pyrazol-4-yl)methanol | 1,1-diphenylpropyl | N-(trans-4-{[(1-(pyridin-2-yl)piperidin-4-yl)carbamoyl]amino}cyclohexyl)acetamide | 428* |
| 84 | (1-methyl-1H-pyrazol-4-yl)methanol | 1,1-diphenylpropyl | N-(2-methyl-2-{[(1-(pyridin-2-yl)piperidin-4-yl)carbamoyl]amino}propyl)acetamide | 829 |
| 85 | (1-methyl-1H-pyrazol-4-yl)methanol | 1,1-diphenylpropyl | N-methyl-piperidin-4-amine | 610 |

TABLE 5-continued

| Ex. | R¹ | R² | R³ | MH+ or MH+/2* |
|---|---|---|---|---|
| 86 | 1-methyl-1H-pyrazol-4-yl-methanol | 1,1-diphenylpropyl | (1-methylpyrrolidin-3-yl)-NH-C(O)-NH-piperidin-4-yl-N-(5-carboxypyridin-2-yl) | 422* |
| 87 | 1-methyl-1H-pyrazol-4-yl-methanol | 1,1-diphenylpropyl | acetamido-propyl-NH-C(O)-NH-ethyl | 682.8 |
| 88 | 1-methyl-1H-pyrazol-4-yl-methanol | 1,1-diphenylpropyl | acetamido-propyl-NH-C(O)-CH₂-N(CH₃)₂ | — |
| 89 | 1-methyl-1H-pyrazol-4-yl-methanol | 1,1-diphenylpropyl | acetamido-trans-cyclohexyl-NH-C(O)-NH-ethyl | 722.9 |

TABLE 5-continued

| Ex. | R¹ | R² | R³ | MH+ or MH+/2* |
|-----|----|----|----|--------------|
| 90 | | | | 722.9 |
| 91 | | | | — |
| 92 | | | | 696.8 |
| 93 | | | | 669.10 |

TABLE 5-continued

| Ex. | R¹ | R² | R³ | MH+ or MH+/2* |
|---|---|---|---|---|
| 94 | 1-methyl-4-(hydroxymethyl)pyrazole | 1,1-diphenylpropyl | acetamido-ethyl-NH-C(O)-NH-ethyl-(4-benzylpiperazin-1-yl) | 422* |
| 95 | 1-methyl-4-(hydroxymethyl)pyrazole | 1,1-diphenylpropyl | acetamido-ethyl-NH-C(O)-NH-(1-(pyridin-2-yl)piperidin-4-yl) | 773 |
| 96 | 1-methyl-4-(hydroxymethyl)pyrazole | 1,1-diphenylpropyl | (3S)-1-methyl-3-(dimethylamino)pyrrolidine | 624 |
| 97 | 1-methyl-4-(hydroxymethyl)pyrazole | 1,1-diphenylpropyl | benzyl 4-(1-methylpyrrolidin-3-yl)piperazine-1-carboxylate | 799 |

TABLE 5-continued

| Ex. | R¹ | R² | R³ | MH+ or MH+/2* |
|---|---|---|---|---|
| 98 | (1-methyl-1H-pyrazol-4-yl)methanol | 1,1-diphenylpropyl | 1,3-bis(1-methylpyrrolidin-3-yl)urea | 70/8 |
| 99 | 5-ethyl-2-methyl-2H-tetrazole | 1,1-diphenylpropyl | 1,3-bis(1-methylpyrrolidin-3-yl)urea | 708 |
| 100 | 5-ethyl-2-methyl-2H-tetrazole | 1,1-diphenylpropyl | N,N,1-trimethylpyrrolidin-3-amine | 624 |
| 101 | 5-ethyl-2-methyl-2H-tetrazole | 1,1-diphenylpropyl | tert-butyl (1-methylpyrrolidin-3-yl)carbamate | 696 |
| 102 | 5-ethyl-2-methyl-2H-tetrazole | 1,1-diphenylpropyl | 1-(1-methylpyrrolidin-3-yl)-3-(pyridin-4-ylmethyl)urea | 730 |
| 103 | 5-ethyl-2-methyl-2H-tetrazole | 1,1-bis(4-hydroxyphenyl)propyl | N,N,1-trimethylpyrrolidin-3-amine | 656 |

TABLE 5-continued

| Ex. | R¹ | R² | R³ | MH+ or MH+/2* |
|---|---|---|---|---|
| 104 | 5-ethyl-2-methyl-2H-tetrazole | 1,1-diphenylpropyl | (S)-1-methyl-N-(pyridin-3-yl)pyrrolidin-3-yl urea | 716 |
| 105 | 5-ethyl-2-methyl-2H-tetrazole | 1,1-diphenylpropyl | (R)-1-methyl-N-(pyridin-3-yl)pyrrolidin-3-yl urea | 716.5 |
| 106 | 5-ethyl-2-methyl-2H-tetrazole | 4,4'-(propane-1,1-diyl)diphenol | (S)-1-methylpyrrolidin-3-amine | 628.3 |
| 107 | 5-ethyl-2-methyl-2H-tetrazole | 4,4'-(propane-1,1-diyl)diphenol | (S)-1-methyl-N-(pyridin-3-yl)pyrrolidin-3-yl urea | 748.4 |
| 108 | 5-ethyl-2-methyl-2H-tetrazole | 1,1-diphenylpropyl | (S)-1-methyl-N-(pyridin-4-yl)pyrrolidin-3-yl urea | 716.4 |

TABLE 5-continued
| Ex. | R¹ | R² | R³ | MH+ or MH+/2* |
|---|---|---|---|---|
| 109 | 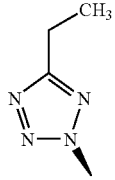 | 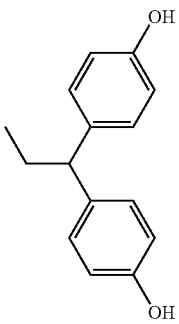 | 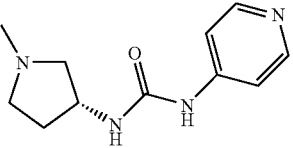 | 748.4 |
| 110 | 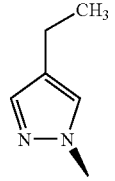 | 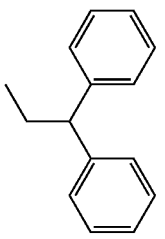 | 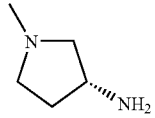 | 594.3 |
| 111 | 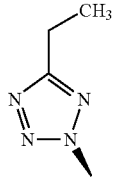 | 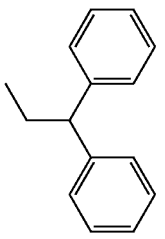 | 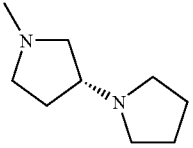 | 650.4 |
| 112 | 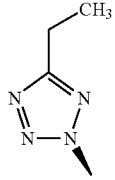 | 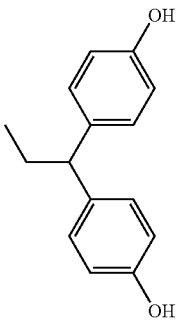 | 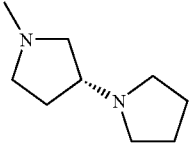 | 682.4 |
| 113 | 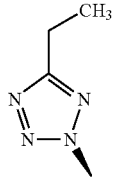 | 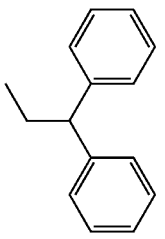 | 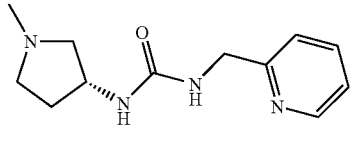 | 730.5 |

TABLE 5-continued

| Ex. | R¹ | R² | R³ | MH+ or MH+/2* |
|---|---|---|---|---|
| 114 | 5-ethyl-2-methyl-2H-tetrazole | 1,1-diphenylpropyl | (S)-1-methylpyrrolidin-3-yl urea with pyridin-3-ylmethyl | 730.5 |
| 115 | 5-ethyl-2-methyl-2H-tetrazole | 1,1-diphenylpropyl | (S)-1-methylpyrrolidin-3-yl urea with (1-methyl-1H-imidazol-4-yl)methyl | 733.5 |
| 116 | 5-ethyl-2-methyl-2H-tetrazole | 1,1-diphenylpropyl | (S)-1-methylpyrrolidin-3-yl urea with 3-hydroxybenzyl | 745.5 |
| 117 | 5-ethyl-2-methyl-2H-tetrazole | 1,1-bis(4-hydroxyphenyl)propyl | (S)-1-methylpyrrolidin-3-yl urea with pyridin-2-ylmethyl | 762.5 |
| 118 | 5-ethyl-2-methyl-2H-tetrazole | 1,1-bis(4-hydroxyphenyl)propyl | (S)-1-methylpyrrolidin-3-yl urea with pyridin-3-ylmethyl | 762.5 |

TABLE 5-continued

| Ex. | R¹ | R² | R³ | MH+ or MH+/2* |
|---|---|---|---|---|
| 119 | 5-ethyl-2-methyl-tetrazole | 1,1-bis(4-hydroxyphenyl)propyl | (3S)-1-methyl-N-(pyridin-4-ylmethyl)pyrrolidin-3-yl urea | 762.5 |
| 120 | 5-ethyl-2-methyl-tetrazole | 1,1-bis(4-hydroxyphenyl)propyl | (3S)-1-methyl-N-((1-methyl-1H-imidazol-4-yl)methyl)pyrrolidin-3-yl urea | 765.5 |
| 121 | (1-methyl-1H-pyrazol-4-yl)methanol | 1,1-diphenylpropyl | (3S)-1-methyl-N-(pyridin-4-ylmethyl)pyrrolidin-3-yl urea | 730.6 |
| 122 | 4-ethyl-2-methyl-2H-1,2,3-triazole | 1,1-diphenylpropyl | (3S)-1-methyl-N-(pyridin-3-yl)pyrrolidin-3-yl urea | 715.5 |
| 123 | 4-ethyl-2-methyl-2H-1,2,3-triazole | 1,1-diphenylpropyl | (3S)-1-methyl-N-(pyridin-2-ylmethyl)pyrrolidin-3-yl urea | 729.54 |

TABLE 5-continued
| Ex. | R¹ | R² | R³ | MH+ or MH+/2* |
|---|---|---|---|---|
| 124 | 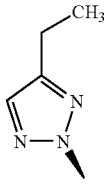 | 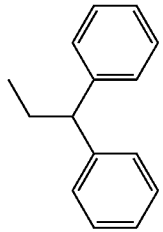 | 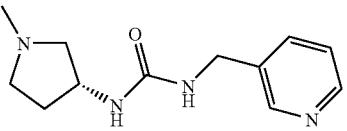 | 729.6 |
| 125 | 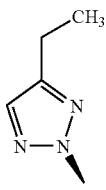 | 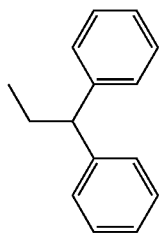 | 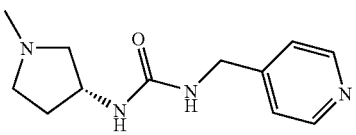 | 729.6 |
| 126 | 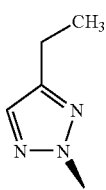 | 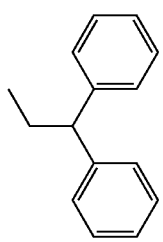 | 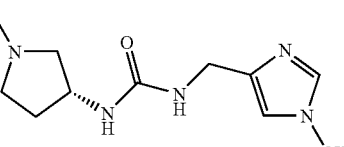 | 732.5 |
| 127 | 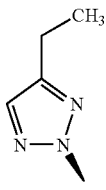 | 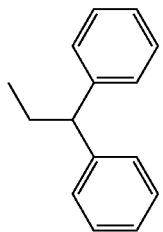 | 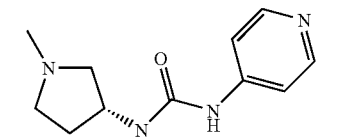 | 715.5 |
| 128 | 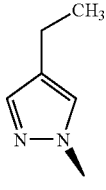 | 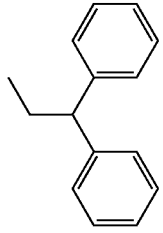 | 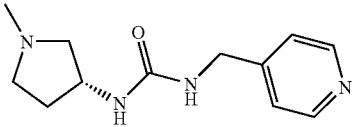 | 728.2 |
| 129 | 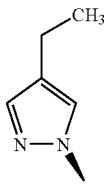 | 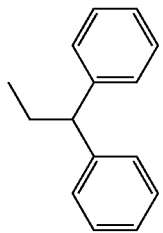 | 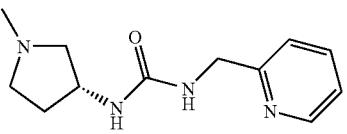 | 728.5 |

TABLE 5-continued

| Ex. | R¹ | R² | R³ | MH+ or MH+/2* |
|---|---|---|---|---|
| 130 | 4-ethyl-1-methylpyrazole | 1,1-diphenylpropyl | (3S)-1-methyl-3-[3-(pyridin-3-ylmethyl)ureido]pyrrolidine | 728.5 |
| 131 | 4-ethyl-1-methylpyrazole | 1,1-diphenylpropyl | (3S)-1-methyl-3-[3-((1-methylimidazol-4-yl)methyl)ureido]pyrrolidine | 731.6 |
| 132 | 4-ethyl-1-methylpyrazole | 1,1-diphenylpropyl | (3S)-1-methyl-3-[3-(3-hydroxybenzyl)ureido]pyrrolidine | 743.6 |
| 133 | 4-ethyl-1-methylpyrazole | 1,1-diphenylpropyl | (3S)-1-methyl-3-(cyclopropanecarboxamido)pyrrolidine | 662.4 |
| 134 | 4-ethyl-1-methylpyrazole | 1,1-diphenylpropyl | (3S)-1-methyl-3-[3-(pyridin-4-yl)ureido]pyrrolidine | 714.5 |
| 135 | 4-ethyl-1-methylpyrazole | 1,1-diphenylpropyl | (3S)-1-methyl-3-(pyrrolidin-1-yl)pyrrolidine | 648.44 |

TABLE 5-continued

| Ex. | R¹ | R² | R³ | MH+ or MH+/2* |
|---|---|---|---|---|
| 136 | 4-ethyl-1-methyl-pyrazole | 1,1-diphenylpropyl | (3R)-1-methyl-N,N-dimethylpyrrolidin-3-amine | 622.4 |
| 137 | 4-ethyl-1-methyl-pyrazole | 1,1-diphenylpropyl | N-methyl-2-(piperidin-1-yl)ethanamine | 636.4 |
| 138 | 4-ethyl-1-methyl-pyrazole | 1,1-diphenylpropyl | trans-N-methylcyclohexane-1,4-diamine | 622.4 |
| 139 | 4-ethyl-2-methyl-1,2,3-triazole | 1,1-diphenylpropyl | 1-methyl-3-(pyrrolidin-1-yl)pyrrolidine | 649.5 |
| 140 | 4-ethyl-2-methyl-1,2,3-triazole | 1,1-diphenylpropyl | (3R)-1-methyl-N,N-dimethylpyrrolidin-3-amine | 623.4 |
| 141 | 4-ethyl-2-methyl-1,2,3-triazole | 1,1-diphenylpropyl | N-methyl-2-(piperidin-1-yl)ethanamine | 637.4 |

TABLE 5-continued

| Ex. | R¹ | R² | R³ | MH+ or MH+/2* |
|---|---|---|---|---|
| 142 | 4-ethyl-2-methyl-2H-1,2,3-triazole | 1,1-diphenylpropyl | trans-N-methyl-cyclohexane-1,4-diamine | 623.4 |
| 143 | 4-ethyl-2-methyl-2H-1,2,3-triazole | 1,1-diphenylpropyl | N-methyl-2-(1-ethyl-1H-imidazol-4-yl)ethanamine | 648.4 |
| 144 | 4-ethyl-1-methyl-1H-pyrazole | 1,1-diphenylpropyl | N-methyl-2-(1-ethyl-1H-imidazol-4-yl)ethanamine | 647.4 |
| 145 | 4-ethyl-2-methyl-2H-1,2,3-triazole | 1,1-diphenylpropyl | 1-(1-methylpyrrolidin-3-yl)-3-(3-hydroxybenzyl)urea | 744.5 |
| 146 | 5-ethyl-2-methyl-2H-tetrazole | 1,1-bis(4-hydroxyphenyl)propyl | 1,3-bis(1-methylpyrrolidin-3-yl)urea | 740.4 |
| 147 | 4-ethyl-1-methyl-1H-pyrazole | 1,1-diphenylpropyl | 1-(1-methylpyrrolidin-3-yl)-3-(pyrrolidin-3-yl)urea | 706.5 |

TABLE 5-continued

| Ex. | R¹ | R² | R³ | MH+ or MH+/2* |
|---|---|---|---|---|
| 148 | 5-ethyl-2-methyl-tetrazole | 1,1-diphenylpropyl | (3S)-1-methylpyrrolidin-3-yl urea CH₂-(2-phenylthiazol-4-yl) | 812.5 |
| 149 | 5-ethyl-2-methyl-tetrazole | 1,1-diphenylpropyl | (3S)-1-methylpyrrolidin-3-yl urea CH₂CH₂-(1H-benzimidazol-2-yl) | 783.55 |
| 150 | 5-ethyl-2-methyl-tetrazole | 1,1-diphenylpropyl | (3S)-1-methylpyrrolidin-3-yl urea CH₂-(quinolin-4-yl) | 780.6 |
| 151 | 5-ethyl-2-methyl-tetrazole | 1,1-diphenylpropyl | (3S)-1-methylpyrrolidin-3-yl urea CH₂-(pyrimidin-4-yl) | 731.5 |
| 152 | 5-ethyl-2-methyl-tetrazole | 1,1-diphenylpropyl | (3S)-1-methylpyrrolidin-3-yl urea CH₂-(4-methoxycarbonylphenyl) | 787.5 |
| 153 | 5-ethyl-2-methyl-tetrazole | 1,1-diphenylpropyl | (3S)-1-methylpyrrolidin-3-yl urea CH₂CH₂-(4-carboxyphenyl) | 787.5 |

TABLE 5-continued

| Ex. | R¹ | R² | R³ | MH+ or MH+/2* |
|---|---|---|---|---|
| 154 | 5-ethyl-2-methyl-tetrazole | 1,1-diphenylpropyl | (S)-1-methylpyrrolidin-3-yl urea-CH₂-C₆H₄-C(=NH)NH₂ | 771.6 |
| 155 | 5-ethyl-2-methyl-tetrazole | 1,1-diphenylpropyl | (S)-1-methylpyrrolidin-3-yl urea-(6-cyanopyridin-3-yl) | 741.5 |
| 156 | 5-ethyl-2-methyl-tetrazole | 1,1-diphenylpropyl | (S)-1-methylpyrrolidin-3-yl urea-(6-methoxypyridin-3-yl) | 746.5 |
| 157 | 5-ethyl-2-methyl-tetrazole | 1,1-diphenylpropyl | (S)-1-methylpyrrolidin-3-yl urea-(3-(1H-tetrazol-5-yl)phenyl) | 783.5 |
| 158 | 5-ethyl-2-methyl-tetrazole | 1,1-diphenylpropyl | (S)-1-methylpyrrolidin-3-yl urea-(4-sulfamoylphenyl) | 795.0 |
| 159 | 5-ethyl-2-methyl-tetrazole | 1,1-diphenylpropyl | (S)-1-methylpyrrolidin-3-yl urea-CH₂-(4-carboxyphenyl) | 774.0 |

TABLE 5-continued

| Ex. | R¹ | R² | R³ | MH+ or MH+/2* |
|---|---|---|---|---|
| 160 | (1-methyl-tetrazol-5-yl)methyl | 1,1-diphenylpropyl | (R)-1-methylpyrrolidin-3-yl urea with 5-methylisoxazol-3-yl | 720.9 |
| 161 | (1-methyl-pyrazol-4-yl)methyl | 1,1-diphenylpropyl | (R)-1-methylpyrrolidin-3-yl urea with 4-sulfamoylphenyl | 792.9 |

Example 67

N-{(R)-1-[9-[(1R,2S,3R,4S)-2,3-Dihydroxy-4-(5-methyl-tetrazol-2-yl)-cyclopentyl]-6-(2,2-diphenyl-ethylamino)-9H-purin-2-yl]-pyrrolidin-3-yl}-methanesulfonamide (1R,2S,3R,5S)-3-[6-(2,2-diphenyl-ethylamino)-2-((R)-pyrrolidin-3-ylamino)-purin-9-yl]-5-(5-methyl-tetrazol-2-yl)-cyclopentane-1,2-diol trifluoroacetate (Example 7) (30 mg, 0.04 mmol) is dissolved in dichloromethane (1 ml). Triethylamine (0.012 ml, 0.088 mmol) and methane sulphonyl chloride (0.003 ml, 0.04 mmol) are added and the reaction mixture is allowed to stand at room temperature over night. The solvent is removed in vacuo. The title compound is obtained after purification by reverse phase column chromatography (Isolute™ C18, 0-100% MeCN in water—0.1% TFA). MS (ES+) m/e 660 (MH+).

Example 68

N-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-methanesulfonamide The title compound is prepared using a procedure analogous to that of N-{(R)-1-[9-[(1R,2S,3R,4S)-2,3-dihydroxy-4-(5-methyl-tetrazol-2-yl)-cyclopentyl]-6-(2,2-diphenyl-ethylamino)-9H-purin-2-yl]-pyrrolidin-3-yl}-methanesulfonamide (Example 67) by replacing (1R,2S,3R,5S)-3-[6-(2,2-diphenyl-ethylamino)-2-((R)-pyrrolidin-3-ylamino)-purin-9-yl]-5-(5-methyl-tetrazol-2-yl)-cyclopentane-1,2-diol trifluoroacetate (Example 7) with (1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48). MS (ES+) m/e 674 (MH+).

Example 69-71

These compounds, namely, 1-((R)-1-{6-(1-Ethyl-propylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-(3,4,5,6-tetrahydro-2H-[1,2']bipyridinyl-4-yl)-urea (Example 69) MS (ES+) m/e 344 (MH+/2);

1-{(R)-1-[9-[(1R,2S,3R,4S)-4-(4-Ethyl-pyrazol-1-yl)-2,3-dihydroxy-cyclopentyl]-6-((S)-1-hydroxymethyl-2-phenyl-ethylamino)-9H-purin-2-yl]-pyrrolidin-3-yl}-3-(3,4,5,6-tetrahydro-2H-[1,2']bipyridinyl-4-yl)-urea (Example 70) MS (ES+) m/e 376 (MH+/2); and 1-((R)-1-{9-[(1R,2S,3R,4S)-4-(4-Ethyl-pyrazol-1-yl)-2,3-dihydroxy-cyclopentyl]-6-phenethylamino-9H-purin-2-yl}-pyrrolidin-3-yl)-3-(3,4,5,6-tetrahydro-2H-[1,2']bipyridinyl-4-yl)-urea (Example 71) MS (ES+) m/e 361 (MH+/2), are prepared using procedures analogous to 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) by replacing (1R,2S,3R,5S)-3-[2-(4-amino-cyclohexylamino)-6-(2,2-diphenyl-ethylamino)-purin-9-yl]-5-(4-methyl-pyrazol-1-yl)-cyclopentane-1,2-diol trifluoroacetate (Example 1) with the appropriate compound, the preparations of which are described herein. (Examples 59, 51 and 55).

Example 72-74

These compounds, namely, 1-(6'-Chloro-3,4,5,6-tetrahydro-2H-[1,2']bipyridinyl-4-yl)-3-{(R)-1-[9-[(1R,2S,3R,4S)-4-(4-ethyl-pyrazol-1-yl)-2,3-dihydroxy-cyclopentyl]-6-((S)-1-hydroxymethyl-2-phenyl-ethylamino)-9H-purin-2-yl]-pyrrolidin-3-yl}-urea (Example 72) MS (ES+) m/e 393 (MH+/2);

1-(6'-Chloro-3,4,5,6-tetrahydro-2H-[1,2']bipyridinyl-4-yl)-3-((R)-1-{9-[(1R,2S,3R,4S)-4-(4-ethyl-pyrazol-1-yl)-2, 3-dihydroxy-cyclopentyl]-6-phenethylamino-9H-purin-2-yl}-pyrrolidin-3-yl)-urea (Example 73) MS (ES+) m/e 378 (MH$^+$/2); and 1-(6'-Chloro-3,4,5,6-tetrahydro-2H-[1,2']bipyridinyl-4-yl)-3-((R)-1-{6-(1-ethyl-propylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-urea (Example 74) MS (ES+) m/e 361 (MH$^+$/2), are prepared using procedures analogous to 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) by replacing (1R,2S,3R,5S)-3-[2-(4-amino-cyclohexylamino)-6-(2,2-diphenyl-ethylamino)-purin-9-yl]-5-(4-methyl-pyrazol-1-yl)-cyclopentane-1,2-diol trifluoroacetate (Example 1) with the appropriate compound, the preparations of which are described herein (Examples 51, 55 and 59), and replacing N-[1-(2-pyridinyl)-4-piperidinyl]-1H-imidazole-1-carboxamide with imidazole-1-carboxylic acid (6'-chloro-3,4,5,6-tetrahydro-2H-[1,2']bipyridinyl-4-yl)-amide.

Example 75

1-(2-Diisopropylamino-ethyl)-3-((R)-1-{9-[(1R,2S,3R,4S)-4-(4-ethyl-pyrazol-1-yl)-2,3-dihydroxy-cyclopentyl]-6-phenethylamino-9H-purin-2-yl}-pyrrolidin-3-yl)-urea This compound is prepared from (1S,2R,3S,5R)-3-(4-ethyl-pyrazol-1-yl)-5-[6-phenethylamino-2-((R)-pyrrolidin-3-ylamino)-purin-9-yl]-cyclopentane-1,2-diol (Example 55) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) replacing N-[1-(2-pyridinyl)-4-piperidinyl]-1H-imidazole-1-carboxamide with imidazole-1-carboxylic acid (2-diisopropylamino-ethyl)-amide. MS (ES+) m/e 688 (MH$^+$).

Example 76

(1R,2S,3R,5S)-3-[2-((R)-3-Amino-pyrrolidin-1-yl)-6-(2,2-diphenyl-ethylamino)-purin-9-yl]-5-(4-hydroxymethyl-pyrazol-1-yl)-cyclopentane-1,2-diol trifluoroacetate This compound is prepared from (1R,2S,3R,5S)-3-[2-chloro-6-(2,2-diphenyl-ethylamino)-purin-9-yl]-5-(4-hydroxymethyl-pyrazol-1-yl)-cyclopentane-1,2-diol (Intermediate BA7) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) replacing the 1-(2-aminoethyl)piperidine with (3R)-(+)-3-amino pyrrolidine. MS (ES+) m/e 596 (MH$^+$).

Example 77

1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-(3,4,5,6-tetrahydro-2H-[1,2']bipyridinyl-4-yl)-urea trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-hydroxymethyl-pyrazol-1-yl)-cyclopentane-1,2-diol trifluoroacetate (Example 76) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42). MS (ES+) m/e 400 (MH$^+$/2)

Example 78

(1R,2S,3R,5S)-3-[2-(1-Benzyl-piperidin-4-ylamino)-6-(2,2-diphenyl-ethylamino)-purin-9-yl]-5-(4-hydroxymethyl-pyrazol-1-yl)-cyclopentane-1,2-diol trifluoroacetate This compound is prepared from (1R,2S,3R,5S)-3-[2-chloro-6-(2,2-diphenyl-ethylamino)-purin-9-yl]-5-(4-hydroxymethyl-pyrazol-1-yl)-cyclopentane-1,2-diol (Intermediate BA7) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 46) replacing 1-(2-aminoethyl)piperidine with 1-benzyl-4-aminopiperidine. MS (ES+) m/e 700 (MH$^+$).

Example 79

4-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-3,4,5,6-tetrahydro-2H-[1,2']bipyridinyl-5'-carboxylic acid ethyl ester trifluoroacetate a) 4-Carbamoyl-3,4,5,6-tetrahydro-2H-[1,2']bipyridinyl-5'-carboxylic Acid Ethyl Ester Ethyl-6-chloronicotinate (1.86 g, 10 mmol) and piperidine-4-carboxamide (1.54 g, 12 mmol) are dissolved in DMSO (7 ml). N,N-Diisopropylethylamine (2.1 ml, 12 mmol) is added and the reaction mixture is heated at 95° C. for 3 hours. Methanol (8 ml) is added as the reaction mixture cools to give a precipitate. The solid is collected, washed with water followed by diethyl ether, and dried in vacuo at 45° C. to yield the title compound as a white solid. MS (ES+) m/e 278 (MH$^+$)

b) 4-Amino-3,4,5,6-tetrahydro-2H-[1,2']bipyridinyl-5'-carboxylic acid ethyl ester A solution comprising 4-carbamoyl-3,4,5,6-tetrahydro-2H-[1,2']bipyridinyl-5'-carboxylic acid ethyl ester (step a) (2.04 g, 7.36-mmol) and bis(trifluoroacetoxy) iodobenzene (3.80 g, 8.83 mmol) in acetonitrile (13 ml) is treated with water (5 ml) and heated to 65° C. for 30 hours. The solvent is partially removed in vacuo and the resulting solution is acidified to pH1 using 12 M HCl. The solution is extracted with ethyl acetate and this organic portion is discarded. The aqueous portion is basified to pH 8-9 using 2M potassium carbonate solution and then extracted with ethyl acetate and dichloromethane. The organic portions are washed with brine, dried (Na$_2$SO$_4$) and concentrated in vacuo. The resulting residue is triturated with diethyl ether followed by diethyl ether/ethyl acetate (1:1, 5×0.7 ml) and dried in vacuo to yield the title compound as an off-white solid. MS (ES+) m/e 250 (MH$^+$)

c) 4-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-3,4,5,6-tetrahydro-2H-[1,2']bipyridinyl-5'-carboxylic acid ethyl ester trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-hydroxymethyl-pyrazol-1-yl)-cyclopentane-1,2-diol trifluoroacetate (Example 76) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) replacing N-[1-(2-pyridinyl)-4-piperidinyl]-1H-imidazole-1-carboxamide with 4-[(imidazole-1-carbonyl)-amino]-3,4,5,6-tetrahydro-2H-[1,2']bipyridinyl-5'-carboxylic acid ethyl ester. MS (ES+) m/e 436 (MH+/2).

Example 80

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid {2-[3-((R)-1-pyridin-2-yl-pyrrolidin-3-yl)-ureido]-ethyl}-amide trifluoroacetate a) 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide trifluoroacetate 9-[(1R,4S)-2,3-dihydroxy-4-(4-hydroxymethyl-pyrazol-1-yl)-cyclopentyl]-6-(2,2-diphenyl-ethylamino)-9H-purine-2-carboxylic acid methyl ester (Example 62) (361 mg, 0.63 mmol) is dissolved in ethyl-1,2-diamine (3.8 g, 63.4 mmol) and the reaction mixture is stirred at 105° C. for 1.5 hours. The solvent in removed in vacuo. The title compound is obtained after purification by reverse phase column chromatography (Isolute™ C18, 0-100% MeCN in water—0.1% TFA).

b) 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid {2-[3-((R)-1-pyridin-2-yl-pyrrolidin-3-yl)-ureido]-ethyl}-amide Trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide trifluoroacetate (first step a) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) replacing N-[1-(2-pyridinyl)-4-piperidinyl]-1H-imidazole-1-carboxamide with imidazole-1-carboxylic acid ((R)-1-pyridin-2-yl-pyrrolidin-3-yl)-amide. MS (ES+) m/e 786 (MH+)

Example 81

9-[(1R,2S,3R,4S)-2,3-Dihydroxy-4-(4-hydroxymethyl-pyrazol-1-yl)-cylopentyl]-6-(2,2-diphenyl-ethylamino)-9H-purine-2-carboxylic acid {2-[3-((S)-1-pyridin-2-yl-pyrrolidin-3-yl)-ureido]-ethyl}-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide trifluoroacetate (Example 80, first step a) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) replacing N-[1-(2-pyridinyl)-4-piperidinyl]-1H-imidazole-1-carboxamide with imidazole-1-carboxylic acid ((S)-1-pyridin-2-yl-pyrrolidin-3-yl)-amide. MS (ES+) m/e 394 (MH+/2).

Example 82

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid {3-[3-(3,4,5,6-tetrahydro-2H-[1,2']bipyridinyl-4-yl)-ureido]-propyl}-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (3-amino-propyl)-amide trifluoroacetate (Example 63) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42). MS (ES+) m/e 815 (MH+)

Example 83

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid {4-[3-(3,4,5,6-tetrahydro-2H-[1,2']bipyridinyl-4-yl)-ureido]-cyclohexyl}-amide trifluoroacetate a) 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid (4-amino-cyclohexyl)-amide trifluoroacetate 9-[(1R,4S)-2,3-dihydroxy-4-(4-hydroxymethyl-pyrazol-1-yl)-cyclopentyl]-6-(2,2-diphenyl-ethylamino)-9H-purine-2-carboxylic acid methyl ester (Example 62) (85 mg, 0.15 mmol) is dissolved in 0.25 ml of toluene. Trans-1,4-diaminocyclohexane (340 mg, 2.98 mmol) is added and the reaction mixture is stirred at 95° C. for 2 hours. The title compound is obtained after purification by reverse phase column chromatography (Isolute™ C18, 0-100% MeCN in water—0.1% TFA).

b) 9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid {4-[3-(3,4,5,6-tetrahydro-2H-[1,2']bipyridinyl-4-yl)-ureido]-cyclohexyl}-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (4-amino-cyclohexyl)-amide trifluoroacetate (first step a) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethyl-amino)-9H-purin-2-ylamino]-cyclohexyl}-3-(3,4,5,6-tetrahydro-2H-[1,2']bipyridinyl-4-yl)-urea trifluoroacetate (Example 42). MS (ES+) m/e 428 (MH+/2)

Example 84

9-[(1R,2S,3R,4S)-2,3-Dihydroxy-4-(4-hydroxym-ethyl-pyrazol-1-yl)-cyclopentyl]-6-(2,2-diphenyl-ethylamino)-9H-purine-2-carboxylic acid {2-methyl-2-[3-(3,4,5,6-tetrahydro-2H-[1,2']bipyridinyl-4-yl)-ureido]-propyl}-amide trifluoroacetate a) 9-[(1R,2S,3R,4S)-2,3-Dihydroxy-4-(4-hydroxym-ethyl-pyrazol-1-yl)-cyclopentyl]-6-(2,2-diphenyl-ethylamino)-9H-purine-2-carboxylic acid (2-amino-2-methyl-propyl)-amide This compound is prepared from 9-[(1R,4S)-2,3-dihydroxy-4-(4-hydroxymethyl-pyrazol-1-yl)-cyclopentyl]-6-(2,2-diphenyl-ethylamino)-9H-purine-2-carboxylic acid methyl ester (Example 62) using a procedure analogous to that of 9-[(1R,2S,3R,4S)-2,3-dihydroxy-4-(4-hydroxym-ethyl-pyrazol-1-yl)-cyclopentyl]-6-(2,2-diphenyl-ethy-lamino)-9H-purine-2-carboxylic acid (4-amino-cyclohexyl)-amide (Example 83, first step a) replacing trans-1,4-diaminocyclohexane with 1,2-diamino-2-methylpropane.

b) 9-[(1R,2S,3R,4S)-2,3-Dihydroxy-4-(4-hydroxym-ethyl-pyrazol-1-yl)-cyclopentyl]-6-(2,2-diphenyl-ethylamino)-9H-purine-2-carboxylic acid {2-methyl-2-[3-(3,4,5,6-tetrahydro-2H-[1,2']bipyridinyl-4-yl)-ureido]-propyl}-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-2-methyl-propyl)-amide (first step a) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42). MS (ES+) m/e 829 (MH+)

Example 85

(1R,2S,3R,5S)-3-[6-(2,2-Diphenyl-ethylamino)-2-(piperidin-4-ylamino)-purin-9-yl]-5-(4-hydroxym-ethyl-pyrazol-1-yl)-cyclopentane-1,2-diol trifluoroacetate (1R,2S,3R,1S)-3-[2-(1-benzyl-piperidin-4-ylamino)-6-(2,2-diphenyl-ethylamino)-purin-9-yl]-5-(4-hydroxymethyl-pyrazol-1-yl)-cyclopentane-1,2-diol trifluoroacetate (Example 78) (50 mg, 0.063 mmol) is dissolved in ethanol (2 ml). Palladium hydroxide (20% on carbon) (45 mg, 0.57 mmol) and ammonium formate (20 mg, 0.057 mmol) are added and the reaction mixture is refluxed for 1.5 hours. The reaction mixture is allowed to cool, the catalyst is filtered off and the solvent is removed in vacuo. The title compound is obtained after purification by reverse phase column chromatography (Isolute™ C18, 0-100% MeCN in water—0.1% TFA). MS (ES+) m/e 610 (MH+).

Example 86

4-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-3,4,5,6-tetrahydro-2H-[1,2']bipyridinyl-5'-carboxylic acid trifluoroacetate 4-(3-{(R)-1-[9-[(1R,2S,3R,4S)-2,3-dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-3,4,5,6-tetrahydro-2H-[1,2']bipyridinyl-5'-carboxylic acid ethyl ester trifluoroacetate (Example 79) (23 mg, 0.023 mmol) is dissolved in methanol (2 ml). Aqueous lithium hydroxide (6 mg, 0.23 mmol) is added and the reaction mixture is stirred at room temperature for 18 hours. The solvent is removed in vacuo. The title compound is obtained after purification by reverse phase column chromatography (Isolute™ C18, 0-100% MeCN in water—0.1% TFA). MS (ES+) m/e 422 (MH+/2).

Example 87

9-[(1R,2S,3R,4S)-2,3-Dihydroxy-4-(4-hydroxym-ethyl-pyrazol-1-yl)-cyclopentyl]-6-(2,2-diphenyl-ethylamino)-9H-purine-2-carboxylic acid [3-(3-ethyl-ureido)-propyl]-amide Trifluoroacetate 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (3-amino-propyl)-amide trifluoroacetate (Example 63) (10 mg, 0.027 mmol) is dissolved in dry DMF (0.25 ml). Ethyl isocyanate (0.92 mg, 0.013 mmol) is dissolved in dry DMF (0.25 ml). The two solutions were combined and triethylamine (>1 eq) is added. The reaction mixture is allowed to stand at room temperature over night. The solvent is removed in vacuo. Purification is carried out using mass directed preparative LC-MS eluting with acetonitrile: water: trifluoroacetic acid to afford the titled compound.

Example 88

9-[(1R,2S,3R,4S)-2,3-Dihydroxy-4-(4-hydroxym-ethyl-pyrazol-1-yl)-cyclopentyl]-6-(2,2-diphenyl-ethylamino)-9H-purine-2-carboxylic acid [3-(2-dim-ethylamino-acetylamino)-propyl]-amide Trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (3-amino-propyl)-amide trifluoroacetate (Example 63) using a procedure analogous to that of 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid [3-(3-ethyl-ureido)-propyl]-amide trifluoroacetate (Example 87) replacing ethyl isocyanate with dimethyl-amino-acetyl chloride hydrochloride.

Example 89

9-[(1R,4S)-2,3-Dihydroxy-4-(4-hydroxymethyl-pyrazol-1-yl)-cyclopentyl]-6-(2,2-diphenyl-ethy-lamino)-9H-purine-2-carboxylic acid [4-(3-ethyl-ureido)-cyclohexyl]-amide trifluoroacetate This compound is prepared from 9-[(1R,2S,3R,4S)-2,3-dihydroxy-4-(4-hydroxymethyl-pyrazol-1-yl)-cyclopentyl]-

6-(2,2-diphenyl-ethylamino)-9H-purine-2-carboxylic acid (4-amino-cyclohexyl)-amide trifluoroacetate (Example 83, first step a) using a procedure analogous to that of 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid [3-(3-ethyl-ureido)-propyl]-amide trifluoroacetate (Example 87).

Example 90

9-[(1R,4S)-2,3-Dihydroxy-4-(4-hydroxymethyl-pyrazol-1-yl)-cyclopentyl]-6-(2,2-diphenyl-ethylamino)-9H-purine-2-carboxylic acid [4-(3,3-dimethyl-ureido)-cyclohexyl]-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (4-amino-cyclohexyl)-amide trifluoroacetate (Example 83, first step a) using a procedure analogous to that of 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid [3-(3-ethyl-ureido)-propyl]-amide trifluoroacetate (Example 87) replacing ethyl isocyanate with dimethylcarbamic chloride.

Example 91

9-[(1R,4S)-2,3-Dihydroxy-4-(4-hydroxymethyl-pyrazol-1-yl)-cyclopentyl]-6-(2,2-diphenyl-ethylamino)-9H-purine-2-carboxylic acid [4-(2-dimethylamino-acetylamino)-cyclohexyl]-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (4-amino-cyclohexyl)-amide trifluoroacetate (Example 83, first step a) using a procedure analogous to that of 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid [3-(3-ethyl-ureido)-propyl]-amide trifluoroacetate (Example 87) replacing ethyl isocyanate with dimethyl-amino-acetyl chloride hydrochloride.

Example 92

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid [2-(3-ethyl-ureido)-2-methyl-propyl]-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-2-methyl-propyl)-amide (Example 84, first step a) using a procedure analogous to that of 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid [3-(3-ethyl-ureido)-propyl]-amide trifluoroacetate (Example 87).

Example 93

9-[(1R,2S,3R,4S)-2,3-Dihydroxy-4-(4-hydroxymethyl-pyrazol-1-yl)-cyclopentyl]-6-(2,2-diphenyl-ethylamino)-9H-purine-2-carboxylic acid [2-(3-ethyl-ureido)-ethyl]-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide trifluoroacetate (Example 80) using a procedure analogous to that of 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid [3-(3-ethyl-ureido)-propyl]-amide trifluoroacetate (Example 87).

Example 94

9-[(1R,2S,3R,4S)-2,3-Dihydroxy-4-(4-hydroxymethyl-pyrazol-1-yl)-cyopentyl]-6-(2,2-diphenyl-ethylamino)-9H-purine-2-carboxylic acid (2-{3-[2-(4-benzyl-piperazin-1-yl)-ethyl]-ureido}-ethyl)-amide trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide trifluoroacetate (Example 80) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42) replacing N-[1-(2-pyridinyl)-4-piperidinyl]-1H-imidazole-1-carboxamide with imidazole-1-carboxylic acid [2-(4-benzyl-piperazin-1-yl)-ethyl]-amide. MS (ES+) m/e 422 (MH$^+$/2)

Example 95

1-{2-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-ylamino]-ethyl}-3-(3,4,5,6-tetrahydro-2H-[1,2']bipyridinyl-4-yl)-urea trifluoroacetate This compound is prepared from 9-[(1R,2S,3R,4S)-2,3-dihydroxy-4-(4-hydroxymethyl-pyrazol-1-yl)-cyclopentyl]-6-(2,2-diphenyl-ethylamino)-9H-purine-2-carboxylic acid (2-amino-ethyl)-amide trifluoroacetate (Example 80) using a procedure analogous to that of 1-{4-[9-[(1R,2S,3R,4S)-2,3-dihydroxy-4-(4-methyl-pyrazol-1-yl)-cyclopentyl]-6-(2,2-diphenyl-ethylamino)-9H-purin-2-ylamino]-cyclohexyl}-3-(3,4,5,6-tetrahydro-2H-[1,2']bipyridinyl-4-yl)-urea trifluoroacetate (Example 42). MS (ES+) m/e 773 (MH$^+$).

Example 96

(1R,2S,3R,5S)-3-[2-((R)-3-Dimethylamino-pyrrolidin-1-yl)-6-(2,2-diphenyl-ethylamino)-purin-9-yl]-5-(4-hydroxymethyl-pyrazol-1-yl)-cyclopentane-1,2-diol This compound is prepared from (1R,2S,3R,5S)-3-[2-chloro-6-(2,2-diphenyl-ethylamino)-purin-9-yl]-5-(4-hydroxymethyl-pyrazol-1-yl)-cyclopentane-1,2-diol (BA7) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 46) replacing 1-(2-amino-ethyl)piperidine with (3R)-(+)-3-(dimethylamino)-pyrrolidine. After purification, the compound is partitioned between DCM and saturated NaHCO$_3$(aq). The organics are dried (MgSO$_4$), filtered and reduced in vacuo to yield the title compound. MS (ES+) m/e 624 (MH$^+$).

Example 97

4-{1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-piperazine-1-carboxylic acid benzyl ester trifluoroacetate a) 4-Pyrrolidin-3-yl-piperazine-1-carboxylic acid benzyl ester 1-N-BOC-3-pyrrolidinone (500 mg, 2.70 mmol), benzyl-1-piperazinecarboxylate (595 mg, 2.70 mmol) and titanium (IV) isopropoxide (960 mg, 3.37 mmol) are stirred under argon for 1 hour. Ethanol (3 ml) and sodium cyanoborohydride (113 mg, 1.80 mmol) are added and the reaction mixture stirred at room temperature over night. The compound is purified by reverse phase column chromatography (Isolute™ C18, 0-100% MeCN in water—0.1% TFA), followed by deprotection using trifluoroacetic acid (5 ml). The solvent is removed in vacuo and the compound is partitioned between chloroform and saturated $NaHCO_3$(aq). The organics are dried ($MgSO_4$), filtered and reduced in vacuo to yield the title compound.

b) 4-{1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-piperazine-1-carboxylic acid benzyl ester trifluoroacetate (1R,2S,3R,5S)-3-[2-chloro-6-(2,2-diphenyl-ethylamino)-purin-9-yl]-5-(4-hydroxymethyl-pyrazol-1-yl)-cyclopentane-1,2-diol (BA7) (2 mg, 0.037 mmol) and 4-pyrrolidin-3-yl-piperazine-1-carboxylic acid benzyl ester (first step a) (106 mg, 0.37 mmol) are dissolved in DMSO (1 ml) and the reaction mixture is heated at 100° C. over night. The compound is purified by reverse phase column chromatography (Isolute™ C18, 0-100% MeCN in water—0.1% TFA). MS (ES+) m/e 799 ($MH^+$)

Example 98

1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-(R)-pyrrolidin-3-yl-urea This compound is prepared from (1R,2S,3R,5S)-3-[2-chloro-6-(2,2-diphenyl-ethylamino)-purin-9-yl]-5-(4-hydroxymethyl-pyrazol-1-yl)-cyclopentane-1,2-diol (BA7) using a procedure analogous to that of 4-{1-[9-[(1R,2S,3R,4S)-2,3-dihydroxy-4-(4-hydroxymethyl-pyrazol-1-yl)-cyclopentyl]-6-(2,2-diphenyl-ethylamino)-9H-purin-2-yl]-pyrrolidin-3-yl}-piperazine-1-carboxylic acid benzyl ester trifluoroacetate (Example 97, second step b) replacing 4-pyrrolidin-3-yl-piperazine-1-carboxylic acid benzyl ester with 1,3-di(R)-pyrrolidin-3-yl-urea (Intermediate EC) and then converting the compound to its free base. MS (ES+) m/e 708 ($MH^+$).

Example 99

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(R)-pyrrolidin-3-yl-urea This compound is prepared from (1R,2S,3R,5S)-3-[2-chloro-6-(2,2-diphenyl-ethylamino)-purin-9-yl]-5-(5-ethyl-tetrazol-2-yl)-cyclopentane-1,2-diol (BA6) using a procedure analogous to that of 4-{1-[9-[(1R,2S,3R,4S)-2,3-dihydroxy-4-(4-hydroxymethyl-pyrazol-1-yl)-cyclopentyl]-6-(2,2-diphenyl-ethylamino)-9H-purin-2-yl]-pyrrolidin-3-yl}-piperazine-1-carboxylic acid benzyl ester trifluoroacetate (Example 97) replacing 4-pyrrolidin-3-yl-piperazine-1-carboxylic acid benzyl ester with 1,3-di(R)-pyrrolidin-3-yl-urea (Intermediate EC) and then converting the compound to its free base. MS (ES+) m/e 708 ($MH^+$).

Example 100

(1R,2S,3R,5S)-3-[2-((R)-3-Dimethylamino-pyrrolidin-1-yl)-6-(2,2-diphenyl-ethylamino)-purin-9-yl]-5-(5-ethyl-tetrazol-2-yl)-cyclopentane-1,2-diol This compound is prepared from (1R,2S,3R,5S)-3-[2-chloro-6-(2,2-diphenyl-ethylamino)-purin-9-yl]-5-(5-ethyl-tetrazol-2-yl)-cyclopentane-1,2-diol (BA6) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) replacing 1-(2-amino-ethyl)piperidine with (3R)-(+)-3-(dimethylamino)pyrrolidine. After purification, the compound is partitioned between DCM and saturated $NaHCO_3$(aq). The organics are dried ($MgSO_4$), filtered and reduced in vacuo to yield the title compound. MS (ES+) m/e 624 ($MH^+$).

Example 101

((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-carbamic acid tert-butyl ester trifluoroacetate This compound is prepared from (1R,2S,3R,5S)-3-[2-chloro-6-(2,2-diphenyl-ethylamino)-purin-9-yl]-5-(5-ethyl-tetrazol-2-yl)-cyclopentane-1,2-diol (BA6) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) replacing 1-(2-amino-ethyl)piperidine with (3R)-(+)-3-(BOC-amino)pyrrolidine. MS (ES+) m/e 696 ($MH^+$).

Example 102

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-4-ylmethyl-urea hydrochloride (1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) (20 mg, 0.034 mmol) and pyridin-4-ylmethyl-carbamic acid phenyl ester (8.4 mg, 0.037 mmol) are dissolved in NMP (0.5 ml) and the reaction mixture is heated at 115° C. for 48 hours. The compound is purified by reverse phase column chromatography (Isolute™ C18, 0-100% MeCN in water—0.1% HCl) MS (ES+) m/e 730 ($MH^+$).

Example 103

(1R,2S,3R,5S)-3-[6-[2,2-Bis-(4-hydroxy-phenyl)-ethylamino]-2-((R)-3-dimethylamino-pyrrolidin-1-yl)-purin-9-yl]-5-(5-ethyl-tetrazol-2-yl)-cyclopentane-1,2-diol hydrochloride This compound is prepared from (1R,2S,3R,5S)-3-{6-[2,2-bis-(4-hydroxy-phenyl)-ethylamino]-2-chloro-purin-9- yl}-5-(5-ethyl-tetrazol-2-yl)-cyclopentane-1,2-diol (BF1) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) replacing 1-(2-amino-ethyl)piperidine with (3R)-(+)-3-(dimethylamino)pyrrolidine. MS (ES+) m/e 656 (MH$^+$).

Example 104

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea hydrochloride (1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) (30 mg, 0.05 mmol) is dissolved in dry THF (1 ml). Pyridine-3-isocyanate (7 mg, 0.06 mmol) is added and the reaction mixture is stirred at room temperature for 2 hours. The solvent is removed in vacuo. The compound is purified by reverse phase column chromatography (Isolute™ C18, 0-100% MeCN in water—0.1% HCl). MS (ES+) m/e 716 (MH$^+$).

Example 105

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea This compound is prepared from (1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48), using a procedure analogues to that of 1-((R)-1-{6-(2,2-diphenyl-ethylamino)-9-[((1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea hydrochloride (Example 104). After purification, the compound is partitioned between DCM and saturated NaHCO$_3$ (aq). The organics are dried (MgSO$_4$), filtered and reduced in vacuo to yield the title compound. MS (ES+) m/e 716.51 (MH$^+$).

Example 106

(1R,2S,3R,5S)-3-{2-((R)-3-Amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol a) ((R)-1-{6-[2,2-bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-carbamic acid tert-butyl ester
This compound is prepared from (1R,2S,3R,5S)-3-{6-[2,2-bis-(4-hydroxy-phenyl)-ethylamino]-2-chloro-purin-9-yl}-5-(5-ethyl-tetrazol-2-yl)-cyclopentane-1,2-diol (Intermediate BF1) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 46) by replacing trans-1,4-diaminocyclohexane with (R)-pyrrolidin-3-yl-carbamic acid tert-butyl ester.

b) (1R,2S,3R,5S)-3-{2-((R)-3-Amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol This compound is prepared from ((R)-1-{6-[2,2-bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-carbamic acid tert-butyl ester (first step a) using a procedure analogous to that of (1R,2S,3R,5S)-3-[2-((R)-3-Amino-pyrrolidin-1-yl)-6-(2,2-diphenyl-ethylamino)-purin-9-yl]-5-(4-hydroxymethyl-pyrazol-1-yl)-cyclopentane-1,2-diol (Intermediate FB, second step b). MS (ES+) m/e 628.30 (MH$^+$).

Example 107

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea This compound is prepared from (1R,2S,3R,5S)-3-{2-((R)-3-amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol (Example 106) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea (Example 105). MS (ES+) m/e 748.41 (MH$^+$).

Example 108

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-4-yl-urea hydrochloride (1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) (30 mg, 0.05 mmol) and pyridin-4-yl-carbamic acid phenyl ester (Intermediate EA) are dissolved in N-methyl 2-pyrrolidone (0.5 ml). The reaction mixture is stirred at 100° C. for 1 hour. The title compound is obtained after purification by reverse phase column chromatography (Isolute™ C18, 0-100% MeCN in water—0.1% HCl). MS (ES+) m/e 752.28 (MH$^+$).

Example 109

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-4-yl-urea hydrochloride This compound is prepared from (1R,2S,3R,5S)-3-{2-((R)-3-amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol (Example 106) using a procedure analogous to that of (1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-4-yl-urea hydrochloride (Example 108). MS (ES+) m/e 748.42 (MH$^+$).

Example 110

(1R,2S,3R,5S)-3-[2-((R)-3-Amino-pyrrolidin-1-yl)-6-(2,2-diphenyl-ethylamino)-purin-9-yl]-5-(4-ethyl-pyrazol-1-yl)-cyclopentane-1,2-diol a) ((R)-1-{6-(2,2-Diphenyl-ethylamino)-9-[(1R,2S, 3R,4S)-4-(4-ethyl-pyrazol-1-yl)-2,3-dihydroxy-cyclopentyl]-9H-purin-2-yl}-pyrrolidin-3-yl)-carbamic acid tert-butyl ester This compound is prepared from (1R,2S,3R,5S)-3-[2-chloro-6-(2,2-diphenyl-ethylamino)-purin-9-yl]-5-(4-ethyl-pyrazol-1-yl)-cyclopentane-1,2-diol. (Intermediate BA8) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) by replacing the trans-1,4-diaminocyclohexane with (R)-pyrrolidin-3-yl-carbamic acid tert-butyl ester.

b) (1R,2S,3R,5S)-3-[2-((R)-3-Amino-pyrrolidin-1-yl)-6-(2,2-diphenyl-ethylamino)-purin-9-yl]-5-(4-ethyl-pyrazol-1-yl)-cyclopentane-1,2-diol ((R)-1-{6-(2,2-diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-carbamic acid tert-butyl ester (first step a) (9.75 g, 14 mmol) is dissolved in methanol (2 ml). (4M) HCl in 1,4-dioxane (15 ml) is added and the reaction mixture is stirred at room temperature over night. The compound is purified by reverse phase column chromatography (Isolute™ C18, 0-100% MeCN in water—0.1% HCl). The compound is partitioned between DCM and saturated NaHCO$_3$(aq). The organics are dried (MgSO$_4$), filtered and reduced in vacuo to yield the title compound. MS (ES+) m/e 594.31 (MH$^+$).

Example 111

(1R,2S,3R,5S)-3-[(R)-2-[1,3']Bipyrrolidinyl-1'-yl-6-(2,2-diphenyl-ethylamino)-purin-9-yl]-5-(5-ethyl-tetrazol-2-yl)-cyclopentane-1,2-diol hydrochloride This compound is prepared from (1R,2S,3R,5S)-3-[2-chloro-6-(2,2-diphenyl-ethylamino)-purin-9-yl]-5-(5-ethyl-tetrazol-2-yl)-cyclopentane-1,2-diol (Intermediate BA6) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) by replacing 1-(2-amino-ethyl)piperidine with (R)-[1,3']bipyrrolidinyl (intermediate EB). MS (ES+) m/e 650.42 (MH$^+$).

Example 112

(1R,2S,3R,5S)-3-{(R)-2-[1,3']Bipyrrolidinyl-1'-yl-6-[2,2-bis-(4-hydroxy-phenyl)-ethylamino]-purin-9-yl}-5-(5-ethyl-tetrazol-2-yl)-cyclopentane-1,2-diol hydrochloride This compound is prepared from (1R,2S,3R,5S)-3-{6-[2,2-bis-(4-hydroxy-phenyl)-ethylamino]-2-chloro-purin-9-yl}-5-(5-ethyl-tetrazol-2-yl)-cyclopentane-1,2-diol (Intermediate BF1) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46) by replacing 1-(2-amino-ethyl)piperidine with (R)-[1,3']bipyrrolidinyl (intermediate EB). MS (ES+) m/e 650.42 (MH$^+$).

Example 113

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (1R,2S,3R,5S)-3-[2-((R)-3-amino-pyrrolidin-1-yl)-6-(2,2-diphenyl-ethylamino)-purin-9-yl]-2-(5-ethyl-tetrazol-2-yl)-cyclopentane-1,2-diol (Example 48) (80 mg, 0.13 mmol) and potassium carbonate (37 mg, 0.27 mmol) are dissolved in THF (1 ml). Phenyl chloroformate (19 µl, 0.15 mmol) is added to the reaction mixture. The reaction mixture is stirred at room temperature for 2 hours. The THF is removed in vacuo and the reaction mixture dissolved in N-methyl 2-pyrrolidone. 2-aminomethylpyridine (75 mg, 0.7 mmol) is added and the reaction mixture is heated at 100° C. for 2 hours. The title compound is obtained after purification by reverse phase column chromatography (Isolute™ C18, 0-100% MeCN in water—0.1% HCl). MS (ES+) m/e 730.50 (MH$^+$).

Example 114

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-ylmethyl-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(1-ethyl-tetrazol-2-yl)-2,3-dihydroxy-cyclopentyl]-9H-purin-2-yl}-pyrrolidin-3-yl)-3-pyridin-2-ylmethyl-urea hydrochloride. (Example 113) by replacing 2-aminomethyl pyridine with 3-aminomethylpyridine. MS (ES+) m/e 730.50 (MH$^+$).

Example 115

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(1-methyl-1H-imidazol-4-ylmethyl)-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with C-(1-methyl-1H-imidazol-4-yl)-methylamine. MS (ES+) m/e 733.49 (MH$^+$).

Example 116

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(3-hydroxy-benzyl)-urea hydrochloride This compound is prepared from ((1R,2S,3R,5S)-3-[2-((R)-3-amino-pyrrolidin-1-yl)-6-(2,2-diphenyl-ethylamino)- purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 3-aminomethyl-phenol. MS (ES+) m/e 745.47 (MH$^+$).

Example 117

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride This compound is prepared from (1R,2S,3R,5S)-3-{2-((R)-3-amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol (Example 106) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113). MS (ES+) m/e 762.53 (MH$^+$).

Example 118

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-ylmethyl-urea hydrochloride This compound is prepared from (1R,2S,3R,5S)-3-{2-((R)-3-amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol (Example 106) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethylpyridine with 3-aminomethylpyridine. MS (ES+) m/e 762.53 (MH$^+$).

Example 119

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-ylmethyl-urea hydrochloride This compound is prepared from (1R,2S,3R,5S)-3-{2-((R)-3-amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol (Example 106) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethylpyridine with 4-aminomethylpyridine. MS (ES+) m/e 762.54 (MH$^+$).

Example 120

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-(1-methyl-1H-imidazol-4-ylmethyl)-urea hydrochloride This compound is prepared from (1R,2S,3R,5S)-3-{2-((R)-3-amino-pyrrolidin-1-yl)-6-[2,2-bis-(4-hydroxy-phenyl)-ethylamino]-purin-9-yl}-5-(5-ethyl-tetrazol-2-yl)-cyclopentane-1,2-diol (Example 106) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethylpyridine with C-(1-methyl-1H-imidazol-4-yl)-methylamine. MS (ES+) m/e 7652.53 (MH$^+$).

Example 121

1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-pyridin-4-ylmethyl-urea This compound is prepared from (1R,2S,3R,5S)-3-[2-((R)-3-amino-pyrrolidin-1-yl)-6-(2,2-diphenyl-ethylamino)-purin-9-yl]-5-(4-hydroxymethyl-pyrazol-1-yl)-cyclopentane-1,2-diol. (Intermediate FB) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethylpyridine with 4-aminomethylpyridine. MS (ES+) m/e 730.55 (MH$^+$).

Example 122

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-pyridin-3-yl-urea hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol. (Intermediate FC) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea (Example 105). MS (ES+) m/e 715.54 (MH$^+$).

Example 123

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-pyridin-2-ylmethyl-urea hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol. (Intermediate FC) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113). MS (ES+) m/e 729.54 (MH$^+$).

Example 124

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-pyridin-3-ylmethyl-urea hydrochloride This compound is prepared from (1R,2S,3R,5S)-3-[2-((R)-3-amino-pyrrolidin-1-yl)-6-(2,2-diphenyl-ethylamino)- purin-9-yl]-5-(4-ethyl-[1,2,3]triazol-2-yl)-cyclopentane-1,2-diol. (Intermediate FC) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethylpyridine with 3-aminomethylpyridine. MS (ES+) m/e 729.55 (MH+).

Example 125

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-pyridin-4-ylmethyl-urea hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol. (Intermediate FC) using a procedure analogous to 1-((R)-1-{6-(2,2-diphenyl-ethylamino)-9-[((1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113), by replacing 2-aminomethyl pyridine with 4-aminomethylpyridine. MS (ES+) m/e 729.55 (MH+).

Example 126

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-(1-methyl-1H-imidazol-4-ylmethyl)-urea hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol. (Intermediate FC) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethylpyridine with C-(1-methyl-1H-imidazol-4-yl)-methylamine. MS (ES+) m/e 732.54 (MH+).

Example 127

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-pyridin-4-yl-urea hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol (Intermediate FC) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-4-yl-urea hydrochloride (Example 108). MS (ES+) m/e 715.54 (MH+).

Example 128

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-pyridin-4-ylmethyl-urea This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol. (Example 110) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 4-aminomethylpyridine. The compound is partitioned between DCM and saturated NaHCO$_{3(aq)}$. The organics are dried (MgSO$_4$), filtered and reduced in vacuo to yield the title compound. MS (ES+) m/e 728.22 (MH+).

Example 129

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-pyridin-2-ylmethyl-urea trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol. (Example 110) using a procedure analogous to that of 1-((R)-1-{6-(2,2-diphenyl-ethylamino)-9-[(1R,2S,3R,4S)-4-(1-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113). MS (ES+) m/e 728.51 (MH+).

Example 130

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-pyridin-3-ylmethyl-urea trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol. (Example 110) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 3-aminomethylpyridine. MS (ES+) m/e 728.52 (MH+).

Example 131

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-(1-methyl-1H-imidazol-4-ylmethyl)-urea trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol (Example 110) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with C-(1-methyl-1H-imidazol-4-yl)-methylamine. MS (ES+) m/e 731.64 (MH+).

Example 132

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-(3-hydroxy-benzyl)-urea trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol. (Example 110) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 3-aminomethyl-phenol. MS (ES+) m/e 743.63 (MH$^+$).

Example 133

Cyclopropanecarboxylic acid ((R)-1-{6-(2,2-diphenyl-ethylamino)-9-[(1R,2S,3R,4S)-4-(4-ethyl-pyrazol-1-yl)-2,3-dihydroxcyclopentyl]-9H-purin-2-yl}-pyrrolidin-3-yl)-amide trifluoroacetate (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol (Example 110) (30 mg, 0.05 mmol) and triethylamine (5 mg, 0.05 mmol) are dissolved in dry THF (0.5 ml). Cyclopropane carboxylic acid chloride (5.2 mg, 0.05 mmol) is added and the reaction mixture is stirred at room temperature over night. The title compound is obtained after purification by reverse phase column chromatography (Isolute™ C18, 0-100% MeCN in water—0.1% TFA). MS (ES+) m/e 662.42 (MH$^+$).

Example 134

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-pyridin-4-yl-urea trifluoroacetate This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol. (Example 110) using a procedure analogous to that of 1-((R)-1-{(6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-4-yl-urea hydrochloride (Example 108). MS (ES+) m/e 714.47 (MH$^+$).

Example 135

(1R,2S,3R,5S)-3-[(R)-2-[1,3']Bipyrrolidinyl-1'-yl-6-(2,2-diphenyl-ethylamino)-purin-9-yl]-5-(4-ethyl-pyrazol-1-yl)-cyclopentane-1,2-diol Trifluoroacetate This compound is prepared from (1R,2S,3R,5S)-3-[2-chloro-6-(2,2-diphenyl-ethylamino)-purin-9-yl]-5-(4-ethyl-pyrazol-1-yl)-cyclopentane-1,2-diol (Intermediate BA8) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 461 by replacing 1-(2-amino-ethyl)piperidine with (R)-[1,3']bipyrrolidinyl (intermediate EB). MS (ES+) m/e 648.44 (MH$^+$).

Example 136

(1R,2S,3R,5S)-3-[2-((R)-3-Dimethylamino-pyrrolidin-1-yl)-6-(2,2-diphenyl-ethylamino)-purin-9-yl]-5-(4-ethyl-pyrazol-1-yl)-cyclopentane-1,2-diol trifluoroacetate This compound is prepared from (1R,2S,3R,5S)-3-[2-chloro-6-(2,2-diphenyl-ethylamino)-purin-9-yl]-5-(4-ethyl-pyrazol-1-yl)-cyclopentane-1,2-diol (Intermediate BA8) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 461 by replacing 1-(2-amino-ethyl)piperidine with (3R)-(+)-3-(dimethylamino)pyrrolidine. MS (ES+) m/e 622.40 (MH$^+$).

Example 137

(1R,2S,3R,5S)-3-[6-(2,2-Diphenyl-ethylamino)-2-(2-piperidin-1-yl-ethylamino)-purin-9-yl]-5-(4-ethyl-pyrazol-1-yl)-cyclopentane-1,2-diol trifluoroacetate This compound is prepared from (1R,2S,3R,5S)-3-[2-chloro-6-(2,2-diphenyl-ethylamino)-purin-9-yl]-5-(4-ethyl-pyrazol-1-yl)-cyclopentane-1,2-diol (Intermediate BA8) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46). MS (ES+) m/e 636.42 (MH$^+$).

Example 138

(1R,2S,3R,5S)-3-[2-(4-Amino-cyclohexylamino)-6-(2,2-diphenyl-ethylamino)-purin-9-yl]-5-(4-ethyl-pyrazol-1-yl)-cyclopentane-1,2-diol trifluoroacetate This compound is prepared from (1R,2S,3R,5S)-3-[2-chloro-6-(2,2-diphenyl-ethylamino)-purin-9-yl]-5-(4-ethyl-pyrazol-1-yl)-cyclopentane-1,2-diol (Intermediate BA8) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 461 by replacing 1-(2-amino-ethyl)piperidine with cyclohexane-1,4-diamine. MS (ES+) m/e 622.42 (MH$^+$).

Example 139

(1R,2S,3R,5S)-3-[(R)-2-[1,3']Bipyrrolidinyl-1'-yl-6-(2,2-diphenyl-ethylamino)-purin-9-yl]-5-(4-ethyl-[1,2,3]triazol-2-yl)-cyclopentane-1,2-diol trifluoroacetate This compound is prepared from 3-[2-chloro-6-(2,2-diphenyl-ethylamino)-purin-9-yl]-5-(4-ethyl-[1,2,3]triazol-1-yl)-cyclopentane-1,2-diol (Intermediate BA9) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 461 by replacing 1-(2-amino-ethyl)piperidine with (R)-[1,3']bipyrrolidinyl (intermediate EB). MS (ES+) m/e 649.46 (MH+).

Example 140

(1R,2S,3R,5S)-3-[2-((R)-3-Dimethylamino-pyrrolidin-1-yl)-6-(2,2-diphenyl-ethylamino)-purin-9-yl]-5-(4-ethyl-[1,2,3]triazol-2-yl)-cyclopentane-1,2-diol trifluoroacetate This compound is prepared from 3-[2-chloro-6-(2,2-diphenyl-ethylamino)-purin-9-yl]-5-(4-ethyl-[1,2,3]triazol-1-yl)-cyclopentane-1,2-diol (Intermediate BA9) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 461 by replacing 1-(2-amino-ethyl)piperidine with (3R)-(+)-3-(dimethylamino)pyrrolidine. MS (ES+) m/e 623.41 (MH+).

Example 141

(1R,2S,3R,5S)-3-[6-(2,2-Diphenyl-ethylamino)-2-(2-piperidin-1-yl-ethylamino)-purin-9-yl]-5-(4-ethyl-[1,2,3]triazol-2-yl)-cyclopentane-1,2-diol trifluoroacetate This compound is prepared from 3-[2-chloro-6-(2,2-diphenyl-ethylamino)-purin-9-yl]-5-(4-ethyl-[1,2,3]triazol-1-yl)-cyclopentane-1,2-diol (Intermediate BA9) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 46). MS (ES+) m/e 637.42 (MH+).

Example 142

(1R,2S,3R,5S)-3-[2-(4-Amino-cyclohexylamino)-6-(2,2-diphenyl-ethylamino)-purin-9-yl]-5-(4-ethyl-[1,2,3]triazol-2-yl)-cyclopentane-1,2-diol trifluoroacetate This compound is prepared from 3-[2-chloro-6-(2,2-diphenyl-ethylamino)-purin-9-yl]-5-(4-ethyl-[1,2,3]triazol-1-yl)-cyclopentane-1,2-diol (Intermediate BA9) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 461 by replacing 1-(2-amino-ethyl)piperidine with cyclohexane-1,4-diamine. MS (ES+) m/e 623.43 (MH+).

Example 143

(1R,2S,3R,5S)-3-{6-(2,2-Diphenyl-ethylamino)-2-[2-(1-ethyl-1H-imidazol-4-yl)-ethylamino]-purin-9-yl}-5-(4-ethyl-[1,2,3]triazol-2-yl)-cyclopentane-1,2-diol trifluoroacetate This compound is prepared from 3-[2-chloro-6-(2,2-diphenyl-ethylamino)-purin-9-yl]-5-(4-ethyl-[1,2,3]triazol-1-yl)-cyclopentane-1,2-diol (Intermediate BA9) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoroacetate (Example 461 by replacing 1-(2-amino-ethyl)piperidine with 2-(1-ethyl-1H-imidazol-4-yl)-ethylamine (intermediate CD). MS (ES+) m/e 648.42 (MH+).

Example 144

(1R,2S,3R,5S)-3-{6-(2,2-Diphenyl-ethylamino)-2-[2-(1-ethyl-1H-imidazol-4-yl)-ethylamino]-purin-9-yl}-5-(4-ethyl-pyrazol-1-yl)-cyclopentane-1,2-diol trifluoroacetate This compound is prepared from (1R,2S,3R,5S)-3-[2-chloro-6-(2,2-diphenyl-ethylamino)-purin-9-yl]-5-(4-ethyl-pyrazol-1-yl)-cyclopentane-1,2-diol (Intermediate BA8) using a procedure analogous to that of (1R,2S,3R,5S)-3-[6-(2,2-diphenyl-ethylamino)-2-(2-piperidin-1-yl-ethylamino)-purin-9-yl]-5-(4-hydroxymethyl-pyrazol-1-yl)-cyclopentane-1,2-diol trifluoro-acetate (Example 461 by replacing 1-(2-amino-ethyl)piperidine with 2-(1-ethyl-1H-imidazol-4-yl)-ethylamine (intermediate CD). MS (ES+) m/e 647.42 (MH+).

Example 145

1-((R)-1-{6-(2,2-Diphenyl-ethylamino)-9-[(1R,2S,3R,4S)-4-(4-ethyl-[1,2,3]triazol-2-yl)-2,3-dihydroxy-cyclopentyl]-9H-purin-2-yl}-pyrrolidin-3-yl)-3-(3-hydroxy-benzyl)-urea hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-[1,2,3]triazol-2-yl)-cyclopentane-1,2-diol. (Intermediate FC) using a procedure analogous to that of 1-((R)-1-{6-(2,2-diphenyl-ethyl-amino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by 2-aminomethyl pyridine with 3-aminomethyl-phenol. MS (ES+) m/e 744.48 (MH+).

Example 146

1-((R)-1-{6-[2,2-Bis-(4-hydroxy-phenyl)-ethylamino]-9-[(1R,2S,3R,4S)-4-(5-ethyl-tetrazol-2-yl)-2,3-dihydroxy-cyclopentyl]-9H-purin-2-yl}-pyrrolidin-3-yl)-3-(R)-pyrrolidin-3-yl-urea hydrochloride A reaction mixture comprising (1R,2S,3R,5S)-3-{6-[2,2-bis-(4-hydroxy-phenyl)-ethylamino]-2-chloro-purin-9-yl}-5-(5-ethyl-tetrazol-2-yl)-cyclopentane-1,2-diol (Intermediate BF1) (2.5 g, 4.80 mmol) and 1,3-di(R)-pyrrolidin-3-yl-urea (Intermediate EC) (2.7 g, 13.6 mmol) in DMSO (8 ml) is heated at 100° C. overnight. The title compound is obtained after purification by reverse phase column chromatography (Isolute™ C18, 0-100% MeCN in water—0.1% HCl). MS (ES+) m/e 740.43 (MH+).

Example 147

1-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-3-(R)-pyrrolidin-3-yl-urea hydrochloride A reaction mixture comprising (1R,2S,3R,5S)-3-[2-chloro-6-(2,2-diphenyl-ethylamino)-purin-9-yl]-5-(4-ethyl-pyrazol-1-yl)-cyclopentane-1,2-diol (Intermediate BA8) (2.5 g, 4.80 mmol) and 1,3-di(R)-pyrrolidin-3-yl-urea (Intermediate EC) (2.7 g, 13.6 mmol) in DMSO (8 ml) is heated at 100° C. overnight. The title compound is obtained after purification by reverse phase column chromatography (Isolute™ C18, 0-100% MeCN in water—0.1% HCl). MS (ES+) m/e 706.47 (MH$^+$).

Example 148

1-((R)-1-{6-(2,2-Diphenyl-ethylamino)-9-[(1R,2S, 3R,4S)-4-(5-ethyl-tetrazol-2-yl)-2,3-dihydroxy-cyclopentyl]-9H-purin-2-yl}-pyrrolidin-3-yl)-3-(2-phenyl-thiazol-4-ylmethyl)-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with C-(2-phenyl-thiazol-4-yl)-methylamine. MS (ES+) m/e 812.46 (MH$^+$).

Example 149

1-[2-(1H-Benzoimidazol-2-yl)-ethyl]-3-((R)-1-{6-(2, 2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 2-(1H-benzoimidazol-2-yl)-ethylamine. MS (ES+) m/e 783.55 (MH$^+$).

Example 150

1-((R)-1-{6-(2,2-Diphenyl-ethylamino)-9-[(1R,2S, 3R,4S)-4-(5-ethyl-tetrazol-2-yl)-2,3-dihydroxy-cyclopentyl]-9H-purin-2-yl}-pyrrolidin-3-yl)-3-quinolin-4-ylmethyl-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with C-quinolin-4-yl-methylamine. MS (ES+) m/e 780.55 (MH$^+$).

Example 151

1-((R)-1-{6-(2,2-Diphenyl-ethylamino)-9-[(1R,2S, 3R,4S)-4-(5-ethyl-tetrazol-2-yl)-2,3-dihydroxy-cyclopentyl]-9H-purin-2-yl}-pyrrolidin-3-yl)-3-pyrimidin-4-ylmethyl-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with C-pyrimidin-4-yl-methylamine. MS (ES+) m/e 731.46 (MH$^+$)

Example 152

4-[3-((R)-1-{6-(2,2-Diphenyl-ethylamino)-9-[(1R, 2S,3R,4S)-4-(5-ethyl-tetrazol-2-yl)-2,3-dihydroxy-cyclopentyl]-9H-purin-2-yl}-pyrrolidin-3-yl)-ureidomethyl]-benzoic acid methyl ester hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxcyclopentyl]-9H-purin-2-yl}-pyrrolidin-3-yl)-3-pyridin-2-ylmethyl-urea hydrochloride (Example 113) by replacing 2-aminomethyl pyridine with 4-aminomethyl-benzoic acid methyl ester. MS (ES+) m/e 787.45 (MH$^+$)

Example 153

4-{2-[3-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-ureido]-ethyl}-benzoic acid hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 4-(2-amino-ethyl)-benzoic acid. MS (ES+) m/e 787.51 (MH$^+$)

Example 154

4-[3-((R)-1-{6-(2,2-Diphenyl-ethylamino)-9-[(1R, 2S,3R,4S)-4-(5-ethyl-tetrazol-2-yl)-2,3-dihydroxy-cyclopentyl]-9H-purin-2-yl}-pyrrolidin-3-yl)-ureidomethyl]-benzamidine hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-2-ylmethyl-urea hydrochloride (Example 113) by replacing 2-aminomethyl pyridine with 4-aminomethyl-benzamidine. MS (ES+) m/e 771.56 (MH$^+$)

Example 155

1-(6-Cyano-pyridin-3-yl)-3-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-urea hydrochloride a) (6-cyano-pyridin-3-yl)-carbamic acid 4-nitro-phenyl ester:
5-amino-2-cyano-pyridine (50 mg, 0.42 mmol) and potassium carbonate (116 mg, 0.84 mmol) are dissolved in N-methyl 2-pyrrolidone (1 ml). 4-Nitrophenyl chloroformate is added and the reaction mixture is stirred at room temperature for 2 hours.

b) 1-(6-Cyano-pyridin-3-yl)-3-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-urea hydrochloride: ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48 (20 mg, 0.03 mmol) is place in a vial with (6-cyano-pyridin-3-yl)-carbamic acid 4-nitro-phenyl ester (0.15 ml of step a) reaction mixture). The reaction mixture is heated at 110° C. over night. The title compound is obtained after purification by reverse phase column chromatography (Isolute™ C18, 0-100% MeCN in water-0.1% HCl). MS (ES+) m/e 741.49 (MH$^+$).

Example 156

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(6-methoxy-pyridin-3-yl)-urea hydrochloride a) (6-Methoxy-pyridin-3-yl)-carbamic acid phenyl ester 5-amino-2-methoxy-pyridine (30 mg, 0.24 mmol) and potassium carbonate (167 mg, 1.20 mmol) are dissolved in N-methyl 2-pyrrolidone (1 ml). Phenyl chloroformate (36 µl, 0.29 mmol) is added and the reaction mixture is stirred at room temperature for 2 hours.

b) 1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(6-methoxy-pyridin-3-yl)-urea hydrochloride ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) (20 mg, 0.03 mmol) is placed in a vial with (6-methoxy-pyridin-3-yl)-carbamic acid phenyl ester (0.28 ml of step a) reaction mixture). The reaction mixture is heated at 110° C. over the weekend. The title compound is obtained after purification by reverse phase column chromatography (Isolute™ C18, 0-100% MeCN in water—0.1% HCl). MS (ES+) m/e 746.53 (MH$^+$).

Example 157

1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-[3-(1H-tetrazol-5-yl)-phenyl]-urea hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(6-methoxy-pyridin-3-yl)-urea hydrochloride (Example 156) by replacing (6-Methoxy-pyridin-3-yl)-carbamic acid phenyl ester with 3-(1H-tetrazol-5-yl)-phenylamine (first step a).
MS (ES+) m/e 783.47 (MH$^+$).

Example 158

4-[3-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-ureido]-benzenesulfonamide hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea (Example 105) by replacing pyridine-3-isocyanate with 4-isocyanato-benzenesulfonamide (Intermediate EE). MS (ES+) m/e 794.97 (MH$^+$).

Example 159

4-[3-((R)-1-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-ureidomethyl]-benzoic acid hydrochloride 4-[3-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-ureidomethyl]-benzoic acid methyl ester hydrochloride. (Example 152) (40 mg, 0.05 mmol) is dissolved in methanol (1 ml). KOH (6 mg, 0.12 mmol) is dissolved in water (0.05 ml) and added to the reaction mixture. The reaction mixture is stirred at room temperature for 48 hours. The title compound is obtained after purification by reverse phase column chromatography (Isolute™ C18, 0-100% MeCN in water—0.1% HCl). MS (ES+) m/e 773.969 (MH$^+$).

Example 160

1-((R)-{6-(2,2-Diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-(5-methyl-isoxazol-3-yl)-urea Hydrochloride This compound is prepared from ((1R,2S,3R,5S)-3-[2-((R)-3-amino-pyrrolidin-1-yl)-6-(2,2-diphenyl-ethylamino)-purin-9-yl]-5-(5-ethyl-tetrazol-2-yl)-cyclopentane-1,2-diol (Example 48) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea (Example 105) by replacing pyridine-3-isocyanate with 3-isocyanato-5-methyl-isoxazole (Intermediate EF). MS (ES+) m/e 720.91 (MH$^+$).

Example 161

4-[3-((R)-1-{6-(2,2-Diphenyl-ethylamino)-9-[(1R,2S,3R,4S)-4-(4-ethyl-pyrazol-1-yl)-2,3-dihydroxy-cyclopentyl]-9H-purin-2-yl}-pyrrolidin-3-yl)-ureido]-benzenesulfonamide Hydrochloride This compound is prepared from (1R,2S,3R,5S)-3-[2-((R)-3-amino-pyrrolidin-1-yl)-6-(2,2-diphenyl-ethylamino)-purin-9-yl]-5-(4-ethyl-pyrazol-1-yl)-cyclopentane-1,2-diol.

(Example 110) using a procedure analogous to that of 1-((R)-1-{6-(2,2-diphenyl-ethylamino)-9-[(1R,2S,3R,4S)-4-(5-ethyl-tetrazol-2-yl)-2,3-dihydroxy-cyclopentyl]-9H-purin-2-yl}-pyrrolidin-3-yl)-3-pyridin-3-yl-urea (Example 105), by replacing pyridine-3-isocyanate with 4-isocyanato-benzenesulfonamide (Intermediate EE). MS (ES+) m/e 792.94 (MH+).

The invention claimed is:
1. A compound of formula I

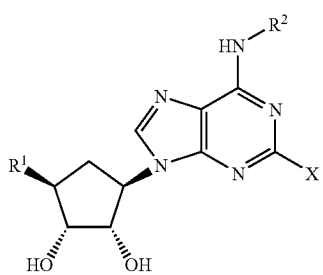

in free or salt form, wherein R¹, R², and R³ are illustrated in the table below:

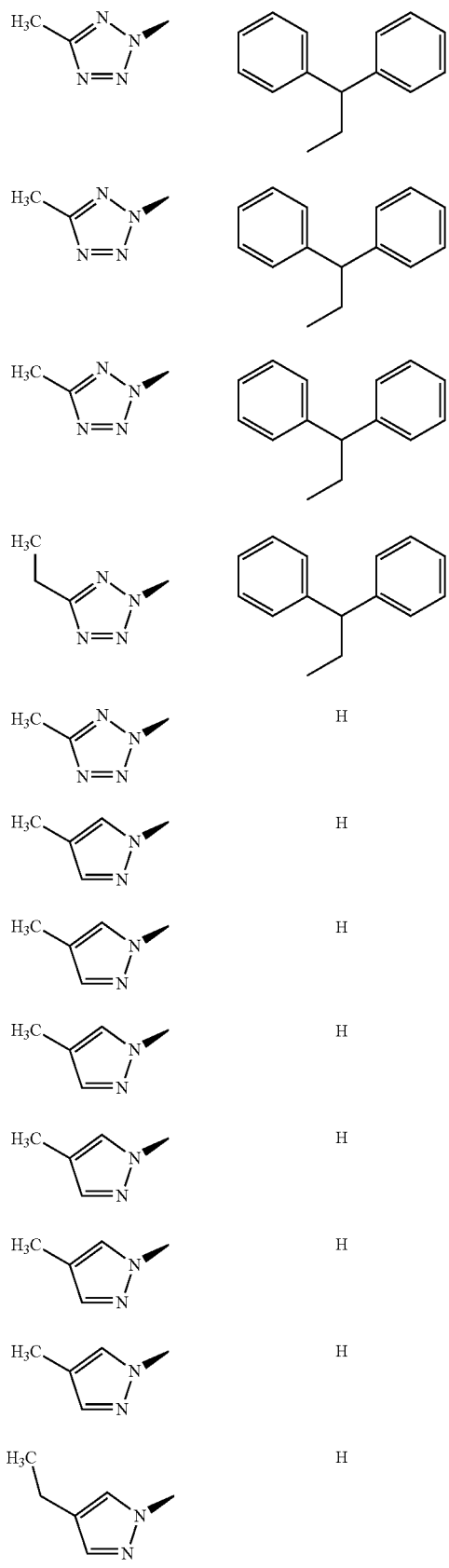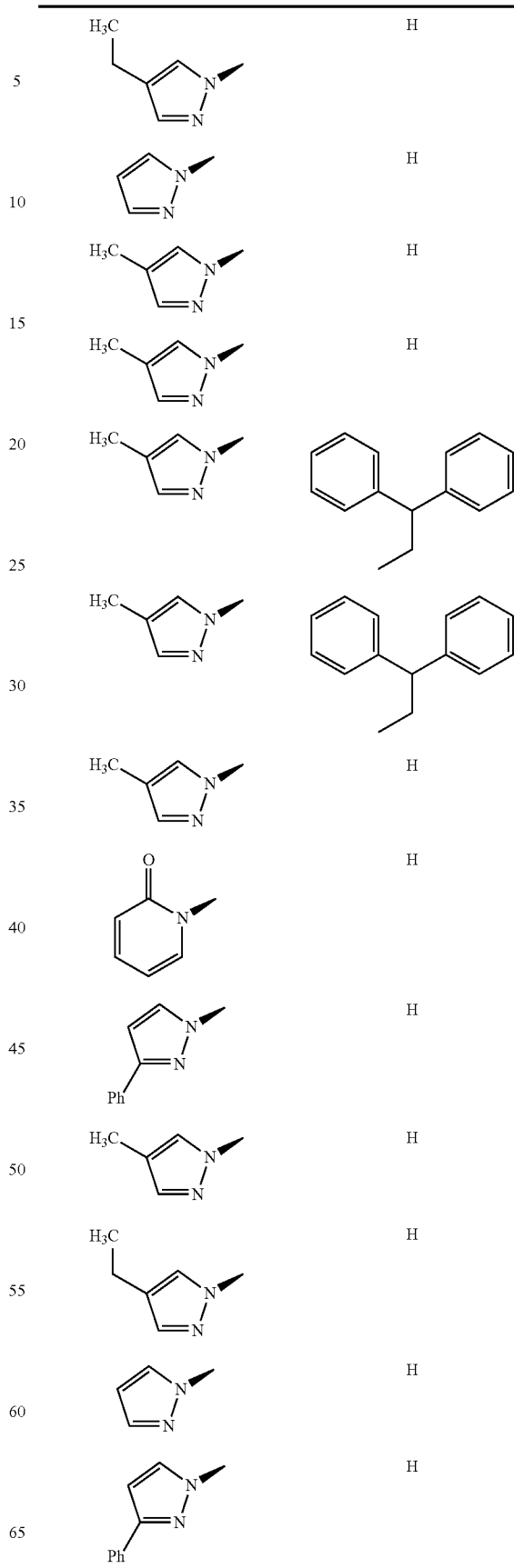

141
-continued

142
-continued

| 143 -continued | | | 144 -continued | |
|---|---|---|---|---|
| 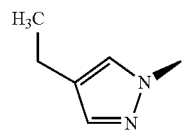 | 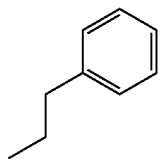 | 5 | 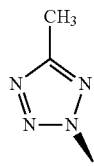 | 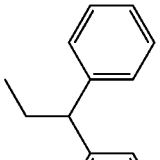 |
| 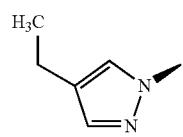 | 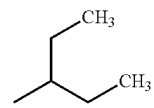 | 10 | | |
| 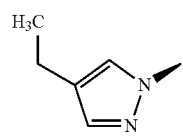 | 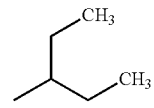 | 15 | 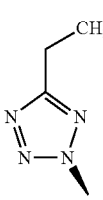 | 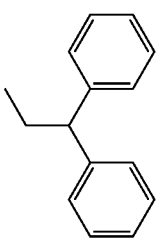 |
| 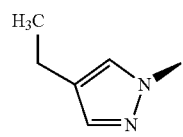 | 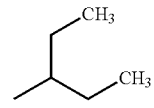 | 20 | | |
| 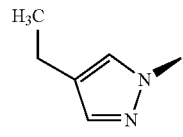 | 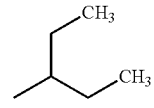 | 25 | 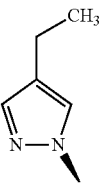 | 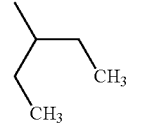 |
| 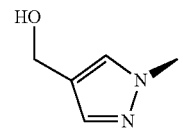 | 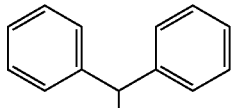 | 30 | 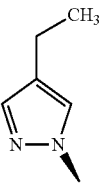 | 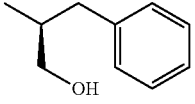 |
| 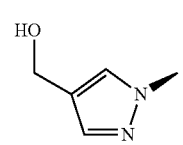 | 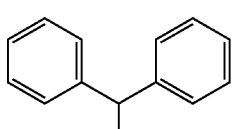 | 35 40 | 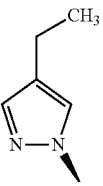 | 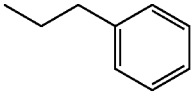 |
| 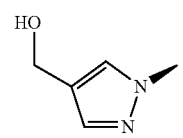 | 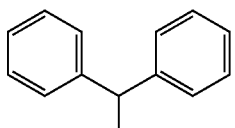 | 45 50 | 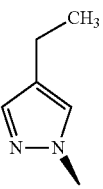 | 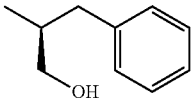 |
| 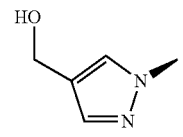 | 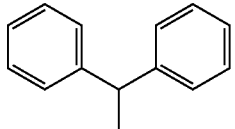 | 55 | 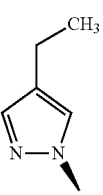 | 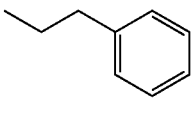 |
| 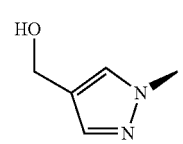 | 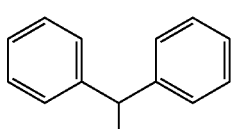 | 60 65 | 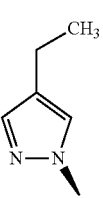 | 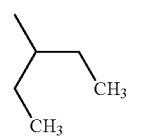 |

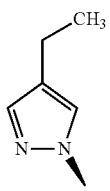 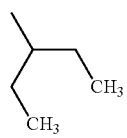 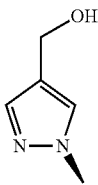 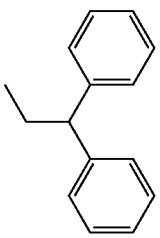
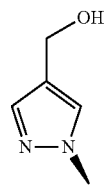 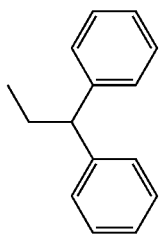 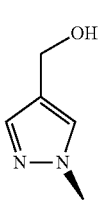 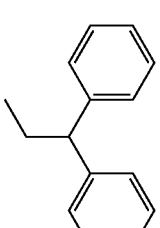
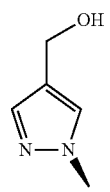 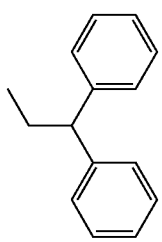 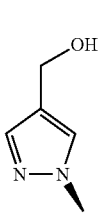 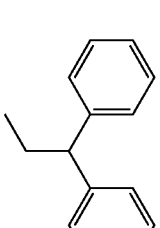
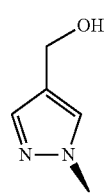 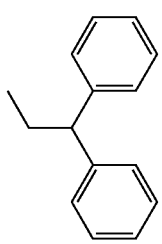 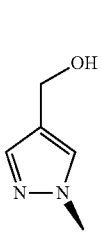 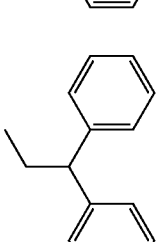
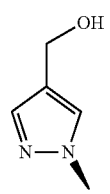 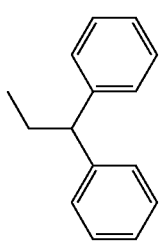 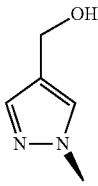 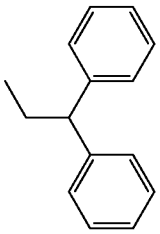
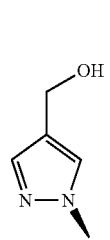 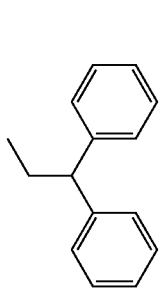 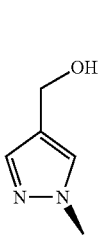 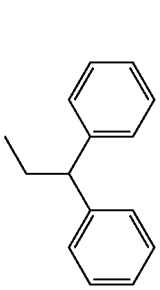

147
-continued
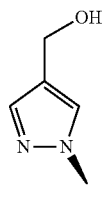 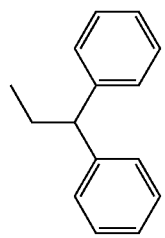
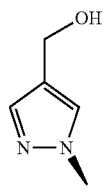 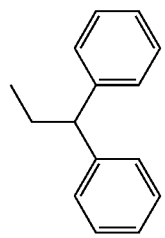
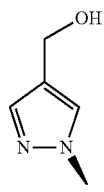 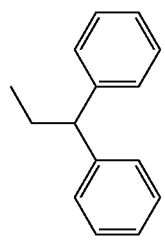
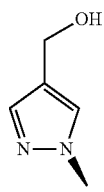 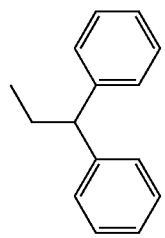
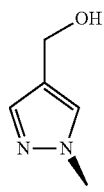 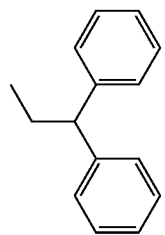
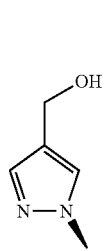 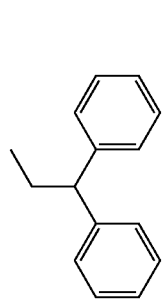
148
-continued
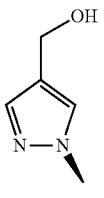 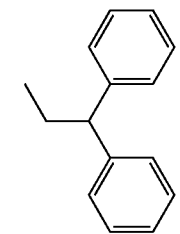
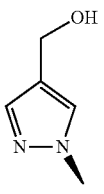 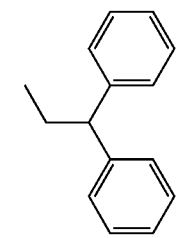
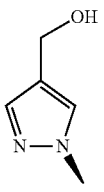 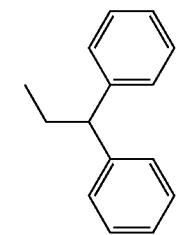
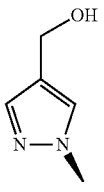 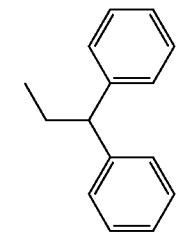
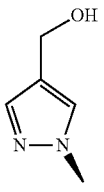 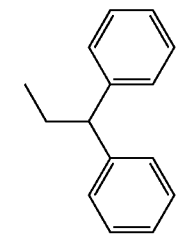
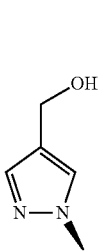 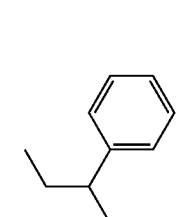

| 149 -continued | | 150 -continued | |
|---|---|---|---|
| 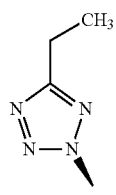 | 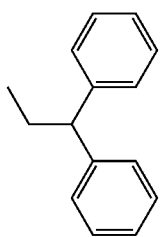 | 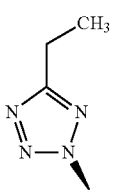 | 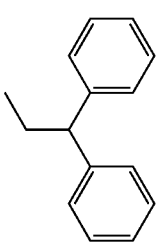 |
| 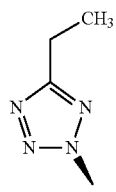 | 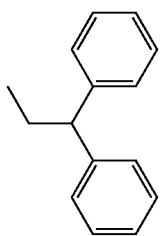 | 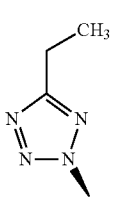 | 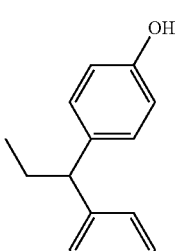 |
| 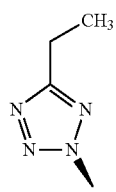 | 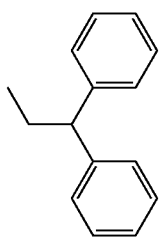 | 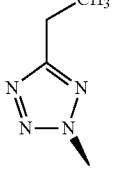 | 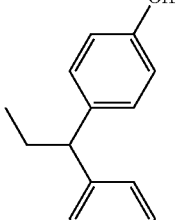 |
| 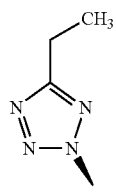 | 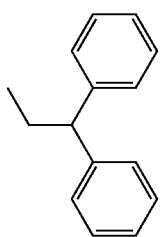 | 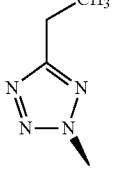 | 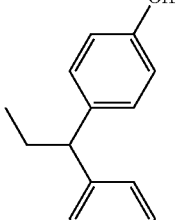 |
| 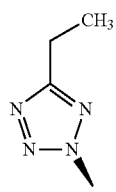 | 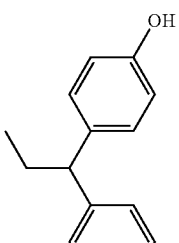 | 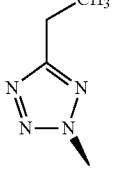 | 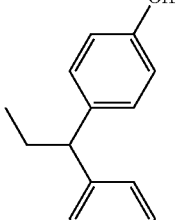 |
| 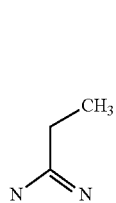 | 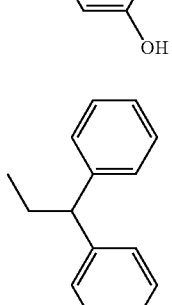 | 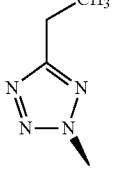 | 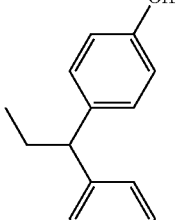 |

| 151 -continued | | 152 -continued | |
|---|---|---|---|
| 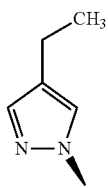 | 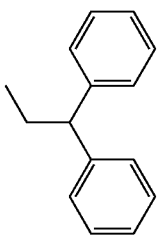 | 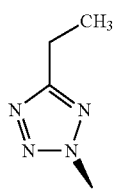 | 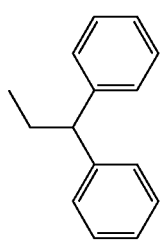 |
| 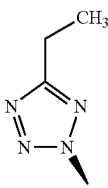 | 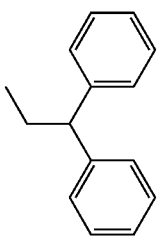 | 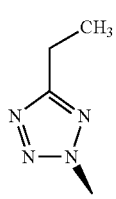 | 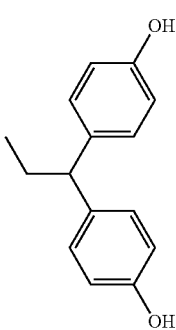 |
| 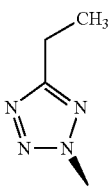 | 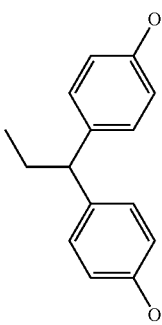 | 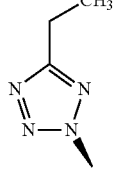 | 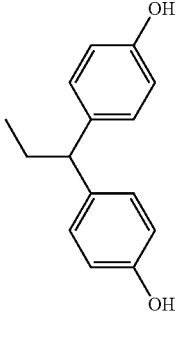 |
| 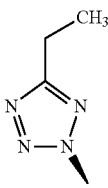 | 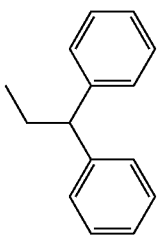 | 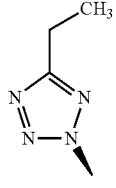 | 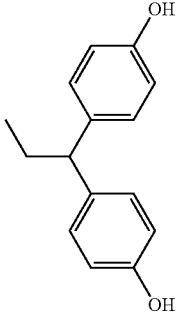 |
| 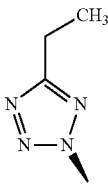 | 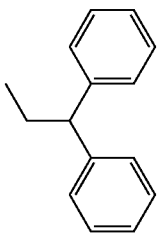 | 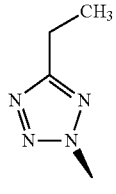 | 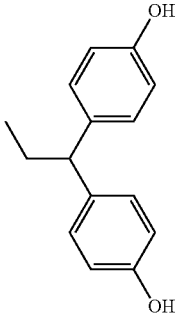 |
| 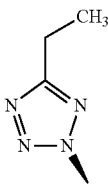 | 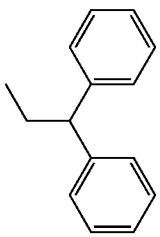 | | |

| 153 -continued | | 154 -continued | |
|---|---|---|---|
| 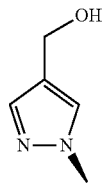 | 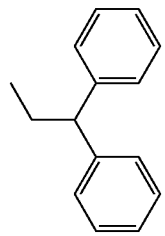 | 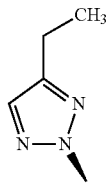 | 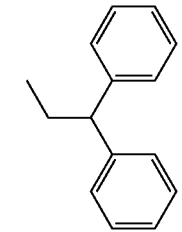 |
| 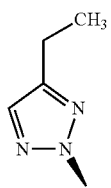 | 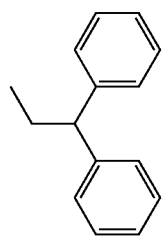 | 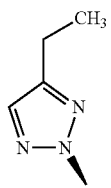 | 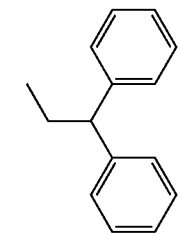 |
| 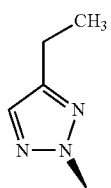 | 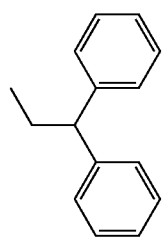 | 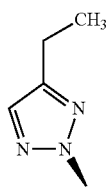 | 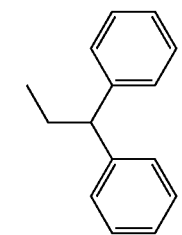 |
| 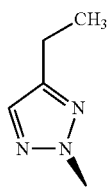 | 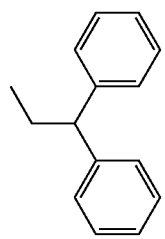 | 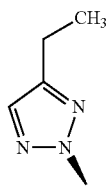 | 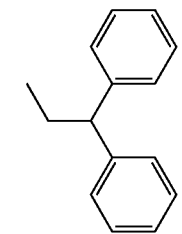 |
| 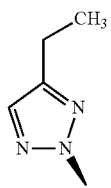 | 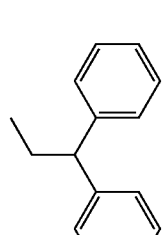 | 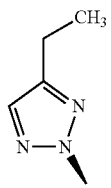 | 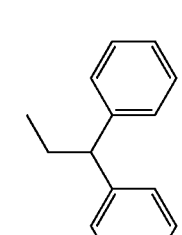 |
| 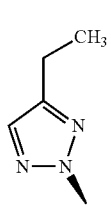 | 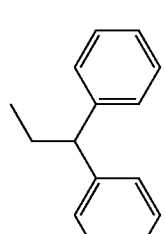 | 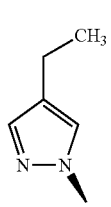 | 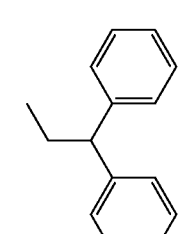 |

| 155 -continued | | 156 -continued | |
|---|---|---|---|
| 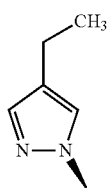 | 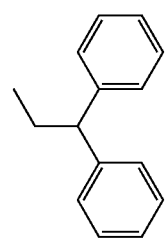 | 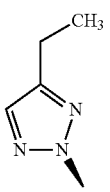 | 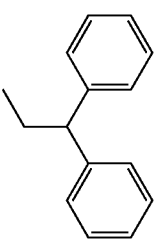 |
| 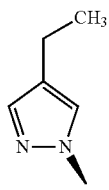 | 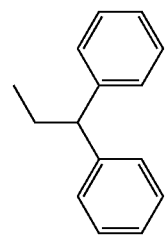 | 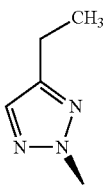 | 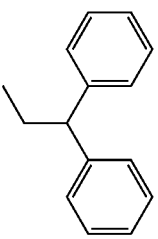 |
| 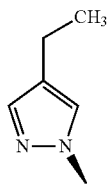 | 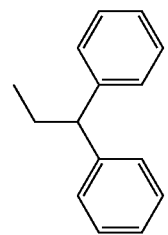 | 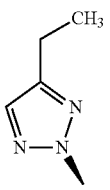 | 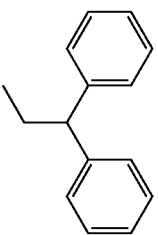 |
| 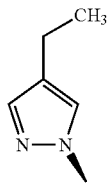 | 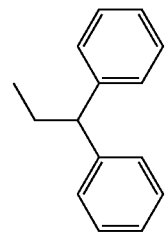 | 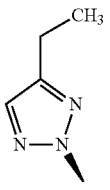 | 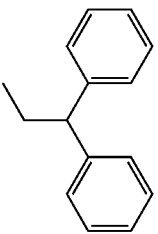 |
| 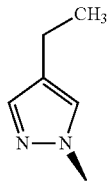 | 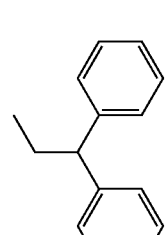 | 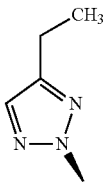 | 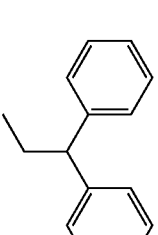 |
| 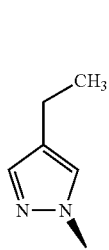 | 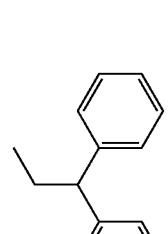 | 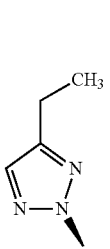 | 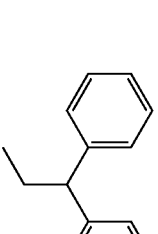 |

| 157 -continued | | 158 -continued | |
|---|---|---|---|
| 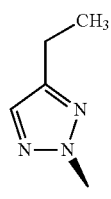 | 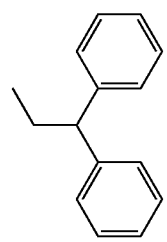 | 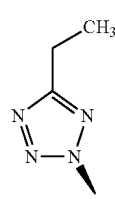 | 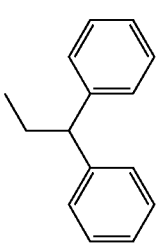 |
| 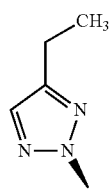 | 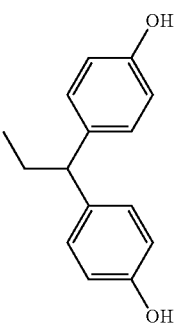 | 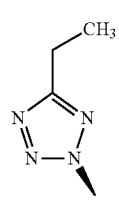 | 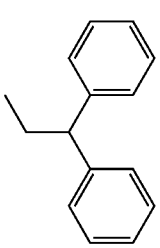 |
| 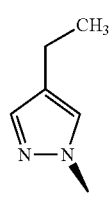 | 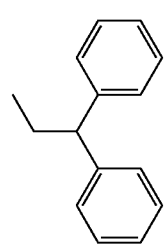 | 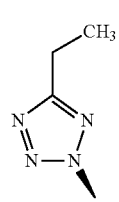 | 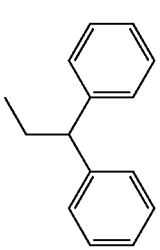 |
| 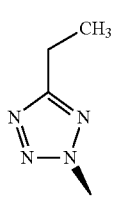 | 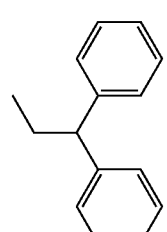 | 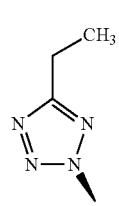 | 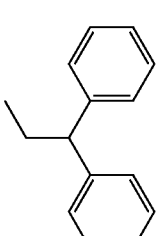 |
| 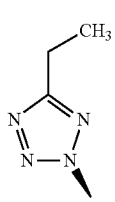 | 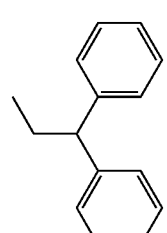 | 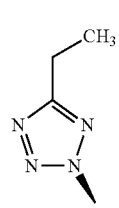 | 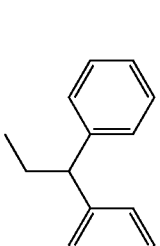 |
| 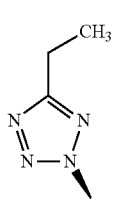 | 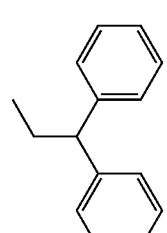 | | |

| 159 -continued | | | 160 -continued |
|---|---|---|---|
| 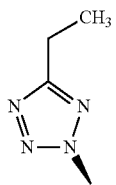 | 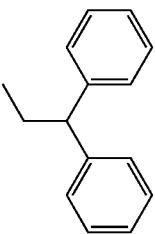 | 5 | 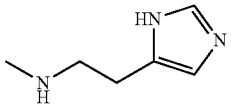 |
| | | 10 | 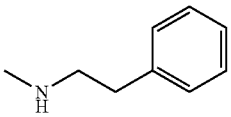 |
| 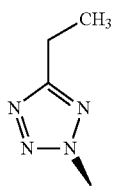 | 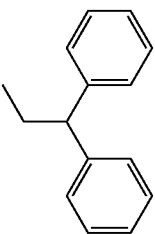 | 15 | 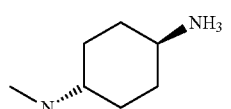 |
| | | 20 | 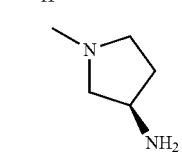 |
| 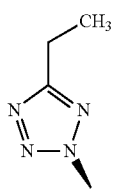 | 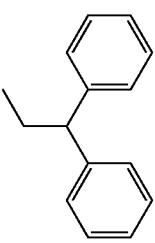 | 25 | 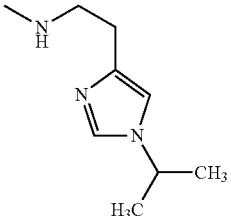 |
| | | 30 | |
| 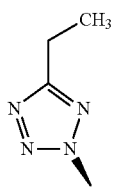 | 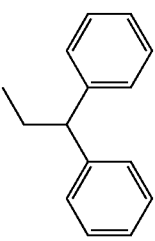 | 35 | 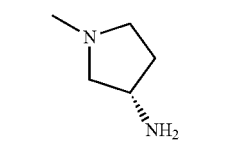 |
| | | 40 | 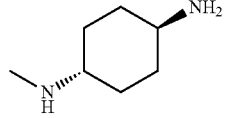 |
| 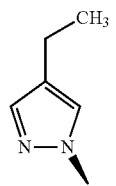 | 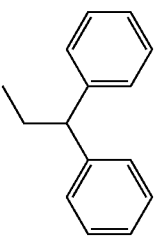 | 45 | 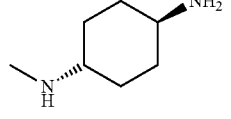 |
| R³ | | 50 | 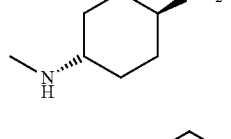 |
| 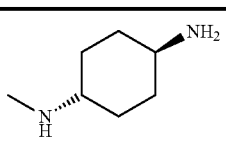 | | 55 | |
| 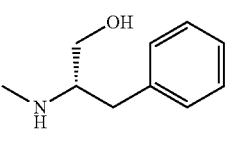 | | 60 | 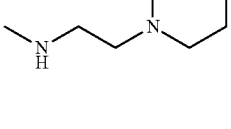 |
| 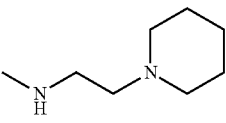 | | 65 | 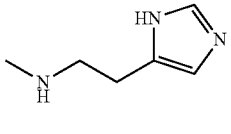 |

161
-continued
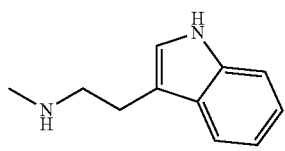
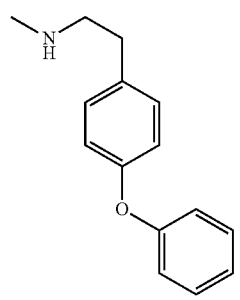
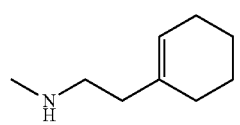
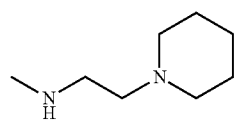
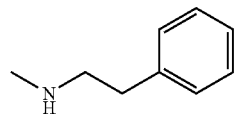
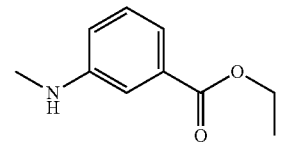
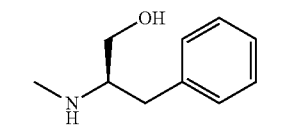
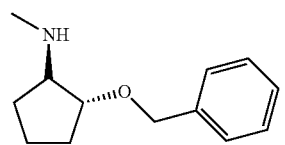
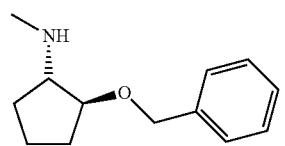
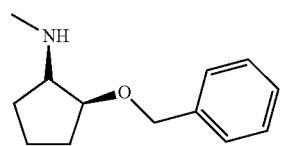
162
-continued
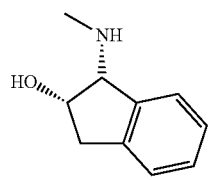
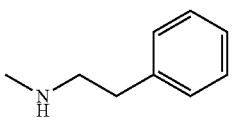
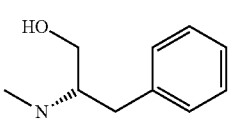
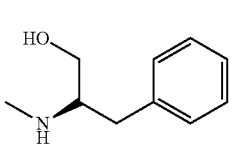
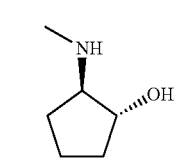
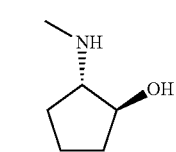
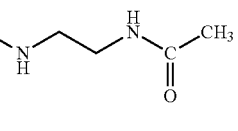
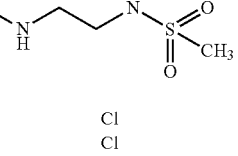
Cl
Cl
Cl
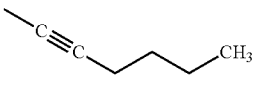
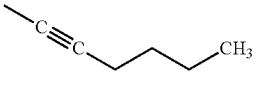
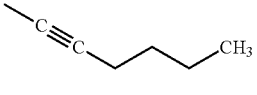
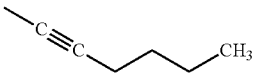

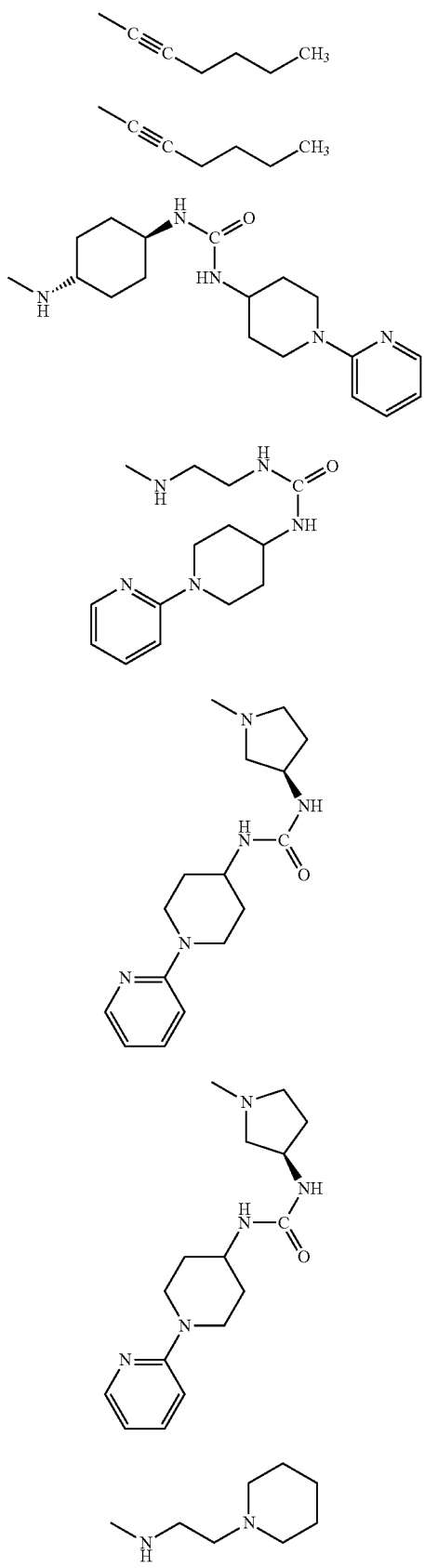
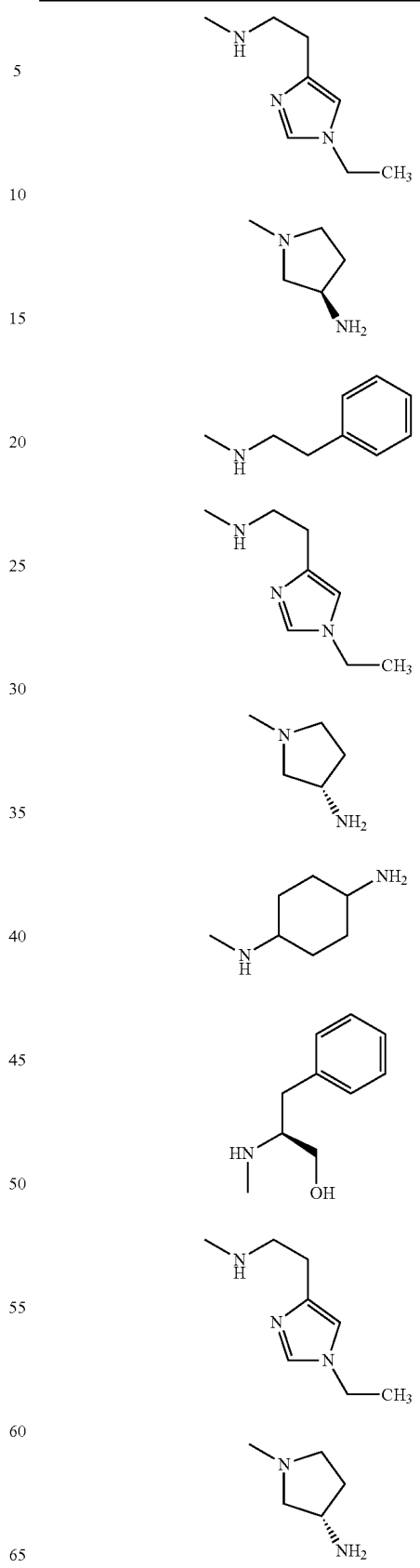

| 165 -continued | 166 -continued |
|---|---|
| 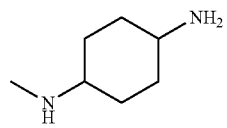 | 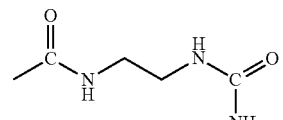 |
| 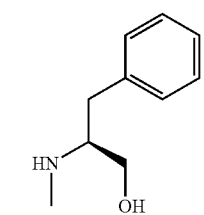 | 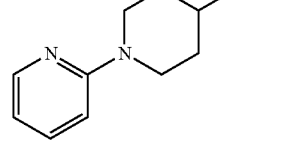 |
| 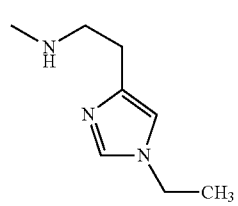 | 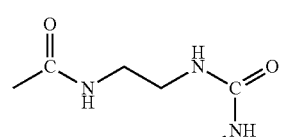 |
| 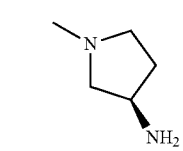 | 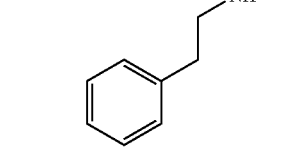 |
| 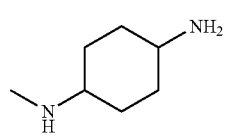 | 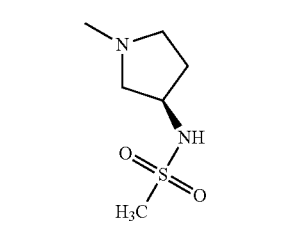 |
| 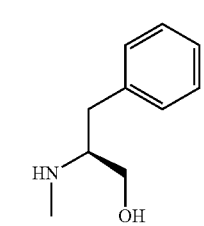 | 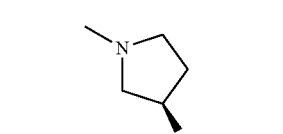 |
| 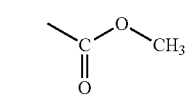 | 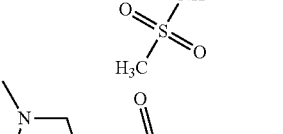 |
| 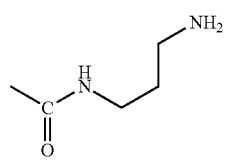 | 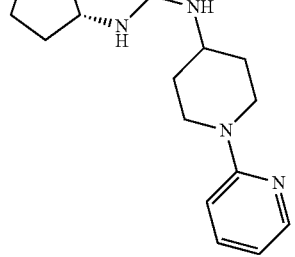 |
| 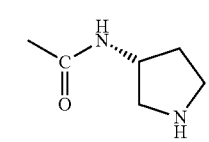 | 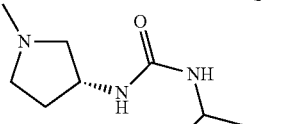 |
|  | 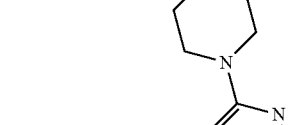 |
|  |  |

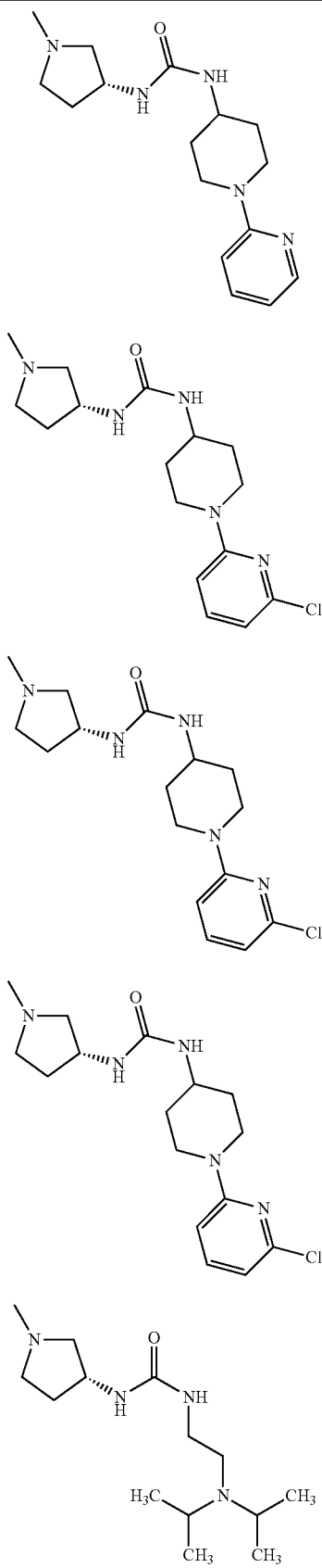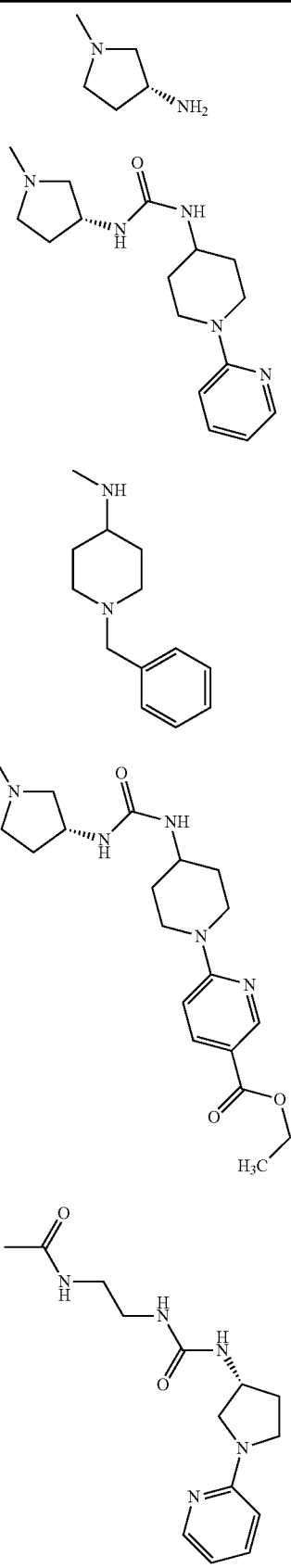

| 169 -continued | 170 -continued |
|---|---|
| 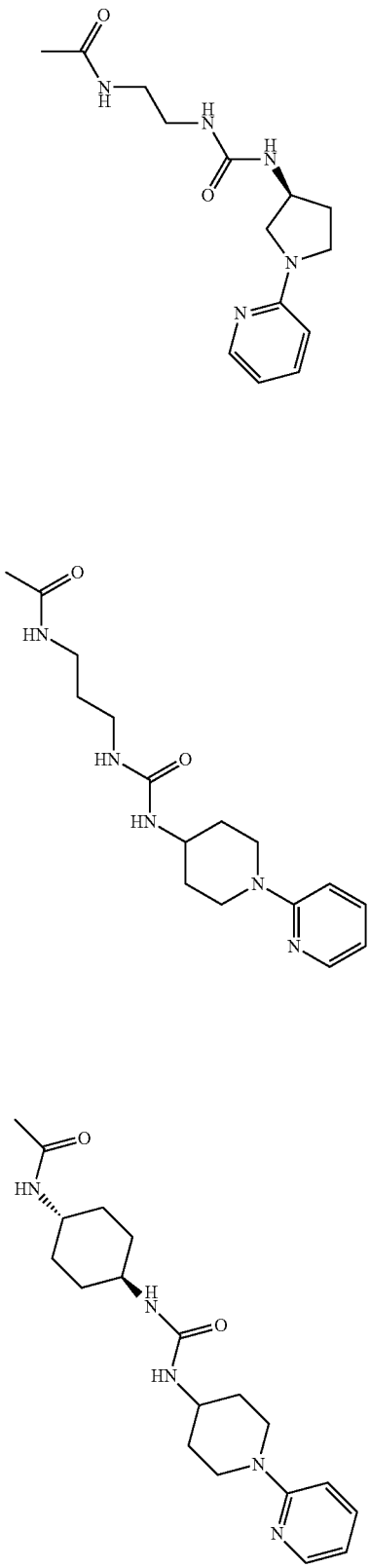 | 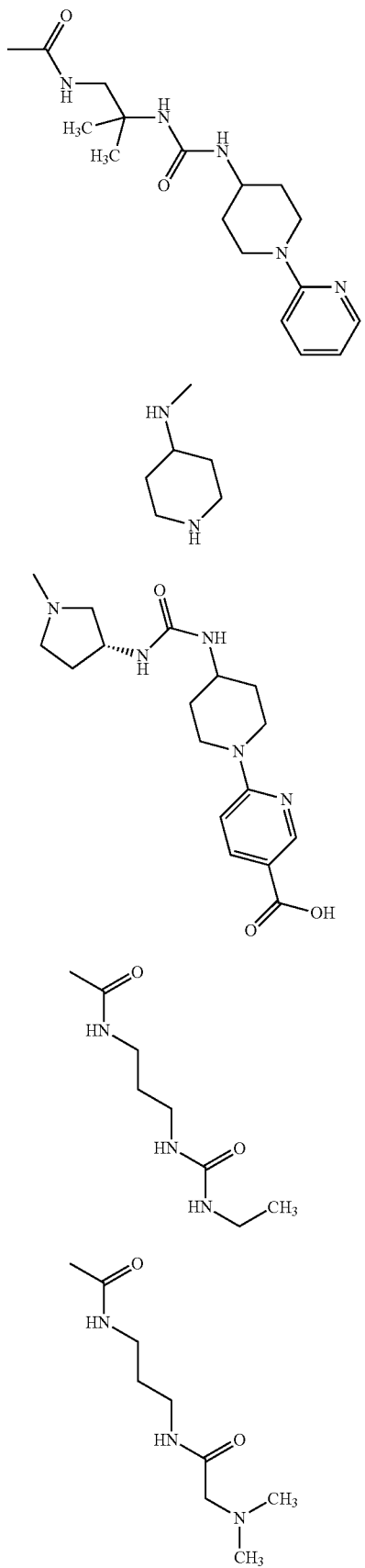 |

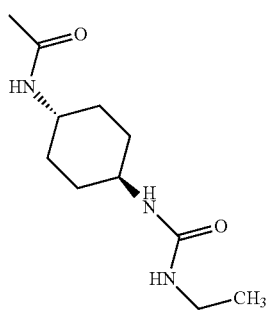
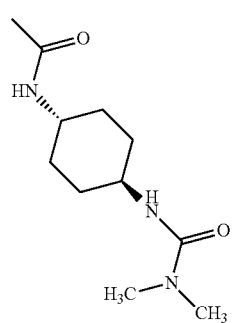
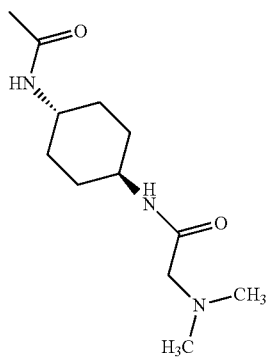
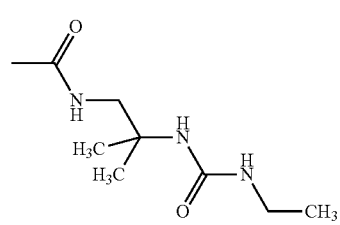
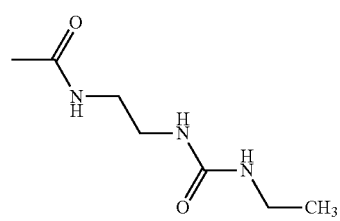
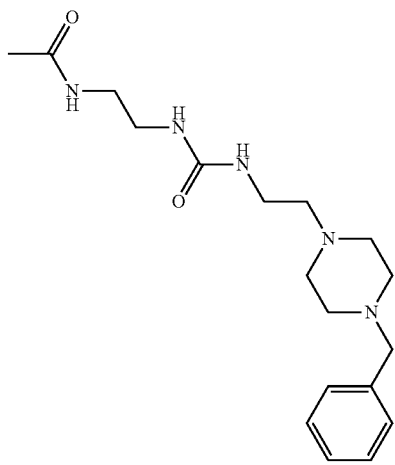
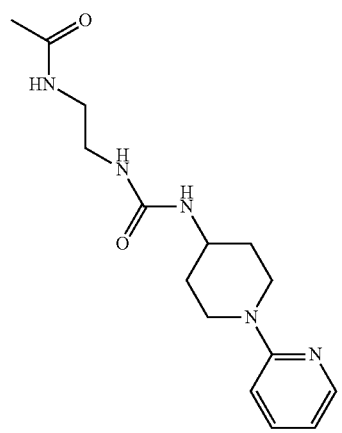
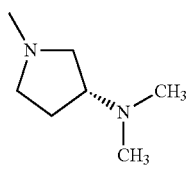
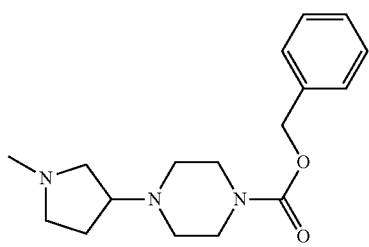
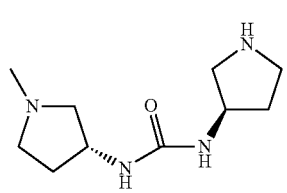

-continued
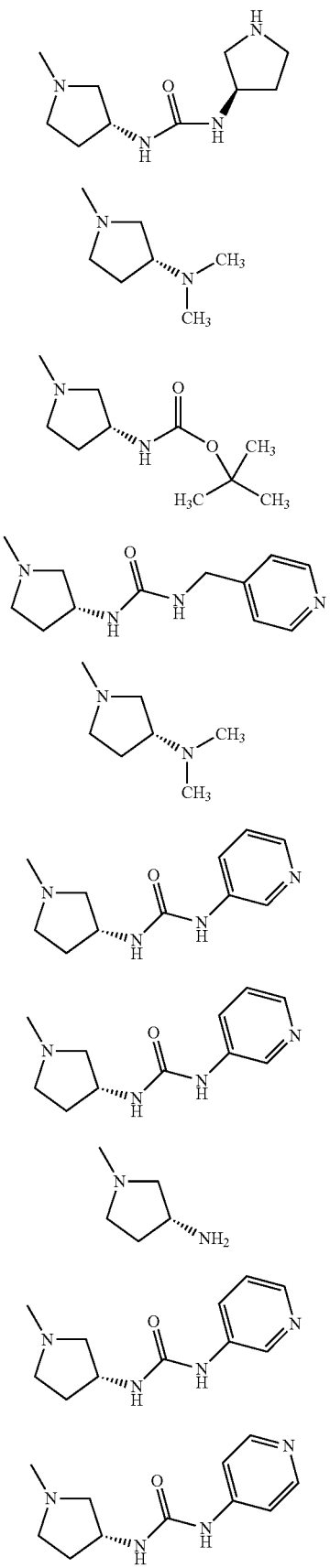
-continued
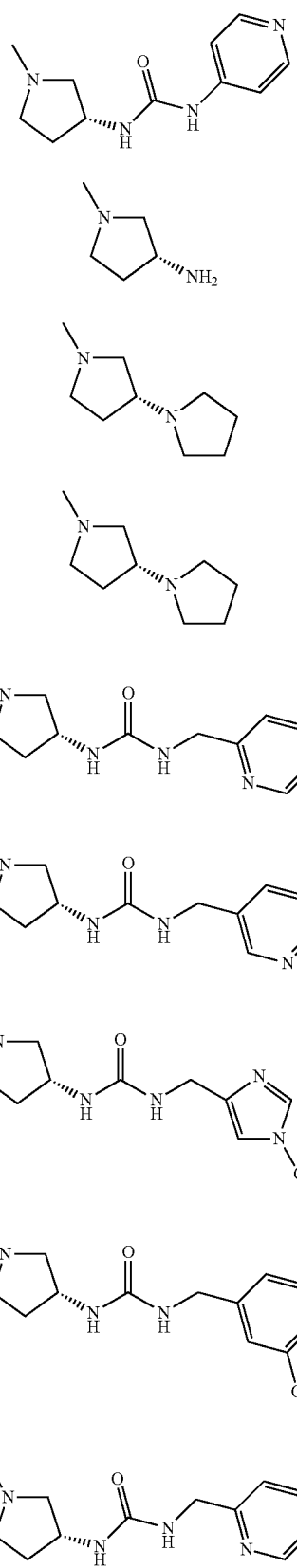

-continued
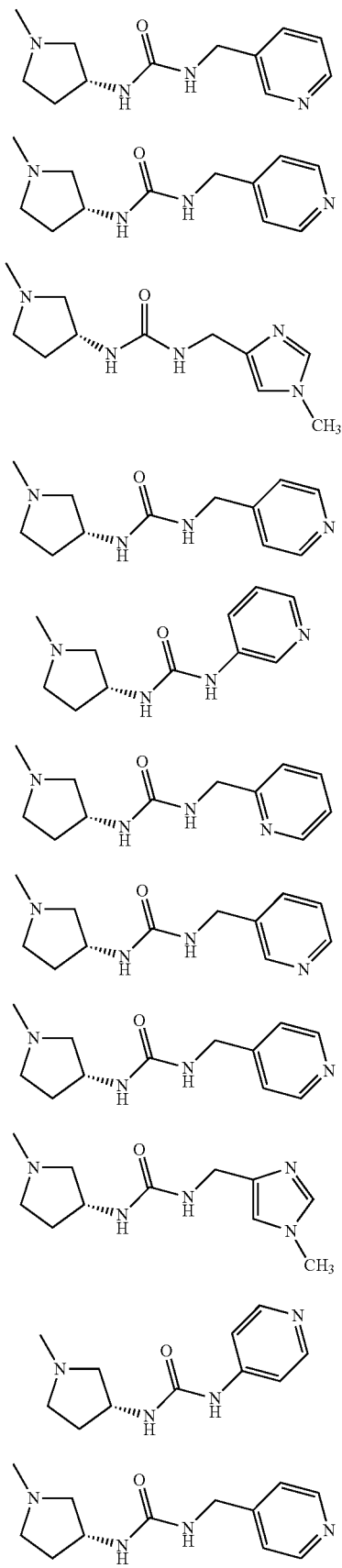
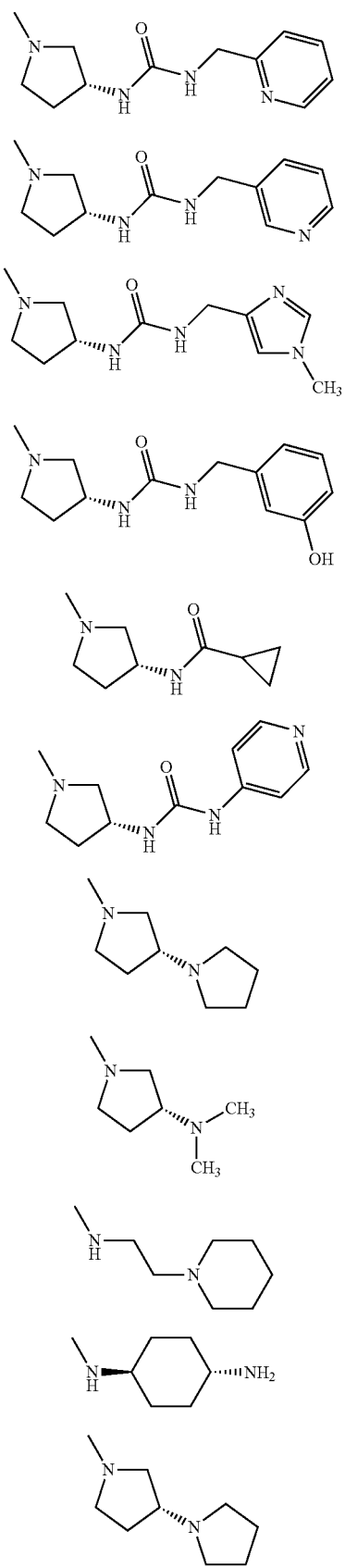

177
-continued
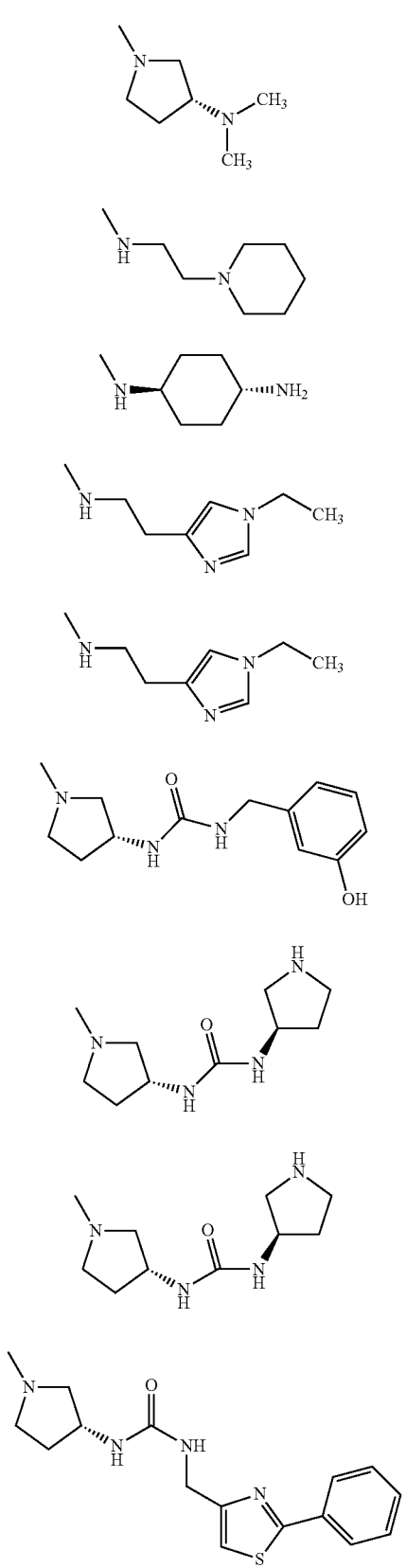
178
-continued
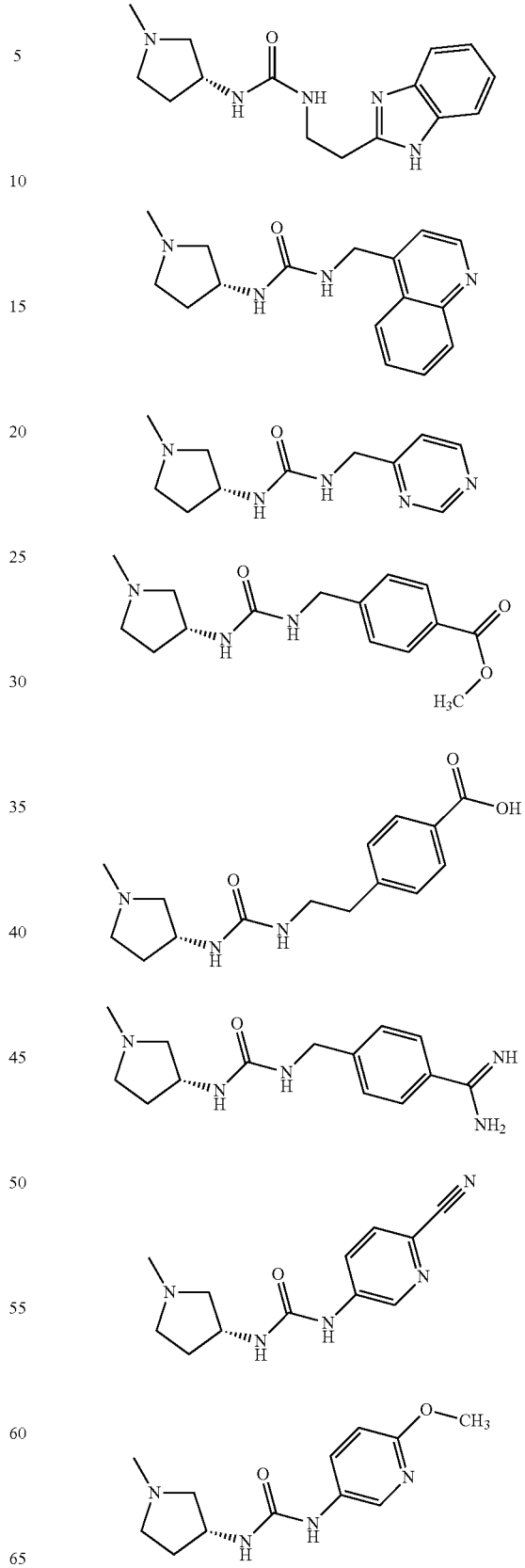

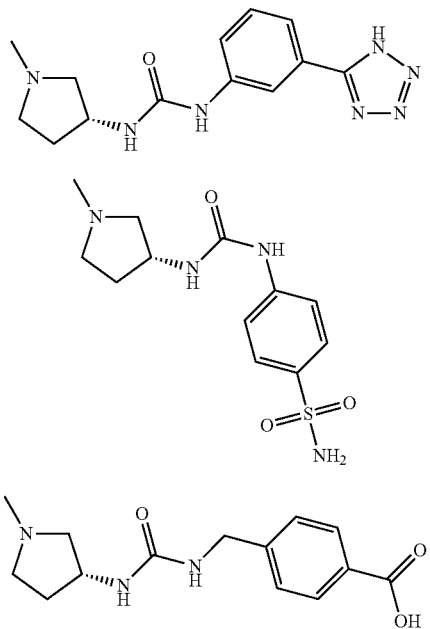
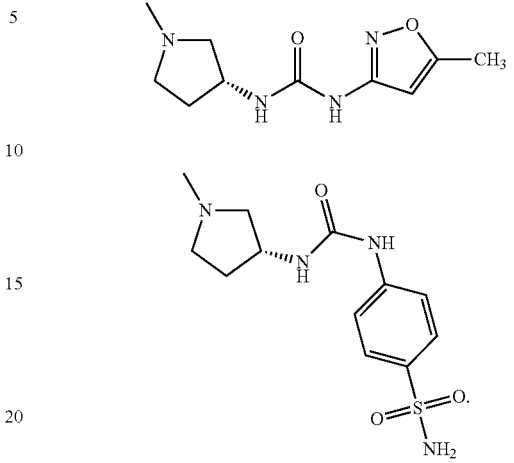
2. The compound of claim 1, wherein $R^1$, $R^2$, and $R^3$ are selected from the group consisting of:
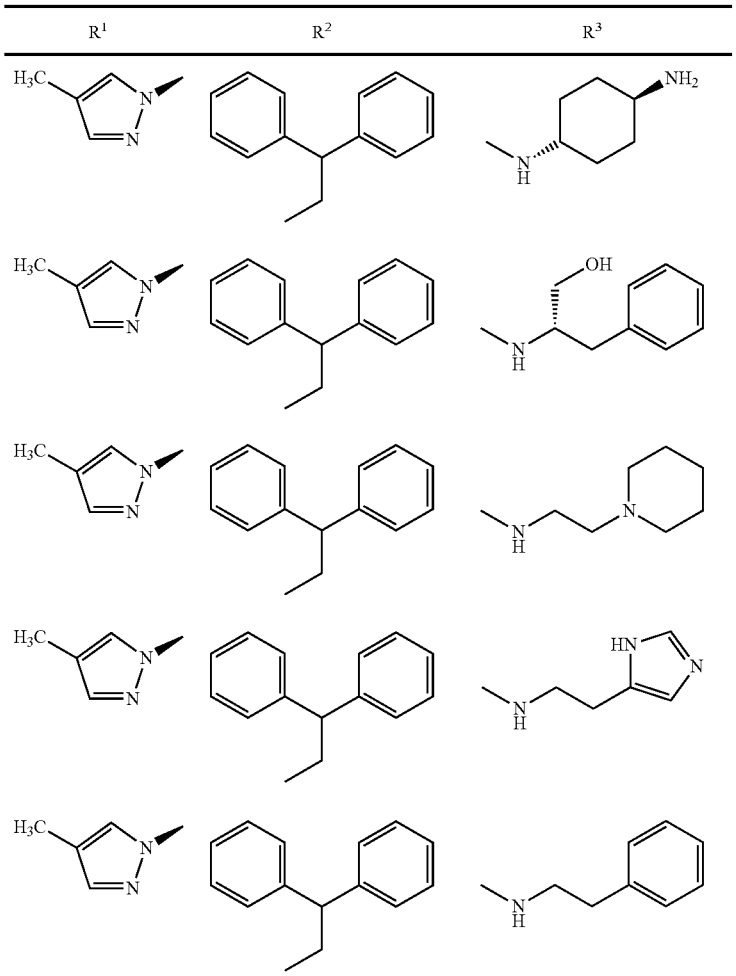

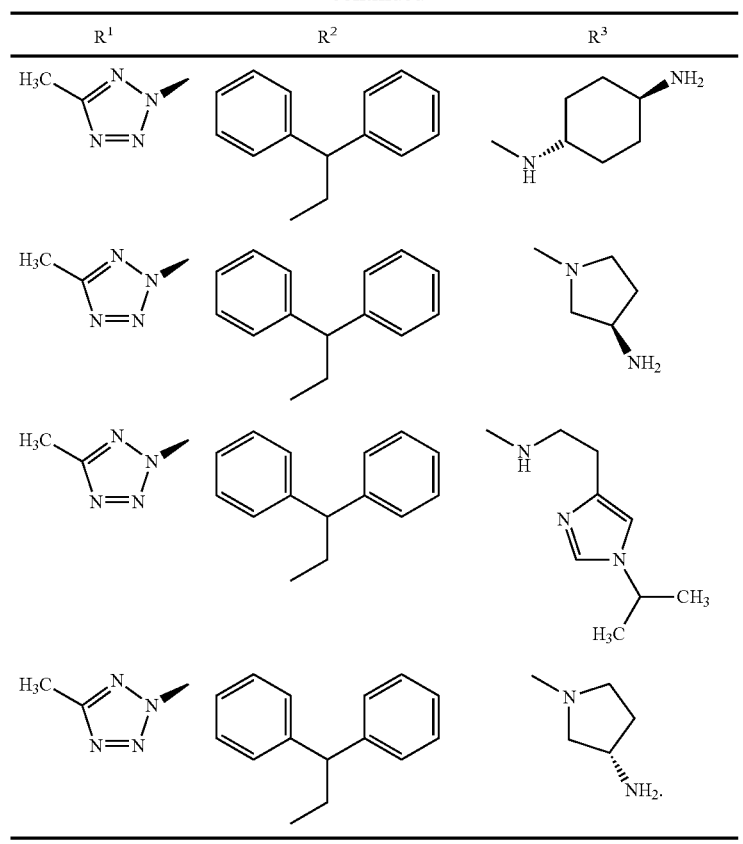
3. The compound of claim 1, wherein $R^1$, $R^2$, and $R^3$ are selected from the group consisting of:
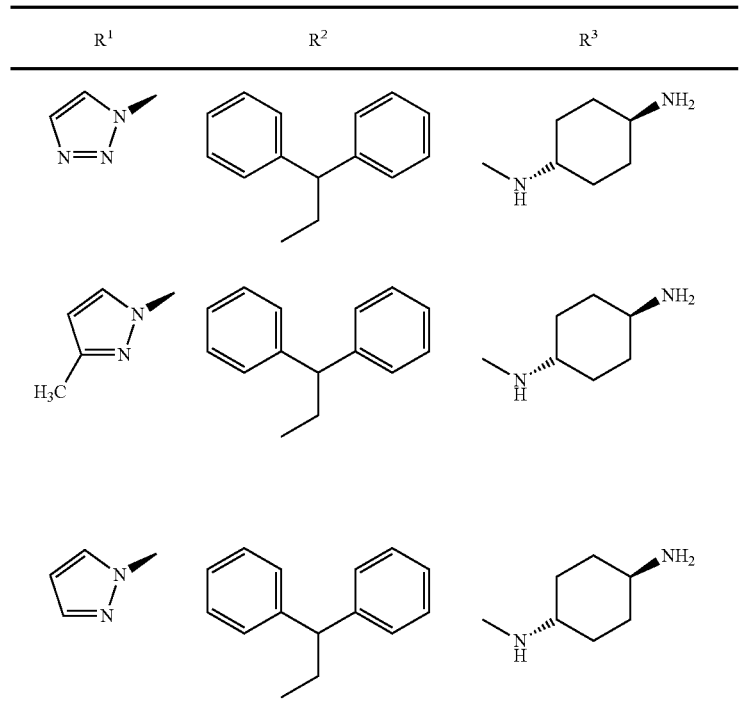

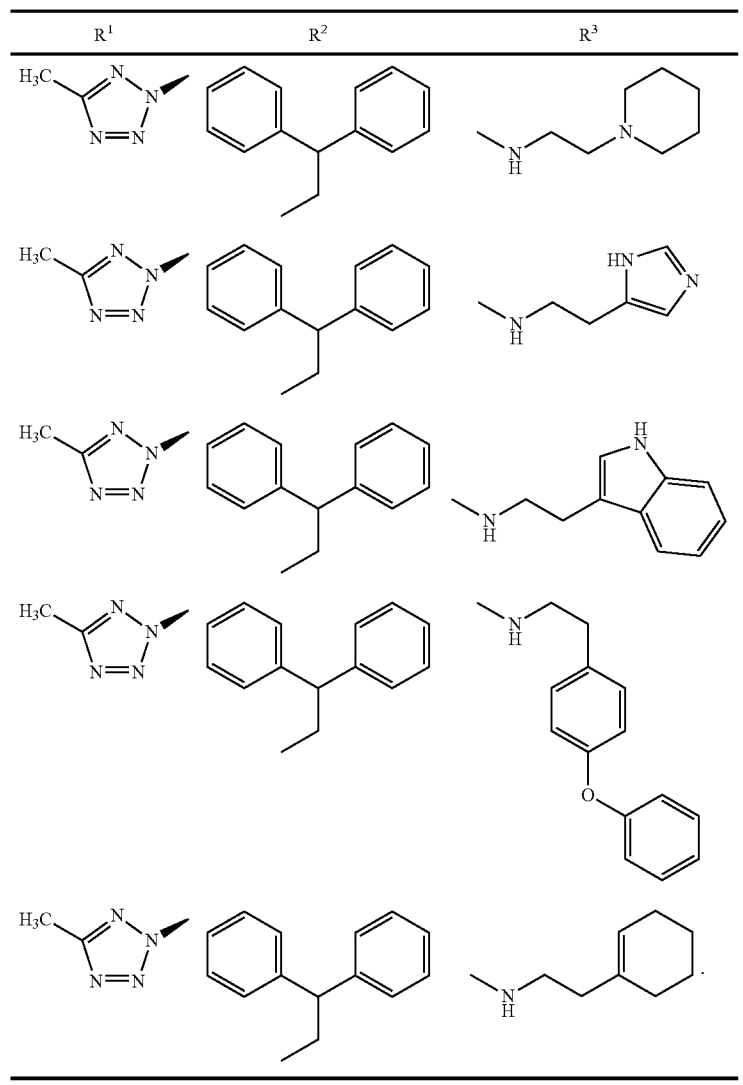
4. The compound of claim 1, wherein $R^1$, $R^2$, and $R^3$ are selected from the group consisting of:
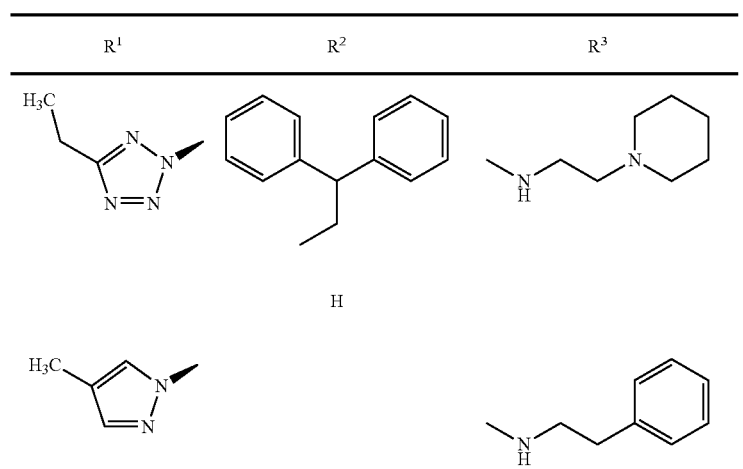

-continued

| R¹ | R² | R³ |
|---|---|---|
| 4-methyl-pyrazol-1-yl | H | ethyl 3-(methylamino)benzoate |
| 4-methyl-pyrazol-1-yl | H | 2-(methylamino)-3-phenylpropan-1-ol |
| 4-methyl-pyrazol-1-yl | H | (1,2)-2-(benzyloxy)-N-methylcyclopentanamine |
| 4-methyl-pyrazol-1-yl | H | (1,2)-2-(benzyloxy)-N-methylcyclopentanamine |
| 4-methyl-pyrazol-1-yl | H | (1,2)-2-(benzyloxy)-N-methylcyclopentanamine |
| 4-methyl-pyrazol-1-yl | H | 1-(methylamino)-2,3-dihydro-1H-inden-2-ol |
| 4-ethyl-pyrazol-1-yl | H | N-methyl-2-phenylethanamine |
| 4-ethyl-pyrazol-1-yl | H | 2-(methylamino)-3-phenylpropan-1-ol |

5. The compound of claim 1, wherein R¹, R², and R³ are selected from the group consisting of:

| R¹ | R² | R³ |
|---|---|---|
| pyrazol-1-yl | H | 2-(methylamino)-3-phenylpropan-1-ol |

-continued
| R¹ | R² | R³ |
|---|---|---|
| 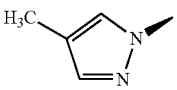 | H | 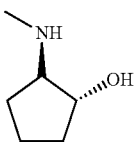 |
| 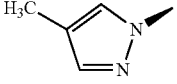 | H | 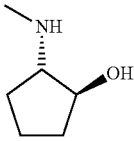 |
| 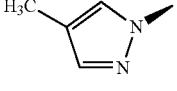 | 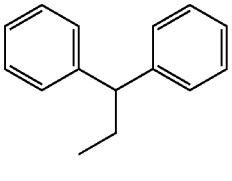 | 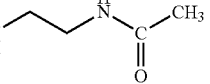 |
| 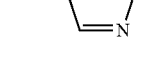 | 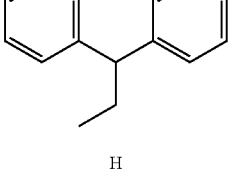 | 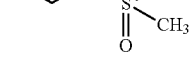 |
| 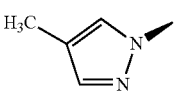 | H | Cl |
| 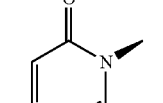 | H | Cl |
| 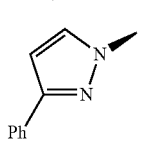 | H | Cl |
| 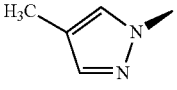 | H | 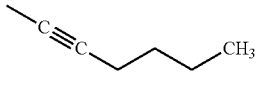 |
| 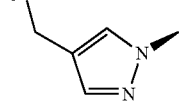 | H | 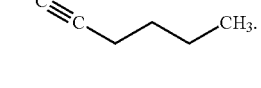 |
6. The compound of claim 1, wherein R¹, R², and R³ are selected from the group consisting of:
| R¹ | R² | R³ |
|---|---|---|
| 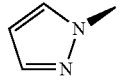 | H | 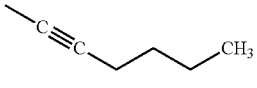 |

-continued
| R¹ | R² | R³ |
|---|---|---|
| 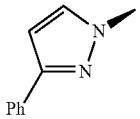 | H |  |
| 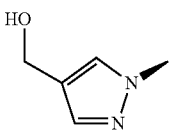 | H |  |
| 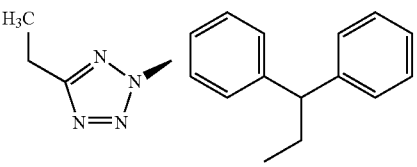 |  | 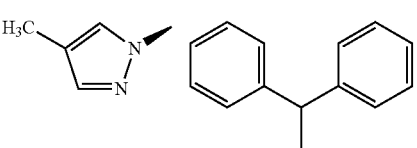 |
| 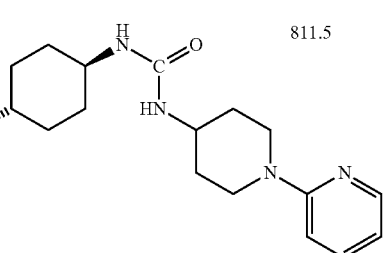 | 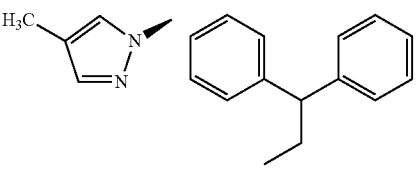 | 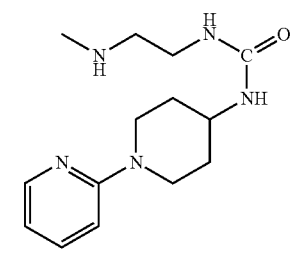 811.5 |
| 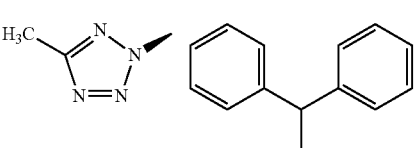 | 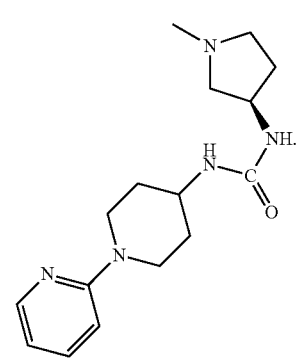 | |

7. The compound of claim 1, wherein $R^1$, $R^2$, and $R^3$ are selected from the group consisting of:
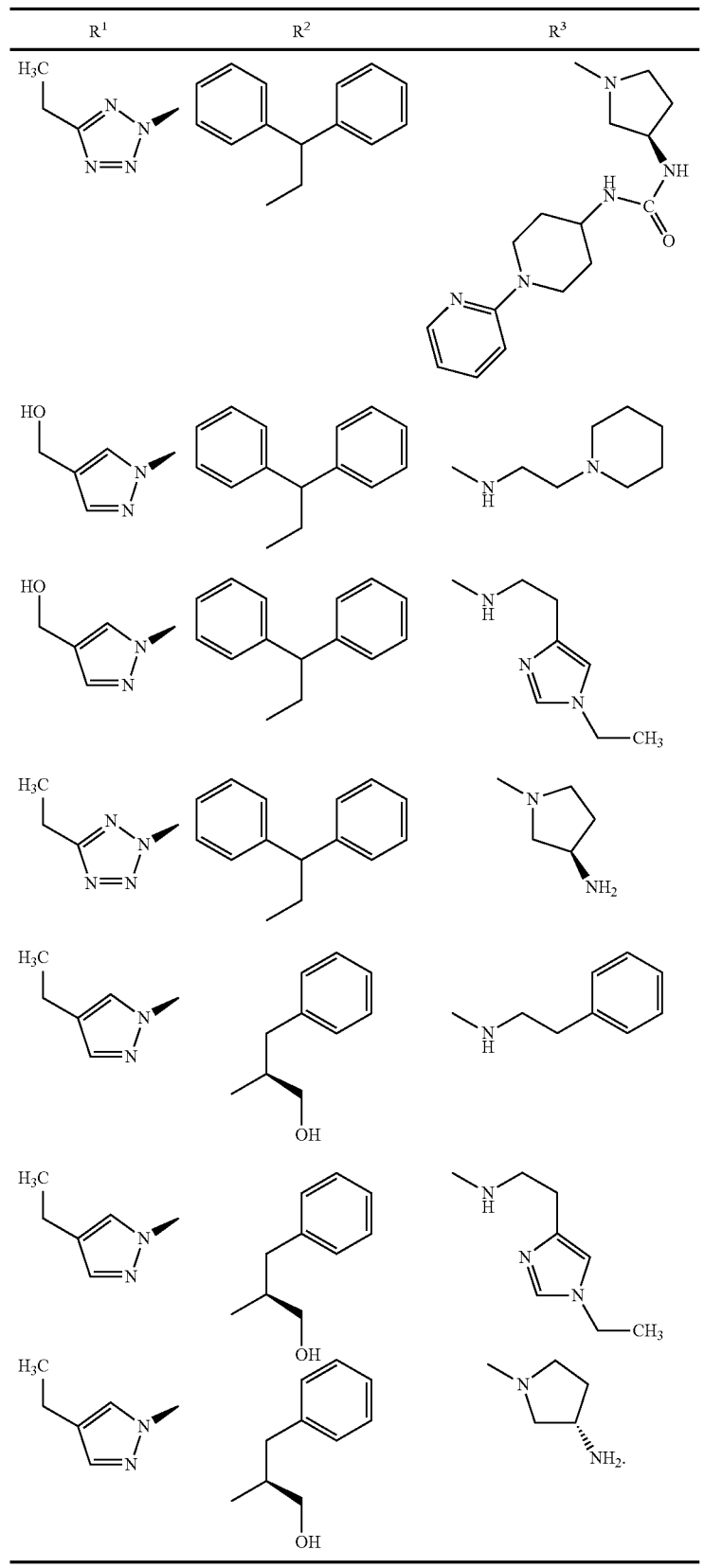

8. The compound of claim 1, wherein $R^1$, $R^2$, and $R^3$ are selected from the group consisting of:
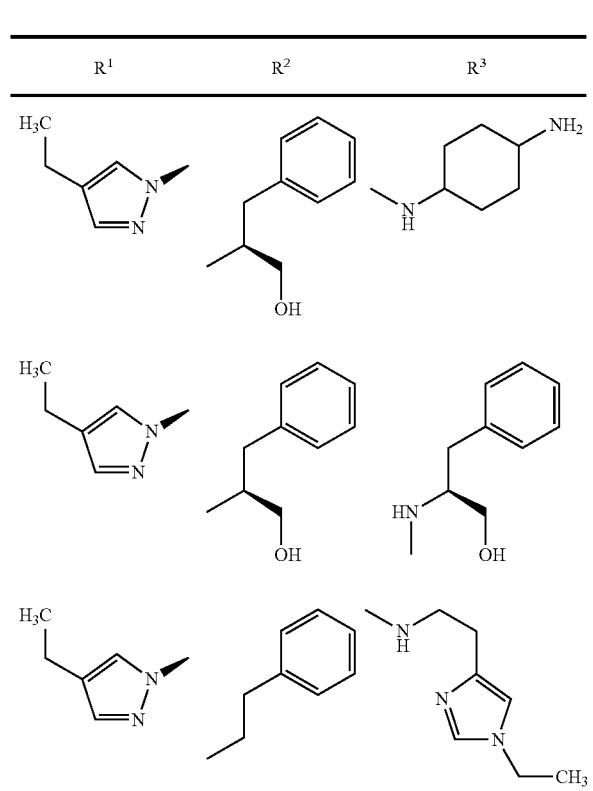
9. The compound of claim 1, wherein $R^1$, $R^2$, and $R^3$ are selected from the group consisting of:

| R¹ | R² | R³ |
|---|---|---|
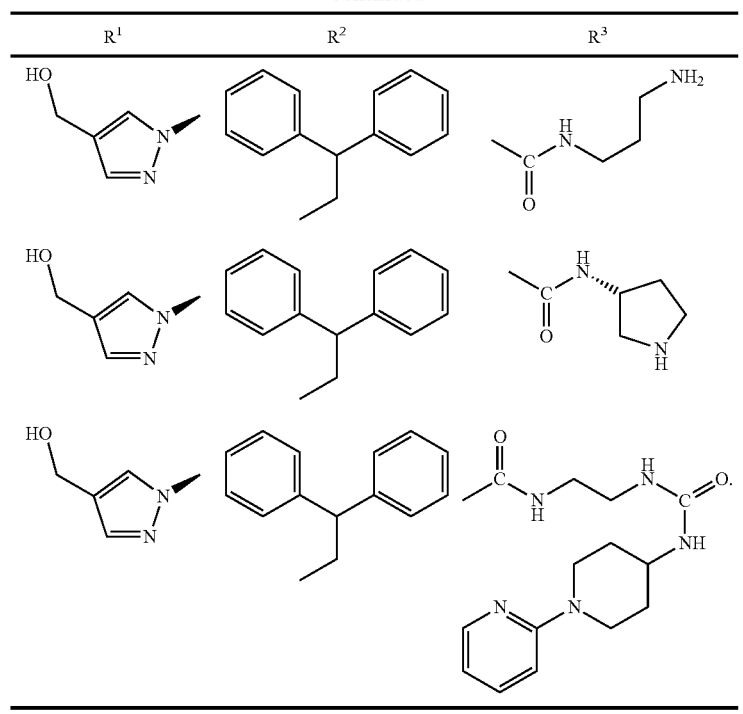
10. The compound of claim 1, wherein R¹, R², and R³ are selected from the group consisting of:
11. The compound of claim 1, wherein R¹, R², and R³ are selected from the group consisting of:
| R¹ | R² | R³ |
|---|---|---|
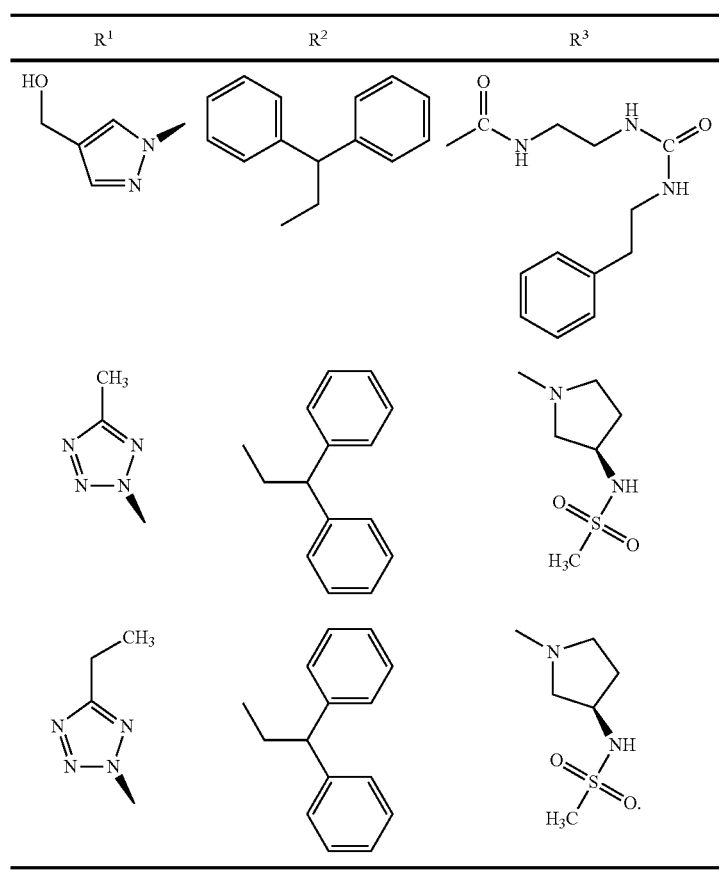

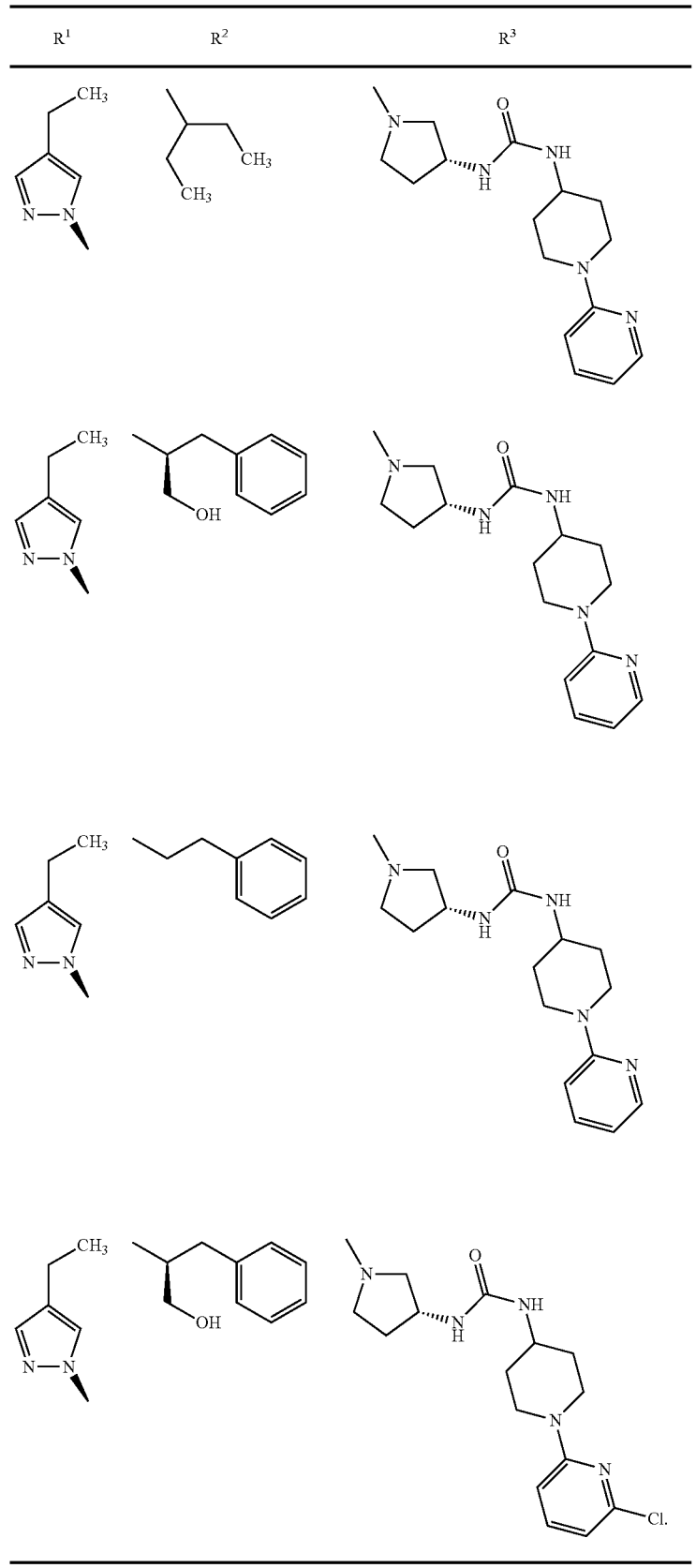

12. The compound of claim 1, wherein $R^1$, $R^2$, and $R^3$ are selected from the group consisting of:
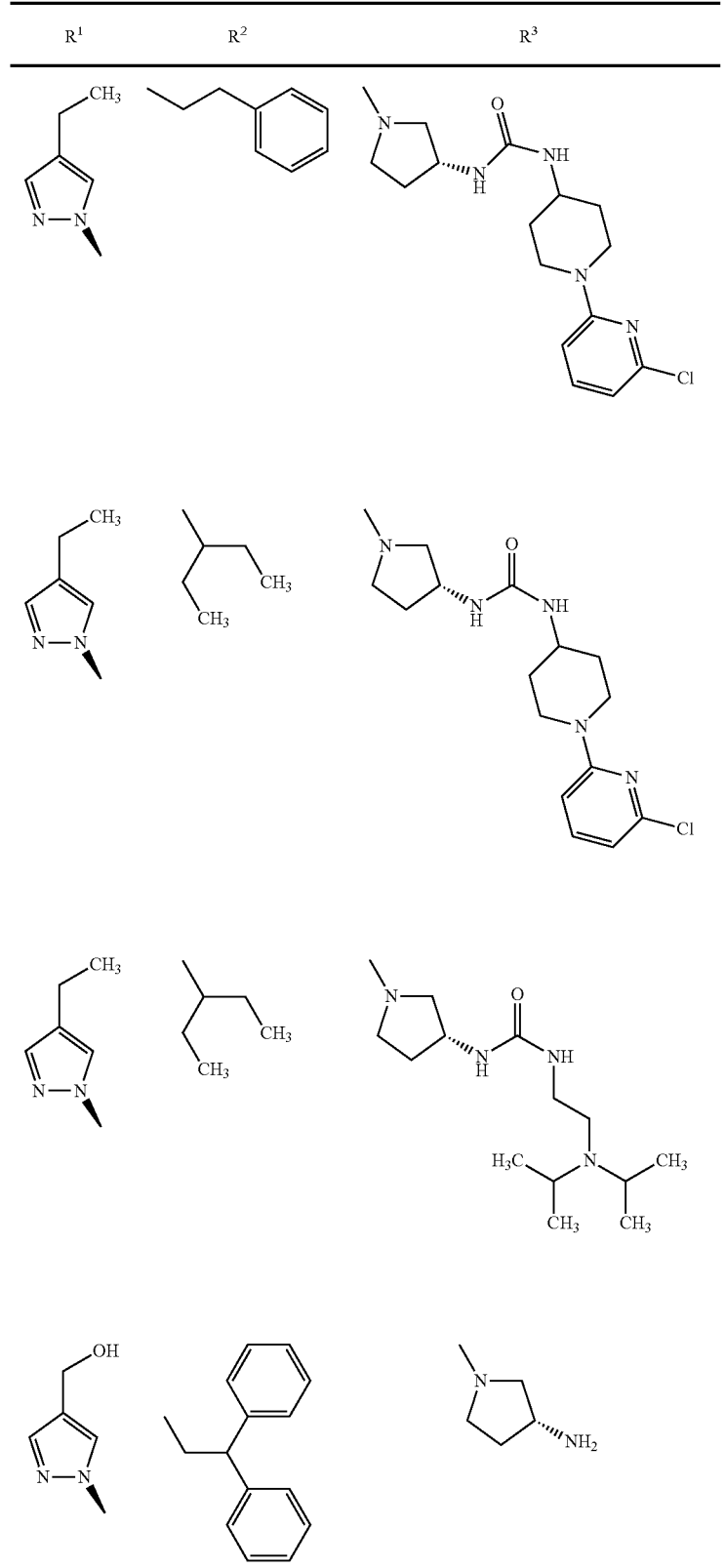

-continued
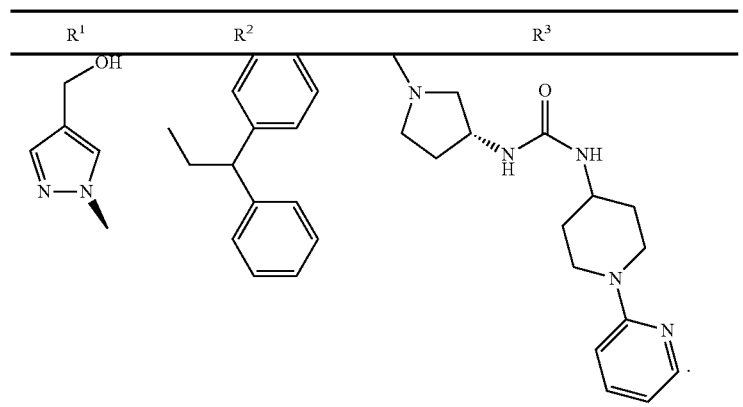
13. The compound of claim 1, wherein R¹, R², and R³ are selected from the group consisting of:
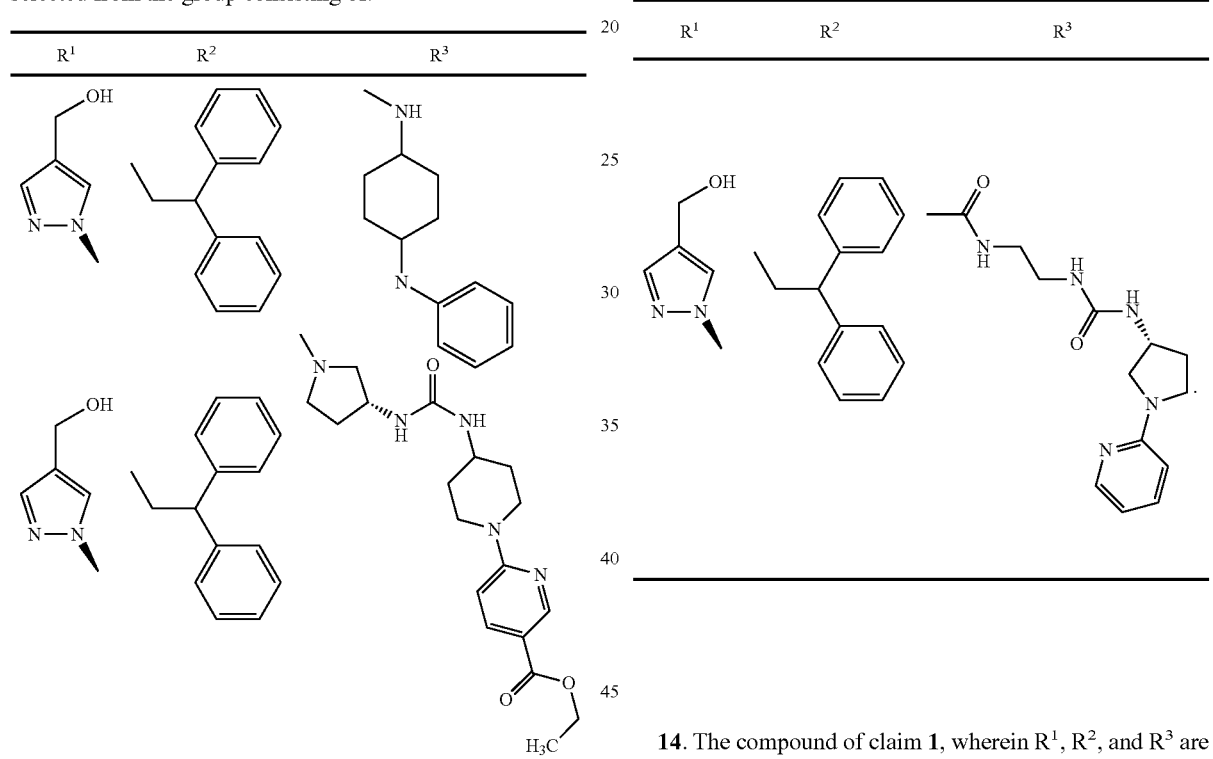
14. The compound of claim 1, wherein R¹, R², and R³ are selected from the group consisting of:
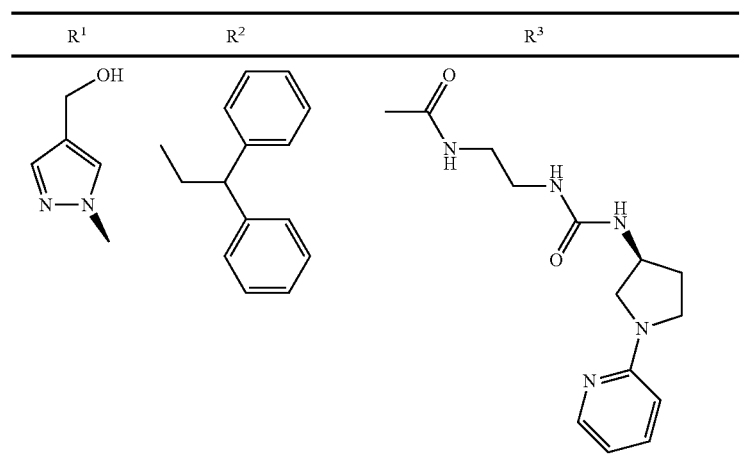

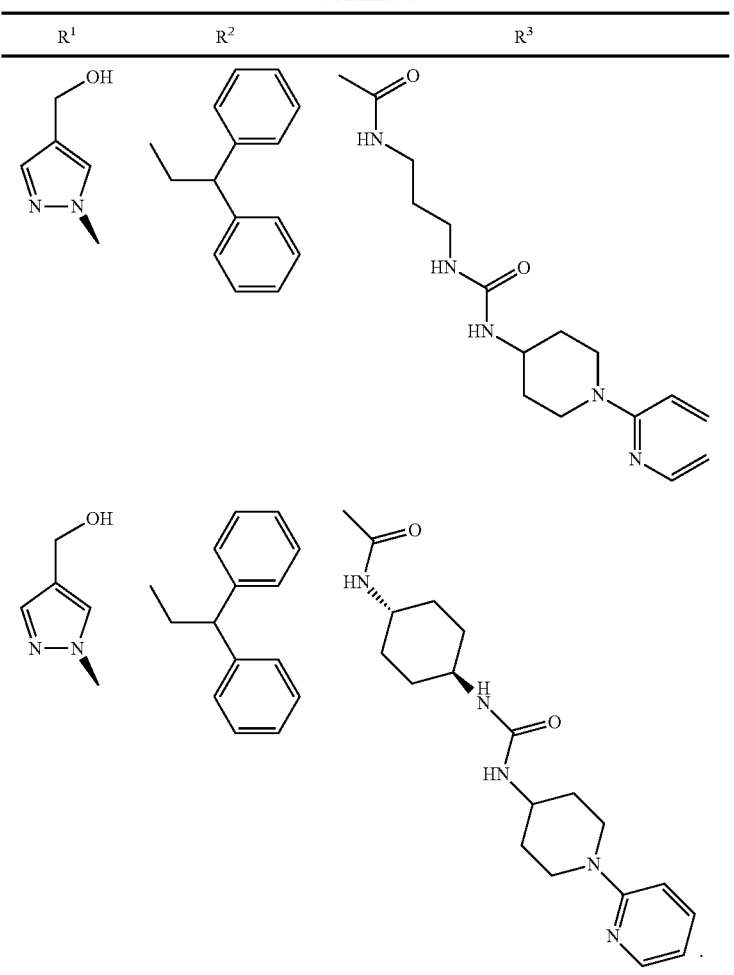
15. The compound of claim 1, wherein $R^1$, $R^2$, and $R^3$ are selected from the group consisting of:
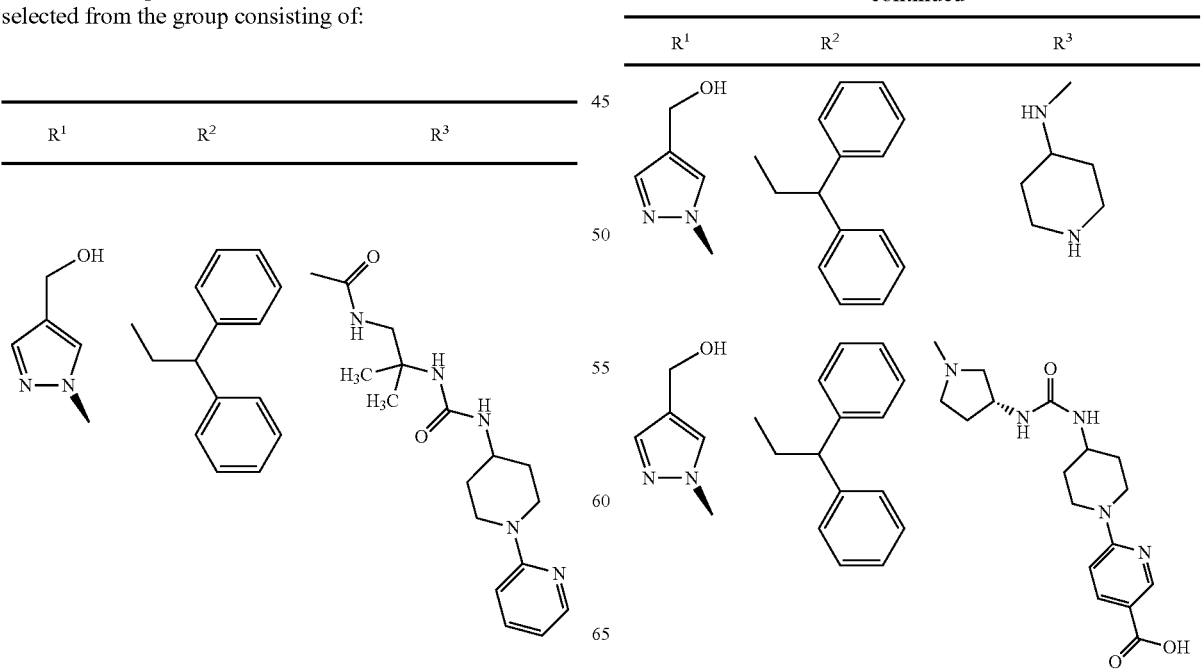

| R¹ | R² | R³ |
|---|---|---|
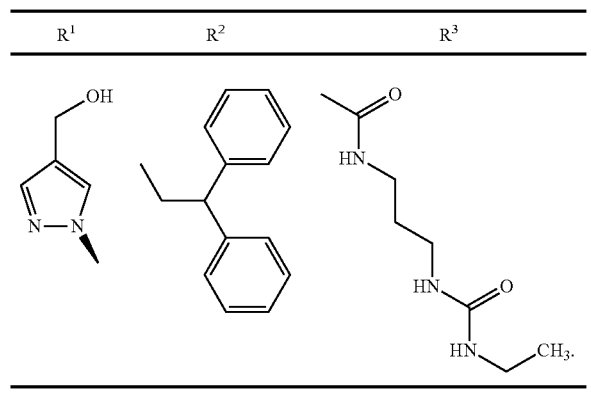
16. The compound of claim 1, wherein R¹, R², and R³ are selected from the group consisting of:
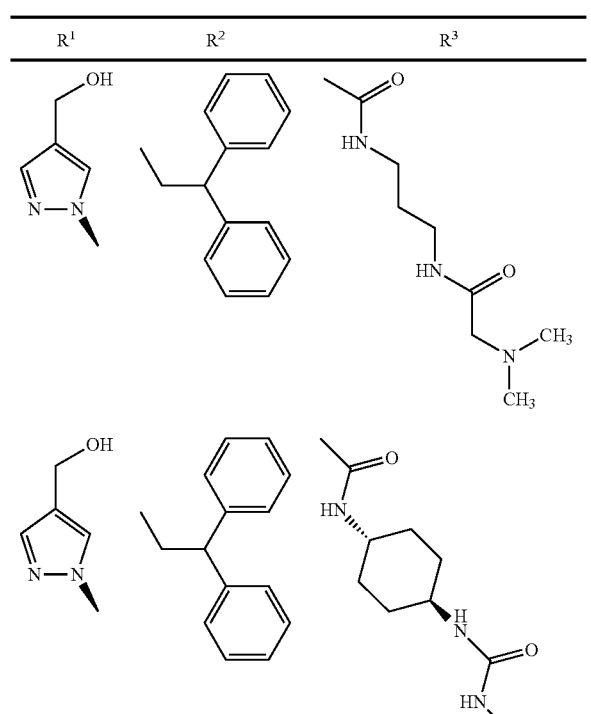
| R¹ | R² | R³ |
|---|---|---|
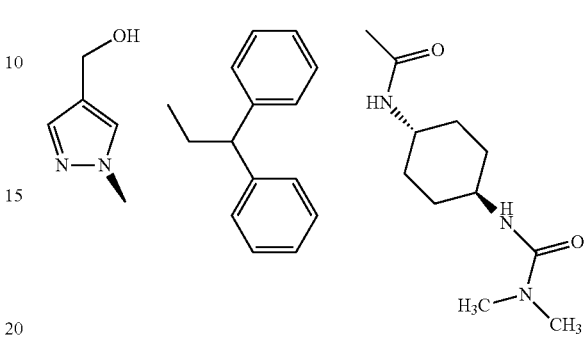
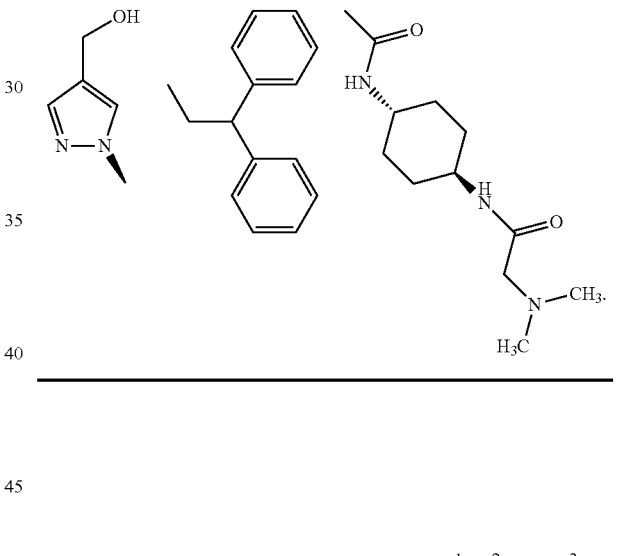
17. The compound of claim 1, wherein R¹, R², and R³ are selected from the group consisting of:
| R¹ | R² | R³ |
|---|---|---|
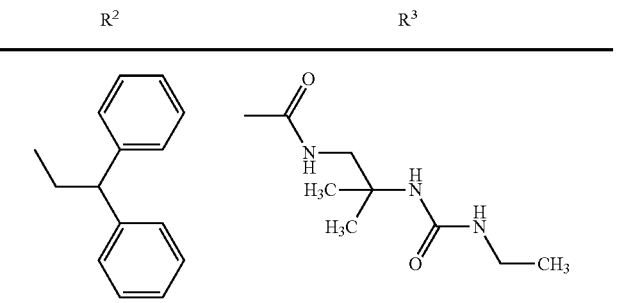

-continued
| R¹ | R² | R³ |
|---|---|---|
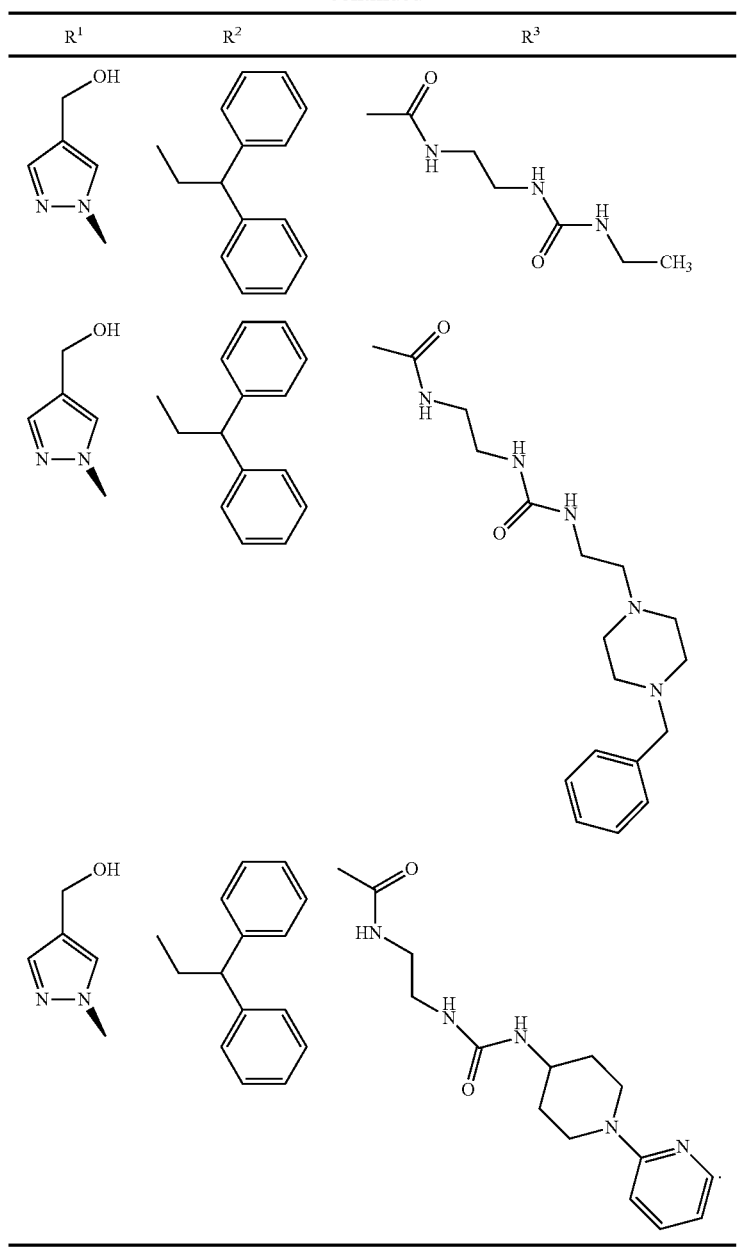
18. The compound of claim 1, wherein R¹, R², and R³ are selected from the group consisting of:
| R¹ | R² | R³ |
|---|---|---|
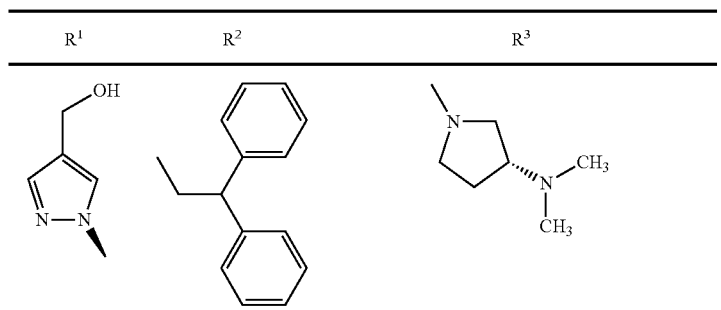

-continued
| R¹ | R² | R³ |
|---|---|---|
| 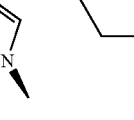 | 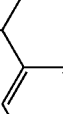 |  |
| 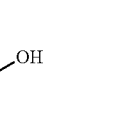 | 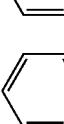 | 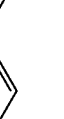 |
| 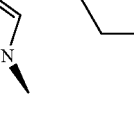 | 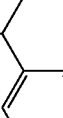 |  |
| 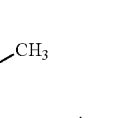 | 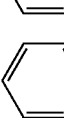 | 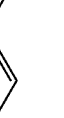 |
| 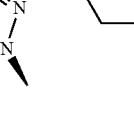 | 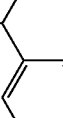 |  |
19. The compound of claim 1, wherein R¹, R², and R³ are selected from the group consisting of:
| R¹ | R² | R³ |
|---|---|---|
| 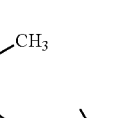 | 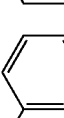 | 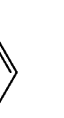 |

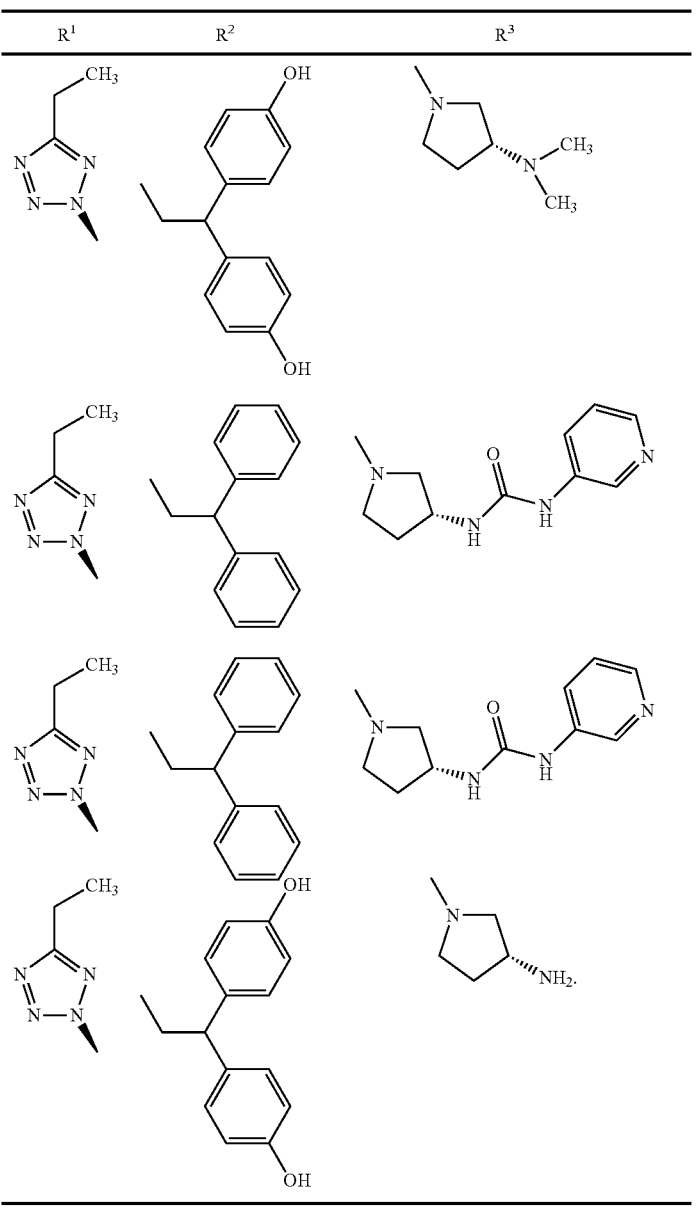
20. The compound of claim 1, wherein $R^1$, $R^2$, and $R^3$ are selected from the group consisting of:
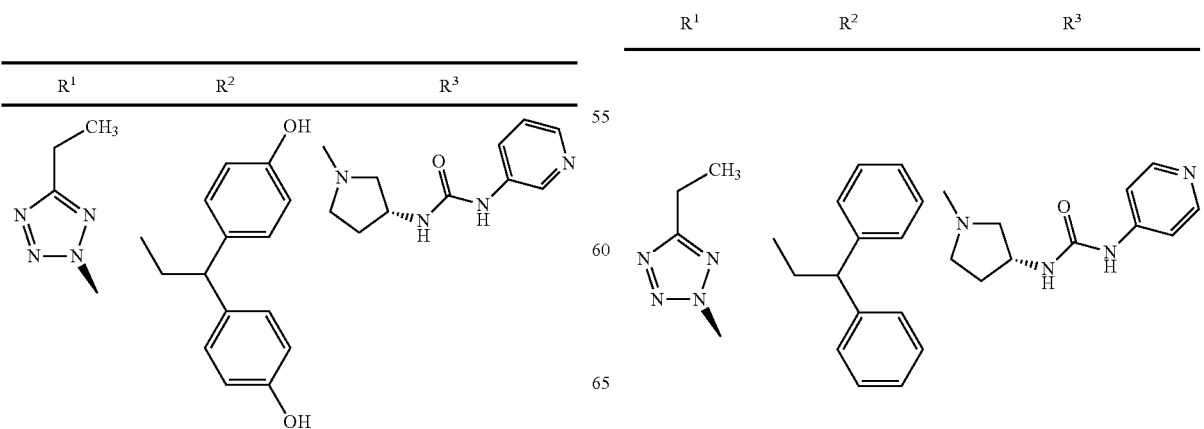

| R¹ | R² | R³ |
|---|---|---|
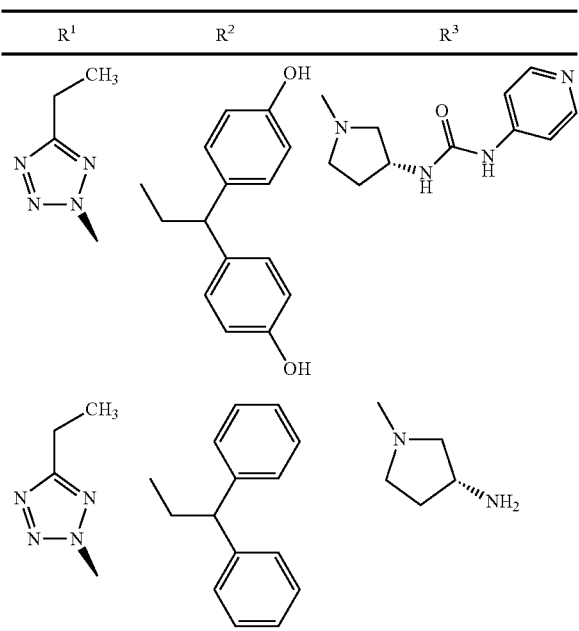
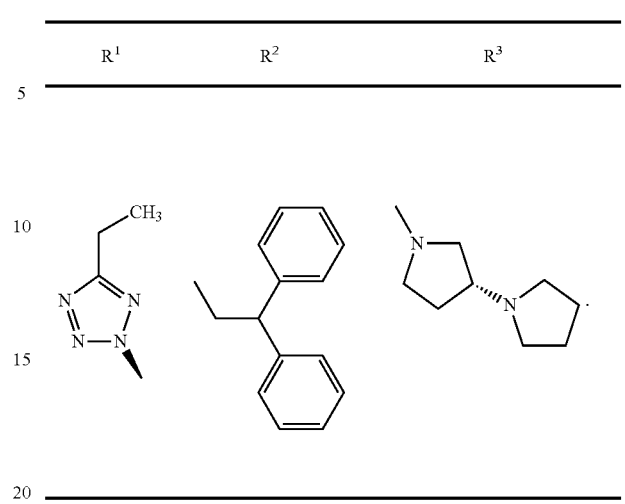
21. The compound of claim 1, wherein R¹, R², and R³ are selected from the group consisting of:
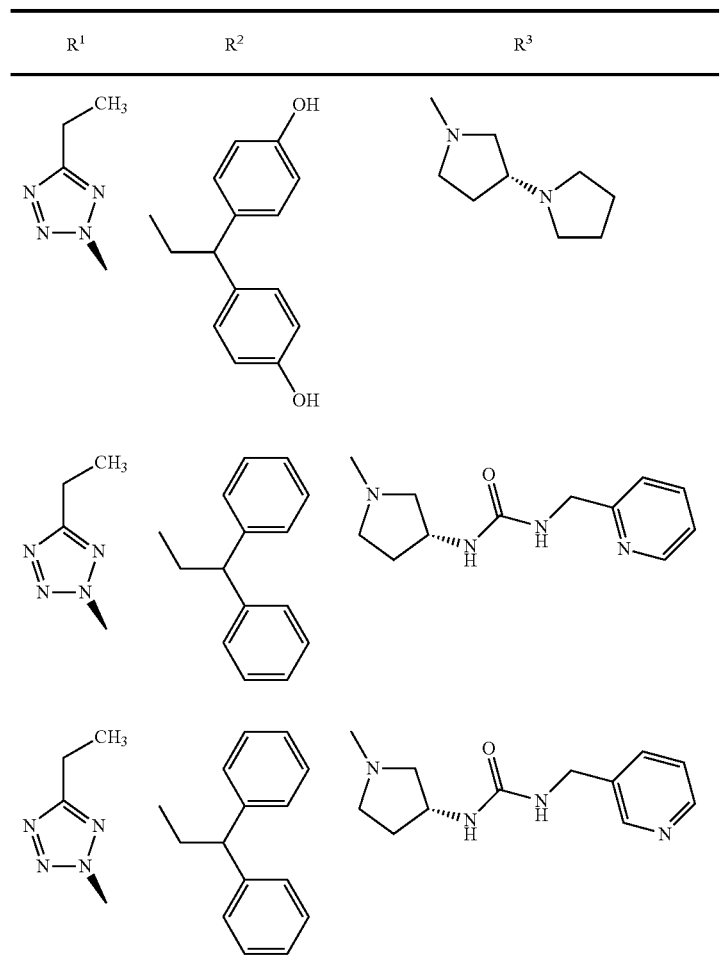

| R¹ | R² | R³ |
|---|---|---|
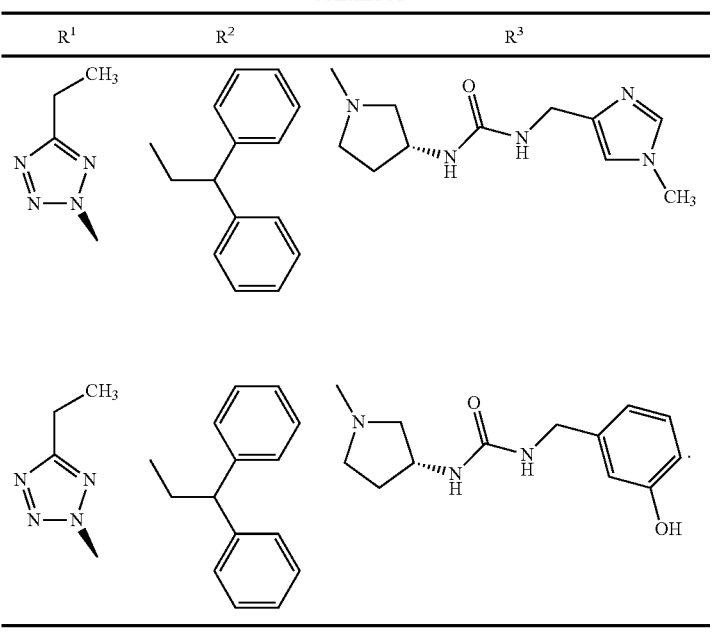
22. The compound of claim 1, wherein R¹, R², and R³ are selected from the group consisting of:
| R¹ | R² | R³ |
|---|---|---|
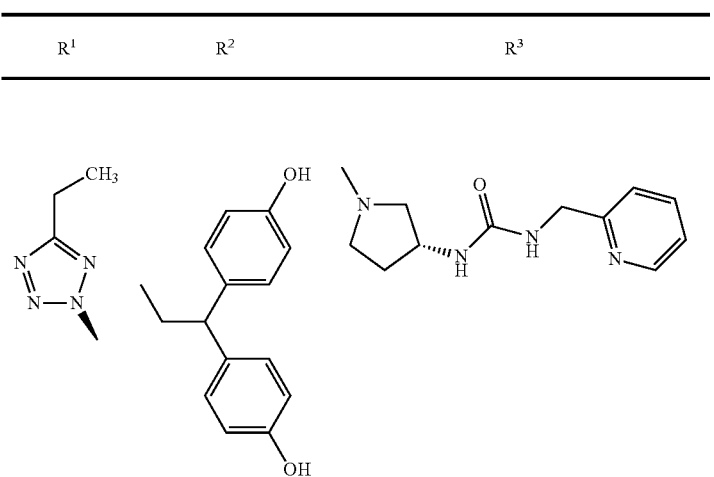
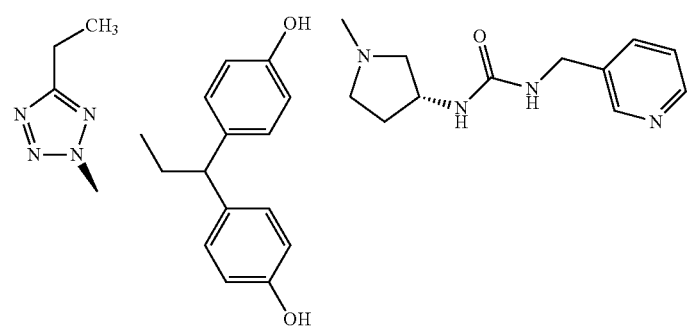

-continued
| R¹ | R² | R³ |
|---|---|---|
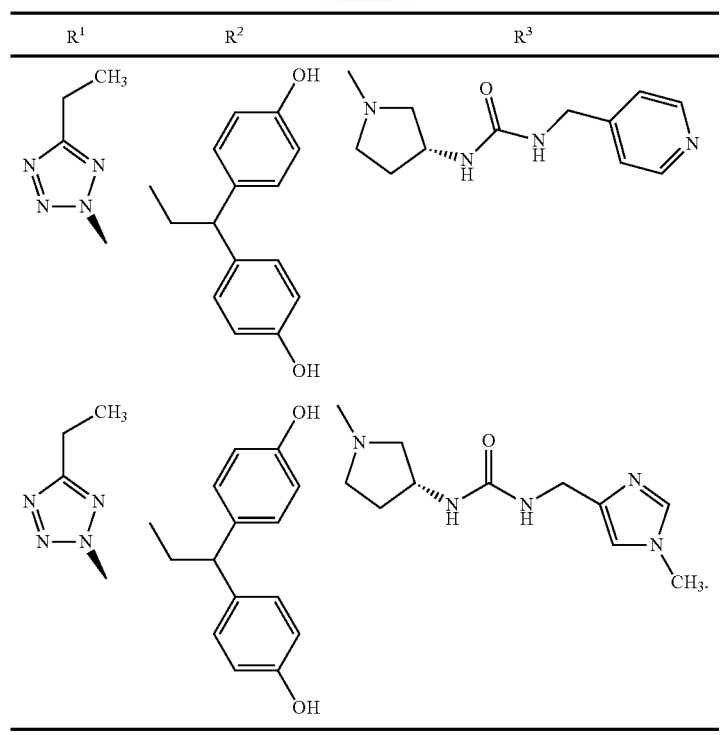
23. The compound of claim 1, wherein R¹, R², and R³ are selected from the group consisting of:
| R¹ | R² | R³ |
|---|---|---|
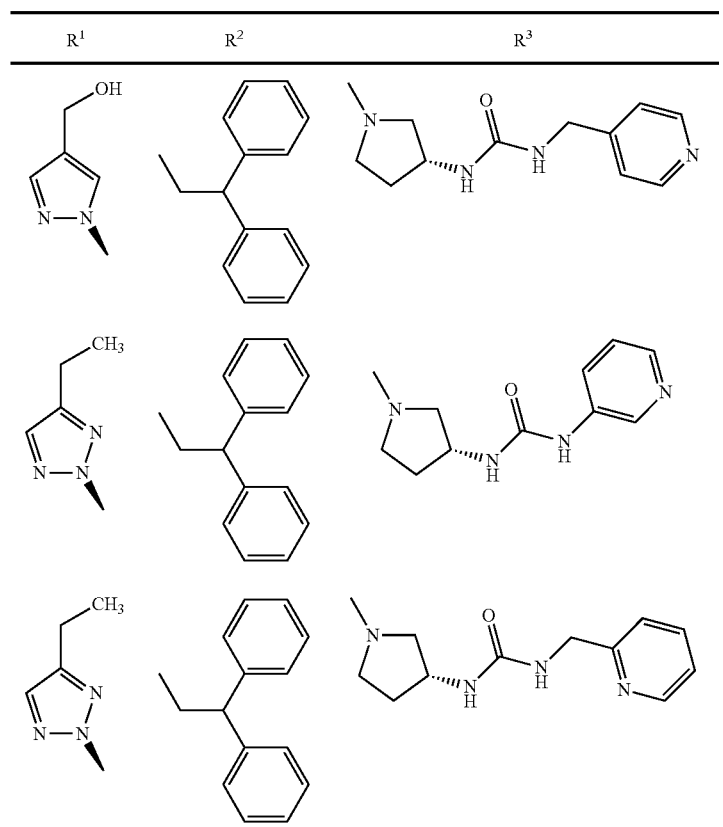

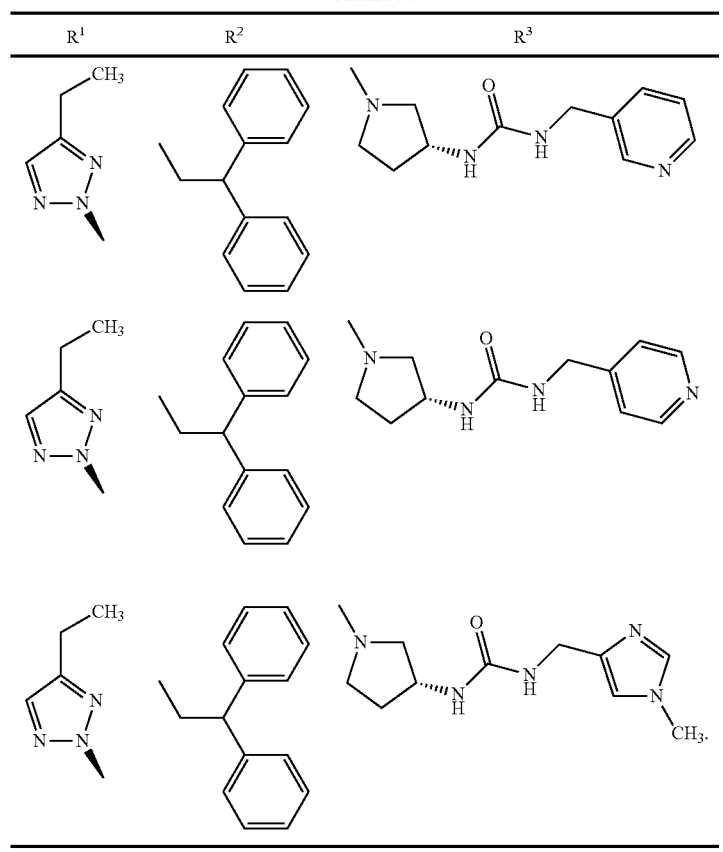
24. The compound of claim 1, wherein $R^1$, $R^2$, and $R^3$ are selected from the group consisting of:
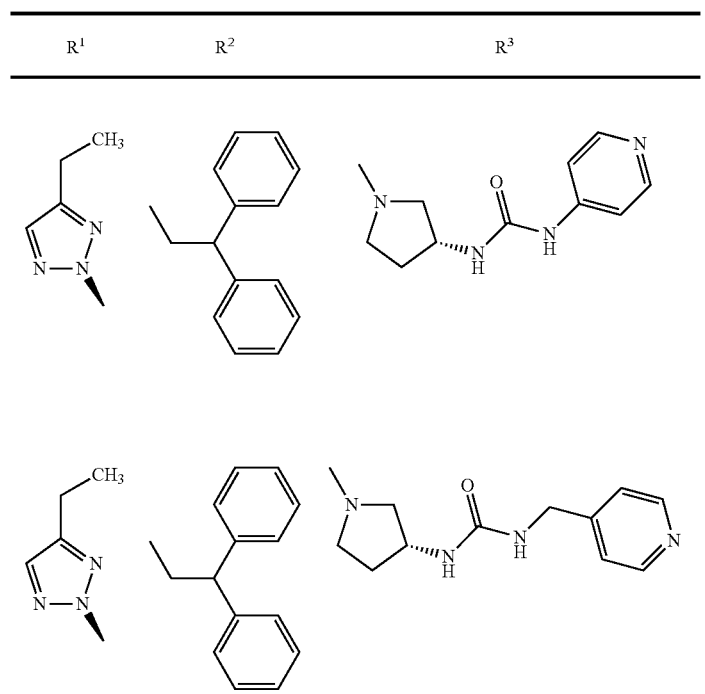

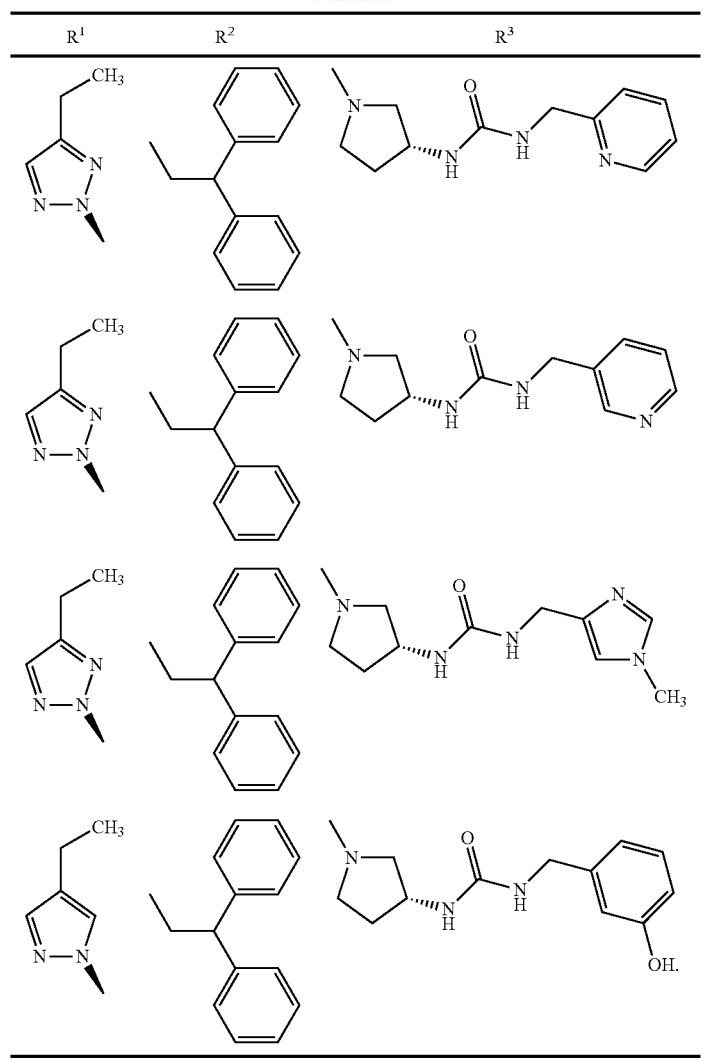
25. The compound of claim 1, wherein $R^1$, $R^2$, and $R^3$ are selected from the group consisting of:
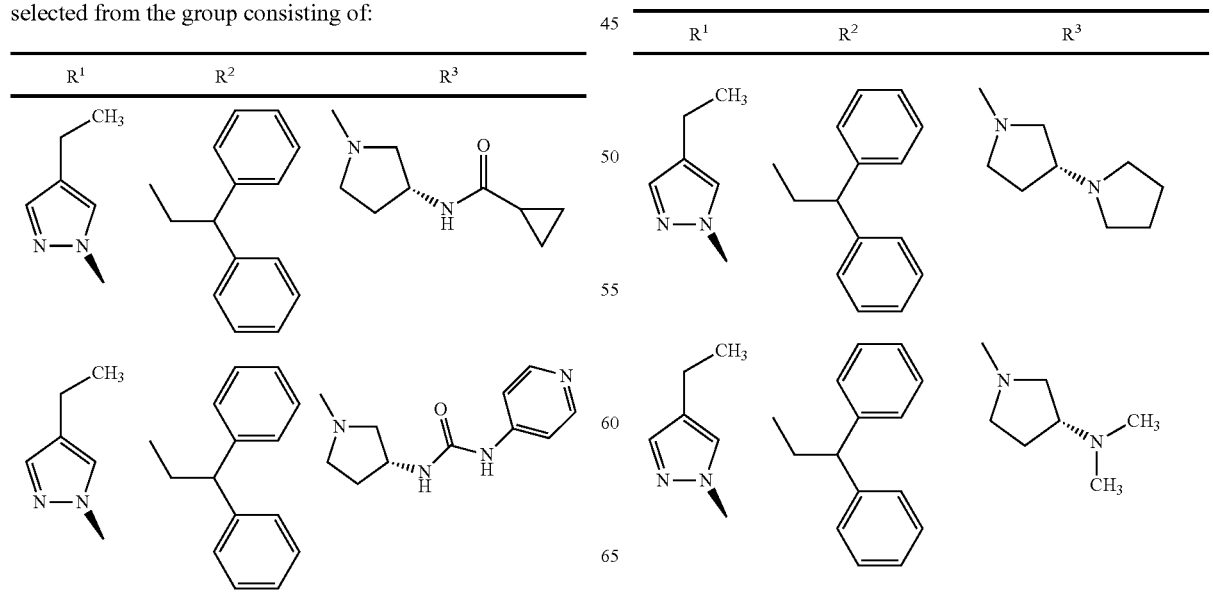

223
-continued
| R¹ | R² | R³ |
|---|---|---|
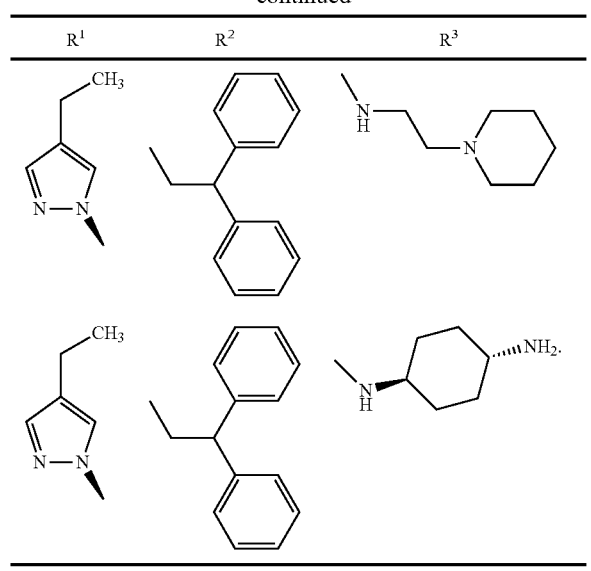
26. The compound of claim 1, wherein R¹, R², and R³ are selected from the group consisting of:
| R¹ | R² | R³ |
|---|---|---|
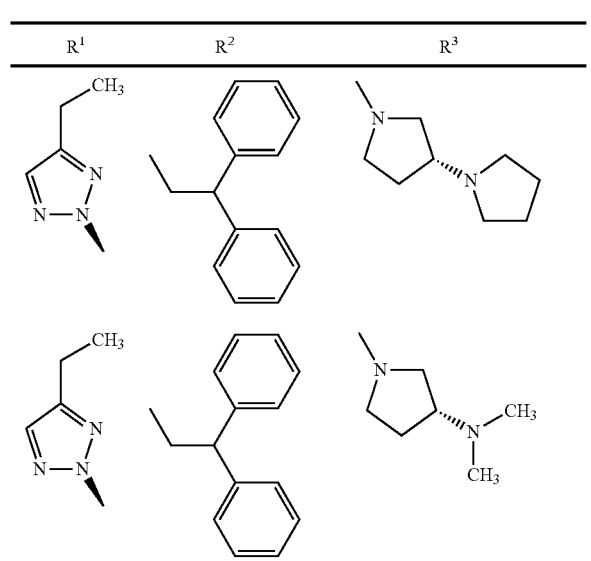
224
-continued
| R¹ | R² | R³ |
|---|---|---|
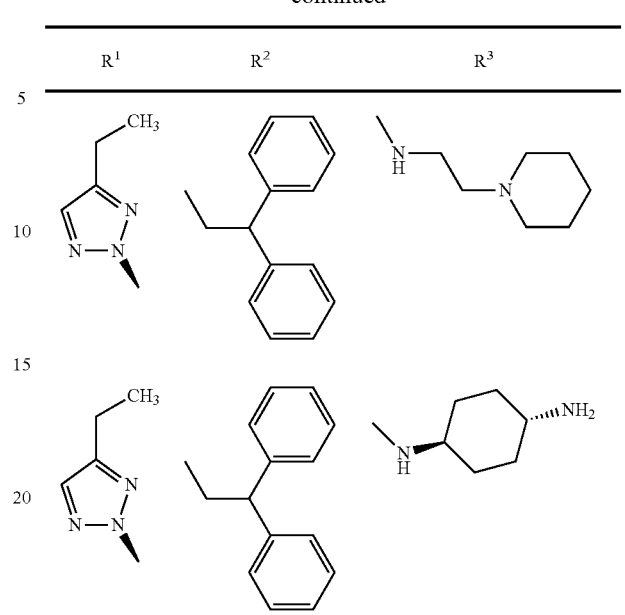
27. The compound of claim 1, wherein R¹, R², and R³ are selected from the group consisting of:
| R¹ | R² | R³ |
|---|---|---|
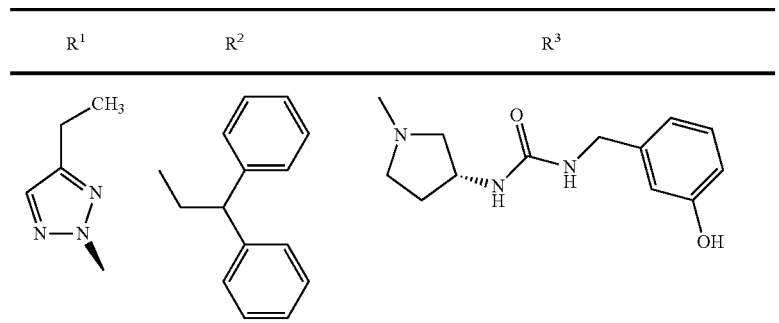

-continued

| R¹ | R² | R³ |
|---|---|---|
| (2-ethyl-tetrazol-5-yl, N-methyl) | 1-(4-hydroxyphenyl)-1-(4-hydroxyphenyl)propyl (bis-4-hydroxyphenyl propyl) | (1-methylpyrrolidin-3-yl)-NH-C(O)-NH-(pyrrolidin-3-yl) |
| (4-ethyl-1-methylpyrazol-1-yl) | 1,1-diphenylpropyl | (1-methylpyrrolidin-3-yl)-NH-C(O)-NH-(pyrrolidin-3-yl) |
| (2-ethyl-tetrazol-5-yl, N-methyl) | 1,1-diphenylpropyl | (1-methylpyrrolidin-3-yl)-NH-C(O)-NH-CH₂-(3-phenyl-isothiazol-5-yl) |
| (2-ethyl-tetrazol-5-yl, N-methyl) | 1,1-diphenylpropyl | (1-methylpyrrolidin-3-yl)-NH-C(O)-NH-CH₂CH₂-(1H-benzimidazol-2-yl) |

28. The compound of claim 1, wherein $R^1$, $R^2$, and $R^3$ are selected from the group consisting of:

| R¹ | R² | R³ |
|---|---|---|
| (2-ethyl-tetrazol-5-yl, N-methyl) | 1,1-diphenylpropyl | (1-methylpyrrolidin-3-yl)-NH-C(O)-NH-CH₂-(quinolin-4-yl) |

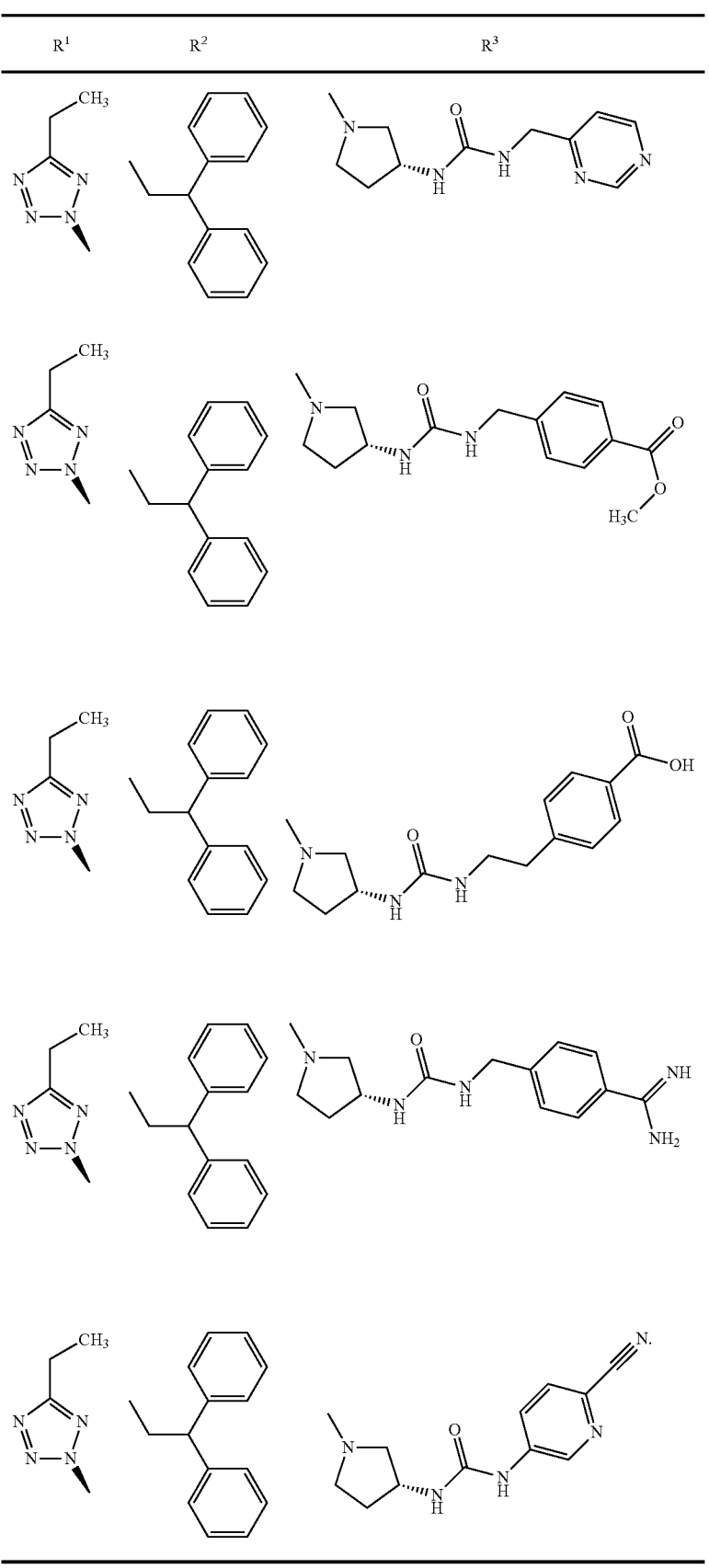

29. The compound of claim 1, wherein $R^1$, $R^2$, and $R^3$ are selected from the group consisting of:
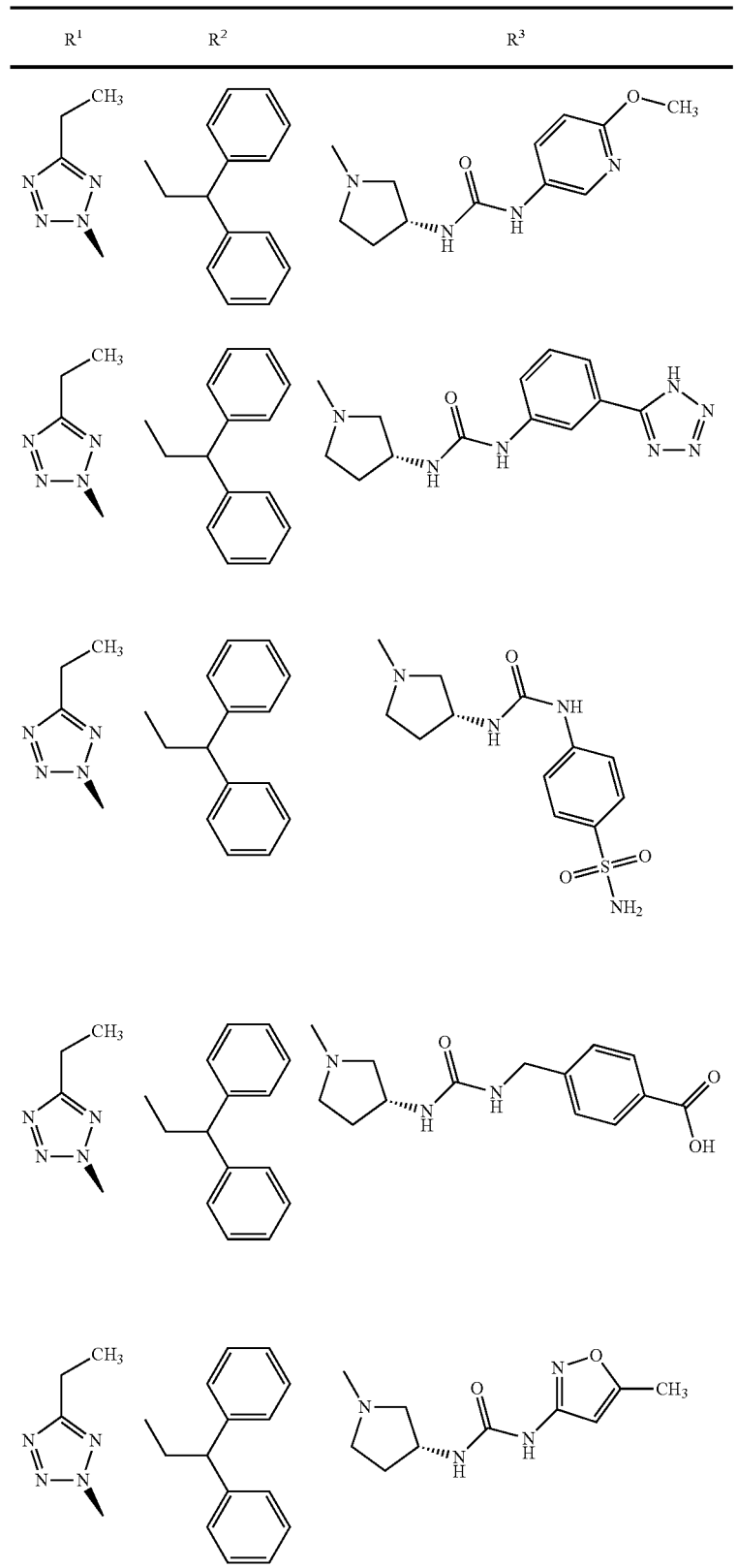

| R¹ | R² | R³ |
|---|---|---|

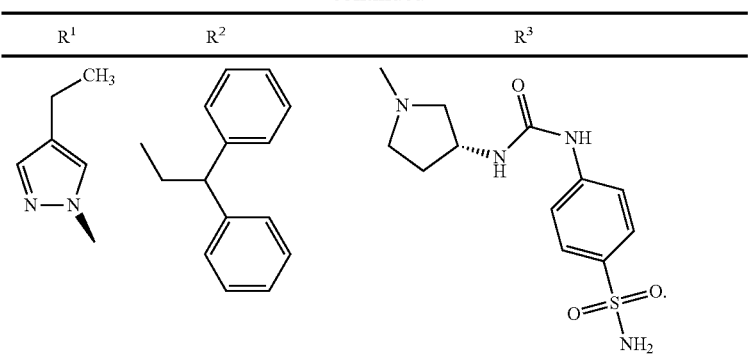

30. A compound according to claim 1 in combination with an anti-inflammatory, bronchodilatory, antihistamine or antitussive drug substance, said compound and said drug substance being in the same or different pharmaceutical composition.

31. A pharmaceutical composition comprising as active ingredient a compound according to claim 1 and a pharmaceutically acceptable diluent or carrier.

* * * * *